US012742196B2

(12) United States Patent
Doudna et al.

(10) Patent No.: US 12,742,196 B2
(45) Date of Patent: *Sep. 22, 2026

(54) METHODS AND COMPOSITIONS FOR DETECTING A TARGET RNA

(71) Applicant: The Regents of the University of California, Oakland, CA (US)

(72) Inventors: Jennifer A. Doudna, Berkeley, CA (US); Mitchell Ray O'Connell, Oakland, CA (US); Alexandra East-Seletsky, San Francisco, CA (US); Spencer Charles Knight, Berkeley, CA (US); James Harrison Doudna Cate, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/492,550

(22) Filed: Oct. 23, 2023

(65) Prior Publication Data

US 2024/0182953 A1 Jun. 6, 2024

Related U.S. Application Data

(60) Continuation of application No. 16/281,939, filed on Feb. 21, 2019, now Pat. No. 11,840,725, which is a continuation of application No. 15/920,222, filed on Mar. 13, 2018, now Pat. No. 10,494,664, which is a division of application No. 15/467,922, filed on Mar. 23, 2017, now Pat. No. 10,337,051.

(60) Provisional application No. 62/378,156, filed on Aug. 22, 2016, provisional application No. 62/351,172, filed on Jun. 16, 2016.

(51) Int. Cl.
*C12Q 1/6823* (2018.01)
*C12N 9/22* (2006.01)

(52) U.S. Cl.
CPC .......... *C12Q 1/6823* (2013.01); *C12N 9/222* (2025.05); *Y02A 50/30* (2018.01)

(58) Field of Classification Search
CPC ...... C12Q 1/6823; C12Q 1/6816; C12Q 1/68; C12Q 1/6818; C12Q 2521/307; C12Q 2537/143; C12Q 2563/107; C12Q 2565/1015; Y02A 50/30; C07K 2319/24; C07K 2319/40; C12N 9/22; C12N 15/113; C12N 2310/20
See application file for complete search history.

(56) References Cited

U.S. PATENT DOCUMENTS

| | | | |
|---|---|---|---|
| 6,773,885 | B1 | 8/2004 | Walder et al. |
| 8,597,886 | B2 | 12/2013 | Smith et al. |
| 8,815,782 | B2 | 8/2014 | Zeiner et al. |
| 9,730,967 | B2 | 8/2017 | Kovarik et al. |
| 9,790,490 | B2 | 10/2017 | Zhang et al. |
| 10,253,365 | B1 | 4/2019 | Doudna et al. |
| 10,266,886 | B2 | 4/2019 | Abudayyeh et al. |
| 10,316,324 | B2 | 6/2019 | Begemann et al. |
| 10,337,051 | B2 | 7/2019 | Doudna et al. |
| 10,494,664 | B2 | 12/2019 | Doudna et al. |
| 10,570,415 | B2 | 2/2020 | Doudna et al. |
| 11,180,743 | B2 | 11/2021 | Doudna et al. |
| 11,371,031 | B2 | 6/2022 | Doudna et al. |
| 11,371,062 | B2 | 6/2022 | Doudna et al. |
| 11,441,137 | B2 | 9/2022 | Doudna et al. |
| 11,453,866 | B2 | 9/2022 | Doudna et al. |
| 11,459,599 | B2 | 10/2022 | Doudna et al. |
| 11,459,600 | B2 | 10/2022 | Doudna et al. |
| 11,739,335 | B2 | 8/2023 | Chevessier-tünnesen et al. |
| 11,795,472 | B2 | 10/2023 | Doudna et al. |
| 11,827,919 | B2 | 11/2023 | Doudna et al. |
| 11,840,725 | B2 | 12/2023 | Doudna et al. |
| 11,873,504 | B2 | 1/2024 | Doudna et al. |
| 11,970,719 | B2 | 4/2024 | Doudna et al. |
| 2012/0252876 | A1 | 10/2012 | Tenenbaum et al. |
| 2013/0123129 | A1 | 5/2013 | Zeiner et al. |
| 2013/0261196 | A1 | 10/2013 | Diamond et al. |
| 2014/0068797 | A1 | 3/2014 | Doudna et al. |
| 2014/0093883 | A1 | 4/2014 | Maples et al. |
| 2014/0273226 | A1 | 9/2014 | Wu |
| 2015/0020223 | A1 | 1/2015 | Zhang et al. |
| 2015/0211058 | A1 | 7/2015 | Carstens |
| 2016/0017366 | A1 | 1/2016 | Chen et al. |
| 2016/0138008 | A1 | 5/2016 | Doudna et al. |
| 2016/0208243 | A1 | 7/2016 | Zhang et al. |

(Continued)

FOREIGN PATENT DOCUMENTS

| | | | |
|---|---|---|---|
| CN | 1886512 | A | 12/2006 |
| CN | 101283089 | A | 10/2008 |

(Continued)

OTHER PUBLICATIONS

Abudayyeh "C2c2 is a single-component programmable RNA-guided RNA-targeting CRISPR effector" Science (2016) 353 (6299): 1-9. (Year: 2016).*
Yang et al. "Using Molecular Beacons for Sensitive Fluorescence Assays of the Enzymatic Cleavage of Nucleic Acids", Methods in Molecular Biology, vol. 335: Fluorescent Energy Transfer Nucleic Acid Probes., (2006), pp. 7 (Year: 2006).*
Pausch, et al., "DNA Interference States of the Hypercompact CRISPR-CasΦ Effector", Nat Struct Mol Biol., Aug. 2021, 28(8):652-661.

(Continued)

*Primary Examiner* — Heather Calamita
(74) *Attorney, Agent, or Firm* — Shweta Chandra; Bozicevic, Field & Francis LLP

(57) ABSTRACT

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample.

19 Claims, 79 Drawing Sheets

Specification includes a Sequence Listing.

(56) References Cited

U.S. PATENT DOCUMENTS

| | | | | |
|---|---|---|---|---|
| 2016/0289659 | A1 | 10/2016 | Doudna et al. | |
| 2017/0037432 | A1 | 2/2017 | Donohoue et al. | |
| 2017/0051276 | A1 | 2/2017 | May et al. | |
| 2017/0175104 | A1 | 6/2017 | Doudna et al. | |
| 2017/0198277 | A1 | 7/2017 | Kmiec et al. | |
| 2017/0211142 | A1 | 7/2017 | Smargon et al. | |
| 2017/0233756 | A1 | 8/2017 | Begemann et al. | |
| 2017/0306335 | A1 | 10/2017 | Zhang et al. | |
| 2017/0321198 | A1* | 11/2017 | Severinov ............. | C12N 15/85 |
| 2017/0321214 | A1 | 11/2017 | Zhang et al. | |
| 2017/0362644 | A1 | 12/2017 | Doudna et al. | |
| 2017/0369870 | A1 | 12/2017 | Gill et al. | |
| 2018/0148735 | A1 | 5/2018 | Begemann et al. | |
| 2018/0201921 | A1 | 7/2018 | Malcolm | |
| 2018/0208976 | A1 | 7/2018 | Doudna et al. | |
| 2018/0208977 | A1 | 7/2018 | Doudna et al. | |
| 2018/0320163 | A1 | 11/2018 | Koonin et al. | |
| 2018/0340218 | A1 | 11/2018 | Abudayyeh et al. | |
| 2018/0346927 | A1 | 12/2018 | Doudna et al. | |
| 2019/0177775 | A1 | 6/2019 | Doudna et al. | |
| 2019/0185933 | A1 | 6/2019 | Zhang et al. | |
| 2019/0276842 | A1 | 9/2019 | Doudna et al. | |
| 2019/0300908 | A1 | 10/2019 | Doudna et al. | |
| 2020/0010878 | A1 | 1/2020 | Doudna et al. | |
| 2020/0010879 | A1 | 1/2020 | Doudna et al. | |
| 2020/0017879 | A1 | 1/2020 | Doudna et al. | |
| 2020/0087640 | A1 | 3/2020 | Doudna et al. | |
| 2020/0115688 | A1 | 4/2020 | Doudna et al. | |
| 2020/0172886 | A1 | 6/2020 | Doudna et al. | |
| 2020/0255858 | A1 | 8/2020 | Doudna et al. | |
| 2020/0299660 | A1 | 9/2020 | Doudna et al. | |
| 2020/0339967 | A1 | 10/2020 | Doudna et al. | |
| 2020/0370028 | A1 | 11/2020 | Doudna et al. | |
| 2021/0017508 | A1 | 1/2021 | Doudna et al. | |
| 2021/0024942 | A1 | 1/2021 | Chen et al. | |
| 2021/0166783 | A1 | 6/2021 | Shmakov et al. | |
| 2021/0209981 | A1 | 7/2021 | Wang | |
| 2021/0214697 | A1 | 7/2021 | Doudna et al. | |
| 2021/0284981 | A1 | 9/2021 | Doudna et al. | |
| 2021/0309981 | A1 | 10/2021 | Doudna et al. | |
| 2022/0396812 | A1 | 12/2022 | Doudna et al. | |
| 2023/0332218 | A1 | 10/2023 | Rauch et al. | |
| 2023/0348872 | A1 | 11/2023 | Doudna et al. | |
| 2024/0167052 | A1 | 5/2024 | Doudna et al. | |
| 2024/0301376 | A1 | 9/2024 | Doudna et al. | |

FOREIGN PATENT DOCUMENTS

| | | | |
|---|---|---|---|
| CN | 103088128 | A | 5/2013 |
| CN | 104620107 | A | 5/2015 |
| CN | 106701830 | A | 5/2017 |
| EP | 1580273 | A1 | 9/2005 |
| EP | 3009511 | A2 | 4/2016 |
| EP | 2825654 | B1 | 4/2017 |
| EP | 3546573 | A1 | 10/2019 |
| EP | 3283625 | B1 | 12/2019 |
| EP | 3665279 | A1 | 6/2020 |
| JP | 2004521606 | A | 7/2004 |
| WO | WO 2014065596 | A1 | 5/2014 |
| WO | WO 2015/071474 | | 5/2015 |
| WO | WO 2015089486 | A2 | 6/2015 |
| WO | WO 2015/139139 | | 9/2015 |
| WO | WO 2015/191693 | | 12/2015 |
| WO | WO 2016/094872 | | 12/2015 |
| WO | WO 2016/106236 | | 12/2015 |
| WO | WO 2016/028843 | | 2/2016 |
| WO | WO 2016/094867 | A1 | 6/2016 |
| WO | WO 2016/205711 | | 6/2016 |
| WO | WO 2016/123243 | | 8/2016 |
| WO | WO 2016166340 | A1 | 10/2016 |
| WO | WO 2016/205613 | | 12/2016 |
| WO | WO 2016/205749 | | 12/2016 |
| WO | WO 2016/205764 | | 12/2016 |
| WO | WO 2017/070605 | | 4/2017 |
| WO | WO 2017/205668 | | 5/2017 |
| WO | WO 2017/120410 | | 7/2017 |
| WO | WO 2017/147345 | | 8/2017 |
| WO | WO 2017/176529 | | 10/2017 |
| WO | WO 2017/218573 | | 12/2017 |
| WO | WO 2017/219027 | | 12/2017 |
| WO | WO 2017/223538 | | 12/2017 |
| WO | WO 2017207589 | A1 | 12/2017 |
| WO | WO 2018027078 | A1 | 2/2018 |
| WO | WO 2018035250 | A1 | 2/2018 |
| WO | WO 2018/064352 | | 4/2018 |
| WO | WO 2018/064371 | | 4/2018 |
| WO | WO 2018/107129 | | 6/2018 |
| WO | WO 2018152418 | A1 | 8/2018 |
| WO | WO 2018/172556 | | 9/2018 |
| WO | WO 2018/195545 | | 10/2018 |
| WO | WO 2018202800 | A1 | 11/2018 |
| WO | WO 2019030695 | A1 | 2/2019 |
| WO | WO 2019/089796 | | 5/2019 |
| WO | WO 2019/089804 | | 5/2019 |
| WO | WO 2019/089808 | | 5/2019 |
| WO | WO 2019/089820 | | 5/2019 |
| WO | WO 2019/126577 | | 6/2019 |
| WO | WO 2019222555 | A1 | 11/2019 |
| WO | WO 2020023529 | A1 | 1/2020 |
| WO | WO 2020098772 | A1 | 5/2020 |

OTHER PUBLICATIONS

Extended European Search Report for EP Patent Application No. 17857442.2, mailed on Jan. 2, 2020, 8 pages.

"How to Choose the Right Cas Variant for Every CRISPR Experiment", Synthego, Chapter 5, Retrieved from the internet <https://www.synthego.com/guide/how-to-use-crispr/cas9-nuclease-variants> on Sep. 11, 2024, , 17 pages.

"Transposase", JGI Accession No. (Taxon ID:Gene ID) 3300013127.a:Ga0172365_100044211, Nov. 5, 2021, 2 pages.

"Transposase", JGI Accession No. (Taxon ID:Gene ID) 3300013123.a:Ga0172368_100090142, Nov. 5, 2021, 2 pages.

"Transposase", JGI Accession No. (Taxon ID:Gene ID) 3300025317.a:Ga0209541_ 1000016152, Nov. 5, 2021, 2 pages.

"Transposase", JGI Accession No. (Taxon ID:Gene ID) 3300025317.a:Ga0209541_1000046133, Nov. 5, 2021, 1 pages.

"Transposase", JGI Accession No. (Taxon ID:Gene ID) 3300013125.a:Ga0172369_100104642, Nov. 5, 2021, 2 pages.

"Transposase", JGI Accession No. (Taxon ID:Gene ID) 3300013130.a:Ga0172363_100165517, Nov. 5, 2021, 2 pages.

"Transposase", JGI Accession No. (Taxon ID:Gene ID) 3300025317.a:Ga0209541_100217848, Nov. 5, 2021, 2 pages.

"Transposase", JGI Accession No. (Taxon ID:Gene ID) 3300025323.a:Ga0209542_100271699, Nov. 5, 2021, 2 pages.

"Transposase", JGI Accession No. 3300025142.a:Ga0210019_10421012, Sep. 1, 2021, 2 pages.

"Transposase", JGI Accession No. 3300025308.a:Ga0209211_100536734, Nov. 9, 2021, 2 pages.

"Transposase", JGI Accession No. 3300025317.a:Ga0209541_100096836, Nov. 9, 2021, 2 pages.

"Transposase", JGI Accession No. 3300025323.a:Ga0209542_1000010711, Nov. 9, 2021, 2 pages.

"Transposase", JGI Accession No. 3300025323.a:Ga0209542_10000107204, Nov. 9, 2021, 2 pages.

"Transposase and inactivated derivatives", JGI Accession No. (Taxon ID: Gene ID) 3300000353.a:ElkS_mat_MD6ADraft_10068983, Nov. 5, 2021, 2 pages.

"Transposase and inactivated derivatives", JGI Accession No. 3300002105.a:C687J26635_100228363, Nov. 9, 2021, 2 pages.

"Transposase and inactivated derivatives", JGI Accession No. (Taxon ID:Gene ID) 3300002966.a:JGI24721J44947_100297402, Nov. 5, 2021, 2 pages.

"Transposase and inactivated derivatives", JGI Accession No. (Taxon ID:Gene ID) 3300002502.a:C687J35174_100502431, Nov. 5, 2021, 2 pages.

"Transposase and inactivated derivatives", JGI Accession No. (Taxon ID:Gene ID) 3300001245.a:JGI12048J13642_102012859, Nov. 5, 2021, 2 pages.

(56) References Cited

OTHER PUBLICATIONS

"Transposase and inactivated derivatives", JGI Accession No. (Taxon ID:Gene ID) 3300001245.a:JGI12048J13642_102012865, Nov. 5, 2021, 2 pages.
"Transposase and inactivated derivatives", JGI Accession No. (Taxon ID:Gene ID) 3300001256.a:JGI12210J13797_103875826, Nov. 5, 2021, 2 pages.
"Transposase and inactivated derivatives", JGI Accession No. (Taxon ID:Gene ID) 3300001256.a:JGI12210J13797_103875833, Nov. 5, 2021, 2 pages.
"Transposase and inactivated derivatives", JGI Accession No. (Taxon ID:Gene ID) 3300005573.a:Ga0078972_100101520, Nov. 5, 2021, 1 page.
"Transposase and inactivated derivatives", JGI Accession No. 3300002502.a:C687J35174_100538264, Sep. 1, 2021, 2 pages.
Bhattacharya et al., "Impact of genetic variation on three dimensional structure and function of proteins", PLoS One, Mar. 15, 2017, 12(3):e0171355:1-22.
Bork et al., "Go hunting in sequence databases but watch out for the traps", Trends in Genetics, Oct. 1996, 12(10):425-427.
Bork, P., "Powers and pitfalls in sequence analysis: the 70% hurdle", Genome Research, Apr. 2000, 10(4):398-400.
Brenner et al., "Errors in genome annotation", Outlook, Apr. 1, 1999, 15(4):132-133.
Burstein, et al., "Major bacterial lineages are essentially devoid of CRISPR-Cas viral defence systems", Nature Communications, Feb. 3, 2016, 7(10613):8 pages.
Doerks et al., "Protein annotation: detective work for function prediction", Trends in Genetics, Jan. 2000, 14(6):248-50.
Fenton et al., "Rheostat positions: A new classification of protein positions relevant to pharmacogenomics", Med Chem Res., Jul. 2020, 9(7):1133-1146.
GenBank, "Rec Name: Full=CRISPR-associated endonuclease Cas12a; AltName: Full=AsCpf1; AltName: Full=CRISPR-associated endonuclease Cpf1", Genbank U2UMQ6.1, UniProtKB reviewed Jun. 2023, 11 pages.
GenBank, "Type VI-a CRISPR-Associated RNA-Guided Ribonuclease Cas13a [Leptotrichia Buccalis]", GenBank: WP_015770004, Retrieved from: https://www.ncbi.nlm.nih.gov/protein/WP_015770004.1, Sep. 28, 2020, 2 pages.
GenBank, "Uncultured bacterium GWB1_scaffold_10668 CRISPR-Cas system-like gene, complete sequence", 2016, 4 pages.
Lander, et al., "Genome Editing by CRISPR/Cas9: A Game Change in the Genetic Manipulation of Protists", J Eukaryot Microbiol., Sep. 2016, 63(5):679-690.
Liu et al., "Synthetic chimeric nucleases function for efficient genome editing", Nat Commun., Dec. 2019, 10(5524):11 pages.
Pausch et al., "CRISPR-CasΦ from huge phages is a hypercompact genome editor", Science, Jul. 17, 2020, 369(6501):333-337.
Sawamura et al., "Generation of biallelic F0 mutants in medaka using the CRISPR/Cas9 system", Genes Cells, Aug. 2017, 22(8):756-763.
Skolnick et al., "From genes to protein structure and function: novel applications of computational approaches in the genomic era", Trends in Biotechnology, Jan. 1, 2000, 18(1):34-39.
Smith et al., "The challenges of genome sequence annotation or "the devil is in the details"", Nature Biotechnology, Nov. 1, 1997, 15(12):1222-1223.
Thorne, et al., "Illuminating Insights into Firefly Luciferase and Other Bioluminescent Reporters Used in Chemical Biology", Chemistry and Biology, Jun. 25, 2010, 17(6):646-657.
Tokuriki et al., "Stability effects of mutations and protein evolvability", Current Opinion in Structural Biology, Oct. 2009, 19(5):596-604.
Wright et al., "Rational design of a split-Cas9 enzyme complex", PNAS, Mar. 10, 2015, 112(10):2984-2989.
Xie et al., "sgRNAcas9: A Software Package for Designing CRISPR sgRNA and Evaluating Potential Off-Target Cleavage Sites", PLoS ONE, Jun. 23, 2014, 9(6):e100448, 9 pages.
Abudayyeh, et al.; "C2c2 is a single-component programmable RNA-guided RNA-targeting CRISPR effector"; Science; vol. 353, No. 6299, 23 pages (Aug. 5, 2016).
Abudayyeh, et al.; "C2c2 is a single-component programmable RNA-guided RNA-targeting CRISPR effector; Supplementary Information"; Science; vol. 353, vol. 6299, 31 pages (Aug. 5, 2016).
Abudayyeh, et al.; "RNA targeting with CRISPR-Cas13"; Nature; vol. 550, 18 pages (Oct. 12, 2017).
Ambion: "RnaseAlert Lab Test Kit v2, User Guide"; 12 pages (Mar. 1, 2013).
Anantharaman, et al.; "Thousands of microbial genomes shed light on interconnected biogeochemical processes in an aquifer system"; Nature Communications; vol. 7, No. 13210, 11 pages (Oct. 24, 2016).
Applied Biosystems/Ambion; "RNaseAlert Lab Test Kit"; 12 pages (2008).
Armitage, et al.; "Hairpin-Forming Peptide Nucleic Acid Oligomers"; Biochemistry; vol. 37, pp. 9417-9425 (1998).
Baker, et al.; "Enigmatic, ultrasmall, uncultivated Archaea"; PNAS; vol. 107, No. 19, pp. 8806-8811 (May 11, 2010).
Barrangou, et al.; "Expanding the CRISPR Toolbox: Targeting RNA with Cas13b"; Molecular Cell; vol. 65, No. 4, pp. 582-584 (Feb. 16, 2017).
Bautista, et al.; "Virus-Induced Dormancy in the Archaeon Sulfolobus islandicus"; mBio; vol. 6, No. 2, 8 pages (2015).
Burstein, et al.; "New CRISPR-Cas systems from uncultivated microbes"; Nature; vol. 542, No. 7640, pp. 237-241 (Feb. 9, 2017).
Chen, et al.; "CRISPR-Cas12a target binding unleashes indiscriminate single-stranded DNase activity"; Science; vol. 360, pp. 436-439 (2018).
Choudhury, et al.; "CRISPR-dCas9 mediated TET1 targeting for selective DNA demethylation at BRCA1 promoter"; Oncotarget; vol. 7, No. 29, pp. 46545-46556 (2016).
Chylinski, et al.; "Classification and evolution of type II CRISPR-Cas systems"; Nucleic Acids Research; vol. 42, No. 10, pp. 6091-6105 (2014).
Clustl; "Omega Multiple Sequence Alignment. https://www.ebi.ac.uk/Tools/msa/clustalo/" [Retrieved from internet Feb. 2, 2022]. Alignment and Percent identity matrix. (Year: 2022).
Cong, et al.; "Multiplex Genome Engineering Using CRISPR/Cas Systems"; Science; vol. 339, No. 6121, pp. 819-823 (Feb. 15, 2013).
Cox, et al.; "RNA editing with CRISPR-Cas13"; Science; vol. 358, No. 6366, 15 pages (Nov. 24, 2017).
CRZ3554.1 (hypothetical protein HHT344_2368 [Herbinix hemicellulosilytica], Gen Bank Accession sequence, priority to Jul. 24, 2015, 1 page) (Year: 2015).
Deltcheva, et al.; "CRISPR RNA maturation by trans-encoded small RNA and host factor RNase III"; Nature; vol. 471, pp. 1-19 (Mar. 31, 2011).
East-Seletsky, et al.; "RNA Targeting by Functionally Orthogonal Type VI-A CRISPR-Cas Enzymes"; Molecular Cell; vol. 66, pp. 373-383 (May 4, 2017).
East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).
Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
GenBank CRL33181.1; Hypothetical protein T1815_05231 [[Eubacterium] rectale], priority to Apr. 6, 2016, 2 pages (Year: 2016).
GenBank CRZ35554 1; "Hypothetical protein HHT355_2368 [Herbinix hemicellulosilytica]"; 1 page (Oct. 11, 2018).
GenBank OHA03494.1 (hypothetical protein A3J58_03210 [*Candidatus sung* bacteria bacterium RIFCSPH IGHO2_02_Full_52_23], NCBI Reference Sequence, priority to Oct. 21, 2016, 2 pages) (Year: 2016).
Gootenberg, et al.; "Multiplexed and portable nucleic acid detection platform with Cas13, Cas12a, and Csm6"; Science; vol. 360, pp. 439-444 (2018).
Gootenberg, et al.; "Nucleic acid detection with CRISPR-Cas13a/C2c2"; Science; 9 pages (Apr. 13, 2017).

(56) References Cited

OTHER PUBLICATIONS

Hale, et al.; "RNA-Guided RNA Cleavage by a CRISPR RNA-Cas Protein Complex"; Cell; vol. 139, No. 5, pp. 945-956 (Nov. 25, 2009).
Hale, et al.; "Target RNA capture and cleavage by the Cmr type III-B CRISPR-Cas effector complex"; Genes & Development; vol. 28, No. 21, pp. 2432-2443 (Nov. 1, 2014).
Harrington, et al.; "Programmed DNA destruction by miniature CRISPR-Cas14 enzymes"; Science; vol. 362, pp. 839-842 (Nov. 16, 2018).
Harrington, et al.; "A scoutRNA Is Required for Some Type V CRISPR-Cas Systems"; Molecular Cell, vol. 79, pp. 416-424.
Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).
Hyun, et al., (2015) "Site-directed mutagenesis in *Arabidopsis thaliana* using dividing tissue-targeted RGEN of the CRISPR/Cas system to generate heritable null alleles" Planta; vol. 241, pp. 271-284.
Karvelis, et al.; "PAM recognition by miniature CRISPR-Cas12f nucleases triggers programmable double-stranded DNA target cleavage"; Nucleic Acids Research; pp. 1-8 (2020).
Kelemen, et al.; "Hypersensitive substrate for ribonucleases"; Nucleic Acids Research; vol. 27, No. 18, pp. 3696-3701 (1999).
Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).
Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Koonin, et al.; "CRISPR-Cas: an adaptive immunity system in prokaryotes"; F1000 Biology Reports; vol. 1, No. 95, 6 pages (Dec. 9, 2009).
Koonin et al., (2017) Diversity, classification and evolution of CRISPR-Cas systems. Current Opinion in Microbiology, 37:67-78 (Year:2017).
Koonin, et al.; "Origins and evolution of CRISPR-Cas systems"; Phil. Trans. R. Soc. B.; vol. 374, No. 1772, 6 pages (Mar. 25, 2019).
Le Cong, et al.; "Multiplex Genome Engineering Using CRISPR/Cas Systems"; Science; vol. 339, pp. 819-823 (Feb. 15, 2013).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "Delivery strategies of the CRISPR-Cas9 gene-editing system for therapeutic applications"; Journal of Controlled Release; vol. 266, pp. 17-26 (2017).
Liu, et al.; "CasX enzymes comprise a distinct family of RNA-guided genome editors"; Nature; vol. 566, pp. 23 pages (Feb. 14, 2019).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Makarova, et al.; "An updated evolutionary classification of CRISPR-Cas systems"; Nat. Rev. Microbiol.; vol. 13, No. 11, pp. 722-736 (Nov. 2015).
Makarova, et al.; "Evolutionary classification of CRISPR-Cas systems: a burst of class 2 and derived variants"; Nature Reviews Microbiology; vol. 18, pp. 67-83 (Feb. 2020).
Makarova, et al.; "SnapShot: Class 2 CRISPR-Cas Systems"; Cell; vol. 168, 2 pages (Jan. 12, 2017).
Mohanraju, et al.; "Diverse evolutionary roots and mechanistic variations of the CRISPR-Cas systems"; Science; vol. 353, No. 6299, 14 pages (Aug. 5, 2016).
NCBI Accession No. KZX85786, May 2, 2016, 2 pages.
NCBI Reference Sequence: WP_012985477.1 (May 18, 2013).
NCBI Reference Sequence: WP_015770004.1 (May 20, 2013).
NCBI Reference Sequence: WP_021746003.1 (Sep. 24, 2013).
NCBI Reference Sequence: WP_021746774.1 (Sep. 24, 2013).
NCBI Reference Sequence: WP_021747205.1 (Sep. 24, 2013).
NCBI Reference Sequence: WP_023911507.1 (Oct. 23, 2013).
NCBI Reference Sequence: WP_034560163.1 (Oct. 22, 2015).
Ngo, et al.; "Computational Complexity, Protein Structure Prediction, and the Levinthal Paradox"; The Protein Folding Problem and Tertiary Structure Prediction; pp. 433 and 492-495 (1994).
O'Connell; "Molecular Mechanisms of RNA Targeting by Cas13-containing Type VI CRISPR-Cas Systems"; J Mol Biol; vol. 431, pp. 66-87 (2019).
OHA03494.1 (hypothetical protein A3J58_03210 [*Candidatus sung* bacteria bacterium RIFCSPH IGHO2_02_FU LL_52_23], NCBI Reference Sequence, priority to Oct. 21, 2016, 2 pages) (Year: 2016).
Price, et al.; "Cas9-mediated targeting of viral RNA in eukaryotic cells"; PNAS; vol. 112, No. 19, pp. 6164-6169 (May 12, 2015).
RNaseAlert Lab Test Kit (Applied Biosystems, Fluorometric RNase Detection Assay, 2008, 12 pages). (Year: 2008).
Sampson, et al.; "A CRISPR/Cas system mediates bacterial innate immune evasion and virulence"; Nature; vol. 497, No. 7448; pp. 254-257 (May 9, 2013).
Sato, et al.; "Highly Sensitive Nuclease Assays Based on Chemically Modified DNA or RNA"; Sensors; vol. 14, No. 7, pp. 12437-12450 (2014).
Shmakov, et al.; "Discovery and functional characterization of diverse Class 2 CRISPR-Cas systems"; Mol. Cell.; vol. 60, No. 3, pp. 385-397 (Nov. 5, 2015).
Shmakov, et al.; "Diversity and evolution of class 2 CRISPR-Cas systems"; Nature Reviews Microbiology; vol. 15, pp. 169-182 (2017).
Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Strauβ, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
Third Party Observations filed on Oct. 15, 2018 in UK patent application No. GB 1804822.3 (18 pages).
Wright, et al.; "Biology and Applications of CRISPR Systems: Harnessing Nature's Toolbox for Genome Engineering"; Cell; vol. 164, pp. 29-44 (2016).
Xie et al. (2013) " RNA-Guided Genome Editing in Plants Using a CRISPR-Cas System." Molecular Plant, vol. 6, No. 6 , pp. 1975-1983.
Yamano, et al.; "Crystal Structure of Cpf1 in Complex with Guide RNA and Target DNA"; Cell; vol. 165, pp. 949-962 (2016).
Yang, et al.; "New CRISPR-Cas systems discovered"; Cell Res.; vol. 27, pp. 313-314 (Feb. 21, 2017).
Yang, et al.; "Using Molecular Beacons for Sensitive Fluorescence Assays of the Enzymatic Cleavage of Nucleic Acids"; Methods in Molecular Biology; vol. 335, pp. 71-81 (2006).
Yan et al., (2018) Cas13d is a compact RNA-Targeting Type VI CRISPR Effector Positively Modulated by a WYL-Domain-Containing Accessory Protein. Molecular Cell, 70(2):327-339 (Year:2018).
Zetsche, et al.; "Cpf1 Is a Single RNA-Guided Endonuclease of a Class 2 CRISPR-Cas System"; Cell; vol. 163, pp. 759-771 (Oct. 22, 2015).
Zhang, et al.; "Design of a Molecular Beacon DNA Probe with Two Fluorophores"; Angew. Chem.; vol. 113, No. 2, pp. 416-419 (2001).

* cited by examiner

FIG. 8A

>Listeria seeligeri (WP_012985477.1)
MWISIKTLIHHLGVLFFCDYMYNRREKKIIEVKTMRITKVEVDRKKVLISRDKNGGKLVY
ENEMQDNTEQIMHHKKSSFYKSVVNKTICRPEQKQMKKLVHGLLQENSQEKIKVSDVTKL
NISNFLNHRFKKSLYYFPENSPDKSEEYRIEINLSQLLEDSLKKQQGTFICWESFSKDME
LYINWAENYISSKTKLIKKSIRNNRIQSTESRSGQLMDRYMKDILNKNKPFDIQSVSEKY
QLEKLTSALKATFKEAKKNDKEINYKLKSTLQNHERQIIEELKENSELNQFNIEIRKHLE
TYFPIKKTNRKVGDIRNLEIGEIQKIVNHRLKNKIVQRILQEGKLASYEIESTVNSNSLQ
KIKIEEAFALKFINACLFASNNLRNMVYPVCKKDILMIGEFKNSFKEIKHKKFIRQWSQF
FSQEITVDDIELASWGLRGAIAPIRNEIIHLKKHSWKKFFNNPTFKVKKSKIINGKTKDV
TSEFLYKETLFKDYFYSELDSVPELIINKMESSKILDYYSSDQLNQVFTIPNFELSLLTS
AVPFAPSFKRVYLKGFDYQNQDEAQPDYNLKLNIYNEKAFNSEAFQAQYSLFKMVYYQVF
LPQFTTNNDLFKSSVDFILTLNKERKGYAKAFQDIRKMNKDEKPSEYMSYIQSQLMLYQK
KQEEKEKINHFEKFINQVFIKGFNSFIEKNRLTYICHPTKNTVPENDNIEIPFHTDMDDS
NIAFWLMCKLLDAKQLSELRNEMIKFSCSLQSTEEISTFTKAREVIGLALLNGEKGCNDW
KELFDDKEAWKKNMSLYVSEELLQSLPYTQEDGQTPVINRSIDLVKKYGTETILEKLFSS
SDDYKVSAKDIAKLHEYDVTEKIAQQESLHKQWIEKPGLARDSAWTKKYQNVINDISNYQ
WAKTKVELTQVRHLHQLTIDLLSRLAGYMSIADRDFQFSSNYILERENSEYRVTSWILLS
ENKNKNKYNDYELYNLKNASIKVSSKNDPQLKVDLKQLRLTLEYLELFDNRLKEKRNNIS
HFNYLNGQLGNSILELFDDARDVLSYDRKLKNAVSKSLKEILSSHGMEVTFKPLYQTNHH
LKIDKLQPKKIHHLGEKSTVSSNQVSNEYCQLVRTLLTMK (SEQ ID NO: 1)

FIG. 8B

>Leptotrichia buccalis (WP_015770004.1)
MKVTKVGGISHKKYTSEGRLVKSESEENRTDERLSALLNMRLDMYIKNPSSTETKENQKR
IGKLKKFFSNKMVYLKDNTLSLKNGKKENIDREYSETDILESDVRDKKNFAVLKKIYLNE
NVNSEELEVFRNDIKKKLNKINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TRFEFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEEKDTYIDFIQKIFLKGFMTYLANNGRLSLIYIGSDEETNTSLAEKKQE
FDKFLKKYEQNNNIKIPYEINEFLREIKLGNILKYTERLNMFYLILKLLNHKELTNLKGS
LEKYQSANKEEAFSDQLELINLLNLDNNRVTEDFELEADEIGKFLDFNGNKVKDNKELKK
FDTNKIYFDGENIIKHRAFYNIKKYGMLNLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIRNYIAHFNYIPHAEISLLEVLENLRKLLSYDRK
LKNAVMKSVVDILKEYGFVATFKIGADKKIGIQTLESEKIVHLKNLKKKKLMTDRNSEEL
CKLVKIMFEYKMEEKKSEN (SEQ ID NO: 2)

FIG. 8C

```
> Leptotrichia shahii  (WP_018451595.1)
MGNLFGHKRWYEVRDKKDFKIKRKVKVKRNYDGNKYILNINENNNKEKIDNNKFIRKYIN
YKKNDNILKEFTRKFHAGNILFKLKGKEGIIRIENNDDFLETEEVVLYIEAYGKSEKLKA
LGITKKKIIDEAIRQGITKDDKKIEIKRQENEEEIEIDIRDEYTNKTLNDCSIILRIIEN
DELETKKSIYEIFKNINMSLYKIIEKIIENETEKVFENRYYEEHLREKLLKDDKIDVILT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDDFSRLHAKEELDLELITFFASTNMELNKIFSRENINN
DENIDFFGGDREKNYVLDKKILNSKIKIIRDLDFIDNKNNITNNFIRKFTKIGTNERNRI
LHAISKERDLQGTQDDYNKVINIIQNLKISDEEVSKALNLDVVFKDKKNIITKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQKMKEIEKDFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTTAYYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL  (SEQ ID NO: 3)
```

FIG. 8D

> Rhodobacter capsulatus (R121) (ETD76934.1) ( U717_11515)
MQIGKVQGRTISEFGDPAGGLKRKISTDGKNRKELPAHLSSDPKALIGQWISGIDKIYRK
PDSRKSDGKAIHSPTPSKMQFDARDDLGEAFWKLVSEAGLAQDSDYDQFKRRLHPYGDKF
QPADSGAKLKFEADPPEPQAFHGRWYGAMSKRGNDAKELAAALYEHLHVDEKRIDGQPKR
NPKTDKFAPGLVVARALGIESSVLPRGMARLARNWGEEEIQTYFVVDVAASVKEVAKAAV
SAAQAFDPPRQVSGRSLSPKVGFALAEHLERVTGSKRCSFDPAAGPSVLALHDEVKKTYK
RLCARGKNAARAFPADKTELLALMRHTHENRVRNQMVRMGRVSEYRGQQAGDLAQSHYWT
SAGQTEIKESEIFVRLWVGAFALAGRSMKAWIDPMGKIVNTEKNDRDLTAAVNIRQVISN
KEMVAEAMARRGIYFGETPELDRLGAEGNEGFVFALLRYLRGCRNQTFHLGARAGFLKEI
RKELEKTRWGKAKEAEHVVLTDKTVAAIRAIIDNDAKALGARLLADLSGAFVAHYASKEH
FSTLYSEIVKAVKDAPEVSSGLPRLKLLLKRADGVRGYVHGLRDTRKHAFATKLPPPPAP
RELDDPATKARYIALLRLYDGPFRAYASGITGTALAGPAARAKEAATALAQSVNVTKAYS
DVMEGRSSRLRPPNDGETLREYLSALTGETATEFRVQIGYESDSENARKQAEFIENYRRD
MLAFMFEDYIRAKGFDWILKIEPGATAMTRAPVLPEPIDTRGQYEHWQAALYLVMHFVPA
SDVSNLLHQLRKWEALQGKYELVQDGDATDQADARREALDLVKRFRDVLVLFLKTGEARF
EGRAAPFDLKPFRALFANPATFDRLFMATPTTARPAEDDPEGDGASEPELRVARTLRGLR
QIARYNHMAVLSDLFAKHKVRDEEVARLAEIEDETQEKSQIVAAQELRTDLHDKVMKCHP
KTISPEERQSYAAAIKTIEEHRFLVGRVYLGDHLRLHRLMMDVIGRLIDYAGAYERDTGT
FLINASKQLGAGADWAVTIAGAANTDARTQTRKDLAHFNVLDRADGTPDLTALVNRAREM
MAYDRKRKNAVPRSILDMLARLGLTLKWQMKDHLLQDATITQAAIKHLDKVRLTVGGPAA
VTEARFSQDYLQMVAAVFNGSVQNPKPRRRDDGDAWHKPPKPATAQSQPDQKPPNKAPSA
GSRLPPPQVGEVYEGVVVKVIDTGSLGFLAVEGVAGNIGLHISRLRRIREDAIIVGRRYR
FRVEIYVPPKSNTSKLNAADLVRID (SEQ ID NO: 4)

FIG. 8E

>WP_034560163.1 WP_034560163.1 hypothetical protein [Carnobacterium gallinarum]
MRITKVKIKLDNKLYQVTMQKEEKYGTLKLNEESRKSTAEILRLKKASFNKSFHSKTINS
QKENKNATIKKNGDYISQIFEKLVGVDTNKNIRKPKMSLTDLKDLPKKDLALFIKRKFKN
DDIVEIKNLDLISLFYNALQKVPGEHFTDESWADFCQEMMPYREYKNKFIERKIILLANS
IEQNKGFSINPETFSKRKRVLHQWAIEVQERGDFSILDEKLSKLAEIYNFKKMCKRVQDE
LNDLEKSMKKGKNPEKEKEAYKKQKNFKIKTIWKDYPYKTHIGLIEKIKENEELNQFNIE
IGKYFEHYFPIKKERCTEDEPYYLNSETIATTVNYQLKNALISYLMQIGKYKQFGLENQV
LDSKKLQEIGIYEGFQTKFMDACVFATSSLKNIIEPMRSGDILGKREFKEAIATSSFVNY
HHFFPYFPFELKGMKDRESELIPFGEQTEAKQMQNIWALRGSVQQIRNEIFHSFDKNQKF
NLPQLDKSNFEFDASENSTGKSQSYIETDYKFLFEAEKNQLEQFFIERIKSSGALEYYPL
KSLEKLFAKKEMKFSLGSQVVAFAPSYKKLVKKGHSYQTATEGTANYLGLSYYNRYELKE
ESFQAQYYLLKLIYQYVFLPNFSQGNSPAFRETVKAILRINKDEARKKMKKNKKFLRKYA
FEQVREMEFKETPDQYMSYLQSEMREEKVRKAEKNDKGFEKNITMNFEKLLMQIFVKGFD
VFLTTFAGKELLLSSEEKVIKETEISLSKKINEREKTLKASIQVEHQLVATNSAISYWLF
CKLLDSRHLNELRNEMIKFKQSRIKFNHTQHAELIQNLLPIVELTILSNDYDEKNDSQNV
DVSAYFEDKSLYETAPYVQTDDRTRVSFRPILKLEKYHTKSLIEALLKDNPQFRVAATDI
QEWMHKREEIGELVEKRKNLHTEWAEGQQTLGAEKREEYRDYCKKIDRFNWKANKVTLTY
LSQLHYLITDLLGRMVGFSALFERDLVYFSRSFSELGGETYHISDYKNLSGVLRLNAEVK
PIKIKNIKVIDNEENPYKGNEPEVKPFLDRLHAYLENVIGIKAVHGKIRNQTAHLSVLQL
ELSMIESMNNLRDLMAYDRKLKNAVTKSMIKILDKHGMILKLKIDENHKNFEIESLIPKE
IIHLKDKAIKTNQVSEEYCQLVLALLTTNPGNQLN (SEQ ID NO: 5)

FIG. 8F

>CRZ35554.1 Herbinix hemicellulosilytica genome assembly TUM3/55, contig 02_T3/55T_contig26, whole genome shotgun sequence
MKLTRRRISGNSVDQKITAAFYRDMSQGLLYYDSEDNDCTDKVIESMDFERSWRGRILKN
GEDDKNPFYMFVKGLVGSNDKIVCEPIDVDSDPDNLDILINKNLTGFGRNLKAPDSNDTL
ENLIRKIQAGIPEEEVLPELKKIKEMIQKDIVNRKEQLLKSIKNNRIPFSLEGSKLVPST
KKMKWLFKLIDVPNKTFNEKMLEKYWEIYDYDKLKANITNRLDKTDKKARSISRAVSEEL
REYHKNLRTNYNRFVSGDRPAAGLDNGGSAKYNPDKEEFLLFLKEVEQYFKKYFPVKSKH
SNKSKDKSLVDKYKNYCSYKVVKKEVNRSIINQLVAGLIQQGKLLYYFYYNDTWQEDFLN
SYGLSYIQVEEAFKKSVMTSLSWGINRLTSFFIDDSNTVKFDDITTKKAKEAIESNYFNK
LRTCSRMQDHFKEKLAFFYPVYVKDKKDRPDDDIENLIVLVKNAIESVSYLRNRTFHFKE
SSLLELLKELDDKNSGQNKIDYSVAAEFIKRDIENLYDVFREQIRSLGIAEYYKADMISD
CFKTCGLEFALYSPKNSLMPAFKNVYKRGANLNKAYIRDKGPKETGDQGQNSYKALEEYR
ELTWYIEVKNNDQSYNAYKNLLQLIYYHAFLPEVRENEALITDFINRTKEWNRKETEERL
NTKNNKKHKNFDENDDITVNTYRYESIPDYQGESLDDYLKVLQRKQMARAKEVNEKEEGN
NNYIQFIRDVVVWAFGAYLENKLKNYKNELQPPLSKENIGLNDTLKELFPEEKVKSPFNI
KCRFSISTFIDNKGKSTDNTSAEAVKTDGKEDEKDKKNIKRKDLLCFYLFLRLLDENEIC
KLQHQFIKYRCSLKERRFPGNRTKLEKETELLAELEELMELVRFTMPSIPEISAKAESGY
DTMIKKYFKDFIEKKVFKNPKTSNLYYHSDSKTPVTRKYMALLMRSAPLHLYKDIFKGYY
LITKKECLEYIKLSNIIKDYQNSLNELHEQLERIKLKSEKQNGKDSLYLDKKDFYKVKEY
VENLEQVARYKHLQHKINFESLYRIFRIHVDIAARMVGYTQDWERDMHFLFKALVYNGVL
EERRFEAIFNNNDDNNDGRIVKKIQNNLNNKNRELVSMLCWNKKLNKNEFGAIIWKRNPI
AHLNHFTQTEQNSKSSLESLINSLRILLAYDRKRQNAVTKTINDLLLNDYHIRIKWEGRV
DEGQIYFNIKEKEDIENEPIIHLKHLHKKDCYIYKNSYMFDKQKEWICNGIKEEVYDKSI
LKCIGNLFKFDYEDKNKSSANPKHT (SEQ ID NO: 6)

FIG. 9A
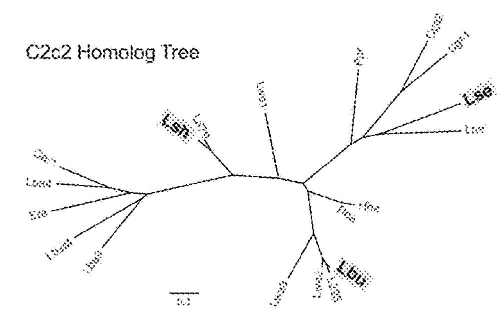
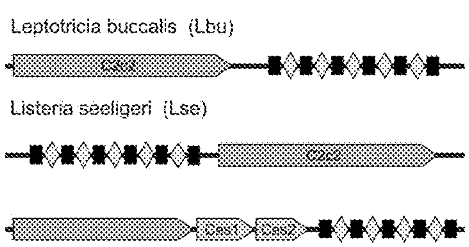
FIG. 9B
FIG. 9C
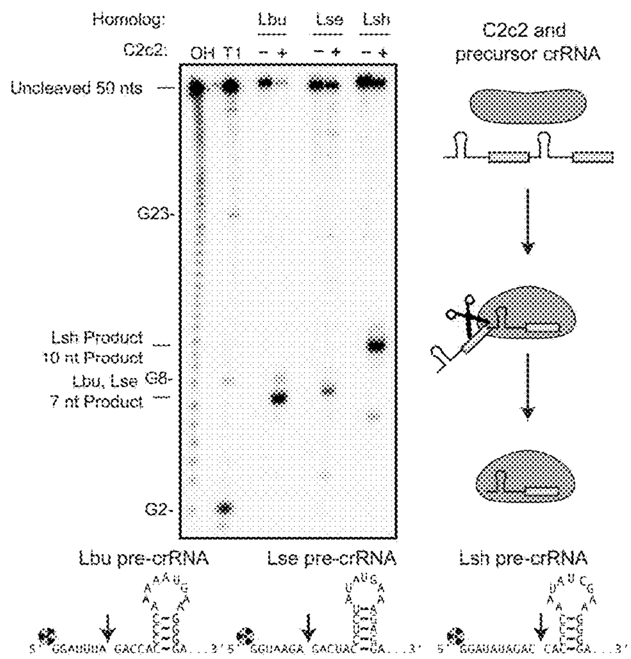

FIG. 10A
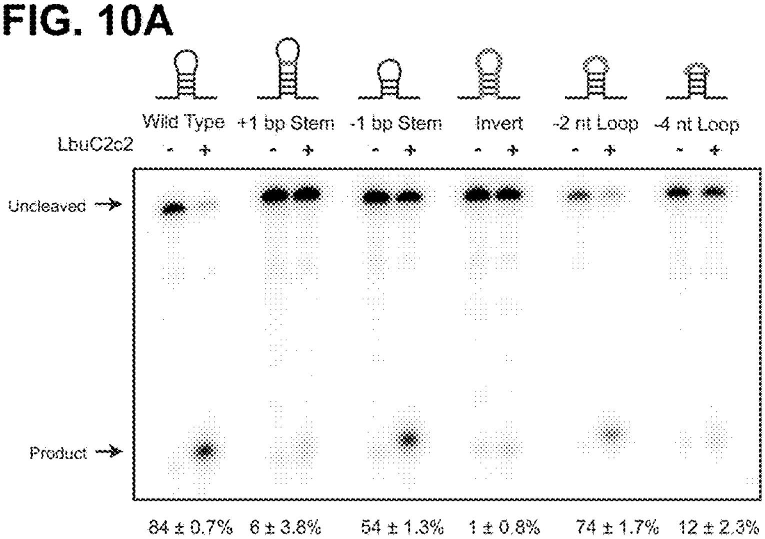
FIG. 10C
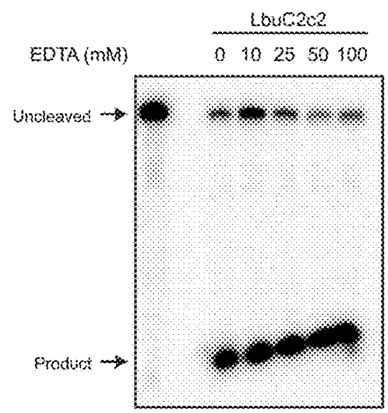
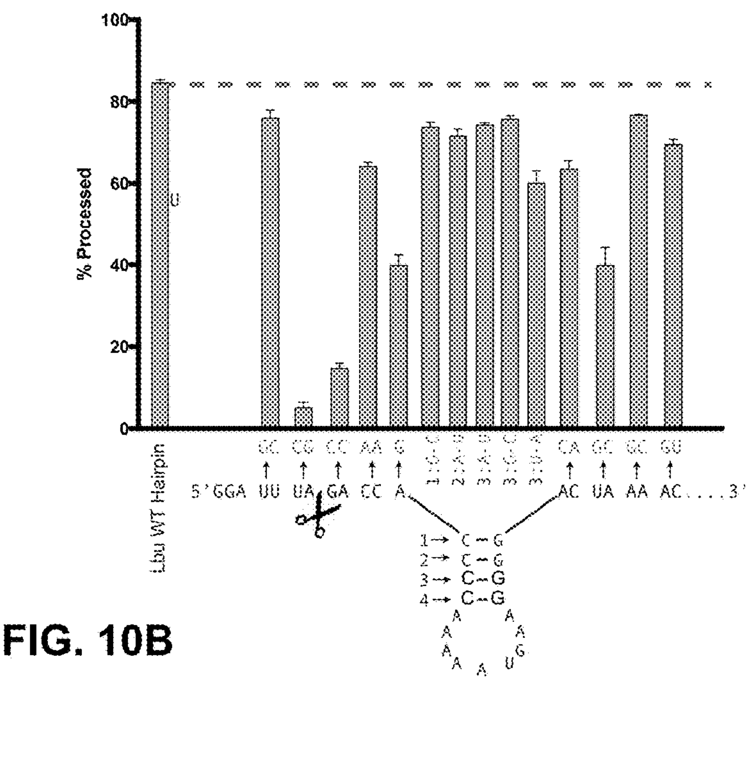
FIG. 10B

FIG. 12A
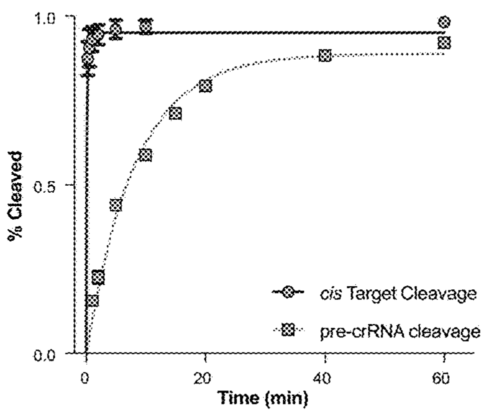
FIG. 12B
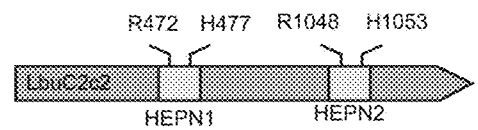
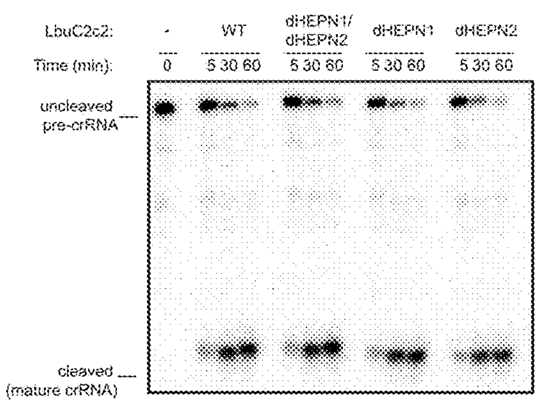
FIG. 12C
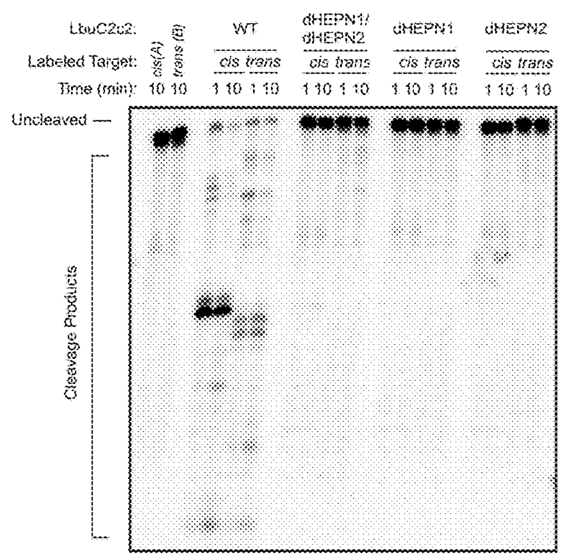
FIG. 12D

FIG. 13A
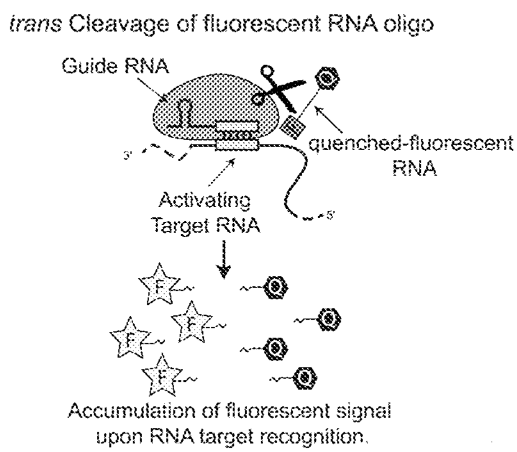
FIG. 13B
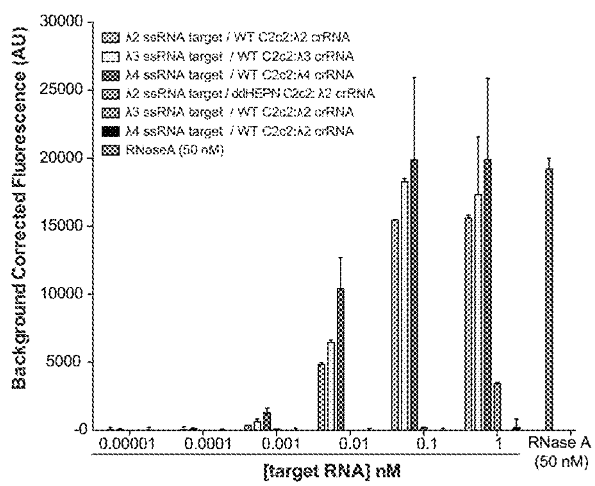
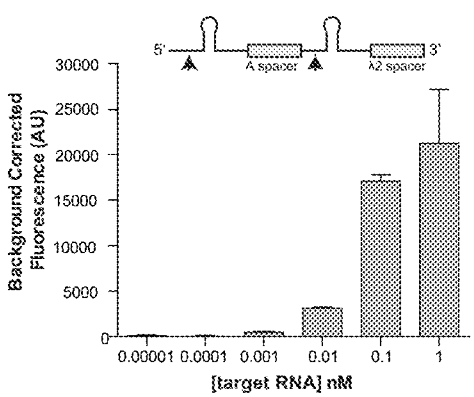
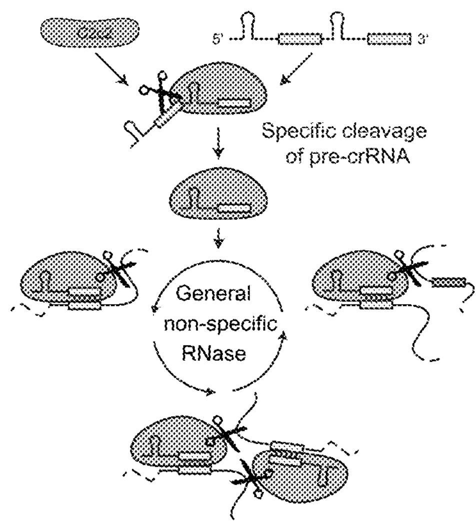
FIG. 13C
FIG. 13D

FIG. 14

Table 2: DNA oligonucleotides used in this study

| Name | Sequence |
|---|---|
| T7_forward_SCK337 | 5'-TAATACGACTCACTATAGG-3' |
| T7_forward_long_AES428 | 5'-CCAAGTAATACGACTCACTATAGG-3' |
| Lbu_R1048A_AES441 | 5'-TAATTAGCAATATAAAGGTCCTTCTTTTCTTGC-3' |
| Lbu_H1053A_AES442 | 5'-CATCGCCGCATTCAATTATATTCCTCACGCCG-3' |
| Lbu_R472A_AES443 | 5'-CCGTGAGCGATGGAAGAAATCGCCTCGTCG-3' |
| Lbu_H477A_AES444 | 5'-TATTGTCGCCTTCAACTTGGAATTAGAAGGTAAGGA-3' |

FIG. 15

Table 3: RNAs used in this study

| Name | Sequence[a] | Used in |
|---|---|---|
| Lbu_pre-crRNA_A_SCK314 | 5'-GGAUUUAGACCACCCCAAAAAUGAAGGGGACUAAAACAGGGGCAGAGAUGAUGACCCU-3' | FIG. 9C, 10A-10C, 12A, C, 16 |
| Lse_pre-crRNA_B_AES484 | 5'-GGUAAGAGACUACCUCUAUAUGAAAGAGGACUAAAACCAAACAUGAUCUGGGUCAUC-3' | FIG. 9C, 16 |
| Lsh_pre-crRNA_A_SCK339 | 5'-GGAUUUAGACCACCCCAAUAUCGAAGGGGACUAAAACAGGGGCAGAGAUGAUGACCCU-3' | FIG. 9C, 16 |
| Lbu_pre-crRNA_invert_SCK321 | 5'-GGAUUUAGACCAGGGGAAGUAAAAACCCCACUAAAACAGGGGCAGAGAUGAUGACCCU-3' | FIG. 10A |
| Lbu_pre-crRNA_5stem_SCK331 | 5'-GGAUUUAGACCACCCCCAAAAAUGAAGGGGGACUAAAACAGGGGCAGAGAUGAUGACCCU-3' | FIG. 10A |
| Lbu_pre-crRNA_7bubble_SCK334 | 5'-GGAUUUAGACCACCCCAUGAAGGGGACUAAAACAGGGGCAGAGAUGAUGACCCU-3' | FIG. 10A |
| Lbu_pre-crRNA_5bubble_SCK335 | 5'-GGAUUUAGACCACCCCAUGAAGGGGACUAAAACAGGGGCAGAGAUGAUGACCCU-3' | FIG. 10A |
| Lbu_pre-crRNA_3stem_SCK342 | 5'-GGAUUUAGACCACCCCAAAAAUGAAGGGCACUAAAACAGGGGCAGAGAUGAUGACCCU-3' | FIG. 10A |
| Lbu_pre-cr_5'_mut1_AES497 | 5'-GGCGUUAGACCACCCCAAAAAUGAAGGGGACUAAAACAGGGGCAGAGAUGAUGACCCU-3' | FIG. 10B, 17 |
| Lbu_pre-cr_5'_mut2_AES496 | 5'-GGAGCUAGACCACCCCAAAAAUGAAGGGGACUAAAACAGGGGCAGAGAUGAUGACCCU-3' | FIG. 10B, 17 |
| Lbu_pre-cr_5'_mut3_AES495 | 5'-GGAUCCAGACCACCCCAAAAAUGAAGGGGACUAAAACAGGGGCAGAGAUGAUGACCCU-3' | FIG. 10B, 17 |
| Lbu_pre-cr_5'_mut4_AES477 | 5'-GGAUUCGGACCACCCCAAAAAUGAAGGGGACUAAAACAGGGGCAGAGAUGAUGACCCU-3' | FIG. 10B, 17 |
| Lbu_pre-cr_5'_mut5_AES482 | 5'-GGAUUUACCCCACCCCAAAAAUGAAGGGGACUAAAACAGGGGCAGAGAUGAUGACCCU-3' | FIG. 10B, 17 |
| Lbu_pre-cr_5'_mut6_AES478 | 5'-GGAUUUAAUCCACCCCAAAAAUGAAGGGGACUAAAACAGGGGCAGAGAUGAUGACCCU-3' | FIG. 10B, 17 |
| Lbu_pre-cr_5'_mut7_AES480 | 5'-GGAUUUAGAAAACCCCAAAAAUGAAGGGGACUAAAACAGGGGCAGAGAUGAUGACCCU-3' | FIG. 10B, 17 |
| Lbu_pre_cr_5'_mut8_AES498 | 5'-GGAUUUAGACCGCCCCAAAAAUGAAGGGGACUAAAACAGGGGCAGAGAUGAUGACCCU-3' | FIG. 10B, 17 |
| Lbu_pre_stem_mut1_AES502 | 5'-GGAUUUAGACCAGCCCAAAAAUGAAGGGCACUAAAACAGGGGCAGAGAUGAUGACCCU-3' | FIG. 10B, 17 |
| Lbu_pre_stem_mut2_AES501 | 5'-GGAUUUAGACCACCGCAAAAAUGAAGCGGACUAAAACAGGGGCAGAGAUGAUGACCCU-3' | FIG. 10B, 17 |
| Lbu_pre_stem_mut3_AES500 | 5'-GGAUUUAGACCACACCAAAAAUGAAGGUGACUAAAACAGGGGCAGAGAUGAUGACCCU-3' | FIG. 10B, 17 |
| Lbu_pre_stem_mut4_AES499 | 5'-GGAUUUAGACCACCACAAAAAUGAAGUGGACUAAAACAGGGGCAGAGAUGAUGACCCU-3' | FIG. 10B, 17 |
| Lbu_pre_stem_mut5_AES504 | 5'-GGAUUUAGACCACUCCAAAAAUGAAGGAGACUAAAACAGGGGCAGAGAUGAUGACCCU-3' | FIG. 10B, 17 |
| Lbu_pre_cr_3'_mut1_AES505 | 5'-GGAUUUAGACCACCCCAAAAAUGAAGGGGCAUAAAACAGGGGCAGAGAUGAUGACCCU-3' | FIG. 10B, 17 |
| Lbu_pre_cr_3'_mut2_AES506 | 5'-GGAUUUAGACCACCCCAAAAAUGAAGGGGACGCAAACAGGGGCAGAGAUGAUGACCCU-3' | FIG. 10B, 17 |
| Lbu_pre_cr_3'_mut3_AES507 | 5'-GGAUUUAGACCACCCCAAAAAUGAAGGGGACUAGCACAGGGGCAGAGAUGAUGACCCU-3' | FIG. 10B, 17 |
| Lbu_pre_cr_3'_mut4_AES508 | 5'-GGAUUUAGACCACCCCAAAAAUGAAGGGGACUAAAGUAGGGGCAGAGAUGAUGACCCU-3' | FIG. 10B, 17 |
| crLbu_A_GG_AES432 | 5'-GGCCACCCCAAAAAUGAAGGGGACUAAAACAGGGGCAGAGAUGAUGACCCU-3' | FIG. 11, 12, 18-20 |
| crLbu_B_AES451 | 5'-GGCCACCCCAAAAAUGAAGGGGACUAAAACACAAACAUGAUCUGGGUCAUC-3' | FIG. 11 |
| A.0_target_AES450 | 5'-GGCACACCCGCAGGGGGGAGCCAAAAGGGUCAUCAUCUCUGCCCCCACAGCAGAAGCCCC-3' | FIG. 11, 12, 20 |
| B_target_AES452 | 5'-GGGAACCCCAAGGCCAACCGCGAGAAGAUGACCCAGAUCAUGUUUGAGACCUUCAACACCCC-3' | FIG. 11, 12, 20 |
| crLbu_Lambda2_AES453 | 5'-GGCCACCCCAAAAAUGAAGGGGACUAAAACAGUGAUAAGUGGAAUGCCAUG-3' | FIG. 13B-13C |
| crLbu_Lambda3_MOC410 | 5'-GGCCACCCCAAAAAUGAAGGGGACUAAAACACUGGUGAACUUCCGAUAGUG-3' | FIG. 13B |
| crLbu_Lambda4_MOC411 | 5'-GGCCACCCCAAAAAUGAAGGGGACUAAAACACAGAUAUAGCCUGGUGGUUC-3' | FIG. 13B |
| Lambda2_target_MOC28 | 5'-GGCUCAAUUUUGACAGCGGUCAUGGCAUUCCACUUAUCACUGGCAUCCUUCCACUC-3' | FIG. 13B-C |
| Lambda3_target_MOC36 | 5'-GGAAAUCAUUCAACACCCGCACUAUCGGAAGUUCACCAGCCAGCCGCAGCACGUU-3' | FIG. 13B |
| Lambda4_target_MOC37 | 5'-GGCAAUAAAAAUGCGCCGCCUGAACCACCAGGCUAUAUCUGCCACUCAUUGUUGUGA-3' | FIG. 13B |
| pre-crLbu_dimer_SCK324 | 5-'GGAUUUAGACCACCCCAAAAAUGAAGGGGACUAAAACAGGGGCAGAGAUGAUGACCCUAUUUAGACCACCCCAAAAAUGA AGGGGACUAAAACAGUGAUAAGUGGAAUGCCAUG-3' | FIG. 13C, 16A-16F |
| crLbu_lambda2_SCK315 | 5'-GGAUUUAGACCACCCCAAAAAUGAAGGGGACUAAAACAGUGAUAAGUGGAAUGCCAUG-3' | FIG. 16A-16F |
| Lbu_pre_cr_5'_4mer1_AES481 | 5'-GGAUUUAAUAAACCCCAAAAAUGAAGGGGACUAAAACAGGGGCAGAGAUGAUGACCCU-3' | FIG. 16A-16F |
| Lbu_pre_cr_5'_4mer2_AES479 | 5'-GGAUUCGAUCCACCCCAAAAAUGAAGGGGACUAAAACAGGGGCAGAGAUGAUGACCCU-3' | FIG. 16A-16F |
| Lbu_pre_cr_5'_4mer3_SCK343 | 5'-GGAUUUAGGAAGCCCCAAAAAUGAAGGGGACUAAAACAGGGGCAGAGAUGAUGACCCU-3' | FIG. 16A-16F |
| Lbu_pre_cr_5'_4mer4_AES503 | 5'-GGAUUUAGACCAGGCCAAAAAUGAAGGCCACUAAAACAGGGGCAGAGAUGAUGACCCU-3' | FIG. 16A-16F |
| crLbu_GuideWalk1_SCK302 | 5'-GGCCACCCCAAAAAUGAAGGGGACUAAAACAUUUUGGCUCCCCCCUGCAAAUGAG-3' | FIG. 18A-18B |
| crLbu_GuideWalk2_SCK303 | 5'-GGCCACCCCAAAAAUGAAGGGGACUAAAACAACCCUUUUGGCUCCCCCCUGCAAA-3' | FIG. 18A-18B |
| crLbu_GuideWalk3_SCK304 | 5'-GGCCACCCCAAAAAUGAAGGGGACUAAAACAGAUGACCCUUUUGGCUCCCCCCUG-3' | FIG. 18A-18B |
| crLbu_GuideWalk4_SCK305 | 5'-GGCCACCCCAAAAAUGAAGGGGACUAAAACAAGAUGAUGACCCUUUUGGCUCCCC-3' | FIG. 18A-18B |
| crLbu_GuideWalk5_SCK306 | 5'-GGCCACCCCAAAAAUGAAGGGGACUAAAACAGCAGAGAUGAUGACCCUUUUGGCU-3' | FIG. 18A-18B |
| crLbu_GuideWalk6_SCK307 | 5'-GGCCACCCCAAAAAUGAAGGGGACUAAAACAGGGGGCAGAGAUGAUGACCCUUUU-3' | FIG. 18A-18B |
| crLbu_GuideWalk7_SCK308 | 5'-GGCCACCCCAAAAAUGAAGGGGACUAAAACACAGAGGGGGCAGAGAUGAUGACCC-3' | FIG. 18A-18B |
| crLbu_GuideWalk8_SCK309 | 5'-GGCCACCCCAAAAAUGAAGGGGACUAAAACAUCAGCAGAGGGGGCAGAGAUGAUG-3' | FIG. 18A-18B |
| A.1_target_U_MOC279 | 5'-GGCUCAUUUGCAGGGGGGAGCCAAAAGGGUCAUCAUCUCUGCCCCCUCUGCUGAUGCCCC-3' | FIG. 18A-18B |
| A.2_target_70nt_AES447 | 5'-GGCCUGACUGCUCUCAUUUGCAGUUGGGAGCCAAAAGGGUCAUCAUCUCUGCCCCCUCUGCUGAUGCCCC-3' | FIG. 18A-18B |
| A.3_target_80nt_AES448 | 5'-GGACCUGUGAAUCCUGACUGCUCUCAUUUGCAGUUGGGAGCCAAAAGGGUCAUCAUCUCUGCCCCCUCUGCUGAUGCCCC-3' | FIG. 18A-18B |
| A.4_5'_ts_shift_AES449 | 5'-GGCACACCCGCAGGGUUUAGCCAAAAGGGUCAUCAUCUCUGCCCCCUCUGCUGAUGCCCC-3' | FIG. 18A-18B |
| crLbu_A_16nt_trunc_SCK282 | 5'-GGCCACCCCAAAAAUGAAGGGGACUAAAACACAGAGAUGAUGACCCU-3' | FIG. 19A-19C |
| crLbu_A_24nt_ext_SCK283 | 5'-GGCCACCCCAAAAAUGAAGGGGACUAAAACAAGAGGGGGCAGAGAUGAUGACCCU-3' | FIG. 19A-19C |
| crLbu_A_mature_GA_SCK340 | 5'-GACCACCCCAAAAAUGAAGGGGACUAAAACAGGGGCAGAGAUGAUGACCCU-3' | FIG. 19A-19C |
| crLbu_A_mature_GGGA_SCK341 | 5'-GGGACCACCCCAAAAAUGAAGGGGACUAAAACAGGGGCAGAGAUGAUGACCCU-3' | FIG. 19A-19C |
| crLbu_A_mature_CCA_AES461 | 5'-CCACCCCAAAAAUGAAGGGGACUAAAACAGGGGCAGAGAUGAUGACCCU-3' | FIG. 19A-19C |

[a]All RNAs were either ordered synthetically (Integrated DNA technologies) or transcribed from a complementary template as described in the Methods

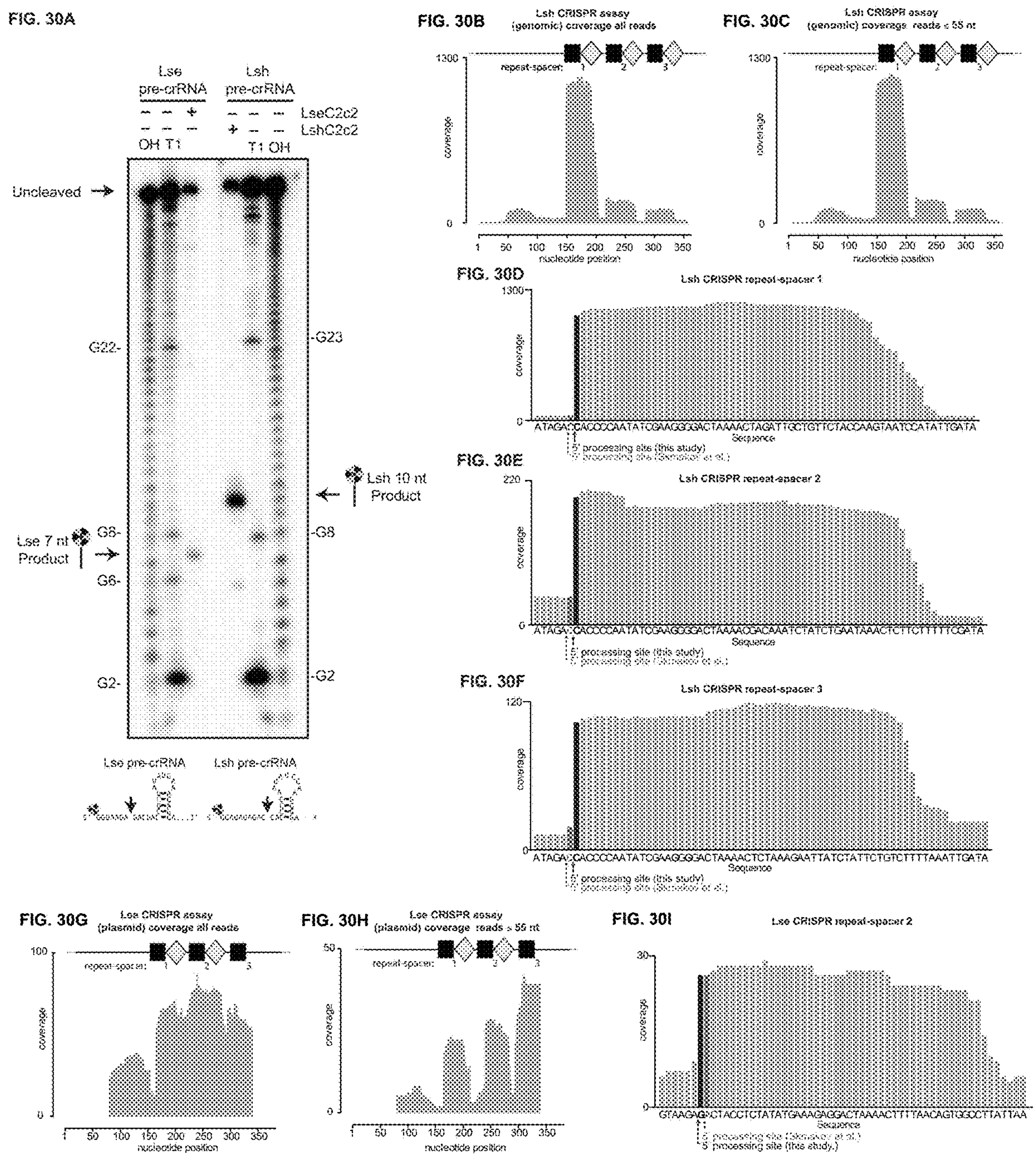
FIG. 30A
Lse pre-crRNA
Lsh pre-crRNA
LseC2c2
LshC2c2
OH T1
T1 OH
Uncleaved
G22-
-G23
Lsh 10 nt Product
Lse 7 nt Product
G8-
-G8
G6-
G2-
-G2
Lse pre-crRNA
Lsh pre-crRNA
FIG. 30B
Lsh CRISPR assay (genomic) coverage all reads
FIG. 30C
Lsh CRISPR assay (genomic) coverage reads ≤ 55 nt
repeat-spacer:
coverage
nucleotide position
FIG. 30D
Lsh CRISPR repeat-spacer 1
ATAGACCACCCCAATATCGAAGGGGACTAAAACTAGATTGCTGTTCTACCAAGTAATCCATATTGATA
Sequence
5' processing site (this study)
FIG. 30E
Lsh CRISPR repeat-spacer 2
FIG. 30F
Lsh CRISPR repeat-spacer 3
ATAGACCACCCCAATATCGAAGGGGACTAAAACTCTAAAGAATTATCTATTCTGTCTTTTAAATTGATA
FIG. 30G
Lse CRISPR assay (plasmid) coverage all reads
FIG. 30H
Lse CRISPR assay (plasmid) coverage reads ≤ 55 nt
FIG. 30I
Lse CRISPR repeat-spacer 2
GTAAGAGACTACCTCTATATGAAAGAGGACTAAAACTTTTAACAGTGGCTTATTAA
5' processing site (this study)

C2c2 Process 025

FIG. 39A
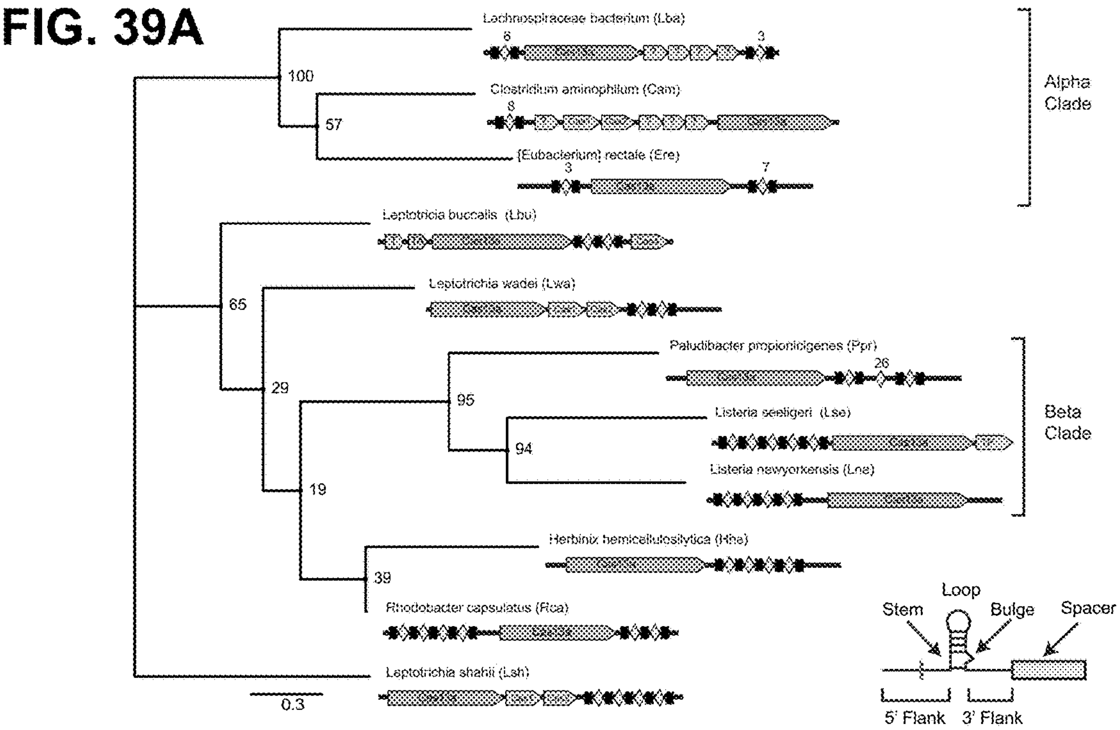
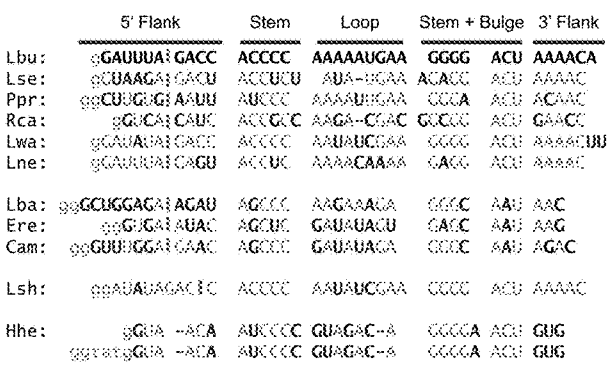
FIG. 39B
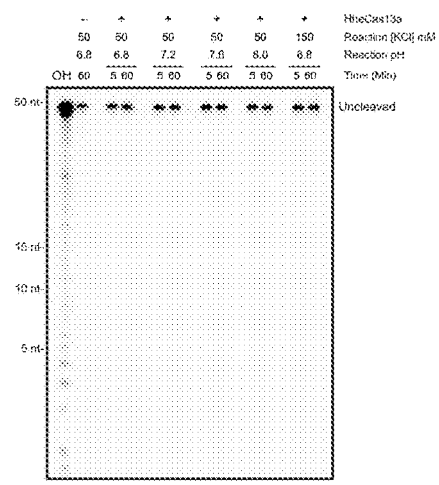
FIG. 39C

FIG. 42A
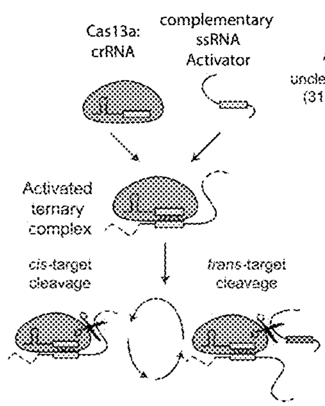
FIG. 42B
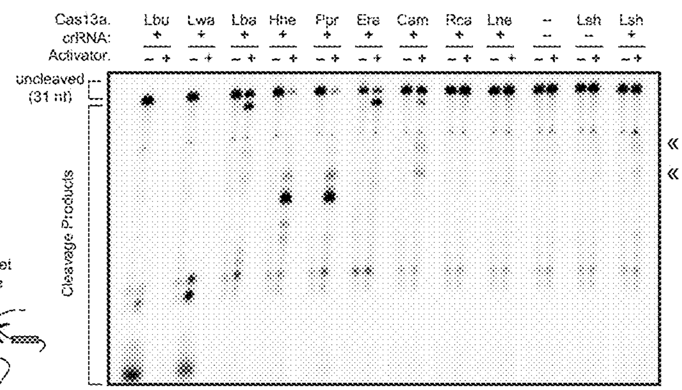
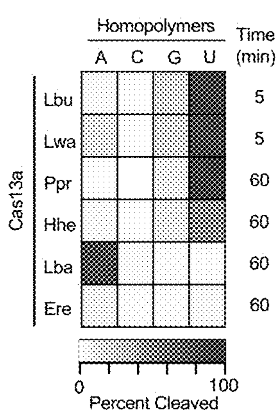
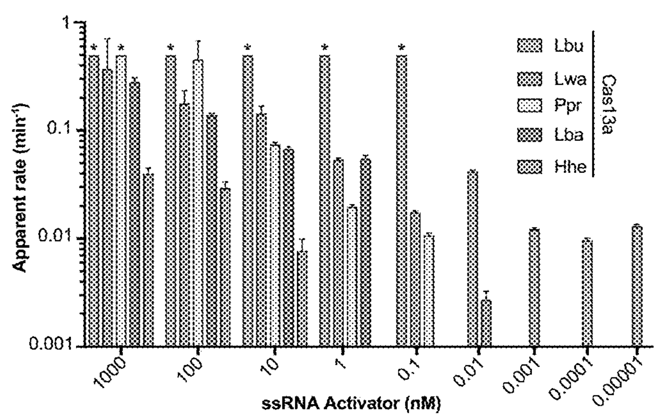
FIG. 42C
FIG. 42D FIG. 44A
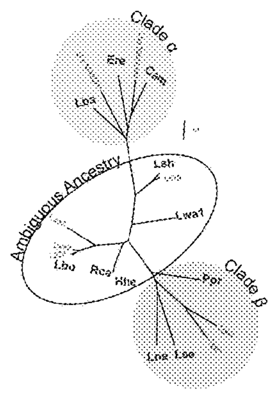
FIG. 44B
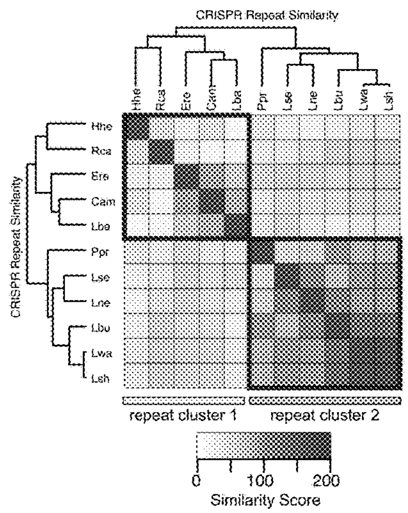
FIG. 44C
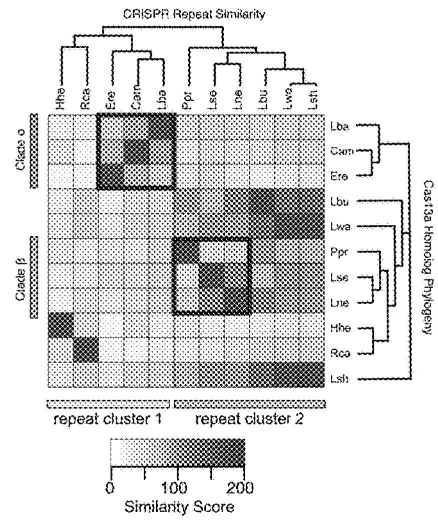
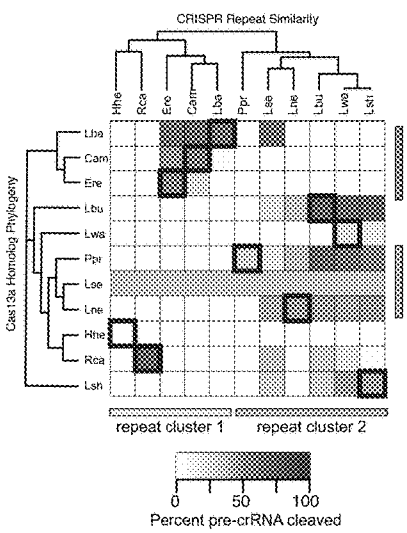
FIG. 44D
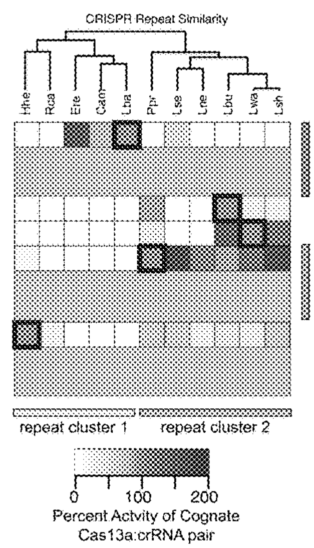
FIG. 44E
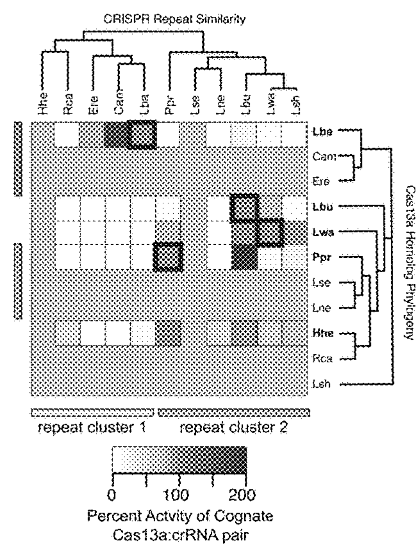
FIG. 44F FIG. 46A
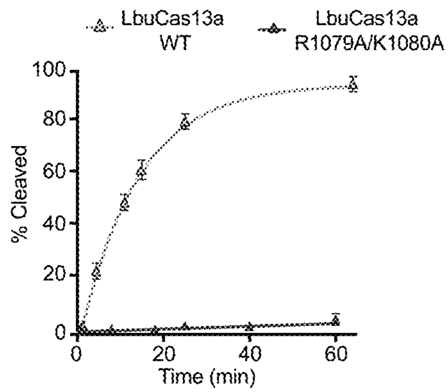
FIG. 46B
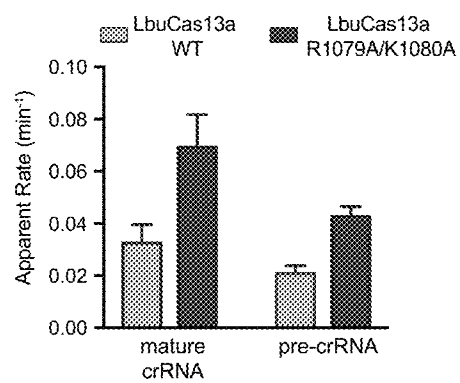
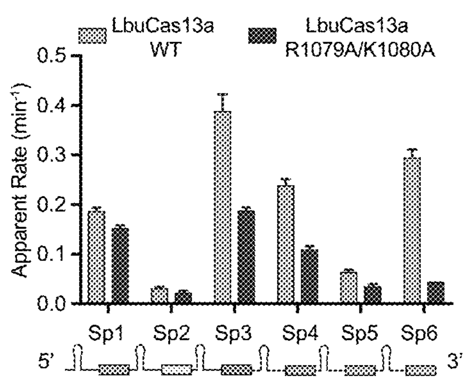
FIG. 46C
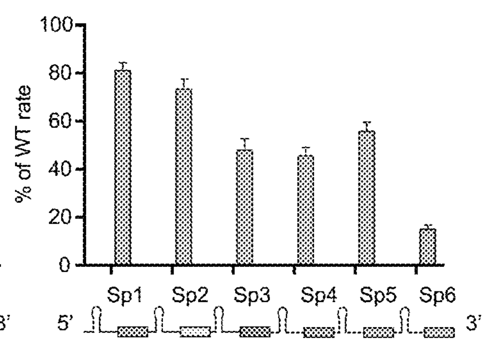
FIG. 46D

Table 4

| Prefix | Species | Strain | Cas13a Accession | Genome Accession | CRISPR array start | CRISPR array stop | CRISPR Repeat Consensus | Mature crRNA handle | Use in Study |
|---|---|---|---|---|---|---|---|---|---|
| Lwa | Leptotrichia wadei | F0279 | ERK53440.1 | AWVM01000026.1 | 24602 | 24774 | GATATAGACCACCCCAATATCGAAGGGGACTAAAACTT | GACCACCCCAAUAUCGAAGGGGACUAAAACUU | Yes |
| Rca | Rhodobacter capsulatus | R121 | ETD76934.1 | AYQC01000019.1 | 321133 | 321440 | TCACATCACCGCCAAGACGACGGCGGACTGAACC | CAUCACCGCCAAGACGACGGCGGACUGAACC | Yes |
| | | | | | 325840 | 326009 | GCAGCACATCACCGCCAAAATGACGGCGGACTGAACCT | not tested | Yes |
| Hhe | Herbinix hemicellulosilytica | T3/55T | CRZ35554.1 | CVTD020000026.1 | 59561 | 59859 | GTAACAATCCCCGTAGACAGGGGAACTGCAAC | not cleaved | No |
| Lbu | Leptotrichia buccalis | DSM 1135 | WP_015770004.1 | NC_013192.1 | 1880132 | 1880237 | GATTTAGACCACCCCAAAAATGAAGGGGACTAAAACA | GACCACCCCAAAAAUGAAGGGGACUAAAACA | Yes |
| Lse | Listeria seeligeri | SLCC3954 | WP_012985477.1 | NC_013891.1 | 1174057 | 1174422 | GTAAGAGACTACCTCTATATGAAAGAGGACTAAAAC | GACUACCUCUAUAUGAAAGAGGACUAAAAC | Yes |
| Ppr | Paludibacter propionicigenes | WB4 | WP_013443710.1 | NC_014734.1 | 223912 | 225653 | CTTGTGAATTATCCCAAAATTGAAGGGAACTACAAC | AAUUAUCCCAAAAUUGAAGGGAACUACAAC | Yes |
| | | | | | | | CTTGTGCATTATCCCAATATTGAAGGGAACTACAAC | not tested | No |
| | | | | | | | CTTGTGCATTATCCCAAAATTGAAGGGAACTAAAAC | not tested | No |
| Lba | Lachnospiraceae bacterium | NK4A179 | WP_022785443.1 | NZ_ATWC01000054.1 | 10469 | 10913 | GCTGGAGAAGATAGCCCAAGAAAGAGGGCAATAAC | AGAUAGCCCAAGAAAGAGGGCAAUAAC | Yes |
| | | | | | 49 | 290 | GTTGATGACAACAGCCCAAGATAGAGGGCAATAAC | GAAGAGCCCAAGAUAGAGGGCAAUAAC | No |
| Ere | [Eubacterium] rectale | T1-815 | WP_055061018.1 | NZ_CVRQ01000008.1 | 63967 | 64487 | GTGAAAGTAGCCCGATATAGAGGGCAATAAC | AAGUAGCCCGAUAUAGAGGGCAAUAAC | Yes |
| | | | | | 58872 | 59187 | GTGAATACAGCTCGATATAGTGAGCAATAAG | AUACAGCUCGAUAUAGUGAGCAAUAAG | No |
| Lny | Listeria newyorkensis | FSL M6-0635 | WP_036091002.1 | NZ_JNFB01000012.1 | 169592 | 169890 | GATTTAGAGTACCTCAAAACAAAAGAGGACTAAAAC | GAGUACCUCAAAACAAAAGAGGACUAAAAC | Yes |
| Cam | Clostridium aminophilum | DSM 10710 | WP_031473346.1 | NZ_JONJ01000012.1 | 1521 | 2181 | GTTTGGAGAACAGCCCGATATAGAGGGCAATAGAC | GAACAGCCCGAUAUAGAGGGCAAUAGAC | Yes |
| Lsh | Leptotrichia shahii | DSM 19757 | WP_018451595.1 | NZ_KB890278.1 | 34127 | 34365 | GATATAGACCACCCCAATATCGAAGGGGACTAAAAC | CACCCCAAUAUCGAAGGGGACUAAAAC | Yes |

FIG. 49

Table 5

| Oligo ID* | Type | Source** | Description | Sequence |
|---|---|---|---|---|
| AES559 | pre-crRNA | SS | Cam pre-crRNA L4 | GGGUUUGGAGAACAGCCCGAUAUAGAGGGCAAUAGACCAGAUAUAGCCUGGUGGUUCAGGC |
| AES557 | pre-crRNA | SS | Ere pre-crRNA2 L4 | GGGUGAAUACAGCUCGAUAUAGUGAGCAAUAAGCAGAUAUAGCCUGGUGGUUCAGGC |
| AES620 | pre-crRNA | SS | Hhe pre-crRNA L4 | GGUAUGUAACAAUCCCCGUAGACAGGGGAACUGCAACCAGAUAUAGCCUGGUGGUUCAGGC |
| AES556 | pre-crRNA | SS | Lba pre-crRNA2 L4 | GGGCUGGAGAAGAUAGCCCAAGAAAGAGGGCAAUAACCAGAUAUAGCCUGGUGGUUCAGGC |
| AES634 | pre-crRNA | SS | Lbu pre-crRNA L4 | GGAUUUAGACCACCCCAAAAAUGAAGGGGACUAAAACACAGAUAUAGCCUGGUGGUUCAGGC |
| AES619 | pre-crRNA | SS | Lne pre-crRNA L4 | GGAUUUAGAGUACCUCAAAACAAAAGAGGACUAAAACCAGAUAUAGCCUGGUGGUUCAGGC |
| AES625 | pre-crRNA | SS | Lse pre-crRNA L4 | GGUAAGAGACUACCUCUAUAUGAAAGAGGACUAAAACCAGAUAUAGCCUGGUGGUUCAGGC |
| AES566 | pre-crRNA | SS | Lsh pre-crRNA L4 | GGAUAUAGACCACCCCAAUAUCGAAGGGGACUAAAACCAGAUAUAGCCUGGUGGUUCAGGC |
| AES553 | pre-crRNA | SS | Lwa pre-crRNA L4 | GGGAUAUAGACCACCCCAAUAUCGAAGGGGACUAAAACUUCAGAUAUAGCCUGGUGGUUCAGGC |
| AES597 | pre-crRNA | SS | Ppr pre-crRNA L4 | GGCUUGUGAAUUAUCCCAAAAUUGAAGGGAACUACAACCAGAUAUAGCCUGGUGGUUCAGGC |
| AES568 | pre-crRNA | SS | Rca pre-crRNA L4 | GGUCACAUCACCGCCAAGACGACGGCGGACUGAACCCAGAUAUAGCCUGGUGGUUCAGGC |
| AES614 | crRNA | HH PCR | HH-Cam crRNA uncleaved | GGUGUUCUCUGAUGAGGCCUUCGGCCGAAACGGUGAAAGCCGUAAGAACAGCCCGAUAUAGAGGGCAAUAGACCAGAUAUAGCCUGGUGGUUCAGGC |
| | | | Cam crRNA L4 | GAACAGCCCGAUAUAGAGGGCAAUAGACCAGAUAUAGCCUGGUGGUUCAGGC |
| AES610 | crRNA | HH PCR | HH-Ere crRNA uncleaved | GGUGUAUUCUGAUGAGGCCUUCGGCCGAAACGGUGAAAGCCGUAAAUACAGCUCGAUAUAGUGAGCAAUAAGCAGAUAUAGCCUGGUGGUUCAGGC |
| | | | Ere crRNA L4 | AAGUAGCCCGAUAUAGAGGGCAAUAACCAGAUAUAGCCUGGUGGUUCAGGC |
| AES612 | crRNA | HH PCR | HH-Lba crRNA uncleaved | GGUAUCUUCUGAUGAGGCCUUCGGCCGAAACGGUGAAAGCCGUAAAGAUAGCCCAAGAAAGAGGGCAAUAACCAGAUAUAGCCUGGUGGUUCAGGC |
| | | | Lba crRNA L4 | AGAUAGCCCAAGAAAGAGGGCAAUAACCAGAUAUAGCCUGGUGGUUCAGGC |
| MOC410 | crRNA | SS | Lbu crRNA L3 | GGCCACCCCAAAAAUGAAGGGGACUAAAACACUGGUGAACUUCCGAUAGUG |
| MOC411 | crRNA | SS | Lbu crRNA L4 | GGCCACCCCAAAAAUGAAGGGGACUAAAACACAGAUAUAGCCUGGUGGUUC |
| SCK340 | crRNA | SS | Lbu crRNA Sp3 | GACCACCCCAAAAAUGAAGGGGACUAAAACAGGGGCAGAGAUGAUGACCCU |
| AES641 | crRNA | SS | Lne crRNA L4 | GAGUACCUCAAAACAAAAGAGGACUAAAACCAGAUAUAGCCUGGUGGUUCAGGC |
| AES646 | crRNA | SS | Lsh crRNA (gggc) L4 | GGGCCACCCCAAUAUCGAAGGGGACUAAAACCAGAUAUAGCCUGGUGGUUCAGGC |
| AES647 | crRNA | SS | Lwa crRNA L4 | GACCACCCCAAUAUCGAAGGGGACUAAAACUUCAGAUAUAGCCUGGUGGUUCAGGC |
| AES639 | crRNA | HH PCR | HH-Ppr crRNA uncleaved | GGAUAAUUCUGAUGAGGCCUUCGGCCGAAACGGUGAAAGCCGUAAAUUAUCCCAAAAUUGAAGGGAACUACAACCAGAUAUAGCCUGGUGGUUCAGGC |
| | | | Ppr crRNA L4 | AAUUAUCCCAAAAUUGAAGGGAACUACAACCAGAUAUAGCCUGGUGGUUCAGGC |
| AES642 | crRNA | HH PCR | HH-Rca crRNA uncleaved | GGGUGAUGCUGAUGAGGCCUUCGGCCGAAACGGUGAAAGCCGUACAUCACCGCCAAGACGACGGCGGACUGAACCAGAUAUAGCCUGGUGGUUCAGGC |
| | | | Rca-crRNA L4 | CATCACCGCCAAGACGACGGCGGACTGAACCAGATATAGCCTGGTGGTTCAGGC |
| AES618 | Target | SS | 18-mer Random | GGCAUGACUAGUCGUACUGCAUCG |
| MOC36 | Target | SS | Sp1/L3 Target | GGAAAUCAUUCAACACCCGCACUAUCGGAAGUUCACCAGCCAGCCGCAGCACGUU |
| MOC37 | Target | SS | Sp2/L4 Target | GGCAAUAAAAAUGCGCCGCCUGAACCACCAGGCUAUAUCUGCCACUCAUUGUUGUGA |
| AES532 | Target | SS | Sp3 Target- 31 mer | GGUCCAAGGGUCAUCAUCUCUGCCCCCACAG |
| AES450 | Target | SS | Sp3 Target- 60 mer | GGCACACCCGCAGGGGGAGCCAAAAGGGUCAUCAUCUCUGCCCCCACAGCAGAAGCCCC |
| AES653 | Target | SS | Sp4 Target | GGACCAUAUAUCGAAAGUUAAGCUAGAAUGUGUCAUAUGGCAG |
| AES452 | Target | SS | Sp5 Target | GGGAACCCCAAGGCCAACCGCGAGAAGAUGACCCAGAUCAUGUUUGAGACCUUCAACACCCC |
| MOC28 | Target | SS | Sp6/L2 Target | GGCUCAAUUUUGACAGCGGUCAUGGCAUUCCACUUAUCACUGGCAUCCUUCCACUC |
| AES652 | Target | IDT | FQ A5 | /56-FAM/rArArArArA/3IABkFQ/ |
| MOC533 | Target | IDT | FQ U5 | /56-FAM/rUrUrUrUrU/3IABkFQ/ |
| AES626 | Target | IDT | Homo A | rArArArArA |
| AES627 | Target | IDT | Homo C | rCrCrCrCrC |
| AES628 | Target | IDT | Homo G | rGrGrGrGrG |
| AES629 | Target | IDT | Homo U | rUrUrUrUrU |
| Lbu-CRISPR Array | pre-crRNA array | PCR | Six-mer Array Leader-Sp1-Sp2-Sp3-Sp4-Sp5-Sp6 | GGGCCGAAUUGAAGGAAGGCCGUCAAGGCCGCAUGCCAUUAAUACGACUCACUAUAGGAUUUAGACCACCCCAAAAAUGAAGGGGACUAAAACACUGGUGAACUUCCGAUAGUGCGGGUGUUGAAUGAUUUAGACCACCCCAAAAAUGAAGGGGACUAAAACACAGAUAUAGCCUGGUGGUUCAGGCGGCGCAUUGAUUUAGACCACCCCAAAAAUGAAGGGGACUAAAACAGGGGCAGAGAUGAUGACCCUUUUGGCUCCCCCGAUUUAGACCACCCCAAAAAUGAAGGGGACUAAAACAAUAUGACACAUUCUAGCUUAACUUUCGAUAUAGAUUUAGACCACCCCAAAAAUGAAGGGGACUAAAACACAAACAUGAUCUGGGUCAUCUUCUCGCGGUUGGAUUUAGACCACCCCAAAAAUGAAGGGGACUAAAACAAUGCCAGUGAUAAGUGGAAUGCCAUGACCGCU |

Table 6

| Cas13a Homolog | rArArArArA | | rCrCrCrCrC | | rGrGrGrGrG | | rUrUrUrUrU | |
|---|---|---|---|---|---|---|---|---|
| | Avg | SD | Avg | SD | Avg | SD | Avg | SD |
| Lbu | 2.66 | 0.15 | 0.96 | 0.09 | 17.83 | 0.79 | 92.69 | 2.10 |
| Lwa | 13.67 | 0.92 | 0.87 | 0.10 | 18.97 | 1.31 | 90.87 | 1.76 |
| Lba | 82.34 | 5.35 | 3.01 | 1.16 | 2.23 | 0.75 | 1.73 | 0.70 |
| Ppr | 1.19 | 0.26 | 0.50 | 0.14 | 10.21 | 6.63 | 93.20 | 4.78 |
| Hhe | 3.56 | 0.51 | 1.01 | 0.12 | 10.34 | 8.55 | 48.04 | 9.07 |
| Ere | 6.32 | 0.18 | 2.42 | 0.03 | 2.37 | 1.58 | 4.25 | 1.99 |

FIG. 52

Table 7

| | | Lbu WT | | CamCas13a | | EreCas13a | | LbaCas13a | | LwaCas13a | | RcaCas13a | | HheCas13a | | PprCas13a | | LshCas13a | | LnyCas13a | |
|---|---|---|---|---|---|---|---|---|---|---|---|---|---|---|---|---|---|---|---|---|---|
| Descriptive ID | RNA ID | Avg | SD | Avg | SD | Avg | SD | Avg | SD | Avg | SD | Avg | SD | Avg | SD | Avg | SD | Avg | SD | Avg | SD |
| pre-crLbu | AES634 | 82.0 | 3.1 | 0.0 | 3.2 | 0.3 | 0.7 | 0.2 | 0.7 | 3.6 | 2.1 | 44.0 | 29.7 | 4.7 | 3.1 | 78.5 | 5.5 | 40.8 | 9.7 | 58.8 | 38.5 |
| pre-crLse | AES625 | 29.1 | 11.9 | 0.8 | 1.3 | 0.3 | 1.7 | 74.7 | 7.6 | 0.9 | 0.9 | 49.3 | 28.4 | -0.5 | 2.2 | 27.0 | 4.7 | 39.9 | 7.8 | 55.9 | 21.1 |
| pre-crLba1 | AES555 | 1.7 | 2.7 | 15.3 | 6.8 | 2.5 | 1.6 | 75.9 | 7.0 | 2.5 | 3.1 | 2.5 | 2.6 | 0.8 | 2.0 | 1.3 | 3.0 | -0.2 | 1.8 | 2.8 | 2.2 |
| pre-crLba2 | AES556 | 0.1 | 1.9 | 7.6 | 2.5 | -0.1 | 3.7 | 75.4 | 7.1 | 0.4 | 3.4 | -0.7 | 4.1 | -1.9 | 5.0 | -2.2 | 5.5 | -2.5 | 4.1 | 0.3 | 7.3 |
| pre-crEre2 | AES557 | 1.6 | 1.4 | 63.9 | 6.0 | 69.7 | 1.7 | 76.2 | 6.4 | 0.7 | 1.4 | -1.4 | 3.8 | -2.2 | 3.7 | -1.4 | 3.5 | -2.7 | 8.3 | -1.8 | 6.3 |
| pre-crEre1 | AES558 | -0.9 | 2.3 | 68.5 | 9.5 | 66.4 | 6.8 | 74.5 | 9.7 | -0.3 | 2.7 | 0.4 | 3.4 | -1.7 | 5.1 | 0.2 | 4.9 | -0.5 | 7.1 | 2.5 | 3.2 |
| pre-crCam | AES559 | -0.1 | 1.2 | 72.1 | 4.4 | 33.6 | 5.0 | 77.7 | 3.4 | 0.7 | 0.9 | -0.2 | 0.4 | -1.2 | 0.6 | -1.3 | 1.1 | -0.6 | 0.7 | 0.6 | 0.3 |
| pre-crLwa | AES553 | 78.4 | 9.4 | 2.8 | 1.8 | 1.1 | 2.6 | 2.6 | 2.0 | 32.7 | 10.1 | 29.4 | 8.6 | 3.5 | 2.3 | 74.4 | 9.3 | 59.9 | 9.5 | 56.6 | 5.8 |
| pre-crLsh | AES566 | 79.0 | 7.0 | 1.3 | 2.7 | 0.8 | 1.7 | 1.9 | 2.4 | 24.0 | 9.4 | 6.1 | 1.8 | 5.4 | 8.1 | 69.0 | 11.5 | 59.9 | 9.6 | 60.9 | 16.6 |
| pre-crRca | AES568 | 1.6 | 1.4 | 0.8 | 2.0 | 1.5 | 2.8 | 2.1 | 2.3 | 4.6 | 2.7 | 80.7 | 3.4 | 5.4 | 3.6 | 4.4 | 2.0 | 5.4 | 5.0 | 4.4 | 3.5 |
| pre-crPpr | AES597 | -1.0 | 2.2 | -0.8 | 1.2 | -1.0 | 1.8 | 2.1 | 2.3 | -1.0 | 2.2 | -0.2 | 2.8 | -1.5 | 2.3 | 41.3 | 4.9 | -1.0 | 2.5 | 1.5 | 1.9 |
| pre-crHhe | AES620 | 5.8 | 4.5 | 3.9 | 14.3 | 1.9 | 10.4 | -1.0 | 6.9 | 0.5 | 4.4 | -2.8 | 9.7 | -6.6 | 5.2 | 3.5 | 9.4 | -6.5 | 6.6 | 3.8 | 10.6 |
| pre-crLne | AES619 | 48.6 | 1.7 | 0.7 | 2.3 | -0.5 | 1.3 | -0.1 | 0.3 | -0.9 | 3.2 | 5.6 | 3.6 | -2.4 | 1.5 | 50.6 | 4.4 | 1.3 | 2.9 | 61.4 | 1.1 |

FIG. 53

Table 8

| | LwaCas13a | | LbaCas13a | | LbuCas13a | | PprCas13a | | HheCas13a | |
|---|---|---|---|---|---|---|---|---|---|---|
| Guide | slope | SE | slope | SE | slope | SE | slope | SE | slope | SE |
| Lwa pre-crRNA | 100.0 | 4.2 | 124.5 | 37.4 | 35.6 | 1.9 | 31.5 | 6.4 | 1.5 | 0.2 |
| Lba pre-crRNA | -0.3 | 0.0 | 0.0 | 0.0 | 1.8 | 0.1 | -0.6 | -0.1 | 100.0 | 15.8 |
| Ere pre-crRNA | -0.2 | 0.0 | -0.1 | 0.0 | 3.2 | 0.2 | 0.0 | 0.0 | 152.5 | 27.3 |
| Cam pre-crRNA | -0.3 | 0.0 | 0.0 | 0.0 | 2.7 | 0.2 | 0.0 | 0.0 | 77.8 | 10.0 |
| Lsh pre-crRNA | 120.7 | 7.7 | 166.0 | 49.8 | 71.7 | 4.8 | 30.7 | 6.3 | 2.4 | 0.3 |
| Rca pre-crRNA | 0.0 | 0.0 | 0.0 | -0.7 | 26.6 | 1.4 | 0.1 | 0.0 | 0.8 | 0.1 |
| Ppr pre-crRNA | 37.4 | 1.4 | 100.0 | 42.4 | 66.4 | 4.3 | 86.7 | 22.8 | 1.5 | 0.2 |
| Lne pre-crRNA | -0.2 | 0.0 | 104.6 | 31.4 | 29.8 | 1.6 | 7.1 | 1.6 | 1.3 | 0.2 |
| Hhe pre-crRNA | 0.0 | 0.0 | 16.2 | 4.9 | 100.0 | 7.3 | -0.1 | 0.0 | 0.8 | 0.1 |
| Lse pre-crRNA | 1.5 | 0.0 | 170.2 | 51.1 | 63.7 | 3.6 | 6.6 | 1.8 | 51.5 | 6.0 |
| Lbu pre-crRNA | 140.0 | 12.0 | 90.0 | 27.0 | 42.6 | 2.2 | 100.0 | 28.0 | 7.8 | 0.9 |

FIG. 54

Table 9

| | LwaCas13a | | LbaCas13a | | LbuCas13a | | PprCas13a | | HheCas13a | |
|---|---|---|---|---|---|---|---|---|---|---|
| Guide | slope | SE | slope | SE | slope | SE | slope | SE | slope | SE |
| Cam crRNA | 0.0 | 0.1 | 174.8 | 50.9 | -0.2 | 0.0 | -0.9 | -0.1 | 7.4 | 0.4 |
| Lba crRNA | -0.4 | -0.1 | 100.0 | 22.3 | 0.0 | 0.0 | -1.2 | -0.1 | 12.6 | 0.7 |
| Ere crRNA | -0.5 | -0.1 | 81.7 | 23.5 | 0.1 | 0.0 | -0.8 | -0.1 | 6.5 | 0.4 |
| Ppr crRNA | 77.8 | 14.3 | 1.5 | 0.2 | 11.6 | 0.7 | 100.0 | 2.6 | 100.0 | 7.5 |
| Lne crRNA | 0.1 | 0.0 | 1.6 | 0.3 | 0.1 | 0.0 | -0.2 | -0.1 | 54.7 | 3.0 |
| Rca crRNA | -0.1 | -0.1 | 3.9 | 0.6 | -0.8 | 0.0 | -0.1 | -0.1 | 50.4 | 2.7 |
| Lsh crRNA | 93.3 | 21.5 | 0.9 | 0.2 | 10.0 | 0.5 | 27.2 | 1.1 | 75.9 | 4.5 |
| Lwa crRNA | 100.0 | 24.3 | 10.6 | 1.7 | 75.7 | 5.5 | 12.8 | 0.4 | 60.4 | 3.7 |
| Lbu crRNA | 98.2 | 18.2 | 21.1 | 3.4 | 100.0 | 6.1 | 398.3 | 20.6 | 92.6 | 7.0 |

FIG. 56A

>WP_012985477.1 WP_012985477.1 hypothetical protein [Listeria seeligeri]
MWISIKTLIHHLGVLFFCDYMYNRREKKIIEVKTMRITKVEVDRKKVLISRDKNGGKLVY
ENEMQDNTEQIMHHKKSSFYKSVVNKTICRPEQKQMKKLVHGLLQENSQEKIKVSDVTKL
NISNFLNHRFKKSLYYFPENSPDKSEEYRIEINLSQLLEDSLKKQQGTFICWESFSKDME
LYINWAENYISSKTKLIKKSIRNNRIQSTESRSGQLMDRYMKDILNKNKPFDIQSVSEKY
QLEKLTSALKATFKEAKKNDKEINYKLKSTLQNHERQIIEELKENSELNQFNIEIRKHLE
TYFPIKKTNRKVGDIRNLEIGEIQKIVNHRLKNKIVQRILQEGKLASYEIESTVNSNSLQ
KIKIEEAFALKFINACLFASNNLRNMVYPVCKKDILMIGEFKNSFKEIKHKKFIRQWSQF
FSQEITVDDIELASWGLRGAIAPIRNEIIHLKKHSWKKFFNNPTFKVKKSKIINGKTKDV
TSEFLYKETLFKDYFYSELDSVPELIINKMESSKILDYYSSDQLNQVFTIPNFELSLLTS
AVPFAPSFKRVYLKGFDYQNQDEAQPDYNLKLNIYNEKAFNSEAFQAQYSLFKMVYYQVF
LPQFTTNNDLFKSSVDFILTLNKERKGYAKAFQDIRKMNKDEKPSEYMSYIQSQLMLYQK
KQEEKEKINHFEKFINQVFIKGFNSFIEKNRLTYICHPTKNTVPENDNIEIPFHTDMDDS
NIAFWLMCKLLDAKQLSELRNEMIKFSCSLQSTEEISTFTKAREVIGLALLNGEKGCNDW
KELFDDKEAWKKNMSLYVSEELLQSLPYTQEDGQTPVINRSIDLVKKYGTETILEKLFSS
SDDYKVSAKDIAKLHEYDVTEKIAQQESLHKQWIEKPGLARDSAWTKKYQNVINDISNYQ
WAKTKVELTQVRHLHQLTIDLLSRLAGYMSIADRDFQFSSNYILERENSEYRVTSWILLS
ENKNKNKYNDYELYNLKNASIKVSSKNDPQLKVDLKQLRLTLEYLELFDNRLKEKRNNIS
HFNYLNGQLGNSILELFDDARDVLSYDRKLKNAVSKSLKEILSSHGMEVTFKPLYQTNHH
LKIDKLQPKKIHHLGEKSTVSSNQVSNEYCQLVRTLLTMK

FIG. 56B

>WP_013443710.1 WP_013443710.1 hypothetical protein [Paludibacter propionicigenes]
MRVSKVKVKDGGKDKMVLVHRKTTGAQLVYSGQPVSNETSNILPEKKRQSFDLSTLNKTI
IKFDTAKKQKLNVDQYKIVEKIFKYPKQELPKQIKAEEILPFLNHKFQEPVKYWKNGKEE
SFNLTLLIVEAVQAQDKRKLQPYYDWKTWYIQTKSDLLKKSIENNRIDLTENLSKRKKAL
LAWETEFTASGSIDLTHYHKVYMTDVLCKMLQDVKPLTDDKGKINTNAYHRGLKKALQNH
QPAIFGTREVPNEANRADNQLSIYHLEVVKYLEHYFPIKTSKRRNTADDIAHYLKAQTLK
TTIEKQLVNAIRANIIQQGKTNHHELKADTTSNDLIRIKTNEAFVLNLTGTCAFAANNIR
NMVDNEQTNDILGKGDFIKSLLKDNTNSQLYSFFFGEGLSTNKAEKETQLWGIRGAVQQI
RNNVNHYKKDALKTVFNISNFENPTITDPKQQTNYADTIYKARFINELEKIPEAFAQQLK
TGGAVSYYTIENLKSLLTTFQFSLCRSTIPFAPGFKKVFNGGINYQNAKQDESFYELMLE
QYLRKENFAEESYNARYFMLKLIYNNLFLPGFTTDRKAFADSVGFVQMQNKKQAEKVNPR
KKEAYAFEAVRPMTAADSIADYMAYVQSELMQEQNKKEEKVAEETRINFEKFVLQVFIKG
FDSFLRAKEFDFVQMPQPQLTATASNQQKADKLNQLEASITADCKLTPQYAKADDATHIA
FYVFCKLLDAAHLSNLRNELIKFRESVNEFKFHHLLEIIEICLLSADVVPTDYRDLYSSE
ADCLARLRPFIEQGADITNWSDLFVQSDKHSPVIHANIELSVKYGTTKLLEQIINKDTQF
KTTEANFTAWNTAQKSIEQLIKQREDHHEQWVKAKNADDKEKQERKREKSNFAQKFIEKH
GDDYLDICDYINTYNWLDNKMHFVHLNRLHGLTIELLGRMAGFVALFDRDFQFFDEQQIA
DEFKLHGFVNLHSIDKKLNEVPTKKIKEIYDIRNKIIQINGNKINESVRANLIQFISSKR
NYYNNAFLHVSNDEIKEKQMYDIRNHIAHFNYLTKDAADFSLIDLINELRELLHYDRKLK
NAVSKAFIDLFDKHGMILKLKLNADHKLKVESLEPKKIYHLGSSAKDKPEYQYCTNQVMM
AYCNMCRSLLEMKK

FIG. 56C

>WP_015770004.1 WP_015770004.1 hypothetical protein [Leptotrichia buccalis]
MKVTKVGGISHKKYTSEGRLVKSESEENRTDERLSALLNMRLDMYIKNPSSTETKENQKR
IGKLKKFFSNKMVYLKDNTLSLKNGKKENIDREYSETDILESDVRDKKNFAVLKKIYLNE
NVNSEELEVFRNDIKKKLNKINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TRFEFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEEKDTYIDFIQKIFLKGFMTYLANNGRLSLIYIGSDEETNTSLAEKKQE
FDKFLKKYEQNNNIKIPYEINEFLREIKLGNILKYTERLNMFYLILKLLNHKELTNLKGS
LEKYQSANKEEAFSDQLELINLLNLDNNRVTEDFELEADEIGKFLDFNGNKVKDNKELKK
FDTNKIYFDGENIIKHRAFYNIKKYGMLNLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIRNYIAHFNYIPHAEISLLEVLENLRKLLSYDRK
LKNAVMKSVVDILKEYGFVATFKIGADKKIGIQTLESEKIVHLKNLKKKKLMTDRNSEEL
CKLVKIMFEYKMEEKKSEN

FIG. 56D

>WP_018451595.1 WP_018451595.1 hypothetical protein [Leptotrichia shahii]
MGNLFGHKRWYEVRDKKDFKIKRKVKVKRNYDGNKYILNINENNNKEKIDNNKFIRKYIN
YKKNDNILKEFTRKFHAGNILFKLKGKEGIIRIENNDDFLETEEVVLYIEAYGKSEKLKA
LGITKKKIIDEAIRQGITKDDKKIEIKRQENEEEIEIDIRDEYTNKTLNDCSIILRIIEN
DELETKKSIYEIFKNINMSLYKIIEKIIENETEKVFENRYYEEHLREKLLKDDKIDVILT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDDFSRLHAKEELDLELITFFASTNMELNKIFSRENINN
DENIDFFGGDREKNYVLDKKILNSKIKIIRDLDFIDNKNNITNNFIRKFTKIGTNERNRI
LHAISKERDLQGTQDDYNKVINIIQNLKISDEEVSKALNLDVVFKDKKNIITKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQKMKEIEKDFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTTAYYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL

FIG. 56E

>ERK53440.1 ERK53440.1 hypothetical protein HMPREF9015_00520
[Leptotrichia wadei F0279]
MYMKITKIDGVSHYKKQDKGILKKKWKDLDERKQREKIEARYNKQIESKIYKEFFRLKNK
KRIEKEEDQNIKSLYFFIKELYLNEKNEEWELKNINLEILDDKERVIKGYKFKEDVYFFK
EGYKEYYLRILFNNLIEKVQNENREKVRKNKEFLDLKEIFKKYKNRKIDLLLKSINNNKI
NLEYKKENVNEEIYGINPTNDREMTFYELLKEIIEKKDEQKSILEEKLDNFDITNFLENI
EKIFNEETEINIIKGKVLNELREYIKEKEENNSDNKLKQIYNLELKKYIENNFSYKKQKS
KSKNGKNDYLYLNFLKKIMFIEEVDEKKEINKEKFKNKINSNFKNLFVQHILDYGKLLYY
KENDEYIKNTGQLETKDLEYIKTKETLIRKMAVLVSFAANSYYNLFGRVSGDILGTEVVK
SSKTNVIKVGSHIFKEKMLNYFFDFEIFDANKIVEILESISYSIYNVRNGVGHFNKLILG
KYKKKDINTNKRIEEDLNNNEEIKGYFIKKRGEIERKVKEKFLSNNLQYYYSKEKIENYF
EVYEFEILKRKIPFAPNFKRIIKKGEDLFNNKNNKKYEYFKNFDKNSAEEKKEFLKTRNF
LLKELYYNNFYKEFLSKKEEFEKIVLEVKEEKKSRGNINNKKSGVSFQSIDDYDTKINIS
DYIASIHKKEMERVEKYNEEKQKDTAKYIRDFVEEIFLTGFINYLEKDKRLHFLKEEFSI
LCNNNNNVVDFNININEEKIKEFLKENDSKTLNLYLFFNMIDSKRISEFRNELVKYKQFT
KKRLDEEKEFLGIKIELYETLIEFVILTREKLDTKKSEEIDAWLVDKLYVKDSNEYKEYE
EILKLFVDEKILSSKEAPYYATDNKTPILLSNFEKTRKYGTQSFLSEIQSNYKYSKVEKE
NIEDYNKKEEIEQKKKSNIEKLQDLKVELHKKWEQNKITEKEIEKYNNTTRKINEYNYLK
NKEELQNVYLLHEMLSDLLARNVAFFNKWERDFKFIVIAIKQFLRENDKEKVNEFLNPPD
NSKGKKVYFSVSKYKNTVENIDGIHKNFMNLIFLNNKFMNRKIDKMNCAIWVYFRNYIAH
FLHLHTKNEKISLISQMNLLIKLFSYDKKVQNHILKSTKTLLEKYNIQINFEISNDKNEV
FKYKIKNRLYSKKGKMLGKNNKFEILENEFLENVKAMLEYSE

FIG. 56F

>WP_022785443.1 WP_022785443.1 hypothetical protein
[Lachnospiraceae bacterium NK4A179]
MKISKVREENRGAKLTVNAKTAVVSENRSQEGILYNDPSRYGKSRKNDEDRDRYIESRLK
SSGKLYRIFNEDKNKRETDELQWFLSEIVKKINRRNGLVLSDMLSVDDRAFEKAFEKYAE
LSYTNRRNKVSGSPAFETCGVDAATAERLKGIISETNFINRIKNNIDNKVSEDIIDRIIA
KYLKKSLCRERVKRGLKKLLMNAFDLPYSDPDIDVQRDFIDYVLEDFYHVRAKSQVSRSI
KNMNMPVQPEGDGKFAITVSKGGTESGNKRSAEKEAFKKFLSDYASLDERVRDDMLRRMR
RLVVLYFYGSDDSKLSDVNEKFDVWEDHAARRVDNREFIKLPLENKLANGKTDKDAERIR
KNTVKELYRNQNIGCYRQAVKAVEEDNNGRYFDDKMLNMFFIHRIEYGVEKIYANLKQVT
EFKARTGYLSEKIWKDLINYISIKYIAMGKAVYNYAMDELNASDKKEIELGKISEEYLSG
ISSFDYELIKAEEMLQRETAVYVAFAARHLSSQTVELDSENSDFLLLKPKGTMDKNDKNK
LASNNILNFLKDKETLRDTILQYFGGHSLWTDFPFDKYLAGGKDDVDFLTDLKDVIYSMR
NDSFHYATENHNNGKWNKELISAMFEHETERMTVVMKDKFYSNNLPMFYKNDDLKKLLID
LYKDNVERASQVPSFNKVFVRKNFPALVRDKDNLGIELDLKADADKGENELKFYNALYYM
FKEIYYNAFLNDKNVRERFITKATKVADNYDRNKERNLKDRIKSAGSDEKKKLREQLQNY
IAENDFGQRIKNIVQVNPDYTLAQICQLIMTEYNQQNNGCMQKKSAARKDINKDSYQHYK
MLLLVNLRKAFLEFIKENYAFVLKPYKHDLCDKADFVPDFAKYVKPYAGLISRVAGSSEL
QKWYIVSRFLSPAQANHMLGFLHSYKQYVWDIYRRASETGTEINHSIAEDKIAGVDITDV
DAVIDLSVKLCGTISSEISDYFKDDEVYAEYISSYLDFEYDGGNYKDSLNRFCNSDAVND
QKVALYYDGEHPKLNRNIILSKLYGERRFLEKITDRVSRSDIVEYYKLKKETSQYQTKGI
FDSEDEQKNIKKFQEMKNIVEFRDLMDYSEIADELQGQLINWIYLRERDLMNFQLGYHYA
CLNNDSNKQATYVTLDYQGKKNRKINGAILYQICAMYINGLPLYYVDKDSSEWTVSDGKE
STGAKIGEFYRYAKSFENTSDCYASGLEIFENISEHDNITELRNYIEHFRYYSSFDRSFL
GIYSEVFDRFFTYDLKYRKNVPTILYNILLQHFVNVRFEFVSGKKMIGIDKKDRKIAKEK
ECARITIREKNGVYSEQFTYKLKNGTVYVDARDKRYLQSIIRLLFYPEKVNMDEMIEVKE
KKKPSDNNTGKGYSKRDRQQDRKEYDKYKEKKKKEGNFLSGMGGNINWDEINAQLKN

FIG. 56G

>ETD76934.1 ETD76934.1 hypothetical protein U717_11515
[Rhodobacter capsulatus R121]
MQIGKVQGRTISEFGDPAGGLKRKISTDGKNRKELPAHLSSDPKALIGQWISGIDKIYRK
PDSRKSDGKAIHSPTPSKMQFDARDDLGEAFWKLVSEAGLAQDSDYDQFKRRLHPYGDKF
QPADSGAKLKFEADPPEPQAFHGRWYGAMSKRGNDAKELAAALYEHLHVDEKRIDGQPKR
NPKTDKFAPGLVVARALGIESSVLPRGMARLARNWGEEEIQTYFVVDVAASVKEVAKAAV
SAAQAFDPPRQVSGRSLSPKVGFALAEHLERVTGSKRCSFDPAAGPSVLALHDEVKKTYK
RLCARGKNAARAFPADKTELLALMRHTHENRVRNQMVRMGRVSEYRGQQAGDLAQSHYWT
SAGQTEIKESEIFVRLWVGAFALAGRSMKAWIDPMGKIVNTEKNDRDLTAAVNIRQVISN
KEMVAEAMARRGIYFGETPELDRLGAEGNEGFVFALLRYLRGCRNQTFHLGARAGFLKEI
RKELEKTRWGKAKEAEHVVLTDKTVAAIRAIIDNDAKALGARLLADLSGAFVAHYASKEH
FSTLYSEIVKAVKDAPEVSSGLPRLKLLLKRADGVRGYVHGLRDTRKHAFATKLPPPPAP
RELDDPATKARYIALLRLYDGPFRAYASGITGTALAGPAARAKEAATALAQSVNVTKAYS
DVMEGRSSRLRPPNDGETLREYLSALTGETATEFRVQIGYESDSENARKQAEFIENYRRD
MLAFMFEDYIRAKGFDWILKIEPGATAMTRAPVLPEPIDTRGQYEHWQAALYLVMHFVPA
SDVSNLLHQLRKWEALQGKYELVQDGDATDQADARREALDLVKRFRDVLVLFLKTGEARF
EGRAAPFDLKPFRALFANPATFDRLFMATPTTARPAEDDPEGDGASEPELRVARTLRGLR
QIARYNHMAVLSDLFAKHKVRDEEVARLAEIEDETQEKSQIVAAQELRTDLHDKVMKCHP
KTISPEERQSYAAAIKTIEEHRFLVGRVYLGDHLRLHRLMMDVIGRLIDYAGAYERDTGT
FLINASKQLGAGADWAVTIAGAANTDARTQTRKDLAHFNVLDRADGTPDLTALVNRAREM
MAYDRKRKNAVPRSILDMLARLGLTLKWQMKDHLLQDATITQAAIKHLDKVRLTVGGPAA
VTEARFSQDYLQMVAAVFNGSVQNPKPRRRDDGDAWHKPPKPATAQSQPDQKPPNKAPSA
GSRLPPPQVGEVYEGVVVKVIDTGSLGFLAVEGVAGNIGLHISRLRRIREDAIIVGRRYR
FRVEIYVPPKSNTSKLNAADLVRID

FIG. 56H

>WP_031473346.1 WP_031473346.1 hypothetical protein
[[Clostridium] aminophilum]
MKFSKVDHTRSAVGIQKATDSVHGMLYTDPKKQEVNDLDKRFDQLNVKAKRLYNVFNQSK
AEEDDDEKRFGKVVKKLNRELKDLLFHREVSRYNSIGNAKYNYYGIKSNPEEIVSNLGMV
ESLKGERDPQKVISKLLLYYLRKGLKPGTDGLRMILEASCGLRKLSGDEKELKVFLQTLD
EDFEKKTFKKNLIRSIENQNMAVQPSNEGDPIIGITQGRFNSQKNEEKSAIERMMSMYAD
LNEDHREDVLRKLRRLNVLYFNVDTEKTEEPTLPGEVDTNPVFEVWHDHEKGKENDRQFA
TFAKILTEDRETRKKEKLAVKEALNDLKSAIRDHNIMAYRCSIKVTEQDKDGLFFEDQRI
NRFWIHHIESAVERILASINPEKLYKLRIGYLGEKVWKDLLNYLSIKYIAVGKAVFHFAM
EDLGKTGQDIELGKLSNSVSGGLTSFDYEQIRADETLQRQLSVEVAFAANNLFRAVVGQT
GKKIEQSKSEENEEDFLLWKAEKIAESIKKEGEGNTLKSILQFFGGASSWDLNHFCAAYG
NESSALGYETKFADDLRKAIYSLRNETFHFTTLNKGSFDWNAKLIGDMFSHEAATGIAVE
RTRFYSNNLPMFYRESDLKRIMDHLYNTYHPRASQVPSFNSVFVRKNFRLFLSNTLNTNT
SFDTEVYQKWESGVYYLFKEIYYNSFLPSGDAHHLFFEGLRRIRKEADNLPIVGKEAKKR
NAVQDFGRRCDELKNLSLSAICQMIMTEYNEQNNGNRKVKSTREDKRKPDIFQHYKMLLL
RTLQEAFAIYIRREEFKFIFDLPKTLYVMKPVEEFLPNWKSGMFDSLVERVKQSPDLQRW
YVLCKFLNGRLLNQLSGVIRSYIQFAGDIQRRAKANHNRLYMDNTQRVEYYSNVLEVVDF
CIKGTSRFSNVFSDYFRDEDAYADYLDNYLQFKDEKIAEVSSFAALKTFCNEEEVKAGIY
MDGENPVMQRNIVMAKLFGPDEVLKNVVPKVTREEIEEYYQLEKQIAPYRQNGYCKSEED
QKKLLRFQRIKNRVEFQTITEFSEIINELLGQLISWSFLRERDLLYFQLGFHYLCLHNDT
EKPAEYKEISREDGTVIRNAILHQVAAMYVGGLPVYTLADKKLAAFEKGEADCKLSISKD
TAGAGKKIKDFFRYSKYVLIKDRMLTDQNQKYTIYLAGLELFENTDEHDNITDVRKYVDH
FKYYATSDENAMSILDLYSEIHDRFFTYDMKYQKNVANMLENILLRHFVLIRPEFFTGSK
KVGEGKKITCKARAQIEIAENGMRSEDFTYKLSDGKKNISTCMIAARDQKYLNTVARLLY
YPHEAKKSIVDTREKKNNKKTNRGDGTFNKQKGTARKEKDNGPREFNDTGFSNTPFAGFD
PFRNS

FIG. 56I

>WP_036091002.1 WP_036091002.1 hypothetical protein [Listeria newyorkensis]
MKITKMRVDGRTIVMERTSKEGQLGYEGIDGNKTTEIIFDKKKESFYKSILNKTVRKPDE
KEKNRRKQAINKAINKEITELMLAVLHQEVPSQKLHNLKSLNTESLTKLFKPKFQNMISY
PPSKGAEHVQFCLTDIAVPAIRDLDEIKPDWGIFFEKLKPYTDWAESYIHYKQTTIQKSI
EQNKIQSPDSPRKLVLQKYVTAFLNGEPLGLDLVAKKYKLADLAESFKLVDLNEDKSANY
KIKACLQQHQRNILDELKEDPELNQYGIEVKKYIQRYFPIKRAPNRSKHARADFLKKELI
ESTVEQQFKNAVYHYVLEQGKMEAYELTDPKTKDLQDIRSGEAFSFKFINACAFASNNLK
MILNPECEKDILGKGNFKKNLPNSTTRSDVVKKMIPFFSDELQNVNFDEAIWAIRGSIQQ
IRNEVYHCKKHSWKSILKIKGFEFEPNNMKYADSDMQKLMDKDIAKIPEFIEEKLKSSGV
VRFYRHDELQSIWEMKQGFSLLTTNAPFVPSFKRVYAKGHDYQTSKNRYYNLDLTTFDIL
EYGEEDFRARYFLTKLVYYQQFMPWFTADNNAFRDAANFVLRLNKNRQQDAKAFINIREV
EEGEMPRDYMGYVQGQIAIHEDSIEDTPNHFEKFISQVFIKGFDRHMRSANLKFIKNPRN
QGLEQSEIEEMSFDIKVEPSFLKNKDDYIAFWIFCKMLDARHLSELRNEMIKYDGHLTGE
QEIIGLALLGVDSRENDWKQFFSSEREYEKIMKGYVVEELYQREPYRQSDGKTPILFRGV
EQARKYGTETVIQRLFDANPEFKVSKCNLAEWERQKETIEETIKRRKELHNEWAKNPKKP
QNNAFFKEYKECCDAIDAYNWHKNKTTLAYVNELHHLLIEILGRYVGYVAIADRDFQCMA
NQYFKHSGITERVEYWGDNRLKSIKKLDTFLKKEGLFVSEKNARNHIAHLNYLSLKSECT
LLYLSERLREIFKYDRKLKNAVSKSLIDILDRHGMSVVFANLKENKHRLVIKSLEPKKLR
HLGGKKIDGGYIETNQVSEEYCGIVKRLLEM

FIG. 56J

>WP_055061018.1 Eubacterium rectale genome assembly T1815, contig T1815_16, whole genome shotgun sequence
MLRRDKEVKKLYNVFNQIQVGTKPKKWNNDEKLSPEENERRAQQKNIKMKNYKWREACSK
YVESSQRIINDVIFYSYRKAKNKLRYMRKNEDILKKMQEAEKLSKFSGGKLEDFVAYTLR
KSLVVSKYDTQEFDSLAAMVVFLECIGKNNISDHEREIVCKLLELIRKDFSKLDPNVKGS
QGANIVRSVRNQNMIVQPQGDRFLFPQVYAKENETVTNKNVEKEGLNEFLLNYANLDDEK
RAESLRKLRRILDVYFSAPNHYEKDMDITLSDNIEKEKFNVWEKHECGKKETGLFVDIPD
VLMEAEAENIKLDAVVEKRERKVLNDRVRKQNIICYRYTRAVVEKYNSNEPLFFENNAIN
QYWIHHIENAVERILKNCKAGKLFKLRKGYLAEKVWKDAINLISIKYIALGKAVYNFALD
DIWKDKKNKELGIVDERIRNGITSFDYEMIKAHENLQRELAVDIAFSVNNLARAVCDMSN
LGNKESDFLLWKRNDIADKLKNKDDMASVSAVLQFFGGKSSWDINIFKDAYKGKKKYNYE
VRFIDDLRKAIYCARNENFHFKTALVNDEKWNTELFGKIFERETEFCLNVEKDRFYSNNL
YMFYQVSELRNMLDHLYSRSVSRAAQVPSYNSVIVRTAFPEYITNVLGYQKPSYDADTLG
KWYSACYYLLKEIYYNSFLQSDRALQLFEKSVKTLSWDDKKQQRAVDNFKDHFSDIKSAC
TSLAQVCQIYMTEYNQQNNQIKKVRSSNDSIFDQPVYQHYKVLLKKAIANAFADYLKNNK
DLFGFIGKPFKANEIREIDKEQFLPDWTSRKYEALCIEVSGSQELQKWYIVGKFLNARSL
NLMVGSMRSYIQYVTDIKRRAASIGNELHVSVHDVEKVEKWVQVIEVCSLLASRTSNQFE
DYFNDKDDYARYLKSYVDFSNVDMPSEYSALVDFSNEEQSDLYVDPKNPKVNRNIVHSKL
FAADHILRDIVEPVSKDNIEEFYSQKAEIAYCKIKGKEITAEEQKAVLKYQKLKNRVELR
DIVEYGEIINELLGQLINWSFMRERDLLYFQLGFHYDCLRNDSKKPEGYKNIKVDENSIK
DAILYQIIGMYVNGVTVYAPEKDGDKLKEQCVKGGVGVKVSAFHRYSKYLGLNEKTLYNA
GLEIFEVVAEHEDIINLRNGIDHFKYYLGDYRSMLSIYSEVFDRFFTYDIKYQKNVLNLL
QNILLRHNVIVEPILESGFKTIGEQTKPGAKLSIRSIKSDTFQYKVKGGTLITDAKDERY
LETIRKILYYAENEEDNLKKSVVVTNADKYEKNKESDDQNKQKEKKNKDNKGKKNEETKS
DAEKNNNERLSYNPFANLNFKLSN

FIG. 56K

>CRZ35554.1 Herbinix hemicellulosilytica genome assembly TUM3/55, contig 02_T3/55T_contig26, whole genome shotgun sequence
MKLTRRRISGNSVDQKITAAFYRDMSQGLLYYDSEDNDCTDKVIESMDFERSWRGRILKN
GEDDKNPFYMFVKGLVGSNDKIVCEPIDVDSDPDNLDILINKNLTGFGRNLKAPDSNDTL
ENLIRKIQAGIPEEEVLPELKKIKEMIQKDIVNRKEQLLKSIKNNRIPFSLEGSKLVPST
KKMKWLFKLIDVPNKTFNEKMLEKYWEIYDYDKLKANITNRLDKTDKKARSISRAVSEEL
REYHKNLRTNYNRFVSGDRPAAGLDNGGSAKYNPDKEEFLLFLKEVEQYFKKYFPVKSKH
SNKSKDKSLVDKYKNYCSYKVVKKEVNRSIINQLVAGLIQQGKLLYYFYYNDTWQEDFLN
SYGLSYIQVEEAFKKSVMTSLSWGINRLTSFFIDDSNTVKFDDITTKKAKEAIESNYFNK
LRTCSRMQDHFKEKLAFFYPVYVKDKKDRPDDDIENLIVLVKNAIESVSYLRNRTFHFKE
SSLLELLKELDDKNSGQNKIDYSVAAEFIKRDIENLYDVFREQIRSLGIAEYYKADMISD
CFKTCGLEFALYSPKNSLMPAFKNVYKRGANLNKAYIRDKGPKETGDQGQNSYKALEEYR
ELTWYIEVKNNDQSYNAYKNLLQLIYYHAFLPEVRENEALITDFINRTKEWNRKETEERL
NTKNNKKHKNFDENDDITVNTYRYESIPDYQGESLDDYLKVLQRKQMARAKEVNEKEEGN
NNYIQFIRDVVVWAFGAYLENKLKNYKNELQPPLSKENIGLNDTLKELFPEEKVKSPFNI
KCRFSISTFIDNKGKSTDNTSAEAVKTDGKEDEKDKKNIKRKDLLCFYLFLRLLDENEIC
KLQHQFIKYRCSLKERRFPGNRTKLEKETELLAELEELMELVRFTMPSIPEISAKAESGY
DTMIKKYFKDFIEKKVFKNPKTSNLYYHSDSKTPVTRKYMALLMRSAPLHLYKDIFKGYY
LITKKECLEYIKLSNIIKDYQNSLNELHEQLERIKLKSEKQNGKDSLYLDKKDFYKVKEY
VENLEQVARYKHLQHKINFESLYRIFRIHVDIAARMVGYTQDWERDMHFLFKALVYNGVL
EERRFEAIFNNNDDNNDGRIVKKIQNNLNNKNRELVSMLCWNKKLNKNEFGAIIWKRNPI
AHLNHFTQTEQNSKSSLESLINSLRILLAYDRKRQNAVTKTINDLLLNDYHIRIKWEGRV
DEGQIYFNIKEKEDIENEPIIHLKHLHKKDCYIYKNSYMFDKQKEWICNGIKEEVYDKSI
LKCIGNLFKFDYEDKNKSSANPKHT

FIG. 57A

Reference sequence (1): 937566624_Eubacterium_rectale
Identities normalised by aligned length.
Colored by: identity + property

1 . . . . : . . . 80

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

81 . 1 . . . . : . 160

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

161 . . . 2 . . . 240

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

241 : . . . . 3 . 320

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%

FIG. 57C 8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

641 7 720

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

721 8 800

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

801 880

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

881 9 960

1 937566624_Eubacterium_rectale 100.0%

Figure 57E:
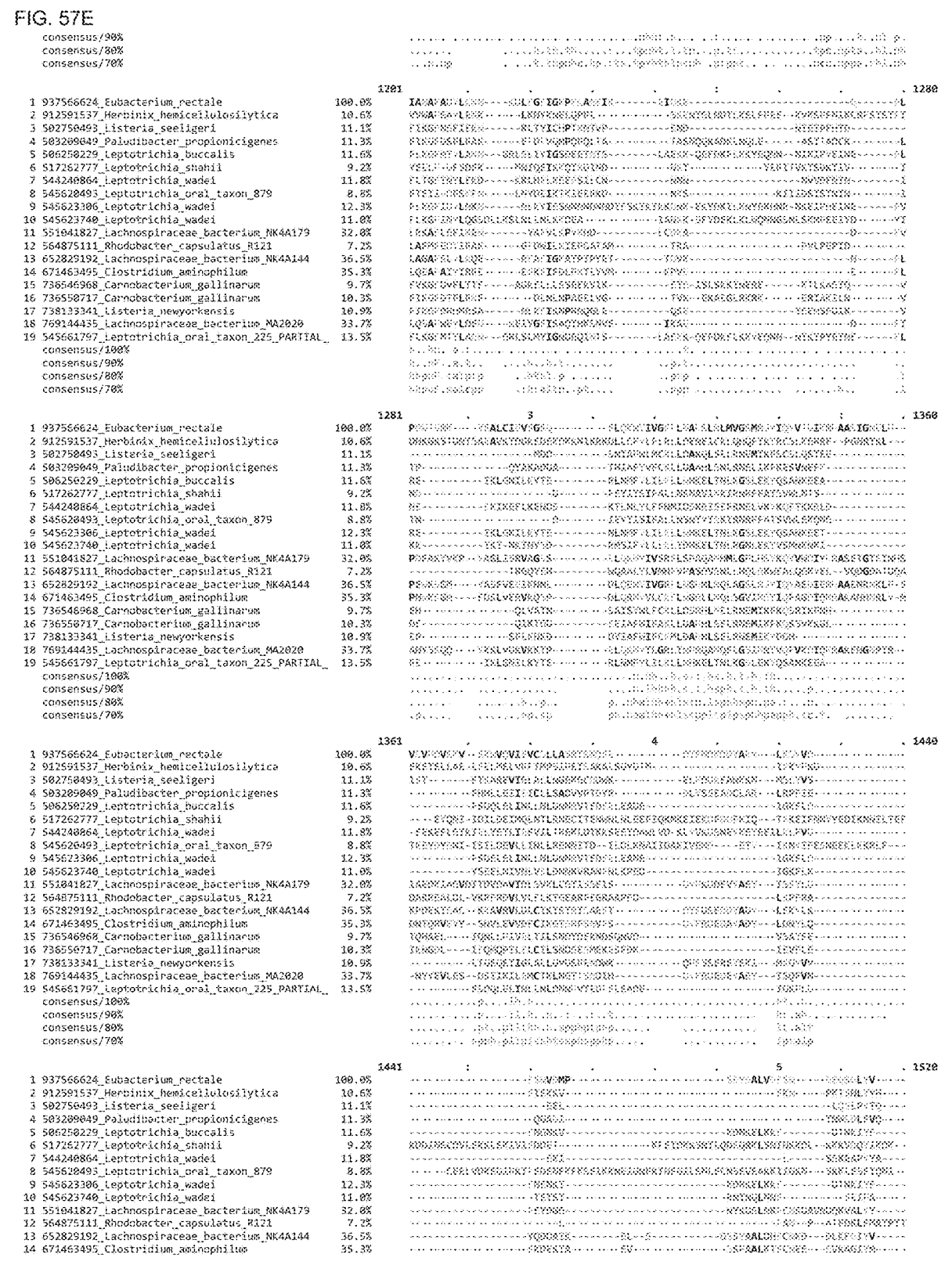

FIG. 57E consensus/90%
consensus/80%
consensus/70%

1201 ... 1280

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

1281 ... 1360

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

1361 ... 1440

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%
15 736546968_Carnobacterium_gallinarum 9.7%
16 736550717_Carnobacterium_gallinarum 10.3%
17 738133341_Listeria_newyorkensis 10.9%
18 769144435_Lachnospiraceae_bacterium_MA2020 33.7%
19 545661797_Leptotrichia_oral_taxon_225_PARTIAL_ 13.5%
consensus/100%
consensus/90%
consensus/80%
consensus/70%

1441 ... 1520

1 937566624_Eubacterium_rectale 100.0%
2 912591537_Herbinix_hemicellulosilytica 10.6%
3 502750493_Listeria_seeligeri 11.1%
4 503209049_Paludibacter_propionicigenes 11.3%
5 506250229_Leptotrichia_buccalis 11.6%
6 517262777_Leptotrichia_shahii 9.2%
7 544240864_Leptotrichia_wadei 11.8%
8 545620493_Leptotrichia_oral_taxon_879 8.8%
9 545623306_Leptotrichia_wadei 12.3%
10 545623740_Leptotrichia_wadei 11.0%
11 551041827_Lachnospiraceae_bacterium_NK4A179 32.0%
12 564875111_Rhodobacter_capsulatus_R121 7.2%
13 652829192_Lachnospiraceae_bacterium_NK4A144 36.5%
14 671463495_Clostridium_aminophilum 35.3%

FIG. 57H

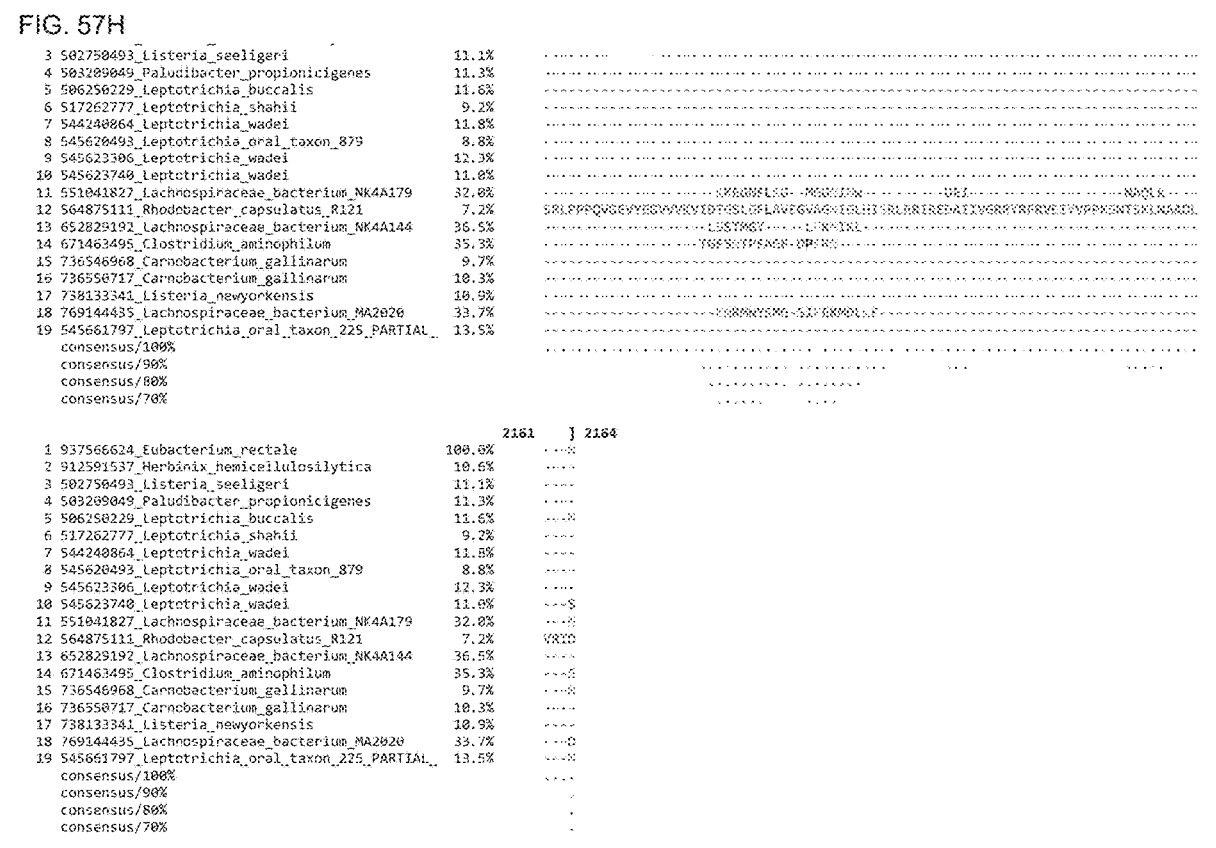

| | | | |
|---|---|---|---|
| 3 | 502750493_Listeria_seeligeri | 11.1% | - |
| 4 | 503209049_Paludibacter_propionicigenes | 11.3% | - |
| 5 | 506250229_Leptotrichia_buccalis | 11.6% | - |
| 6 | 517262777_Leptotrichia_shahii | 9.2% | - |
| 7 | 544240864_Leptotrichia_wadei | 11.8% | - |
| 8 | 545620493_Leptotrichia_oral_taxon_879 | 8.8% | - |
| 9 | 545623306_Leptotrichia_wadei | 12.3% | - |
| 10 | 545623740_Leptotrichia_wadei | 11.0% | - |
| 11 | 551041827_Lachnospiraceae_bacterium_NK4A179 | 32.0% | ---SKRGNFLSG--MGGIPN------UKI------NAQLK--- |
| 12 | 564875111_Rhodobacter_capsulatus_R121 | 7.2% | SRLPPPQVGEVYEGVVVKVIDTGSLGFLAVEGVAGxIGLHIxRLDRIREDAIIVGRRVRFRVEIVPPKGNTSKLNAAGL |
| 13 | 652829192_Lachnospiraceae_bacterium_NK4A144 | 36.5% | ---LSSTKGY----LFKxIKL--- |
| 14 | 671463495_Clostridium_aminophilum | 35.3% | ---YGFSKTPSAGN-DPxKx--- |
| 15 | 736546968_Carnobacterium_gallinarum | 9.7% | - |
| 16 | 736550717_Carnobacterium_gallinarum | 10.3% | - |
| 17 | 738133341_Listeria_newyorkensis | 10.9% | - |
| 18 | 769144435_Lachnospiraceae_bacterium_MA2020 | 33.7% | ---KGRNKYSMG-SIFKKNDLxF--- |
| 19 | 545661797_Leptotrichia_oral_taxon_225_PARTIAL_ | 13.5% | - |
| | consensus/100% | | |
| | consensus/90% | | |
| | consensus/80% | | |
| | consensus/70% | | |

| | | | 2161 ] 2164 |
|---|---|---|---|
| 1 | 937566624_Eubacterium_rectale | 100.0% | ---N |
| 2 | 912591537_Herbinix_hemicellulosilytica | 10.6% | ---- |
| 3 | 502750493_Listeria_seeligeri | 11.1% | ---- |
| 4 | 503209049_Paludibacter_propionicigenes | 11.3% | ---- |
| 5 | 506250229_Leptotrichia_buccalis | 11.6% | ---N |
| 6 | 517262777_Leptotrichia_shahii | 9.2% | ---- |
| 7 | 544240864_Leptotrichia_wadei | 11.8% | ---- |
| 8 | 545620493_Leptotrichia_oral_taxon_879 | 8.8% | ---- |
| 9 | 545623306_Leptotrichia_wadei | 12.3% | ---- |
| 10 | 545623740_Leptotrichia_wadei | 11.0% | ---S |
| 11 | 551041827_Lachnospiraceae_bacterium_NK4A179 | 32.0% | ---N |
| 12 | 564875111_Rhodobacter_capsulatus_R121 | 7.2% | VRID |
| 13 | 652829192_Lachnospiraceae_bacterium_NK4A144 | 36.5% | ---- |
| 14 | 671463495_Clostridium_aminophilum | 35.3% | ---E |
| 15 | 736546968_Carnobacterium_gallinarum | 9.7% | ---N |
| 16 | 736550717_Carnobacterium_gallinarum | 10.3% | ---- |
| 17 | 738133341_Listeria_newyorkensis | 10.9% | ---- |
| 18 | 769144435_Lachnospiraceae_bacterium_MA2020 | 33.7% | ---D |
| 19 | 545661797_Leptotrichia_oral_taxon_225_PARTIAL_ | 13.5% | ---N |
| | consensus/100% | | |
| | consensus/90% | | |
| | consensus/80% | | |
| | consensus/70% | | |

SEQUENCE LISTING

```
Sequence total quantity: 322
SEQ ID NO: 1             moltype = AA  length = 1120
FEATURE                  Location/Qualifiers
source                   1..1120
                         mol_type = protein
                         organism = Listeria seeligeri
SEQUENCE: 1
MWISIKTLIH HLGVLFFCDY MYNRREKKII EVKTMRITKV EVDRKKVLIS RDKNGGKLVY  60
ENEMQDNTEQ IMHHKKSSFY KSVVNKTICR PEQKQMKKLV HGLLQENSQE KIKVSDVTKL  120
NISNFLNHRF KKSLYYFPEN SPDKSEEYRI EINLSQLLED SLKKQQGTFI CWESFSKDME  180
LYINWAENYI SSKTKLIKKS IRNNRIQSTE SRSGQLMDRY MKDILNKNKP FDIQSVSEKY  240
QLEKLTSALK ATFKEAKKND KEINYKLKST LQNHERQIIE ELKENSELNQ FNIEIRKHLE  300
TYFPIKKTNR KVGDIRNLEI GEIQKIVNHR LKNKIVQRIL QEGKLASYEI ESTVNSNSLQ  360
KIKIEEAFAL KFINACLFAS NNLRNMVYPV CKKDILMIGE FKNSFKEIKH KKFIRQWSQF  420
FSQEITVDDI ELASWGLRGA IAPIRNEIIH LKKHSWKKFF NNPTFKVKKS KIINGKTKDV  480
TSEFLYKETL FKDYFYSELD SVPELIINKM ESSKILDYYS SDQLNQVFTI PNFELSLLTS  540
AVPFAPSFKR VYLKGFDYQN QDEAQPDYNL KLNIYNEKAF NSEAFQAQYS LFKMVYYQVF  600
LPQFTTNNDL FKSSVDFILT LNKERKGYAK AFQDIRKMNK DEKPSEYMSY IQSQLMLYQK  660
KQEEKEKINH FEKFINQVFI KGFNSFIEKN RLTYICHPTK NTVPENDNIE IPFHTDMDDS  720
NIAFWLMCKL LDAKQLSELR NEMIKFSCSL QSTEEISTFT KAREVIGLAL LNGEKGCNDW  780
KELFDDKEAW KKNMSLYVSE ELLQSLPYTQ EDGQTPVINR SIDLVKKYGT ETILEKLFSS  840
SDDYKVSAKD IAKLHEYDVT EKIAQQESLH KQWIEKPGLA RDSAWTKKYQ NVINDISNYQ  900
WAKTKVELTQ VRHLHQLTID LLSRLAGYMS IADRDFQFSS NYILERENSE YRVTSWILLS  960
ENKNKNKYND YELYNLKNAS IKVSSKNDPQ LKVDLKQLRL TLEYLELFDN RLKEKRNNIS  1020
HFNYLNGQLG NSILELFDDA RDVLSYDRKL KNAVSKSLKE ILSSHGMEVT FKPLYQTNHH  1080
LKIDKLQPKK IHHLGEKSTV SSNQVSNEYC QLVRTLLTMK                        1120

SEQ ID NO: 2             moltype = AA  length = 1159
FEATURE                  Location/Qualifiers
source                   1..1159
                         mol_type = protein
                         organism = Leptotrichia buccalis
SEQUENCE: 2
MKVTKVGGIS HKKYTSEGRL VKSESEENRT DERLSALLNM RLDMYIKNPS STETKENQKR  60
IGKLKKFFSN KMVYLKDNTL SLKNGKKENI DREYSETDIL ESDVRDKKNF AVLKKIYLNE  120
```

-continued

```
NVNSEELEVF RNDIKKKLNK INSLKYSFEK NKANYQKINE NNIEKVEGKS KRNIIYDYYR  180
ESAKRDAYVS NVKEAFDKLY KEEDIAKLVL EIENLTKLEK YKIREFYHEI IGRKNDKENF  240
AKIIYEEIQN VNNMKELIEK VPDMSELKKS QVFYKYYLDK EELNDKNIKY AFCHFVEIEM  300
SQLLKNYVYK RLSNISNDKI KRIFEYQNLK KLIENKLLNK LDTYVRNCGK YNYYLQDGEI  360
ATSDFIARNR QNEAFLRNII GVSSVAYFSL RNILETENEN DITGRMRGKT VKNNKGEEKY  420
VSGEVDKIYN ENKKNEVKEN LKMFYSYDFN MDNKNEIEDF FANIDEAISS IRHGIVHFNL  480
ELEGKDIFAF KNIAPSEISK KMFQNEINEK KLKLKIFRQL NSANVFRYLE KYKILNYLKR  540
TRFEFVNKNI PFVPSFTKLY SRIDDLKNSL GIYWKTPKTN DDNKTKEIID AQIYLLKNIY  600
YGEFLNYFMS NNGNFFEISK EIIELNKNDK RNLKTGFYKL QKFEDIQEKI PKEYLANIQS  660
LYMINAGNQD EEEKDTYIDF IQKIFLKGFM TYLANNGRLS LIYIGSDEET NTSLAEKKQE  720
FDKFLKKYEQ NNNIKIPYEI NEFLREIKLG NILKYTERLN MFYLILKLLN HKELTNLKGS  780
LEKYQSANKE EAFSDQLELI NLLNLDNNRV TEDFELEADE IGKFLDFNGN KVKDNKELKK  840
FDTNKIYFDG ENIIKHRAFY NIKKYGMLNL LEKIADKAGY KISIEELKKY SNKKNEIEKN  900
HKMQENLHRK YARPRKDEKF TDEDYESYKQ AIENIEEYTH LKNKVEFNEL NLLQGLLLRI  960
LHRLVGYTSI WERDLRFRLK GEFPENQYIE EIFNFENKKN VKYKGGQIVE KYIKFYKELH  1020
QNDEVKINKY SSANIKVLKQ EKKDLYIRNY IAHFNYIPHA EISLLEVLEN LRKLLSYDRK  1080
LKNAVMKSVV DILKEYGFVA TFKIGADKKI GIQTLESEKI VHLKNLKKKK LMTDRNSEEL  1140
CKLVKIMFEY KMEEKKSEN                                               1159

SEQ ID NO: 3           moltype = AA  length = 1389
FEATURE                Location/Qualifiers
source                 1..1389
                       mol_type = protein
                       organism = Leptotrichia shahii
SEQUENCE: 3
MGNLFGHKRW YEVRDKKDFK IKRKVKVKRN YDGNKYILNI NENNNKEKID NNKFIRKYIN  60
YKKNDNILKE FTRKFHAGNI LFKLKGKEGI IRIENNDDFL ETEEVVLYIE AYGKSEKLKA  120
LGITKKKIID EAIRQGITKD DKKIEIKRQE NEEEIEIDIR DEYTNKTLND CSIILRIIEN  180
DELETKKSIY EIFKNINMSL YKIIEKIIEN ETEKVFENRY YEEHLREKLL KDDKIDVILT  240
NFMEIREKIK SNLEILGFVK FYLNVGGDKK KSKNKKMLVE KILNINVDLT VEDIADFVIK  300
ELEFWNITKR IEKVKKVNNE FLEKRRNRTY IKSYVLLDKH EKFKIERENK KDKIVKFFVE  360
NIKNNSIKEK IEKILAEFKI DELIKKLEKE LKKGNCDTEI FGIFKKHYKV NFDSKKFSKK  420
SDEEKELYKI IYRYLKGRIE KILVNEQKVR LKKMEKIEIE KILNESILSE KILKRVKQYT  480
LEHIMYLGKL RHNDIDMTTV NTDDFSRLHA KEELDLELIT FFASTNMELN KIFSRENINN  540
DENIDFFGGD REKNYVLDKK ILNSKIKIIR DLDFIDNKNN ITNNFIRKFT KIGTNERNRI  600
LHAISKERDL QGTQDDYNKV INIIQNLKIS DEEVSKALNL DVVFKDKKNI ITKINDIKIS  660
EENNNDIKYL PSFSKVLPEI LNLYRNNPKN EPFDTIETEK IVLNALIYVN KELYKKLILE  720
DDLEENESKN IFLQELKKTL GNIDEIDENI IENYYKNAQI SASKGNNKAI KKYQKKVIEC  780
YIGYLRKNYE ELFDFSDFKM NIQEIKKQIK DINDNKTYER ITVKTSDKTI VINDDFEYII  840
SIFALLNSNA VINKIRNRFF ATSVWLNTSE YQNIIDILDE IMQLNTLRNE CITENWNLNL  900
EEFIQKMKEI EKDFDDFKIQ TKKEIFNNYY EDIKNNILTE FKDDINGCDV LEKKLEKIVI  960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNLFLNIGNP NFDKIYGLIS  1080
NDIKMADAKF LFNIDGKNIR KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VFEVFKKDVN LDYDELKKKF KLIGNNDILE RLMKPKKVSV LELESYNSDY IKNLIIELLT  1380
KIENTNDTL                                                          1389

SEQ ID NO: 4           moltype = AA  length = 1285
FEATURE                Location/Qualifiers
source                 1..1285
                       mol_type = protein
                       organism = Rhodobacter capsulatus
SEQUENCE: 4
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA AALYEHLHVD EKRIDGQPKR  180
NPKTDKFAPG LVVARALGIE SSVLPRGMAR LARNWGEEEI QTYFVVDVAA SVKEVAKAAV  240
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRSSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTDARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FRVEIYVPPK SNTSKLNAAD LVRID                                        1285
```

-continued

```
SEQ ID NO: 5            moltype = AA  length = 1175
FEATURE                 Location/Qualifiers
source                  1..1175
                        mol_type = protein
                        organism = Carnobacterium gallinarum
SEQUENCE: 5
MRITKVKIKL DNKLYQVTMQ KEEKYGTLKL NEESRKSTAE ILRLKKASFN KSFHSKTINS  60
QKENKNATIK KNGDYISQIF EKLVGVDTNK NIRKPKMSLT DLKDLPKKDL ALFIKRKFKN  120
DDIVEIKNLD LISLFYNALQ KVPGEHFTDE SWADFCQEMM PYREYKNKFI ERKIILLANS  180
IEQNKGFSIN PETFSKRKRV LHQWAIEVQE RGDFSILDEK LSKLAEIYNF KKMCKRVQDE  240
LNDLEKSMKK GKNPEKEKEA YKKQKNFKIK TIWKDYPYKT HIGLIEKIKE NEELNQFNIE  300
IGKYFEHYFP IKKERCTEDE PYYLNSETIA TTVNYQLKNA LISYLMQIGK YKQFGLENQV  360
LDSKKLQEIG IYEGFQTKFM DACVFATSSL KNIIEPMRSG DILGKREFKE AIATSSFVNY  420
HHFFPYFPFE LKGMKDRESE LIPFGEQTEA KQMQNIWALR GSVQQIRNEI FHSFDKNQKF  480
NLPQLDKSNF EFDASENSTG KSQSYIETDY KFLFEAEKNQ LEQFFIERIK SSGALEYYPL  540
KSLEKLFAKK EMKFSLGSQV VAFAPSYKKL VKKGHSYQTA TEGTANYLGL SYYNRYELKE  600
ESFQAQYYLL KLIYQYVFLP NFSQGNSPAF RETVKAILRI NKDEARKKMK KNKKFLRKYA  660
FEQVREMEFK ETPDQYMSYL QSEMREEKVR KAEKNDKGFE KNITMNFEKL LMQIFVKGFD  720
VFLTTFAGKE LLLSSEEKVI KETEISLSKK INEREKTLKA SIQVEHQLVA TNSAISYWLF  780
CKLLDSRHLN ELRNEMIKFK QSRIKFNHTQ HAELIQNLLP IVELTILSND YDEKNDSQNV  840
DVSAYFEDKS LYETAPYVQT DDRTRVSFRP ILKLEKYHTK SLIEALLKDN PQFRVAATDI  900
QEWMHKREEI GELVEKRKNL HTEWAEGQQT LGAEKREEYR DYCKKIDRFN WKANKVTLTY  960
LSQLHYLITD LLGRMVGFSA LFERDLVYFS RSFSELGGET YHISDYKNLS GVLRLNAEVK  1020
PIKIKNIKVI DNEENPYKGN EPEVKPFLDR LHAYLENVIG IKAVHGKIRN QTAHLSVLQL  1080
ELSMIESMNN LRDLMAYDRK LKNAVTKSMI KILDKHGMIL KLKIDENHKN FEIESLIPKE  1140
IIHLKDKAIK TNQVSEEYCQ LVLALLTTNP GNQLN                           1175

SEQ ID NO: 6            moltype = AA  length = 1285
FEATURE                 Location/Qualifiers
source                  1..1285
                        mol_type = protein
                        organism = Herbinix hemicellulosilytica
SEQUENCE: 6
MKLTRRRISG NSVDQKITAA FYRDMSQGLL YYDSEDNDCT DKVIESMDFE RSWRGRILKN  60
GEDDKNPFYM FVKGLVGSND KIVCEPIDVD SDPDNLDILI NKNLTGFGRN LKAPDSNDTL  120
ENLIRKIQAG IPEEEVLPEL KKIKEMIQKD IVNRKEQLLK SIKNNRIPFS LEGSKLVPST  180
KKMKWLFKLI DVPNKTFNEK MLEKYWEIYD YDKLKANITN RLDKTDKKAR SISRAVSEEL  240
REYHKNLRTN YNRFVSGDRP AAGLDNGGSA KYNPDKEEFL LFLKEVEQYF KKYFPVKSKH  300
SNKSKDKSLV DKYKNYCSYK VVKKEVNRSI INQLVAGLIQ QGKLLYYFYY NDTWQEDFLN  360
SYGLSYIQVE EAFKKSVMTS LSWGINRLTS FFIDDSNTVK FDDITTKKAK EAIESNYFNK  420
LRTCSRMQDH FKEKLAFFYP VYVKDKKDRP DDDIENLIVL VKNAIESVSY LRNRTFHFKE  480
SSLLELLKEL DDKNSGQNKI DYSVAAEFIK RDIENLYDVF REQIRSLGIA EYYKADMISD  540
CFKTCGLEFA LYSPKNSLMP AFKNVYKRGA NLNKAYIRDK GPKETGDQGQ NSYKALEEYR  600
ELTWYIEVKN NDQSYNAYKN LLQLIYYHAF LPEVRENEAL ITDFINRTKE WNRKETEERL  660
NTKNNKKHKN FDENDDITVN TYRYESIPDY QGESLDDYLK VLQRKQMARA KEVNEKEEGN  720
NNYIQFIRDV VVWAFGAYLE NKLKNYKNEL QPPLSKENIG LNDTLKELFP EEKVKSPFNI  780
KCRFSISTFI DNKGKSTDNT SAEAVKTDGK EDEKDKKNIK RKDLLCFYLF LRLLDENEIC  840
KLQHQFIKYR CSLKERRFPG NRTKLEKETE LLAELEELME LVRFTMPSIP EISAKAESGY  900
DTMIKKYFKD FIEKKVFKNP KTSNLYYHSD SKTPVTRKYM ALLMRSAPLH LYKDIFKGYY  960
LITKKECLEY IKLSNIIKDY QNSLNELHEQ LERIKLKSEK QNGKDSLYLD KKDFYKVKEY  1020
VENLEQVARY KHLQHKINFE SLYRIFRIHV DIAARMVGYT QDWERDMHFL FKALVYNGVL  1080
EERRFEAIFN NNDDNNDGRI VKKIQNNLNN KNRELVSMLC WNKKLNKNEF GAIIWKRNPI  1140
AHLNHFTQTE QNSKSSLESL INSLRILLAY DRKRQNAVTK TINDLLLNDY HIRIKWEGRV  1200
DEGQIYFNIK EKEDIENEPI IHLKHLHKKD CYIYKNSYMF DKQKEWICNG IKEEVYDKSI  1260
LKCIGNLFKF DYEDKNKSSA NPKHT                                      1285

SEQ ID NO: 7            moltype = RNA  length = 30
FEATURE                 Location/Qualifiers
source                  1..30
                        mol_type = other RNA
                        organism = Listeria seeligeri
SEQUENCE: 7
gactacctct atatgaaaga ggactaaaac                                 30

SEQ ID NO: 8            moltype = RNA  length = 29
FEATURE                 Location/Qualifiers
source                  1..29
                        mol_type = other RNA
                        organism = Leptotrichia shahii
SEQUENCE: 8
ccaccccaat atcgaagggg actaaaaca                                  29

SEQ ID NO: 9            moltype = RNA  length = 31
FEATURE                 Location/Qualifiers
source                  1..31
                        mol_type = other RNA
                        organism = Leptotrichia buccalis
SEQUENCE: 9
gaccacccca aaaatgaagg ggactaaaac a                               31
```

```
SEQ ID NO: 10          moltype = RNA  length = 50
FEATURE                Location/Qualifiers
source                 1..50
                       mol_type = other RNA
                       organism = Listeria seeligeri
SEQUENCE: 10
gactacctct atatgaaaga ggactaaaac caaacatgat ctgggtcatc             50

SEQ ID NO: 11          moltype = RNA  length = 55
FEATURE                Location/Qualifiers
source                 1..55
                       mol_type = other RNA
                       organism = Listeria seeligeri
SEQUENCE: 11
taagagacta cctctatatg aaagaggact aaaaccaaac atgatctggg tcatc       55

SEQ ID NO: 12          moltype = RNA  length = 49
FEATURE                Location/Qualifiers
source                 1..49
                       mol_type = other RNA
                       organism = Leptotrichia shahii
SEQUENCE: 12
ccaccccaat atcgaagggg actaaaacag gggcagagat gatgaccct              49

SEQ ID NO: 13          moltype = RNA  length = 58
FEATURE                Location/Qualifiers
source                 1..58
                       mol_type = other RNA
                       organism = Leptotrichia shahii
SEQUENCE: 13
ggatttagac caccccaata tcgaagggga ctaaaacagg ggcagagatg atgaccct    58

SEQ ID NO: 14          moltype = RNA  length = 51
FEATURE                Location/Qualifiers
source                 1..51
                       mol_type = other RNA
                       organism = Leptotrichia buccalis
SEQUENCE: 14
gaccacccca aaaatgaagg ggactaaaac aggggcagag atgatgaccc t           51

SEQ ID NO: 15          moltype = RNA  length = 56
FEATURE                Location/Qualifiers
source                 1..56
                       mol_type = other RNA
                       organism = Leptotrichia buccalis
SEQUENCE: 15
atttagacca ccccaaaaat gaaggggact aaaacagggg cagagatgat gaccct      56

SEQ ID NO: 16          moltype = RNA  length = 27
FEATURE                Location/Qualifiers
source                 1..27
                       mol_type = other RNA
                       organism = synthetic construct
SEQUENCE: 16
agatagccca agaaagaggg caataac                                      27

SEQ ID NO: 17          moltype = RNA  length = 32
FEATURE                Location/Qualifiers
source                 1..32
                       mol_type = other RNA
                       organism = synthetic construct
SEQUENCE: 17
gtaacaatcc ccgtagacag gggaactgca ac                                32

SEQ ID NO: 18          moltype = RNA  length = 31
FEATURE                Location/Qualifiers
source                 1..31
                       mol_type = other RNA
                       organism = synthetic construct
SEQUENCE: 18
catcaccgcc aagacgacgg cggactgaac c                                 31

SEQ ID NO: 19          moltype = RNA  length = 30
FEATURE                Location/Qualifiers
source                 1..30
                       mol_type = other RNA
                       organism = synthetic construct
SEQUENCE: 19
```

```
aattatccca aaattgaagg gaactacaac                                  30

SEQ ID NO: 20           moltype = RNA  length = 30
FEATURE                 Location/Qualifiers
source                  1..30
                        mol_type = other RNA
                        organism = synthetic construct
SEQUENCE: 20
gagtacctca aaacaaaaga ggactaaaac                                  30

SEQ ID NO: 21           moltype = RNA  length = 32
FEATURE                 Location/Qualifiers
source                  1..32
                        mol_type = other RNA
                        organism = synthetic construct
SEQUENCE: 21
gaccacccca atatcgaagg ggactaaaac tt                               32

SEQ ID NO: 22           moltype = RNA  length = 27
FEATURE                 Location/Qualifiers
source                  1..27
                        mol_type = other RNA
                        organism = synthetic construct
SEQUENCE: 22
caccccaata tcgaagggga ctaaaac                                     27

SEQ ID NO: 23           moltype = RNA  length = 27
FEATURE                 Location/Qualifiers
source                  1..27
                        mol_type = other RNA
                        organism = synthetic construct
SEQUENCE: 23
aagtagcccg atatagaggg caataac                                     27

SEQ ID NO: 24           moltype = RNA  length = 27
FEATURE                 Location/Qualifiers
source                  1..27
                        mol_type = other RNA
                        organism = synthetic construct
SEQUENCE: 24
atacagctcg atatagtgag caataag                                     27

SEQ ID NO: 25           moltype = RNA  length = 34
FEATURE                 Location/Qualifiers
source                  1..34
                        mol_type = other RNA
                        organism = synthetic construct
SEQUENCE: 25
tcacatcacc gccaagacga cggcggactg aacc                             34

SEQ ID NO: 26           moltype = RNA  length = 28
FEATURE                 Location/Qualifiers
source                  1..28
                        mol_type = other RNA
                        organism = synthetic construct
SEQUENCE: 26
gaacagcccg atatagaggg caatagac                                    28

SEQ ID NO: 27           moltype = RNA  length = 60
FEATURE                 Location/Qualifiers
source                  1..60
                        mol_type = other RNA
                        organism = synthetic construct
SEQUENCE: 27
ggctcatttg caggggggag ccaaaagggt catcatctct gccccctctg ctgatgcccc  60

SEQ ID NO: 28           moltype = RNA  length = 51
FEATURE                 Location/Qualifiers
source                  1..51
                        mol_type = other RNA
                        organism = synthetic construct
SEQUENCE: 28
gaccacccca aaaatgaagg ggactaaaac aggggcagag atgatgaccc t          51

SEQ ID NO: 29           moltype = RNA  length = 50
FEATURE                 Location/Qualifiers
source                  1..50
                        mol_type = other RNA
                        organism = synthetic construct
```

```
SEQUENCE: 29
gactacctct atatgaaaga ggactaaaac caaacatgat ctgggtcatc            50

SEQ ID NO: 30          moltype = RNA  length = 55
FEATURE                Location/Qualifiers
source                 1..55
                       mol_type = other RNA
                       organism = synthetic construct
SEQUENCE: 30
taagagacta cctctatatg aaagaggact aaaaccaaac atgatctggg tcatc      55

SEQ ID NO: 31          moltype = RNA  length = 49
FEATURE                Location/Qualifiers
source                 1..49
                       mol_type = other RNA
                       organism = synthetic construct
SEQUENCE: 31
ccaccccaat atcgaagggg actaaaacag gggcagagat gatgaccct             49

SEQ ID NO: 32          moltype = RNA  length = 58
FEATURE                Location/Qualifiers
source                 1..58
                       mol_type = other RNA
                       organism = synthetic construct
SEQUENCE: 32
ggatttagac caccccaata tcgaagggga ctaaaacagg ggcagagatg atgaccct   58

SEQ ID NO: 33          moltype = RNA  length = 51
FEATURE                Location/Qualifiers
source                 1..51
                       mol_type = other RNA
                       organism = synthetic construct
SEQUENCE: 33
gaccacccca aaaatgaagg ggactaaaac aggggcagag atgatgaccc t          51

SEQ ID NO: 34          moltype = RNA  length = 56
FEATURE                Location/Qualifiers
source                 1..56
                       mol_type = other RNA
                       organism = synthetic construct
SEQUENCE: 34
atttagacca ccccaaaaat gaaggggact aaaacagggg cagagatgat gaccct     56

SEQ ID NO: 35          moltype = RNA  length = 30
FEATURE                Location/Qualifiers
source                 1..30
                       mol_type = other RNA
                       organism = synthetic construct
SEQUENCE: 35
ggatttagac caccccaaaa atgaagggga                                  30

SEQ ID NO: 36          moltype = RNA  length = 30
FEATURE                Location/Qualifiers
source                 1..30
                       mol_type = other RNA
                       organism = synthetic construct
SEQUENCE: 36
ggtaagagac tacctctata tgaaagagga                                  30

SEQ ID NO: 37          moltype = RNA  length = 30
FEATURE                Location/Qualifiers
source                 1..30
                       mol_type = other RNA
                       organism = synthetic construct
SEQUENCE: 37
ggatatagac caccccaata tcgaagggga                                  30

SEQ ID NO: 38          moltype = RNA  length = 37
FEATURE                Location/Qualifiers
source                 1..37
                       mol_type = other RNA
                       organism = synthetic construct
SEQUENCE: 38
ggatttagac caccccaaaa atgaagggga ctaaaac                          37

SEQ ID NO: 39          moltype = RNA  length = 14
FEATURE                Location/Qualifiers
source                 1..14
                       mol_type = other RNA
```

```
                      organism = synthetic construct
SEQUENCE: 39
aaacgaccac aagg                                                  14

SEQ ID NO: 40         moltype = RNA  length = 19
FEATURE               Location/Qualifiers
source                1..19
                      mol_type = other RNA
                      organism = synthetic construct
SEQUENCE: 40
ccaagaaacg accacaagg                                             19

SEQ ID NO: 41         moltype = RNA  length = 19
FEATURE               Location/Qualifiers
source                1..19
                      mol_type = other RNA
                      organism = synthetic construct
SEQUENCE: 41
aaagcaaaaa aggccccgc                                             19

SEQ ID NO: 42         moltype = RNA  length = 23
FEATURE               Location/Qualifiers
source                1..23
                      mol_type = other RNA
                      organism = synthetic construct
SEQUENCE: 42
cacgccgcac aaaacccacg ccg                                        23

SEQ ID NO: 43         moltype = RNA  length = 25
FEATURE               Location/Qualifiers
source                1..25
                      mol_type = other RNA
                      organism = synthetic construct
SEQUENCE: 43
ccggagcgag gaagaaacgc ccgcg                                      25

SEQ ID NO: 44         moltype = RNA  length = 25
FEATURE               Location/Qualifiers
source                1..25
                      mol_type = other RNA
                      organism = synthetic construct
SEQUENCE: 44
agcgcccaac ggaaagaagg aagga                                      25

SEQ ID NO: 45         moltype = RNA  length = 58
FEATURE               Location/Qualifiers
source                1..58
                      mol_type = other RNA
                      organism = synthetic construct
SEQUENCE: 45
ggatttagac caccccaaaa atgaagggga ctaaaacagg ggcagagatg atgaccct    58

SEQ ID NO: 46         moltype = RNA  length = 57
FEATURE               Location/Qualifiers
source                1..57
                      mol_type = other RNA
                      organism = synthetic construct
SEQUENCE: 46
ggtaagagac tacctctata tgaaagagga ctaaaaccaa acatgatctg ggtcatc     57

SEQ ID NO: 47         moltype = RNA  length = 58
FEATURE               Location/Qualifiers
source                1..58
                      mol_type = other RNA
                      organism = synthetic construct
SEQUENCE: 47
ggatttagac caccccaata tcgaagggga ctaaaacagg ggcagagatg atgaccct    58

SEQ ID NO: 48         moltype = RNA  length = 58
FEATURE               Location/Qualifiers
source                1..58
                      mol_type = other RNA
                      organism = synthetic construct
SEQUENCE: 48
ggatttagac caggggaagt aaaaacccca ctaaaacagg ggcagagatg atgaccct    58

SEQ ID NO: 49         moltype = RNA  length = 60
FEATURE               Location/Qualifiers
source                1..60
```

-continued

```
                        mol_type = other RNA
                        organism = synthetic construct
SEQUENCE: 49
ggatttagac cacccccaaa aatgaagggg gactaaaaca ggggcagaga tgatgaccct  60

SEQ ID NO: 50           moltype = RNA  length = 54
FEATURE                 Location/Qualifiers
source                  1..54
                        mol_type = other RNA
                        organism = synthetic construct
SEQUENCE: 50
ggatttagac caccccatga aggggactaa aacaggggca gagatgatga ccct        54

SEQ ID NO: 51           moltype = RNA  length = 54
FEATURE                 Location/Qualifiers
source                  1..54
                        mol_type = other RNA
                        organism = synthetic construct
SEQUENCE: 51
ggatttagac caccccatga aggggactaa aacaggggca gagatgatga ccct        54

SEQ ID NO: 52           moltype = RNA  length = 58
FEATURE                 Location/Qualifiers
source                  1..58
                        mol_type = other RNA
                        organism = synthetic construct
SEQUENCE: 52
ggatttagac caccccaaaa atgaagggca ctaaaacagg ggcagagatg atgaccct    58

SEQ ID NO: 53           moltype = RNA  length = 58
FEATURE                 Location/Qualifiers
source                  1..58
                        mol_type = other RNA
                        organism = synthetic construct
SEQUENCE: 53
ggcgttagac caccccaaaa atgaagggga ctaaaacagg ggcagagatg atgaccct    58

SEQ ID NO: 54           moltype = RNA  length = 58
FEATURE                 Location/Qualifiers
source                  1..58
                        mol_type = other RNA
                        organism = synthetic construct
SEQUENCE: 54
ggagctagac caccccaaaa atgaagggga ctaaaacagg ggcagagatg atgaccct    58

SEQ ID NO: 55           moltype = RNA  length = 58
FEATURE                 Location/Qualifiers
source                  1..58
                        mol_type = other RNA
                        organism = synthetic construct
SEQUENCE: 55
ggatccagac caccccaaaa atgaagggga ctaaaacagg ggcagagatg atgaccct    58

SEQ ID NO: 56           moltype = RNA  length = 58
FEATURE                 Location/Qualifiers
source                  1..58
                        mol_type = other RNA
                        organism = synthetic construct
SEQUENCE: 56
ggattcggac caccccaaaa atgaagggga ctaaaacagg ggcagagatg atgaccct    58

SEQ ID NO: 57           moltype = RNA  length = 58
FEATURE                 Location/Qualifiers
source                  1..58
                        mol_type = other RNA
                        organism = synthetic construct
SEQUENCE: 57
ggatttaccc caccccaaaa atgaagggga ctaaaacagg ggcagagatg atgaccct    58

SEQ ID NO: 58           moltype = RNA  length = 58
FEATURE                 Location/Qualifiers
source                  1..58
                        mol_type = other RNA
                        organism = synthetic construct
SEQUENCE: 58
ggatttaatc caccccaaaa atgaagggga ctaaaacagg ggcagagatg atgaccct    58

SEQ ID NO: 59           moltype = RNA  length = 58
FEATURE                 Location/Qualifiers
```

```
source                  1..58
                        mol_type = other RNA
                        organism = synthetic construct
SEQUENCE: 59
ggatttagaa aaccccaaaa atgaagggga ctaaaacagg ggcagagatg atgaccct    58

SEQ ID NO: 60           moltype = RNA  length = 58
FEATURE                 Location/Qualifiers
source                  1..58
                        mol_type = other RNA
                        organism = synthetic construct
SEQUENCE: 60
ggatttagac cgccccaaaa atgaagggga ctaaaacagg ggcagagatg atgaccct    58

SEQ ID NO: 61           moltype = RNA  length = 58
FEATURE                 Location/Qualifiers
source                  1..58
                        mol_type = other RNA
                        organism = synthetic construct
SEQUENCE: 61
ggatttagac cagcccaaaa atgaagggca ctaaaacagg ggcagagatg atgaccct    58

SEQ ID NO: 62           moltype = RNA  length = 58
FEATURE                 Location/Qualifiers
source                  1..58
                        mol_type = other RNA
                        organism = synthetic construct
SEQUENCE: 62
ggatttagac caccgcaaaa atgaagcgga ctaaaacagg ggcagagatg atgaccct    58

SEQ ID NO: 63           moltype = RNA  length = 58
FEATURE                 Location/Qualifiers
source                  1..58
                        mol_type = other RNA
                        organism = synthetic construct
SEQUENCE: 63
ggatttagac cacaccaaaa atgaaggtga ctaaaacagg ggcagagatg atgaccct    58

SEQ ID NO: 64           moltype = RNA  length = 58
FEATURE                 Location/Qualifiers
source                  1..58
                        mol_type = other RNA
                        organism = synthetic construct
SEQUENCE: 64
ggatttagac caccacaaaa atgaagtgga ctaaaacagg ggcagagatg atgaccct    58

SEQ ID NO: 65           moltype = RNA  length = 58
FEATURE                 Location/Qualifiers
source                  1..58
                        mol_type = other RNA
                        organism = synthetic construct
SEQUENCE: 65
ggatttagac cactccaaaa atgaaggaga ctaaaacagg ggcagagatg atgaccct    58

SEQ ID NO: 66           moltype = RNA  length = 58
FEATURE                 Location/Qualifiers
source                  1..58
                        mol_type = other RNA
                        organism = synthetic construct
SEQUENCE: 66
ggatttagac caccccaaaa atgaaggggc ataaaacagg ggcagagatg atgaccct    58

SEQ ID NO: 67           moltype = RNA  length = 58
FEATURE                 Location/Qualifiers
source                  1..58
                        mol_type = other RNA
                        organism = synthetic construct
SEQUENCE: 67
ggatttagac caccccaaaa atgaagggga cgcaaacagg ggcagagatg atgaccct    58

SEQ ID NO: 68           moltype = RNA  length = 58
FEATURE                 Location/Qualifiers
source                  1..58
                        mol_type = other RNA
                        organism = synthetic construct
SEQUENCE: 68
ggatttagac caccccaaaa atgaagggga ctagcacagg ggcagagatg atgaccct    58

SEQ ID NO: 69           moltype = RNA  length = 58
```

```
FEATURE                Location/Qualifiers
source                 1..58
                       mol_type = other RNA
                       organism = synthetic construct
SEQUENCE: 69
ggatttagac caccccaaaa atgaagggga ctaaagtagg ggcagagatg atgaccct    58

SEQ ID NO: 70          moltype = RNA  length = 51
FEATURE                Location/Qualifiers
source                 1..51
                       mol_type = other RNA
                       organism = synthetic construct
SEQUENCE: 70
ggccacccca aaaatgaagg ggactaaaac aggggcagag atgatgaccc t           51

SEQ ID NO: 71          moltype = RNA  length = 51
FEATURE                Location/Qualifiers
source                 1..51
                       mol_type = other RNA
                       organism = synthetic construct
SEQUENCE: 71
ggccacccca aaaatgaagg ggactaaaac acaaacatga tctgggtcat c           51

SEQ ID NO: 72          moltype = RNA  length = 60
FEATURE                Location/Qualifiers
source                 1..60
                       mol_type = other RNA
                       organism = synthetic construct
SEQUENCE: 72
ggcacacccg cagggggggag ccaaaagggt catcatctct gcccccacag cagaagcccc  60

SEQ ID NO: 73          moltype = RNA  length = 62
FEATURE                Location/Qualifiers
source                 1..62
                       mol_type = other RNA
                       organism = synthetic construct
SEQUENCE: 73
gggaacccca aggccaaccg cgagaagatg acccagatca tgtttgagac cttcaacacc  60
cc                                                                 62

SEQ ID NO: 74          moltype = RNA  length = 51
FEATURE                Location/Qualifiers
source                 1..51
                       mol_type = other RNA
                       organism = synthetic construct
SEQUENCE: 74
ggccacccca aaaatgaagg ggactaaaac agtgataagt ggaatgccat g           51

SEQ ID NO: 75          moltype = RNA  length = 51
FEATURE                Location/Qualifiers
source                 1..51
                       mol_type = other RNA
                       organism = synthetic construct
SEQUENCE: 75
ggccacccca aaaatgaagg ggactaaaac actggtgaac ttccgatagt g           51

SEQ ID NO: 76          moltype = RNA  length = 51
FEATURE                Location/Qualifiers
source                 1..51
                       mol_type = other RNA
                       organism = synthetic construct
SEQUENCE: 76
ggccacccca aaaatgaagg ggactaaaac acagatatag cctggtggtt c           51

SEQ ID NO: 77          moltype = RNA  length = 56
FEATURE                Location/Qualifiers
source                 1..56
                       mol_type = other RNA
                       organism = synthetic construct
SEQUENCE: 77
ggctcaattt tgacagcggt catggcattc cacttatcac tggcatcctt ccactc      56

SEQ ID NO: 78          moltype = RNA  length = 55
FEATURE                Location/Qualifiers
source                 1..55
                       mol_type = other RNA
                       organism = synthetic construct
SEQUENCE: 78
ggaaatcatt caacacccgc actatcggaa gttcaccagc cagccgcagc acgtt       55
```

```
SEQ ID NO: 79           moltype = RNA  length = 57
FEATURE                 Location/Qualifiers
source                  1..57
                        mol_type = other RNA
                        organism = synthetic construct
SEQUENCE: 79
ggcaataaaa atgcgccgcc tgaaccacca ggctatatct gccactcatt gttgtga     57

SEQ ID NO: 80           moltype = RNA  length = 114
FEATURE                 Location/Qualifiers
source                  1..114
                        mol_type = other RNA
                        organism = synthetic construct
SEQUENCE: 80
ggatttagac caccccaaaa atgaagggga ctaaaacagg ggcagagatg atgaccctat  60
ttagaccacc ccaaaaatga aggggactaa aacagtgata agtggaatgc catg        114

SEQ ID NO: 81           moltype = RNA  length = 58
FEATURE                 Location/Qualifiers
source                  1..58
                        mol_type = other RNA
                        organism = synthetic construct
SEQUENCE: 81
ggatttagac caccccaaaa atgaagggga ctaaaacagt gataagtgga atgccatg    58

SEQ ID NO: 82           moltype = RNA  length = 58
FEATURE                 Location/Qualifiers
source                  1..58
                        mol_type = other RNA
                        organism = synthetic construct
SEQUENCE: 82
ggatttaata aaccccaaaa atgaagggga ctaaaacagg ggcagagatg atgaccct    58

SEQ ID NO: 83           moltype = RNA  length = 58
FEATURE                 Location/Qualifiers
source                  1..58
                        mol_type = other RNA
                        organism = synthetic construct
SEQUENCE: 83
ggattcgatc caccccaaaa atgaagggga ctaaaacagg ggcagagatg atgaccct    58

SEQ ID NO: 84           moltype = RNA  length = 58
FEATURE                 Location/Qualifiers
source                  1..58
                        mol_type = other RNA
                        organism = synthetic construct
SEQUENCE: 84
ggatttagga agccccaaaa atgaagggga ctaaaacagg ggcagagatg atgaccct    58

SEQ ID NO: 85           moltype = RNA  length = 58
FEATURE                 Location/Qualifiers
source                  1..58
                        mol_type = other RNA
                        organism = synthetic construct
SEQUENCE: 85
ggatttagac caggccaaaa atgaaggcca ctaaaacagg ggcagagatg atgaccct    58

SEQ ID NO: 86           moltype = RNA  length = 55
FEATURE                 Location/Qualifiers
source                  1..55
                        mol_type = other RNA
                        organism = synthetic construct
SEQUENCE: 86
ggccacccca aaaatgaagg ggactaaaac attttggctc cccctgcaa atgag        55

SEQ ID NO: 87           moltype = RNA  length = 55
FEATURE                 Location/Qualifiers
source                  1..55
                        mol_type = other RNA
                        organism = synthetic construct
SEQUENCE: 87
ggccacccca aaaatgaagg ggactaaaac aacccttttg gctccccct gcaaa        55

SEQ ID NO: 88           moltype = RNA  length = 55
FEATURE                 Location/Qualifiers
source                  1..55
                        mol_type = other RNA
                        organism = synthetic construct
```

```
SEQUENCE: 88
ggccacccca aaaatgaagg ggactaaaac agatgaccct tttggctccc ccctg      55

SEQ ID NO: 89          moltype = RNA  length = 55
FEATURE                Location/Qualifiers
source                 1..55
                       mol_type = other RNA
                       organism = synthetic construct
SEQUENCE: 89
ggccacccca aaaatgaagg ggactaaaac aagatgatga cccttttggc tcccc      55

SEQ ID NO: 90          moltype = RNA  length = 55
FEATURE                Location/Qualifiers
source                 1..55
                       mol_type = other RNA
                       organism = synthetic construct
SEQUENCE: 90
ggccacccca aaaatgaagg ggactaaaac agcagagatg atgacccttt tggct      55

SEQ ID NO: 91          moltype = RNA  length = 55
FEATURE                Location/Qualifiers
source                 1..55
                       mol_type = other RNA
                       organism = synthetic construct
SEQUENCE: 91
ggccacccca aaaatgaagg ggactaaaac aggggggcaga gatgatgacc ctttt      55

SEQ ID NO: 92          moltype = RNA  length = 55
FEATURE                Location/Qualifiers
source                 1..55
                       mol_type = other RNA
                       organism = synthetic construct
SEQUENCE: 92
ggccacccca aaaatgaagg ggactaaaac acagaggggg cagagatgat gaccc      55

SEQ ID NO: 93          moltype = RNA  length = 55
FEATURE                Location/Qualifiers
source                 1..55
                       mol_type = other RNA
                       organism = synthetic construct
SEQUENCE: 93
ggccacccca aaaatgaagg ggactaaaac atcagcagag ggggcagaga tgatg      55

SEQ ID NO: 94          moltype = RNA  length = 60
FEATURE                Location/Qualifiers
source                 1..60
                       mol_type = other RNA
                       organism = synthetic construct
SEQUENCE: 94
ggctcatttg caggggggag ccaaaagggt catcatctct gccccctctg ctgatgcccc  60

SEQ ID NO: 95          moltype = RNA  length = 70
FEATURE                Location/Qualifiers
source                 1..70
                       mol_type = other RNA
                       organism = synthetic construct
SEQUENCE: 95
ggcctgactg ctctcatttg cagttgggag ccaaaagggt catcatctct gccccctctg  60
ctgatgcccc                                                         70

SEQ ID NO: 96          moltype = RNA  length = 80
FEATURE                Location/Qualifiers
source                 1..80
                       mol_type = other RNA
                       organism = synthetic construct
SEQUENCE: 96
ggacctgtga atcctgactg ctctcatttg cagttgggag ccaaaagggt catcatctct  60
gccccctctg ctgatgcccc                                              80

SEQ ID NO: 97          moltype = RNA  length = 60
FEATURE                Location/Qualifiers
source                 1..60
                       mol_type = other RNA
                       organism = synthetic construct
SEQUENCE: 97
ggcacacccg cagggtttag ccaaaagggt catcatctct gccccctctg ctgatgcccc  60

SEQ ID NO: 98          moltype = RNA  length = 47
FEATURE                Location/Qualifiers
```

```
source                  1..47
                        mol_type = other RNA
                        organism = synthetic construct
SEQUENCE: 98
ggccacccca aaaatgaagg ggactaaaac acagagatga tgaccct                47

SEQ ID NO: 99           moltype = RNA  length = 55
FEATURE                 Location/Qualifiers
source                  1..55
                        mol_type = other RNA
                        organism = synthetic construct
SEQUENCE: 99
ggccacccca aaaatgaagg ggactaaaac aagaggggc agagatgatg accct        55

SEQ ID NO: 100          moltype = RNA  length = 51
FEATURE                 Location/Qualifiers
source                  1..51
                        mol_type = other RNA
                        organism = synthetic construct
SEQUENCE: 100
gaccacccca aaaatgaagg ggactaaaac aggggcagag atgatgaccc t           51

SEQ ID NO: 101          moltype = RNA  length = 53
FEATURE                 Location/Qualifiers
source                  1..53
                        mol_type = other RNA
                        organism = synthetic construct
SEQUENCE: 101
gggaccaccc caaaaatgaa ggggactaaa acaggggcag agatgatgac cct         53

SEQ ID NO: 102          moltype = RNA  length = 49
FEATURE                 Location/Qualifiers
source                  1..49
                        mol_type = other RNA
                        organism = synthetic construct
SEQUENCE: 102
ccaccccaaa aatgaagggg actaaaacag gggcagagat gatgaccct              49

SEQ ID NO: 103          moltype = RNA  length = 38
FEATURE                 Location/Qualifiers
source                  1..38
                        mol_type = other RNA
                        organism = synthetic construct
SEQUENCE: 103
ggattcgatc caccccaaaa atgaagggga ctaaaaca                          38

SEQ ID NO: 104          moltype = RNA  length = 38
FEATURE                 Location/Qualifiers
source                  1..38
                        mol_type = other RNA
                        organism = synthetic construct
SEQUENCE: 104
ggatttaata aaccccaaaa atgaagggga ctaaaaca                          38

SEQ ID NO: 105          moltype = RNA  length = 38
FEATURE                 Location/Qualifiers
source                  1..38
                        mol_type = other RNA
                        organism = synthetic construct
SEQUENCE: 105
ggatttagga agccccaaaa atgaagggga ctaaaaca                          38

SEQ ID NO: 106          moltype = RNA  length = 38
FEATURE                 Location/Qualifiers
source                  1..38
                        mol_type = other RNA
                        organism = synthetic construct
SEQUENCE: 106
ggatttagac caggccaaaa atgaaggcca ctaaaaca                          38

SEQ ID NO: 107          moltype = RNA  length = 38
FEATURE                 Location/Qualifiers
source                  1..38
                        mol_type = other RNA
                        organism = synthetic construct
SEQUENCE: 107
ggatttagac caccccaaaa atgaagggga ctaaaaca                          38

SEQ ID NO: 108          moltype = RNA  length = 38
```

```
FEATURE                Location/Qualifiers
source                 1..38
                       mol_type = other RNA
                       organism = synthetic construct
SEQUENCE: 108
ggcgttagac caccccaaaa atgaagggga ctaaaaca                          38

SEQ ID NO: 109         moltype = RNA  length = 38
FEATURE                Location/Qualifiers
source                 1..38
                       mol_type = other RNA
                       organism = synthetic construct
SEQUENCE: 109
ggagctagac caccccaaaa atgaagggga ctaaaaca                          38

SEQ ID NO: 110         moltype = RNA  length = 38
FEATURE                Location/Qualifiers
source                 1..38
                       mol_type = other RNA
                       organism = synthetic construct
SEQUENCE: 110
ggatccagac caccccaaaa atgaagggga ctaaaaca                          38

SEQ ID NO: 111         moltype = RNA  length = 38
FEATURE                Location/Qualifiers
source                 1..38
                       mol_type = other RNA
                       organism = synthetic construct
SEQUENCE: 111
ggattcggac caccccaaaa atgaagggga ctaaaaca                          38

SEQ ID NO: 112         moltype = RNA  length = 38
FEATURE                Location/Qualifiers
source                 1..38
                       mol_type = other RNA
                       organism = synthetic construct
SEQUENCE: 112
ggatttaccc caccccaaaa atgaagggga ctaaaaca                          38

SEQ ID NO: 113         moltype = RNA  length = 38
FEATURE                Location/Qualifiers
source                 1..38
                       mol_type = other RNA
                       organism = synthetic construct
SEQUENCE: 113
ggatttaatc caccccaaaa atgaagggga ctaaaaca                          38

SEQ ID NO: 114         moltype = RNA  length = 38
FEATURE                Location/Qualifiers
source                 1..38
                       mol_type = other RNA
                       organism = synthetic construct
SEQUENCE: 114
ggatttagaa aaccccaaaa atgaagggga ctaaaaca                          38

SEQ ID NO: 115         moltype = RNA  length = 38
FEATURE                Location/Qualifiers
source                 1..38
                       mol_type = other RNA
                       organism = synthetic construct
SEQUENCE: 115
ggatttagac cgccccaaaa atgaagggga ctaaaaca                          38

SEQ ID NO: 116         moltype = RNA  length = 38
FEATURE                Location/Qualifiers
source                 1..38
                       mol_type = other RNA
                       organism = synthetic construct
SEQUENCE: 116
ggatttagac caccgcaaaa atgaagggca ctaaaaca                          38

SEQ ID NO: 117         moltype = RNA  length = 38
FEATURE                Location/Qualifiers
source                 1..38
                       mol_type = other RNA
                       organism = synthetic construct
SEQUENCE: 117
ggatttagac cagcccaaaa atgaagggca ctaaaaca                          38
```

```
SEQ ID NO: 118          moltype = RNA  length = 38
FEATURE                 Location/Qualifiers
source                  1..38
                        mol_type = other RNA
                        organism = synthetic construct
SEQUENCE: 118
ggatttagac caccacaaaa atgaagtgga ctaaaaca                          38

SEQ ID NO: 119          moltype = RNA  length = 38
FEATURE                 Location/Qualifiers
source                  1..38
                        mol_type = other RNA
                        organism = synthetic construct
SEQUENCE: 119
ggatttagac cacaccaaaa atgaaggtga ctaaaaca                          38

SEQ ID NO: 120          moltype = RNA  length = 38
FEATURE                 Location/Qualifiers
source                  1..38
                        mol_type = other RNA
                        organism = synthetic construct
SEQUENCE: 120
ggatttagac cactccaaaa atgaaggaga ctaaaaca                          38

SEQ ID NO: 121          moltype = RNA  length = 38
FEATURE                 Location/Qualifiers
source                  1..38
                        mol_type = other RNA
                        organism = synthetic construct
SEQUENCE: 121
ggatttagac caccccaaaa atgaaggggc ataaaaca                          38

SEQ ID NO: 122          moltype = RNA  length = 38
FEATURE                 Location/Qualifiers
source                  1..38
                        mol_type = other RNA
                        organism = synthetic construct
SEQUENCE: 122
ggatttagac caccccaaaa atgaagggga cgcaaaca                          38

SEQ ID NO: 123          moltype = RNA  length = 38
FEATURE                 Location/Qualifiers
source                  1..38
                        mol_type = other RNA
                        organism = synthetic construct
SEQUENCE: 123
ggatttagac caccccaaaa atgaagggga ctagcaca                          38

SEQ ID NO: 124          moltype = RNA  length = 38
FEATURE                 Location/Qualifiers
source                  1..38
                        mol_type = other RNA
                        organism = synthetic construct
SEQUENCE: 124
ggatttagac caccccaaaa atgaagggga ctaaagta                          38

SEQ ID NO: 125          moltype = RNA  length = 60
FEATURE                 Location/Qualifiers
source                  1..60
                        mol_type = other RNA
                        organism = synthetic construct
SEQUENCE: 125
ggctcatttg cagggtttag ccaaaagggt catcatctct gccccctctg ctgatgcccc  60

SEQ ID NO: 126          moltype = RNA  length = 60
FEATURE                 Location/Qualifiers
source                  1..60
                        mol_type = other RNA
                        organism = synthetic construct
SEQUENCE: 126
ggcacacccg cagggtttag ccaaaagggt catcatctct gccccctctg ctgatgcccc  60

SEQ ID NO: 127          moltype = RNA  length = 60
FEATURE                 Location/Qualifiers
source                  1..60
                        mol_type = other RNA
                        organism = synthetic construct
SEQUENCE: 127
ggcacacccg caggggggag ccaaaagggt catcatctct gccccctctg ctgatgcccc  60
```

```
SEQ ID NO: 128          moltype = RNA  length = 62
FEATURE                 Location/Qualifiers
source                  1..62
                        mol_type = other RNA
                        organism = synthetic construct
SEQUENCE: 128
gggaacccca aggccaaccg cgagaagatg acccagatca tgtttgagac cttcaacacc  60
cc                                                                 62

SEQ ID NO: 129          moltype = RNA  length = 70
FEATURE                 Location/Qualifiers
source                  1..70
                        mol_type = other RNA
                        organism = synthetic construct
SEQUENCE: 129
ggcctgactg ctctcatttg cagttgggag ccaaaagggt catcatctct gccccctctg  60
ctgatgcccc                                                         70

SEQ ID NO: 130          moltype = RNA  length = 80
FEATURE                 Location/Qualifiers
source                  1..80
                        mol_type = other RNA
                        organism = synthetic construct
SEQUENCE: 130
ggacctgtga atcctgactg ctctcatttg cagttgggag ccaaaagggt catcatctct  60
gccccctctg ctgatgcccc                                              80

SEQ ID NO: 131          moltype = RNA  length = 60
FEATURE                 Location/Qualifiers
source                  1..60
                        mol_type = other RNA
                        organism = synthetic construct
SEQUENCE: 131
ggctcatttg cagggtttag ccaaaagggt catcatctct gccccctctg ctgatgcccc  60

SEQ ID NO: 132          moltype = RNA  length = 31
FEATURE                 Location/Qualifiers
source                  1..31
                        mol_type = other RNA
                        organism = synthetic construct
SEQUENCE: 132
gaccacccca aaaatgaagg ggactaaaac a                                 31

SEQ ID NO: 133          moltype = RNA  length = 31
FEATURE                 Location/Qualifiers
source                  1..31
                        mol_type = other RNA
                        organism = synthetic construct
SEQUENCE: 133
ggccacccca aaaatgaagg ggactaaaac a                                 31

SEQ ID NO: 134          moltype = RNA  length = 33
FEATURE                 Location/Qualifiers
source                  1..33
                        mol_type = other RNA
                        organism = synthetic construct
SEQUENCE: 134
gggaccaccc caaaaatgaa ggggactaaa aca                               33

SEQ ID NO: 135          moltype = RNA  length = 29
FEATURE                 Location/Qualifiers
source                  1..29
                        mol_type = other RNA
                        organism = synthetic construct
SEQUENCE: 135
ccaccccaaa aatgaagggg actaaaaca                                    29

SEQ ID NO: 136          moltype = RNA  length = 30
FEATURE                 Location/Qualifiers
source                  1..30
                        mol_type = other RNA
                        organism = synthetic construct
SEQUENCE: 136
ggatttagac caccccaaaa atgaagggga                                   30

SEQ ID NO: 137          moltype = RNA  length = 30
FEATURE                 Location/Qualifiers
source                  1..30
```

```
                        mol_type = other RNA
                        organism = synthetic construct
SEQUENCE: 137
ggtaagagac tacctctata tgaaagagga                                   30

SEQ ID NO: 138          moltype = RNA  length = 30
FEATURE                 Location/Qualifiers
source                  1..30
                        mol_type = other RNA
                        organism = synthetic construct
SEQUENCE: 138
ggatatagac caccccaata tcgaaggga                                    30

SEQ ID NO: 139          moltype = DNA  length = 68
FEATURE                 Location/Qualifiers
source                  1..68
                        mol_type = other DNA
                        organism = synthetic construct
SEQUENCE: 139
atagaccacc ccaatatcga aggggactaa aactagattg ctgttctacc aagtaatcca  60
tattgata                                                           68

SEQ ID NO: 140          moltype = DNA  length = 69
FEATURE                 Location/Qualifiers
source                  1..69
                        mol_type = other DNA
                        organism = synthetic construct
SEQUENCE: 140
atagaccacc ccaatatcga aggggactaa aacgacaaat ctatctgaat aaactcttct  60
ttttcgata                                                          69

SEQ ID NO: 141          moltype = DNA  length = 69
FEATURE                 Location/Qualifiers
source                  1..69
                        mol_type = other DNA
                        organism = synthetic construct
SEQUENCE: 141
atagaccacc ccaatatcga aggggactaa aactctaaag aattatctat tctgtctttt  60
aaattgata                                                          69

SEQ ID NO: 142          moltype = DNA  length = 57
FEATURE                 Location/Qualifiers
source                  1..57
                        mol_type = other DNA
                        organism = synthetic construct
SEQUENCE: 142
gtaagagact acctctatat gaaagaggac taaaactttt aacagtggcc ttattaa     57

SEQ ID NO: 143          moltype = RNA  length = 38
FEATURE                 Location/Qualifiers
source                  1..38
                        mol_type = other RNA
                        organism = synthetic construct
SEQUENCE: 143
ggattcgatc caccccaaaa atgaagggga ctaaaaca                          38

SEQ ID NO: 144          moltype = RNA  length = 38
FEATURE                 Location/Qualifiers
source                  1..38
                        mol_type = other RNA
                        organism = synthetic construct
SEQUENCE: 144
ggatttaata aaccccaaaa atgaagggga ctaaaaca                          38

SEQ ID NO: 145          moltype = RNA  length = 38
FEATURE                 Location/Qualifiers
source                  1..38
                        mol_type = other RNA
                        organism = synthetic construct
SEQUENCE: 145
ggatttagga agccccaaaa atgaagggga ctaaaaca                          38

SEQ ID NO: 146          moltype = RNA  length = 38
FEATURE                 Location/Qualifiers
source                  1..38
                        mol_type = other RNA
                        organism = synthetic construct
SEQUENCE: 146
ggatttagac caggccaaaa atgaaggcca ctaaaaca                          38
```

```
SEQ ID NO: 147          moltype = RNA  length = 31
FEATURE                 Location/Qualifiers
source                  1..31
                        mol_type = other RNA
                        organism = synthetic construct
SEQUENCE: 147
ggccacccca aaaatgaagg ggactaaaac a                                  31

SEQ ID NO: 148          moltype = RNA  length = 33
FEATURE                 Location/Qualifiers
source                  1..33
                        mol_type = other RNA
                        organism = synthetic construct
SEQUENCE: 148
gggaccaccc caaaaatgaa ggggactaaa aca                                33

SEQ ID NO: 149          moltype = RNA  length = 29
FEATURE                 Location/Qualifiers
source                  1..29
                        mol_type = other RNA
                        organism = synthetic construct
SEQUENCE: 149
ccaccccaaa aatgaagggg actaaaaca                                     29

SEQ ID NO: 150          moltype = RNA  length = 16
FEATURE                 Location/Qualifiers
source                  1..16
                        mol_type = other RNA
                        organism = synthetic construct
SEQUENCE: 150
ggatttagac caccccc                                                  16

SEQ ID NO: 151          moltype = RNA  length = 17
FEATURE                 Location/Qualifiers
source                  1..17
                        mol_type = other RNA
                        organism = synthetic construct
SEQUENCE: 151
ggtaagagac tacctct                                                  17

SEQ ID NO: 152          moltype = RNA  length = 17
FEATURE                 Location/Qualifiers
source                  1..17
                        mol_type = other RNA
                        organism = synthetic construct
SEQUENCE: 152
ggcttgtgaa ttatccc                                                  17

SEQ ID NO: 153          moltype = RNA  length = 15
FEATURE                 Location/Qualifiers
source                  1..15
                        mol_type = other RNA
                        organism = synthetic construct
SEQUENCE: 153
ggtcacatca ccgcc                                                    15

SEQ ID NO: 154          moltype = RNA  length = 16
FEATURE                 Location/Qualifiers
source                  1..16
                        mol_type = other RNA
                        organism = synthetic construct
SEQUENCE: 154
ggatatagac caccccc                                                  16

SEQ ID NO: 155          moltype = RNA  length = 16
FEATURE                 Location/Qualifiers
source                  1..16
                        mol_type = other RNA
                        organism = synthetic construct
SEQUENCE: 155
ggatttagag tacctc                                                   16

SEQ ID NO: 156          moltype = RNA  length = 19
FEATURE                 Location/Qualifiers
source                  1..19
                        mol_type = other RNA
                        organism = synthetic construct
SEQUENCE: 156
```

```
gggctggaga agatagccc                                                   19

SEQ ID NO: 157          moltype = RNA  length = 15
FEATURE                 Location/Qualifiers
source                  1..15
                        mol_type = other RNA
                        organism = synthetic construct
SEQUENCE: 157
gggtgaatac agctc                                                       15

SEQ ID NO: 158          moltype = RNA  length = 18
FEATURE                 Location/Qualifiers
source                  1..18
                        mol_type = other RNA
                        organism = synthetic construct
SEQUENCE: 158
gggtttggag aacagccc                                                    18

SEQ ID NO: 159          moltype = RNA  length = 16
FEATURE                 Location/Qualifiers
source                  1..16
                        mol_type = other RNA
                        organism = synthetic construct
SEQUENCE: 159
ggatatagac cacccc                                                      16

SEQ ID NO: 160          moltype = RNA  length = 13
FEATURE                 Location/Qualifiers
source                  1..13
                        mol_type = other RNA
                        organism = synthetic construct
SEQUENCE: 160
ggtaacaatc ccc                                                         13

SEQ ID NO: 161          moltype = RNA  length = 38
FEATURE                 Location/Qualifiers
source                  1..38
                        mol_type = other RNA
                        organism = synthetic construct
SEQUENCE: 161
ggatttagac caccccaaaa atgaagggga ctaaaaca                              38

SEQ ID NO: 162          moltype = RNA  length = 37
FEATURE                 Location/Qualifiers
source                  1..37
                        mol_type = other RNA
                        organism = synthetic construct
SEQUENCE: 162
ggtaagagac tacctctata tgaaagagga ctaaaac                               37

SEQ ID NO: 163          moltype = RNA  length = 38
FEATURE                 Location/Qualifiers
source                  1..38
                        mol_type = other RNA
                        organism = synthetic construct
SEQUENCE: 163
ggcttgtgaa ttatcccaaa attgaaggga actacaac                              38

SEQ ID NO: 164          moltype = RNA  length = 36
FEATURE                 Location/Qualifiers
source                  1..36
                        mol_type = other RNA
                        organism = synthetic construct
SEQUENCE: 164
ggtcacatca ccgccaagac gacggcggac tgaacc                                36

SEQ ID NO: 165          moltype = RNA  length = 39
FEATURE                 Location/Qualifiers
source                  1..39
                        mol_type = other RNA
                        organism = synthetic construct
SEQUENCE: 165
ggatatagac caccccaata tcgaagggga ctaaaactt                             39

SEQ ID NO: 166          moltype = RNA  length = 37
FEATURE                 Location/Qualifiers
source                  1..37
                        mol_type = other RNA
                        organism = synthetic construct
```

```
SEQUENCE: 166
ggatttagag tacctcaaaa caaaagagga ctaaaac                    37

SEQ ID NO: 167          moltype = RNA  length = 37
FEATURE                 Location/Qualifiers
source                  1..37
                        mol_type = other RNA
                        organism = synthetic construct
SEQUENCE: 167
gggctggaga agatagccca agaaagaggg caataac                    37

SEQ ID NO: 168          moltype = RNA  length = 33
FEATURE                 Location/Qualifiers
source                  1..33
                        mol_type = other RNA
                        organism = synthetic construct
SEQUENCE: 168
gggtgaatac agctcgatat agtgagcaat aag                        33

SEQ ID NO: 169          moltype = RNA  length = 37
FEATURE                 Location/Qualifiers
source                  1..37
                        mol_type = other RNA
                        organism = synthetic construct
SEQUENCE: 169
gggtttggag aacagcccga tatagagggc aatagac                    37

SEQ ID NO: 170          moltype = RNA  length = 37
FEATURE                 Location/Qualifiers
source                  1..37
                        mol_type = other RNA
                        organism = synthetic construct
SEQUENCE: 170
ggatatagac caccccaata tcgaagggga ctaaaac                    37

SEQ ID NO: 171          moltype = RNA  length = 31
FEATURE                 Location/Qualifiers
source                  1..31
                        mol_type = other RNA
                        organism = synthetic construct
SEQUENCE: 171
ggtaacaatc cccgtagaca ggggaactgt g                          31

SEQ ID NO: 172          moltype = RNA  length = 34
FEATURE                 Location/Qualifiers
source                  1..34
                        mol_type = other RNA
                        organism = synthetic construct
SEQUENCE: 172
ggaggtaaca atccccgtag acaggggaac tgtg                       34

SEQ ID NO: 173          moltype = AA  length = 25
FEATURE                 Location/Qualifiers
source                  1..25
                        mol_type = protein
                        organism = synthetic construct
SEQUENCE: 173
AFCHFVEIEM SQLLKNYVYK RLSNI                                 25

SEQ ID NO: 174          moltype = AA  length = 26
FEATURE                 Location/Qualifiers
source                  1..26
                        mol_type = protein
                        organism = synthetic construct
SEQUENCE: 174
IIYRYLKGRI EKILVNEQKV RLKKME                                26

SEQ ID NO: 175          moltype = AA  length = 22
FEATURE                 Location/Qualifiers
source                  1..22
                        mol_type = protein
                        organism = synthetic construct
SEQUENCE: 175
LFLKEVEQYF KKYFPVKSKH SN                                    22

SEQ ID NO: 176          moltype = AA  length = 19
FEATURE                 Location/Qualifiers
source                  1..19
                        mol_type = protein
```

```
                         organism = synthetic construct
SEQUENCE: 176
YWIHHIENAV ERILKNCKA                                              19

SEQ ID NO: 177           moltype = AA  length = 22
FEATURE                  Location/Qualifiers
source                   1..22
                         mol_type = protein
                         organism = synthetic construct
SEQUENCE: 177
QFNIEIRKHL ETYFPIKKTN RK                                          22

SEQ ID NO: 178           moltype = AA  length = 22
FEATURE                  Location/Qualifiers
source                   1..22
                         mol_type = protein
                         organism = synthetic construct
SEQUENCE: 178
IYHLEVVKYL EHYFPIKTSK RR                                          22

SEQ ID NO: 179           moltype = AA  length = 22
FEATURE                  Location/Qualifiers
source                   1..22
                         mol_type = protein
                         organism = synthetic construct
SEQUENCE: 179
IYNLELKKYI ENNFSYKKQK SK                                          22

SEQ ID NO: 180           moltype = AA  length = 19
FEATURE                  Location/Qualifiers
source                   1..19
                         mol_type = protein
                         organism = synthetic construct
SEQUENCE: 180
FFIHRIEYGV EKIYANLKQ                                              19

SEQ ID NO: 181           moltype = AA  length = 16
FEATURE                  Location/Qualifiers
source                   1..16
                         mol_type = protein
                         organism = synthetic construct
SEQUENCE: 181
ALHDEVKKTY KRLCAR                                                 16

SEQ ID NO: 182           moltype = AA  length = 19
FEATURE                  Location/Qualifiers
source                   1..19
                         mol_type = protein
                         organism = synthetic construct
SEQUENCE: 182
FWIHHIESAV ERILASINP                                              19

SEQ ID NO: 183           moltype = AA  length = 22
FEATURE                  Location/Qualifiers
source                   1..22
                         mol_type = protein
                         organism = synthetic construct
SEQUENCE: 183
QYGIEVKKYI QRYFPIKRAP NR                                          22

SEQ ID NO: 184           moltype = AA  length = 26
FEATURE                  Location/Qualifiers
source                   1..26
                         mol_type = protein
                         organism = synthetic construct
SEQUENCE: 184
ENLRKLLSYD RKLKNAVMKS VVDILK                                      26

SEQ ID NO: 185           moltype = AA  length = 25
FEATURE                  Location/Qualifiers
source                   1..25
                         mol_type = protein
                         organism = synthetic construct
SEQUENCE: 185
DRVSNLLSYS TRYNNSTYAS VFEVF                                       25

SEQ ID NO: 186           moltype = AA  length = 26
FEATURE                  Location/Qualifiers
source                   1..26
```

-continued

```
                        mol_type = protein
                        organism = synthetic construct
SEQUENCE: 186
NSLRILLAYD RKRQNAVTKT INDLLL                                    26

SEQ ID NO: 187          moltype = AA  length = 27
FEATURE                 Location/Qualifiers
source                  1..27
                        mol_type = protein
                        organism = synthetic construct
SEQUENCE: 187
SEVFDRFFTY DIKYQKNVLN LLQNILL                                   27

SEQ ID NO: 188          moltype = AA  length = 26
FEATURE                 Location/Qualifiers
source                  1..26
                        mol_type = protein
                        organism = synthetic construct
SEQUENCE: 188
DDARDVLSYD RKLKNAVSKS LKEILS                                    26

SEQ ID NO: 189          moltype = AA  length = 26
FEATURE                 Location/Qualifiers
source                  1..26
                        mol_type = protein
                        organism = synthetic construct
SEQUENCE: 189
NELRELLHYD RKLKNAVSKA FIDLFD                                    26

SEQ ID NO: 190          moltype = AA  length = 26
FEATURE                 Location/Qualifiers
source                  1..26
                        mol_type = protein
                        organism = synthetic construct
SEQUENCE: 190
NLLIKLFSYD KKVQNHILKS TKTLLE                                    26

SEQ ID NO: 191          moltype = AA  length = 27
FEATURE                 Location/Qualifiers
source                  1..27
                        mol_type = protein
                        organism = synthetic construct
SEQUENCE: 191
SEVFDRFFTY DLKYRKNVPT ILYNILL                                   27

SEQ ID NO: 192          moltype = AA  length = 26
FEATURE                 Location/Qualifiers
source                  1..26
                        mol_type = protein
                        organism = synthetic construct
SEQUENCE: 192
NRAREMMAYD RKRKNAVPRS ILDMLA                                    26

SEQ ID NO: 193          moltype = AA  length = 27
FEATURE                 Location/Qualifiers
source                  1..27
                        mol_type = protein
                        organism = synthetic construct
SEQUENCE: 193
SEIHDRFFTY DMKYQKNVAN MLENILL                                   27

SEQ ID NO: 194          moltype = AA  length = 26
FEATURE                 Location/Qualifiers
source                  1..26
                        mol_type = protein
                        organism = synthetic construct
SEQUENCE: 194
ERLREIFKYD RKLKNAVSKS LIDILD                                    26

SEQ ID NO: 195          moltype = AA  length = 29
FEATURE                 Location/Qualifiers
source                  1..29
                        mol_type = protein
                        organism = synthetic construct
SEQUENCE: 195
YAFCHFVEIE MSQLLKNYVY KRLSNISND                                 29

SEQ ID NO: 196          moltype = AA  length = 27
FEATURE                 Location/Qualifiers
```

-continued

```
source                  1..27
                        mol_type = protein
                        organism = synthetic construct
SEQUENCE: 196
IIYRYLKGRI EKILVNEQKV RLKKMEK                                       27

SEQ ID NO: 197          moltype = AA  length = 25
FEATURE                 Location/Qualifiers
source                  1..25
                        mol_type = protein
                        organism = synthetic construct
SEQUENCE: 197
LFLKEVEQYF KKYFPVKSKH SNKSK                                         25

SEQ ID NO: 198          moltype = AA  length = 19
FEATURE                 Location/Qualifiers
source                  1..19
                        mol_type = protein
                        organism = synthetic construct
SEQUENCE: 198
YWIHHIENAV ERILKNCKA                                                19

SEQ ID NO: 199          moltype = AA  length = 23
FEATURE                 Location/Qualifiers
source                  1..23
                        mol_type = protein
                        organism = synthetic construct
SEQUENCE: 199
QFNIEIRKHL ETYFPIKKTN RKV                                           23

SEQ ID NO: 200          moltype = AA  length = 25
FEATURE                 Location/Qualifiers
source                  1..25
                        mol_type = protein
                        organism = synthetic construct
SEQUENCE: 200
IYHLEVVKYL EHYFPIKTSK RRNTA                                         25

SEQ ID NO: 201          moltype = AA  length = 25
FEATURE                 Location/Qualifiers
source                  1..25
                        mol_type = protein
                        organism = synthetic construct
SEQUENCE: 201
IYNLELKKYI ENNFSYKKQK SKSKN                                         25

SEQ ID NO: 202          moltype = AA  length = 27
FEATURE                 Location/Qualifiers
source                  1..27
                        mol_type = protein
                        organism = synthetic construct
SEQUENCE: 202
IIYRYLKGRI EKILVNEQKV RLKKMEK                                       27

SEQ ID NO: 203          moltype = AA  length = 29
FEATURE                 Location/Qualifiers
source                  1..29
                        mol_type = protein
                        organism = synthetic construct
SEQUENCE: 203
YAFCHFVEIE MSQLLKNYVY KRLSNISND                                     29

SEQ ID NO: 204          moltype = AA  length = 31
FEATURE                 Location/Qualifiers
source                  1..31
                        mol_type = protein
                        organism = synthetic construct
SEQUENCE: 204
FAFCYFVEIE VNNLLKENVY KIKRFNESNK K                                  31

SEQ ID NO: 205          moltype = AA  length = 19
FEATURE                 Location/Qualifiers
source                  1..19
                        mol_type = protein
                        organism = synthetic construct
SEQUENCE: 205
FFIHRIEYGV EKIYANLKQ                                                19

SEQ ID NO: 206          moltype = AA  length = 15
```

-continued

```
FEATURE                Location/Qualifiers
source                 1..15
                       mol_type = protein
                       organism = synthetic construct
SEQUENCE: 206
ALHDEVKKTY KRLCA                                                15

SEQ ID NO: 207         moltype = AA  length = 19
FEATURE                Location/Qualifiers
source                 1..19
                       mol_type = protein
                       organism = synthetic construct
SEQUENCE: 207
FWIHRIENAV ERILGSIND                                            19

SEQ ID NO: 208         moltype = AA  length = 19
FEATURE                Location/Qualifiers
source                 1..19
                       mol_type = protein
                       organism = synthetic construct
SEQUENCE: 208
FWIHHIESAV ERILASINP                                            19

SEQ ID NO: 209         moltype = AA  length = 23
FEATURE                Location/Qualifiers
source                 1..23
                       mol_type = protein
                       organism = synthetic construct
SEQUENCE: 209
QFNIEIGKYF EHYFPIKKER CTE                                       23

SEQ ID NO: 210         moltype = AA  length = 22
FEATURE                Location/Qualifiers
source                 1..22
                       mol_type = protein
                       organism = synthetic construct
SEQUENCE: 210
QFNIELGKYF EHYFPKTGKK ES                                        22

SEQ ID NO: 211         moltype = AA  length = 25
FEATURE                Location/Qualifiers
source                 1..25
                       mol_type = protein
                       organism = synthetic construct
SEQUENCE: 211
QYGIEVKKYI QRYFPIKRAP NRSKH                                     25

SEQ ID NO: 212         moltype = AA  length = 19
FEATURE                Location/Qualifiers
source                 1..19
                       mol_type = protein
                       organism = synthetic construct
SEQUENCE: 212
FWIHLIENEV ERLYNGIEN                                            19

SEQ ID NO: 213         moltype = AA  length = 29
FEATURE                Location/Qualifiers
source                 1..29
                       mol_type = protein
                       organism = synthetic construct
SEQUENCE: 213
YVFCHFVEIE MSKLLKNYVY KKPSNISND                                 29

SEQ ID NO: 214         moltype = AA  length = 26
FEATURE                Location/Qualifiers
source                 1..26
                       mol_type = protein
                       organism = synthetic construct
SEQUENCE: 214
ENLRKLLSYD RKLKNAVMKS VVDILK                                    26

SEQ ID NO: 215         moltype = AA  length = 25
FEATURE                Location/Qualifiers
source                 1..25
                       mol_type = protein
                       organism = synthetic construct
SEQUENCE: 215
DRVSNLLSYS TRYNNSTYAS VFEVF                                     25
```

-continued

```
SEQ ID NO: 216          moltype = AA  length = 26
FEATURE                 Location/Qualifiers
source                  1..26
                        mol_type = protein
                        organism = synthetic construct
SEQUENCE: 216
NSLRILLAYD RKRQNAVTKT INDLLL                                       26

SEQ ID NO: 217          moltype = AA  length = 27
FEATURE                 Location/Qualifiers
source                  1..27
                        mol_type = protein
                        organism = synthetic construct
SEQUENCE: 217
SEVFDRFFTY DIKYQKNVLN LLQNILL                                      27

SEQ ID NO: 218          moltype = AA  length = 26
FEATURE                 Location/Qualifiers
source                  1..26
                        mol_type = protein
                        organism = synthetic construct
SEQUENCE: 218
DDARDVLSYD RKLKNAVSKS LKEILS                                       26

SEQ ID NO: 219          moltype = AA  length = 26
FEATURE                 Location/Qualifiers
source                  1..26
                        mol_type = protein
                        organism = synthetic construct
SEQUENCE: 219
NELRELLHYD RKLKNAVSKA FIDLFD                                       26

SEQ ID NO: 220          moltype = AA  length = 26
FEATURE                 Location/Qualifiers
source                  1..26
                        mol_type = protein
                        organism = synthetic construct
SEQUENCE: 220
NLLIKLFSYD KKVQNHILKS TKTLLE                                       26

SEQ ID NO: 221          moltype = AA  length = 25
FEATURE                 Location/Qualifiers
source                  1..25
                        mol_type = protein
                        organism = synthetic construct
SEQUENCE: 221
DRVSNLLSYS TRYNNSTYAS VFEVF                                        25

SEQ ID NO: 222          moltype = AA  length = 26
FEATURE                 Location/Qualifiers
source                  1..26
                        mol_type = protein
                        organism = synthetic construct
SEQUENCE: 222
ENLRKLLSYD RKLKNAIMKS IVDILK                                       26

SEQ ID NO: 223          moltype = AA  length = 26
FEATURE                 Location/Qualifiers
source                  1..26
                        mol_type = protein
                        organism = synthetic construct
SEQUENCE: 223
EELRNLLKYD RKLKNAVMKS IKDIFK                                       26

SEQ ID NO: 224          moltype = AA  length = 27
FEATURE                 Location/Qualifiers
source                  1..27
                        mol_type = protein
                        organism = synthetic construct
SEQUENCE: 224
SEVFDRFFTY DLKYRKNVPT ILYNILL                                      27

SEQ ID NO: 225          moltype = AA  length = 26
FEATURE                 Location/Qualifiers
source                  1..26
                        mol_type = protein
                        organism = synthetic construct
SEQUENCE: 225
NRAREMMAYD RKRKNAVPRS ILDMLA                                       26
```

```
SEQ ID NO: 226          moltype = AA  length = 27
FEATURE                 Location/Qualifiers
source                  1..27
                        mol_type = protein
                        organism = synthetic construct
SEQUENCE: 226
SEFFDRFFTY DMKYQKNVVN VLENILL                                          27

SEQ ID NO: 227          moltype = AA  length = 27
FEATURE                 Location/Qualifiers
source                  1..27
                        mol_type = protein
                        organism = synthetic construct
SEQUENCE: 227
SEIHDRFFTY DMKYQKNVAN MLENILL                                          27

SEQ ID NO: 228          moltype = AA  length = 26
FEATURE                 Location/Qualifiers
source                  1..26
                        mol_type = protein
                        organism = synthetic construct
SEQUENCE: 228
NNLRDLMAYD RKLKNAVTKS MIKILD                                           26

SEQ ID NO: 229          moltype = AA  length = 26
FEATURE                 Location/Qualifiers
source                  1..26
                        mol_type = protein
                        organism = synthetic construct
SEQUENCE: 229
NDLRKLMSYD RKLKNAVTKA IIKILD                                           26

SEQ ID NO: 230          moltype = AA  length = 26
FEATURE                 Location/Qualifiers
source                  1..26
                        mol_type = protein
                        organism = synthetic construct
SEQUENCE: 230
ERLREIFKYD RKLKNAVSKS LIDILD                                           26

SEQ ID NO: 231          moltype = AA  length = 27
FEATURE                 Location/Qualifiers
source                  1..27
                        mol_type = protein
                        organism = synthetic construct
SEQUENCE: 231
SEVFDRFFTY DMKLRKNVVN MLYNILL                                          27

SEQ ID NO: 232          moltype = AA  length = 26
FEATURE                 Location/Qualifiers
source                  1..26
                        mol_type = protein
                        organism = synthetic construct
SEQUENCE: 232
ENLRKLLSYD RKLKNAIMKS IVDILK                                           26

SEQ ID NO: 233          moltype = RNA  length = 24
FEATURE                 Location/Qualifiers
source                  1..24
                        mol_type = other RNA
                        organism = synthetic construct
SEQUENCE: 233
ggcatgacta gtcgtactgc atcg                                             24

SEQ ID NO: 234          moltype = RNA  length = 31
FEATURE                 Location/Qualifiers
source                  1..31
                        mol_type = other RNA
                        organism = synthetic construct
SEQUENCE: 234
ggtccaaggg tcatcatctc tgcccccaca g                                     31

SEQ ID NO: 235          moltype = DNA  length = 38
FEATURE                 Location/Qualifiers
source                  1..38
                        mol_type = other DNA
                        organism = synthetic construct
SEQUENCE: 235
```

```
gatatagacc accccaatat cgaaggggac taaaactt                             38

SEQ ID NO: 236          moltype = DNA  length = 34
FEATURE                 Location/Qualifiers
source                  1..34
                        mol_type = other DNA
                        organism = synthetic construct
SEQUENCE: 236
tcacatcacc gccaagacga cggcggactg aacc                                 34

SEQ ID NO: 237          moltype = DNA  length = 38
FEATURE                 Location/Qualifiers
source                  1..38
                        mol_type = other DNA
                        organism = synthetic construct
SEQUENCE: 237
ggagcacatc accgccaaaa tgacggcgga ctgaacct                             38

SEQ ID NO: 238          moltype = DNA  length = 32
FEATURE                 Location/Qualifiers
source                  1..32
                        mol_type = other DNA
                        organism = synthetic construct
SEQUENCE: 238
gtaacaatcc ccgtagacag gggaactgca ac                                   32

SEQ ID NO: 239          moltype = DNA  length = 37
FEATURE                 Location/Qualifiers
source                  1..37
                        mol_type = other DNA
                        organism = synthetic construct
SEQUENCE: 239
gatttagacc accccaaaaa tgaaggggac taaaaca                              37

SEQ ID NO: 240          moltype = DNA  length = 36
FEATURE                 Location/Qualifiers
source                  1..36
                        mol_type = other DNA
                        organism = synthetic construct
SEQUENCE: 240
gtaagagact acctctatat gaaagaggac taaaac                               36

SEQ ID NO: 241          moltype = DNA  length = 36
FEATURE                 Location/Qualifiers
source                  1..36
                        mol_type = other DNA
                        organism = synthetic construct
SEQUENCE: 241
cttgtgaatt atcccaaaat tgaagggaac tacaac                               36

SEQ ID NO: 242          moltype = DNA  length = 36
FEATURE                 Location/Qualifiers
source                  1..36
                        mol_type = other DNA
                        organism = synthetic construct
SEQUENCE: 242
cttgtggatt atcccaatat tgaagggaac tacaac                               36

SEQ ID NO: 243          moltype = DNA  length = 36
FEATURE                 Location/Qualifiers
source                  1..36
                        mol_type = other DNA
                        organism = synthetic construct
SEQUENCE: 243
cttgtggatt atcccaaaat tgaagggaac taaaac                               36

SEQ ID NO: 244          moltype = DNA  length = 35
FEATURE                 Location/Qualifiers
source                  1..35
                        mol_type = other DNA
                        organism = synthetic construct
SEQUENCE: 244
gctggagaag atagcccaag aaagagggca ataac                                35

SEQ ID NO: 245          moltype = DNA  length = 35
FEATURE                 Location/Qualifiers
source                  1..35
                        mol_type = other DNA
                        organism = synthetic construct
```

```
SEQUENCE: 245
gttgatgaga agagcccaag atagagggca ataac                            35

SEQ ID NO: 246          moltype = DNA  length = 31
FEATURE                 Location/Qualifiers
source                  1..31
                        mol_type = other DNA
                        organism = synthetic construct
SEQUENCE: 246
gtgaaagtag cccgatatag agggcaataa c                                31

SEQ ID NO: 247          moltype = DNA  length = 31
FEATURE                 Location/Qualifiers
source                  1..31
                        mol_type = other DNA
                        organism = synthetic construct
SEQUENCE: 247
gtgaatacag ctcgatatag tgagcaataa g                                31

SEQ ID NO: 248          moltype = DNA  length = 36
FEATURE                 Location/Qualifiers
source                  1..36
                        mol_type = other DNA
                        organism = synthetic construct
SEQUENCE: 248
gatttagagt acctcaaaac aaaagaggac taaaac                           36

SEQ ID NO: 249          moltype = DNA  length = 35
FEATURE                 Location/Qualifiers
source                  1..35
                        mol_type = other DNA
                        organism = synthetic construct
SEQUENCE: 249
gtttggagaa cagcccgata tagagggcaa tagac                            35

SEQ ID NO: 250          moltype = DNA  length = 36
FEATURE                 Location/Qualifiers
source                  1..36
                        mol_type = other DNA
                        organism = synthetic construct
SEQUENCE: 250
gatatagacc accccaatat cgaaggggac taaaac                           36

SEQ ID NO: 251          moltype = RNA  length = 32
FEATURE                 Location/Qualifiers
source                  1..32
                        mol_type = other RNA
                        organism = synthetic construct
SEQUENCE: 251
gaccacccca atatcgaagg ggactaaaac tt                               32

SEQ ID NO: 252          moltype = RNA  length = 31
FEATURE                 Location/Qualifiers
source                  1..31
                        mol_type = other RNA
                        organism = synthetic construct
SEQUENCE: 252
catcaccgcc aagacgacgg cggactgaac c                                31

SEQ ID NO: 253          moltype = RNA  length = 31
FEATURE                 Location/Qualifiers
source                  1..31
                        mol_type = other RNA
                        organism = synthetic construct
SEQUENCE: 253
gaccacccca aaaatgaagg ggactaaaac a                                31

SEQ ID NO: 254          moltype = RNA  length = 30
FEATURE                 Location/Qualifiers
source                  1..30
                        mol_type = other RNA
                        organism = synthetic construct
SEQUENCE: 254
gactacctct atatgaaaga ggactaaaac                                  30

SEQ ID NO: 255          moltype = RNA  length = 30
FEATURE                 Location/Qualifiers
source                  1..30
                        mol_type = other RNA
```

```
                         organism = synthetic construct
SEQUENCE: 255
aattatccca aaattgaagg gaactacaac                                  30

SEQ ID NO: 256           moltype = RNA  length = 27
FEATURE                  Location/Qualifiers
source                   1..27
                         mol_type = other RNA
                         organism = synthetic construct
SEQUENCE: 256
agatagccca agaaagaggg caataac                                     27

SEQ ID NO: 257           moltype = RNA  length = 27
FEATURE                  Location/Qualifiers
source                   1..27
                         mol_type = other RNA
                         organism = synthetic construct
SEQUENCE: 257
gaagagccca agatagaggg caataac                                     27

SEQ ID NO: 258           moltype = RNA  length = 27
FEATURE                  Location/Qualifiers
source                   1..27
                         mol_type = other RNA
                         organism = synthetic construct
SEQUENCE: 258
aagtagcccg atatagaggg caataac                                     27

SEQ ID NO: 259           moltype = RNA  length = 27
FEATURE                  Location/Qualifiers
source                   1..27
                         mol_type = other RNA
                         organism = synthetic construct
SEQUENCE: 259
atacagctcg atatagtgag caataag                                     27

SEQ ID NO: 260           moltype = RNA  length = 30
FEATURE                  Location/Qualifiers
source                   1..30
                         mol_type = other RNA
                         organism = synthetic construct
SEQUENCE: 260
gagtacctca aaacaaaaga ggactaaaac                                  30

SEQ ID NO: 261           moltype = RNA  length = 28
FEATURE                  Location/Qualifiers
source                   1..28
                         mol_type = other RNA
                         organism = synthetic construct
SEQUENCE: 261
gaacagcccg atatagaggg caatagac                                    28

SEQ ID NO: 262           moltype = RNA  length = 27
FEATURE                  Location/Qualifiers
source                   1..27
                         mol_type = other RNA
                         organism = synthetic construct
SEQUENCE: 262
caccccaata tcgaagggga ctaaaac                                     27

SEQ ID NO: 263           moltype = RNA  length = 61
FEATURE                  Location/Qualifiers
source                   1..61
                         mol_type = other RNA
                         organism = synthetic construct
SEQUENCE: 263
gggtttggag aacagcccga tatagagggc aatagaccag atatagcctg gtggttcagg  60
c                                                                 61

SEQ ID NO: 264           moltype = RNA  length = 57
FEATURE                  Location/Qualifiers
source                   1..57
                         mol_type = other RNA
                         organism = synthetic construct
SEQUENCE: 264
gggtgaatac agctcgatat agtgagcaat aagcagatat agcctggtgg ttcaggc     57

SEQ ID NO: 265           moltype = RNA  length = 61
FEATURE                  Location/Qualifiers
```

```
source                  1..61
                        mol_type = other RNA
                        organism = synthetic construct
SEQUENCE: 265
ggtatgtaac aatccccgta gacaggggaa ctgcaaccag atatagcctg gtggttcagg  60
c                                                                  61

SEQ ID NO: 266          moltype = RNA  length = 61
FEATURE                 Location/Qualifiers
source                  1..61
                        mol_type = other RNA
                        organism = synthetic construct
SEQUENCE: 266
gggctggaga agatagccca agaaagaggg caataaccag atatagcctg gtggttcagg  60
c                                                                  61

SEQ ID NO: 267          moltype = RNA  length = 62
FEATURE                 Location/Qualifiers
source                  1..62
                        mol_type = other RNA
                        organism = synthetic construct
SEQUENCE: 267
ggatttagac caccccaaaa atgaagggga ctaaaacaca gatatagcct ggtggttcag  60
gc                                                                 62

SEQ ID NO: 268          moltype = RNA  length = 61
FEATURE                 Location/Qualifiers
source                  1..61
                        mol_type = other RNA
                        organism = synthetic construct
SEQUENCE: 268
ggatttagag tacctcaaaa caaaagagga ctaaaaccag atatagcctg gtggttcagg  60
c                                                                  61

SEQ ID NO: 269          moltype = RNA  length = 61
FEATURE                 Location/Qualifiers
source                  1..61
                        mol_type = other RNA
                        organism = synthetic construct
SEQUENCE: 269
ggtaagagac tacctctata tgaaagagga ctaaaaccag atatagcctg gtggttcagg  60
c                                                                  61

SEQ ID NO: 270          moltype = RNA  length = 61
FEATURE                 Location/Qualifiers
source                  1..61
                        mol_type = other RNA
                        organism = synthetic construct
SEQUENCE: 270
ggatatagac caccccaata tcgaagggga ctaaaaccag atatagcctg gtggttcagg  60
c                                                                  61

SEQ ID NO: 271          moltype = RNA  length = 64
FEATURE                 Location/Qualifiers
source                  1..64
                        mol_type = other RNA
                        organism = synthetic construct
SEQUENCE: 271
gggatataga ccaccccaat atcgaagggg actaaaactt cagatatagc ctggtggttc  60
aggc                                                               64

SEQ ID NO: 272          moltype = RNA  length = 62
FEATURE                 Location/Qualifiers
source                  1..62
                        mol_type = other RNA
                        organism = synthetic construct
SEQUENCE: 272
ggcttgtgaa ttatcccaaa attgaaggga actacaacca gatatagcct ggtggttcag  60
gc                                                                 62

SEQ ID NO: 273          moltype = RNA  length = 60
FEATURE                 Location/Qualifiers
source                  1..60
                        mol_type = other RNA
                        organism = synthetic construct
SEQUENCE: 273
ggtcacatca ccgccaagac gacggcggac tgaacccaga tatagcctgg tggttcaggc  60

SEQ ID NO: 274          moltype = RNA  length = 98
```

```
FEATURE                Location/Qualifiers
source                 1..98
                       mol_type = other RNA
                       organism = synthetic construct
SEQUENCE: 274
ggtgttctct gatgaggcct tcgggccgaa acggtgaaag ccgtaagaac agcccgatat  60
agagggcaat agaccagata tagcctggtg gttcaggc                          98

SEQ ID NO: 275         moltype = RNA  length = 52
FEATURE                Location/Qualifiers
source                 1..52
                       mol_type = other RNA
                       organism = synthetic construct
SEQUENCE: 275
gaacagcccg atatagaggg caatagacca gatatagcct ggtggttcag gc          52

SEQ ID NO: 276         moltype = RNA  length = 97
FEATURE                Location/Qualifiers
source                 1..97
                       mol_type = other RNA
                       organism = synthetic construct
SEQUENCE: 276
ggtgtattct gatgaggcct tcgggccgaa acggtgaaag ccgtaaatac agctcgatat  60
agtgagcaat aagcagatat agcctggtgg ttcaggc                           97

SEQ ID NO: 277         moltype = RNA  length = 51
FEATURE                Location/Qualifiers
source                 1..51
                       mol_type = other RNA
                       organism = synthetic construct
SEQUENCE: 277
aagtagcccg atatagaggg caataaccag atatagcctg gtggttcagg c           51

SEQ ID NO: 278         moltype = RNA  length = 97
FEATURE                Location/Qualifiers
source                 1..97
                       mol_type = other RNA
                       organism = synthetic construct
SEQUENCE: 278
ggtatcttct gatgaggcct tcgggccgaa acggtgaaag ccgtaaagat agcccaagaa  60
agagggcaat aaccagatat agcctggtgg ttcaggc                           97

SEQ ID NO: 279         moltype = RNA  length = 51
FEATURE                Location/Qualifiers
source                 1..51
                       mol_type = other RNA
                       organism = synthetic construct
SEQUENCE: 279
agatagccca agaaagaggg caataaccag atatagcctg gtggttcagg c           51

SEQ ID NO: 280         moltype = RNA  length = 51
FEATURE                Location/Qualifiers
source                 1..51
                       mol_type = other RNA
                       organism = synthetic construct
SEQUENCE: 280
ggccacccca aaaatgaagg ggactaaaac actggtgaac ttccgatagt g           51

SEQ ID NO: 281         moltype = RNA  length = 51
FEATURE                Location/Qualifiers
source                 1..51
                       mol_type = other RNA
                       organism = synthetic construct
SEQUENCE: 281
ggccacccca aaaatgaagg ggactaaaac acagatatag cctggtggtt c           51

SEQ ID NO: 282         moltype = RNA  length = 51
FEATURE                Location/Qualifiers
source                 1..51
                       mol_type = other RNA
                       organism = synthetic construct
SEQUENCE: 282
gaccacccca aaaatgaagg ggactaaaac aggggcagag atgatgaccc t           51

SEQ ID NO: 283         moltype = RNA  length = 54
FEATURE                Location/Qualifiers
source                 1..54
                       mol_type = other RNA
                       organism = synthetic construct
```

```
SEQUENCE: 283
gagtacctca aaacaaaaga ggactaaaac cagatatagc ctggtggttc aggc       54

SEQ ID NO: 284          moltype = RNA  length = 55
FEATURE                 Location/Qualifiers
source                  1..55
                        mol_type = other RNA
                        organism = synthetic construct
SEQUENCE: 284
gggccacccc aatatcgaag gggactaaaa ccagatatag cctggtggtt caggc      55

SEQ ID NO: 285          moltype = RNA  length = 56
FEATURE                 Location/Qualifiers
source                  1..56
                        mol_type = other RNA
                        organism = synthetic construct
SEQUENCE: 285
gaccacccca atatcgaagg ggactaaaac ttcagatata gcctggtggt tcaggc     56

SEQ ID NO: 286          moltype = RNA  length = 99
FEATURE                 Location/Qualifiers
source                  1..99
                        mol_type = other RNA
                        organism = synthetic construct
SEQUENCE: 286
ggataattct gatgaggcct tcgggccgaa acggtgaaag ccgtaaatta tcccaaaatt  60
gaagggaact acaaccagat atagcctggt ggttcaggc                         99

SEQ ID NO: 287          moltype = RNA  length = 54
FEATURE                 Location/Qualifiers
source                  1..54
                        mol_type = other RNA
                        organism = synthetic construct
SEQUENCE: 287
aattatccca aaattgaagg gaactacaac cagatatagc ctggtggttc aggc       54

SEQ ID NO: 288          moltype = RNA  length = 99
FEATURE                 Location/Qualifiers
source                  1..99
                        mol_type = other RNA
                        organism = synthetic construct
SEQUENCE: 288
gggtgatgct gatgaggcct tcgggccgaa acggtgaaag ccgtacatca ccgccaagac  60
gacggcggac tgaaccagat atagcctggt ggttcaggc                         99

SEQ ID NO: 289          moltype = RNA  length = 46
FEATURE                 Location/Qualifiers
source                  1..46
                        mol_type = other RNA
                        organism = synthetic construct
SEQUENCE: 289
cacaccgcca agacgacggc ggacgaacca gaaagccggg gcaggc                 46

SEQ ID NO: 290          moltype = RNA  length = 24
FEATURE                 Location/Qualifiers
source                  1..24
                        mol_type = other RNA
                        organism = synthetic construct
SEQUENCE: 290
ggcatgacta gtcgtactgc atcg                                         24

SEQ ID NO: 291          moltype = RNA  length = 55
FEATURE                 Location/Qualifiers
source                  1..55
                        mol_type = other RNA
                        organism = synthetic construct
SEQUENCE: 291
ggaaatcatt caacacccgc actatcggaa gttcaccagc cagccgcagc acgtt      55

SEQ ID NO: 292          moltype = RNA  length = 57
FEATURE                 Location/Qualifiers
source                  1..57
                        mol_type = other RNA
                        organism = synthetic construct
SEQUENCE: 292
ggcaataaaa atgcgccgcc tgaaccacca ggctatatct gccactcatt gttgtga    57

SEQ ID NO: 293          moltype = RNA  length = 31
FEATURE                 Location/Qualifiers
```

```
source                  1..31
                        mol_type = other RNA
                        organism = synthetic construct
SEQUENCE: 293
ggtccaaggg tcatcatctc tgcccccaca g                              31

SEQ ID NO: 294          moltype = RNA  length = 60
FEATURE                 Location/Qualifiers
source                  1..60
                        mol_type = other RNA
                        organism = synthetic construct
SEQUENCE: 294
ggcacacccg caggggggag ccaaaagggt catcatctct gcccccacag cagaagcccc  60

SEQ ID NO: 295          moltype = RNA  length = 43
FEATURE                 Location/Qualifiers
source                  1..43
                        mol_type = other RNA
                        organism = synthetic construct
SEQUENCE: 295
ggaccatata tcgaaagtta agctagaatg tgtcatatgg cag                 43

SEQ ID NO: 296          moltype = RNA  length = 62
FEATURE                 Location/Qualifiers
source                  1..62
                        mol_type = other RNA
                        organism = synthetic construct
SEQUENCE: 296
gggaacccca aggccaaccg cgagaagatg acccagatca tgtttgagac cttcaacacc  60
cc                                                                 62

SEQ ID NO: 297          moltype = RNA  length = 56
FEATURE                 Location/Qualifiers
source                  1..56
                        mol_type = other RNA
                        organism = synthetic construct
SEQUENCE: 297
ggctcaattt tgacagcggt catggcattc cacttatcac tggcatcctt ccactc      56

SEQ ID NO: 298          moltype = RNA  length = 470
FEATURE                 Location/Qualifiers
source                  1..470
                        mol_type = other RNA
                        organism = synthetic construct
SEQUENCE: 298
gggcgaattg aaggaaggcc gtcaaggccg catgccatta atacgactca ctataggatt  60
tagaccaccc caaaaatgaa ggggactaaa acactggtga acttccgata gtgcgggtgt  120
tgaatgattt agaccacccc aaaaatgaag gggactaaaa cacagatata gcctggtggt  180
tcaggcggcg cattgattta gaccacccca aaaatgaagg ggactaaaac aggggcagag  240
atgatgaccc ttttggctcc cccgatttag accaccccaa aaatgaaggg gactaaaaca  300
atatgacaca ttctagctta actttcgata tagatttaga ccaccccaaa aatgaagggg  360
actaaaacac aaacatgatc tgggtcatct tctcgcggtt ggatttagac caccccaaaa  420
atgaagggga ctaaaacaat gccagtgata agtggaatgc catgaccgct             470

SEQ ID NO: 299          moltype = AA  length = 1154
FEATURE                 Location/Qualifiers
source                  1..1154
                        mol_type = protein
                        organism = Paludibacter propionicigenes
SEQUENCE: 299
MRVSKVKVKD GGKDKMVLVH RKTTGAQLVY SGQPVSNETS NILPEKKRQS FDLSTLNKTI  60
IKFDTAKKQK LNVDQYKIVE KIFKYPKQEL PKQIKAEEIL PFLNHKFQEP VKYWKNGKEE  120
SFNLTLLIVE AVQAQDKRKL QPYYDWKTWY IQTKSDLLKK SIENNRIDLT ENLSKRKKAL  180
LAWETEFTAS GSIDLTHYHK VYMTDVLCKM LQDVKPLTDD KGKINTNAYH RGLKKALQNH  240
QPAIFGTREV PNEANRADNQ LSIYHLEVVK YLEHYFPIKT SKRRNTADDI AHYLKAQTLK  300
TTIEKQLVNA IRANIIQQGK TNHHELKADT TSNDLIRIKT NEAFVLNLTG TCAFAANNIR  360
NMVDNEQTND ILGKGDFIKS LLKDNTNSQL YSFFFGEGLS TNKAEKETQL WGIRGAVQQI  420
RNNVNHYKKD ALKTVFNISN FENPTITDPK QQTNYADTIY KARFINELEK IPEAFAQQLK  480
TGGAVSYYTI ENLKSLLTTF QFSLCRSTIP FAPGFKKVFN GGINYQNAKQ DESFYELMLE  540
QYLRKENFAE ESYNARYFML KLIYNNLFLP GFTTDRKAFA DSVGFVQMQN KKQAEKVNPR  600
KKEAYAFEAV RPMTAADSIA DYMAYVQSEL MQEQNKKEEK VAEETRINFE KFVLQVFIKG  660
FDSFLRAKEF DFVQMPQPQL TATASNQQKA DKLNQLEASI TADCKLTPQY AKADDATHIA  720
FYVFCKLLDA AHLSNLRNEL IKFRESVNEF KFHHLLEIIE ICLLSADVVP TDYRDLYSSE  780
ADCLARLRPF IEQGADITNW SDLFVQSDKH SPVIHANIEL SVKYGTTKLL EQIINKDTQF  840
KTTEANFTAW NTAQKSIEQL IKQREDHHEQ WVKAKNADDK EKQERKREKS NFAQKFIEKH  900
GDDYLDICDY INTYNWLDNK MHFVHLNRLH GLTIELLGRM AGFVALFDRD FQFFDEQQIA  960
DEFKLHGFVN LHSIDKKLNE VPTKKIKEIY DIRNKIIQIN GNKINESVRA NLIQFISSKR  1020
NYYNNAFLHV SNDEIKEKQM YDIRNHIAHF NYLTKDAADF SLIDLINELR ELLHYDRKLK  1080
NAVSKAFIDL FDKHGMILKL KLNADHKLKV ESLEPKKIYH LGSSAKDKPE YQYCTNQVMM  1140
```

```
AYCNMCRSLL EMKK                                                  1154

SEQ ID NO: 300          moltype = AA  length = 1182
FEATURE                 Location/Qualifiers
source                  1..1182
                        mol_type = protein
                        organism = Leptotrichia wadei
SEQUENCE: 300
MYMKITKIDG VSHYKKQDKG ILKKKWKDLD ERKQREKIEA RYNKQIESKI YKEFFRLKNK  60
KRIEKEEDQN IKSLYFFIKE LYLNEKNEEW ELKNINLEIL DDKERVIKGY KFKEDVYFFK  120
EGYKEYYLRI LFNNLIEKVQ NENREKVRKN KEFLDLKEIF KKYKNRKIDL LLKSINNNKI  180
NLEYKKENVN EEIYGINPTN DREMTFYELL KEIIEKKDEQ KSILEEKLDN FDITNFLENI  240
EKIFNEETEI NIIKGKVLNE LREYIKEKEE NNSDNKLKQI YNLELKKYIE NNFSYKKQKS  300
KSKNGKNDYL YLNFLKKIMF IEEVDEKKEI NKEKFKNKIN SNFKNLFVQH ILDYGKLLYY  360
KENDEYIKNT GQLETKDLEY IKTKETLIRK MAVLVSFAAN SYYNLFGRVS GDILGTEVVK  420
SSKTNVIKVG SHIFKEKMLN YFFDFEIFDA NKIVEILESI SYSIYNVRNG VGHFNKLILG  480
KYKKKDINTN KRIEEDLNNN EEIKGYFIKK RGEIERKVKE KFLSNNLQYY YSKEKIENYF  540
EVYEFEILKR KIPFAPNFKR IIKKGEDLFN NKNNKKYEYF KNFDKNSAEE KKEFLKTRNF  600
LLKELYYNNF YKEFLSKKEE FEKIVLEVKE EKKSRGNINN KKSGVSFQSI DDYDTKINIS  660
DYIASIHKKE MERVEKYNEE KQKDTAKYIR DFVEEIFLTG FINYLEKDKR LHFLKEEFSI  720
LCNNNNNVVD FNININEEKI KEFLKENDSK TLNLYLFFNM IDSKRISEFR NELVKYKQFT  780
KKRLDEEKEF LGIKIELYET LIEFVILTRE KLDTKKSEEI DAWLVDKLYV KDSNEYKEYE  840
EILKLFVDEK ILSSKEAPYY ATDNKTPILL SNFEKTRKYG TQSFLSEIQS NYKYSKVEKE  900
NIEDYNKKEE IEQKKKSNIE KLQDLKVELH KKWEQNKITE KEIEKYNNTT RKINEYNYLK  960
NKEELQNVYL LHEMLSDLLA RNVAFFNKWE RDFKFIVIAI KQFLRENDKE KVNEFLNPPD  1020
NSKGKKVYFS VSKYKNTVEN IDGIHKNFMN LIFLNNKFMN RKIDKMNCAI WVYFRNYIAH  1080
FLHLHTKNEK ISLISQMNLL IKLFSYDKKV QNHILKSTKT LLEKYNIQIN FEISNDKNEV  1140
FKYKIKNRLY SKKGKMLGKN NKFEILENEF LENVKAMLEY SE                   1182

SEQ ID NO: 301          moltype = AA  length = 1437
FEATURE                 Location/Qualifiers
REGION                  1..1437
                        note = Lachnospiraceae bacterium
source                  1..1437
                        mol_type = protein
                        organism = unidentified
SEQUENCE: 301
MKISKVREEN RGAKLTVNAK TAVVSENRSQ EGILYNDPSR YGKSRKNDED RDRYIESRLK  60
SSGKLYRIFN EDKNKRETDE LQWFLSEIVK KINRRNGLVL SDMLSVDDRA FEKAFEKYAE  120
LSYTNRRNKV SGSPAFETCG VDAATAERLK GIISETNFIN RIKNNIDNKV SEDIIDRIIA  180
KYLKKSLCRE RVKRGLKKLL MNAFDLPYSD PDIDVQRDFI DYVLEDFYHV RAKSQVSRSI  240
KNMNMPVQPE GDGKFAITVS KGGTESGNKR SAEKEAFKKF LSDYASLDER VRDDMLRRMR  300
RLVVLYFYGS DDSKLSDVNE KFDVWEDHAA RRVDNREFIK LPLENKLANG KTDKDAERIR  360
KNTVKELYRN QNIGCYRQAV KAVEEDNNGR YFDDKMLNMF FIHRIEYGVE KIYANLKQVT  420
EFKARTGYLS EKIWKDLINY ISIKYIAMGK AVYNYAMDEL NASDKKEIEL GKISEEYLSG  480
ISSFDYELIK AEEMLQRETA VYVAFAARHL SSQTVELDSE NSDFLLLKPK GTMDKNDKNK  540
LASNNILNFL KDKETLRDTI LQYFGGHSLW TDFPFDKYLA GGKDDVDFLT DLKDVIYSMR  600
NDSFHYATEN HNNGKWNKEL ISAMFEHETE RMTVVMKDKF YSNNLPMFYK NDDLKKLLID  660
LYKDNVERAS QVPSFNKVFV RKNFPALVRD KDNLGIELDL KADADKGENE LKFYNALYYM  720
FKEIYYNAFL NDKNVRERFI TKATKVADNY DRNKERNLKD RIKSAGSDEK KKLREQLQNY  780
IAENDFGQRI KNIVQVNPDY TLAQICQLIM TEYNQQNNGC MQKKSAARKD INKDSYQHYK  840
MLLLVNLRKA FLEFIKENYA FVLKPYKHDL CDKADFVPDF AKYVKPYAGL ISRVAGSSEL  900
QKWYIVSRFL SPAQANHMLG FLHSYKQYVW DIYRRASETG TEINHSIAED KIAGVDITDV  960
DAVIDLSVKL CGTISSEISD YFKDDEVYAE YISSYLDFEY DGGNYKDSLN RFCNSDAVND  1020
QKVALYYDGE HPKLNRNIIL SKLYGERRFL EKITDRVSRS DIVEYYKLKK ETSQYQTKGI  1080
FDSEDEQKNI KKFQEMKNIV EFRDLMDYSE IADELQGQLI NWIYLRERDL MNFQLGYHYA  1140
CLNNDSNKQA TYVTLDYQGK KNRKINGAIL YQICAMYING LPLYYVDKDS SEWTVSDGKE  1200
STGAKIGEFY RYAKSFENTS DCYASGLEIF ENISEHDNIT ELRNYIEHFR YYSSFDRSFL  1260
GIYSEVFDRF FTYDLKYRKN VPTILYNILL QHFVNVRFEF VSGKKMIGID KKDRKIAKEK  1320
ECARITIREK NGVYSEQFTY KLKNGTVYVD ARDKRYLQSI IRLLFYPEKV NMDEMIEVKE  1380
KKKPSDNNTG KGYSKRDRQQ DRKEYDKYKE KKKKEGNFLS GMGGNINWDE INAQLKN    1437

SEQ ID NO: 302          moltype = AA  length = 1385
FEATURE                 Location/Qualifiers
source                  1..1385
                        mol_type = protein
                        organism = Clostridium aminophilum
SEQUENCE: 302
MKFSKVDHTR SAVGIQKATD SVHGMLYTDP KKQEVNDLDK RFDQLNVKAK RLYNVFNQSK  60
AEEDDDEKRF GKVVKKLNRE LKDLLFHREV SRYNSIGNAK YNYYGIKSNP EEIVSNLGMV  120
ESLKGERDPQ KVISKLLLYY LRKGLKPGTD GLRMILEASC GLRKLSGDEK ELKVFLQTLD  180
EDFEKKTFKK NLIRSIENQN MAVQPSNEGD PIIGITQGRF NSQKNEEKSA IERMMSMYAD  240
LNEDHREDVL RKLRRLNVLY FNVDTEKTEE PTLPGEVDTN PVFEVWHDHE KGKENDRQFA  300
TFAKILTEDR ETRKKEKLAV KEALNDLKSA IRDHNIMAYR CSIKVTEQDK DGLFFEDQRI  360
NRFWIHHIES AVERILASIN PEKLYKLRIG YLGEKVWKDL LNYLSIKYIA VGKAVFHFAM  420
EDLGKTGQDI ELGKLSNSVS GGLTSFDYEQ IRADETLQRQ LSVEVAFAAN NLFRAVVGQT  480
GKKIEQSKSE ENEEDFLLWK AEKIAESIKK EGEGNTLKSI LQFFGGASSW DLNHFCAAYG  540
NESSALGYET KFADDLRKAI YSLRNETFHF TTLNKGSFDW NAKLIGDMFS HEAATGIAVE  600
RTRFYSNNLP MFYRESDLKR IMDHLYNTYH PRASQVPSFN SVFVRKNFRL FLSNTLNTNT  660
```

-continued

```
SFDTEVYQKW ESGVYYLFKE IYYNSFLPSG DAHHLFFEGL RRIRKEADNL PIVGKEAKKR  720
NAVQDFGRRC DELKNLSLSA ICQMIMTEYN EQNNGNRKVK STREDKRKPD IFQHYKMLLL  780
RTLQEAFAIY IRREEFKFIF DLPKTLYVMK PVEEFLPNWK SGMFDSLVER VKQSPDLQRW  840
YVLCKFLNGR LLNQLSGVIR SYIQFAGDIQ RRAKANHNRL YMDNTQRVEY YSNVLEVVDF  900
CIKGTSRFSN VFSDYFRDED AYADYLDNYL QFKDEKIAEV SSFAALKTFC NEEEVKAGIY  960
MDGENPVMQR NIVMAKLFGP DEVLKNVVPK VTREEIEEYY QLEKQIAPYR QNGYCKSEED  1020
QKKLLRFQRI KNRVEFQTIT EFSEIINELL GQLISWSFLR ERDLLYFQLG FHYLCLHNDT  1080
EKPAEYKEIS REDGTVIRNA ILHQVAAMYV GGLPVYTLAD KKLAAFEKGE ADCKLSISKD  1140
TAGAGKKIKD FFRYSKYVLI KDRMLTDQNQ KYTIYLAGLE LFENTDEHDN ITDVRKYVDH  1200
FKYYATSDEN AMSILDLYSE IHDRFFTYDM KYQKNVANML ENILLRHFVL IRPEFFTGSK  1260
KVGEGKKITC KARAQIEIAE NGMRSEDFTY KLSDGKKNIS TCMIAARDQK YLNTVARLLY  1320
YPHEAKKSIV DTREKKNNKK TNRGDGTFNK QKGTARKEKD NGPREFNDTG FSNTPFAGFD  1380
PFRNS                                                              1385

SEQ ID NO: 303          moltype = AA  length = 1051
FEATURE                 Location/Qualifiers
source                  1..1051
                        mol_type = protein
                        organism = Listeria newyorkensis
SEQUENCE: 303
MKITKMRVDG RTIVMERTSK EGQLGYEGID GNKTTEIIFD KKKESFYKSI LNKTVRKPDE  60
KEKNRRKQAI NKAINKEITE LMLAVLHQEV PSQKLHNLKS LNTESLTKLF KPKFQNMISY  120
PPSKGAEHVQ FCLTDIAVPA IRDLDEIKPD WGIFFEKLKP YTDWAESYIH YKQTTIQKSI  180
EQNKIQSPDS PRKLVLQKYV TAFLNGEPLG LDLVAKKYKL ADLAESFKLV DLNEDKSANY  240
KIKACLQQHQ RNILDELKED PELNQYGIEV KKYIQRYFPI KRAPNRSKHA RADFLKKELI  300
ESTVEQQFKN AVYHYVLEQG KMEAYELTDP KTKDLQDIRS GEAFSFKFIN ACAFASNNLK  360
MILNPECEKD ILGKGNFKKN LPNSTTRSDV VKKMIPFFSD ELQNVNFDEA IWAIRGSIQQ  420
IRNEVYHCKK HSWKSILKIK GFEFEPNNMK YADSDMQKLM DKDIAKIPEF IEEKLKSSGV  480
VRFYRHDELQ SIWEMKQGFS LLTTNAPFVP SFKRVYAKGH DYQTSKNRYY NLDLTTFDIL  540
EYGEEDFRAR YFLTKLVYYQ QFMPWFTADN NAFRDAANFV LRLNKNRQQD AKAFINIREV  600
EEGEMPRDYM GYVQGQIAIH EDSIEDTPNH FEKFISQVFI KGFDRHMRSA NLKFIKNPRN  660
QGLEQSEIEE MSFDIKVEPS FLKNKDDYIA FWIFCKMLDA RHLSELRNEM IKYDGHLTGE  720
QEIIGLALLG VDSRENDWKQ FFSSEREYEK IMKGYVVEEL YQREPYRQSD GKTPILFRGV  780
EQARKYGTET VIQRLFDANP EFKVSKCNLA EWERQKETIE ETIKRRKELH NEWAKNPKKP  840
QNNAFFKEYK ECCDAIDAYN WHKNKTTLAY VNELHHLLIE ILGRYVGYVA IADRDFQCMA  900
NQYFKHSGIT ERVEYWGDNR LKSIKKLDTF LKKEGLFVSE KNARNHIAHL NYLSLKSECT  960
LLYLSERLRE IFKYDRKLKN AVSKSLIDIL DRHGMSVVFA NLKENKHRLV IKSLEPKKLR  1020
HLGGKKIDGG YIETNQVSEE YCGIVKRLLE M                                1051

SEQ ID NO: 304          moltype = AA  length = 1344
FEATURE                 Location/Qualifiers
REGION                  1..1344
                        note = Eubacterium rectale genome assembly T1815
source                  1..1344
                        mol_type = protein
                        organism = unidentified
SEQUENCE: 304
MLRRDKEVKK LYNVFNQIQV GTKPKKWNND EKLSPEENER RAQQKNIKMK NYKWREACSK  60
YVESSQRIIN DVIFYSYRKA KNKLRYMRKN EDILKKMQEA EKLSKFSGGK LEDFVAYTLR  120
KSLVVSKYDT QEFDSLAAMV VFLECIGKNN ISDHEREIVC KLLELIRKDF SKLDPNVKGS  180
QGANIVRSVR NQNMIVQPQG DRFLFPQVYA KENETVTNKN VEKEGLNEFL LNYANLDDEK  240
RAESLRKLRR ILDVYFSAPN HYEKDMDITL SDNIEKEKFN VWEKHECGKK ETGLFVDIPD  300
VLMEAEAENI KLDAVVEKRE RKVLNDRVRK QNIICYRYTR AVVEKYNSNE PLFFENNAIN  360
QYWIHHIENA VERILKNCKA GKLFKLRKGY LAEKVWKDAI NLISIKYIAL GKAVYNFALD  420
DIWKDKKNKE LGIVDERIRN GITSFDYEMI KAHENLQREL AVDIAFSVNN LARAVCDMSN  480
LGNKESDFLL WKRNDIADKL KNKDDMASVS AVLQFFGGKS SWDINIFKDA YKGKKKYNYE  540
VRFIDDLRKA IYCARNENFH FKTALVNDEK WNTELFGKIF ERETEFCLNV EKDRFYSNNL  600
YMFYQVSELR NMLDHLYSRS VSRAAQVPSY NSVIVRTAFP EYITNVLGYQ KPSYDADTLG  660
KWYSACYYLL KEIYYNSFLQ SDRALQLFEK SVKTLSWDDK KQQRAVDNFK DHFSDIKSAC  720
TSLAQVCQIY MTEYNQQNNQ IKKVRSSNDS IFDQPVYQHY KVLLKKAIAN AFADYLKNNK  780
DLFGFIGKPF KANEIREIDK EQFLPDWTSR KYEALCIEVS GSQELQKWYI VGKFLNARSL  840
NLMVGSMRSY IQYVTDIKRR AASIGNELHV SVHDVEKVEK WVQVIEVCSL LASRTSNQFE  900
DYFNDKDDYA RYLKSYVDFS NVDMPSEYSA LVDFSNEEQS DLYVDPKNPK VNRNIVHSKL  960
FAADHILRDI VEPVSKDNIE EFYSQKAEIA YCKIKGKEIT AEEQKAVLKY QKLKNRVELR  1020
DIVEYGEIIN ELLGQLINWS FMRERDLLYF QLGFHYDCLR NDSKKPEGYK NIKVDENSIK  1080
DAILYQIIGM YVNGVTVYAP EKDGDKLKEQ CVKGGVGVKV SAFHRYSKYL GLNEKTLYNA  1140
GLEIFEVVAE HEDIINLRNG IDHFKYYLGD YRSMLSIYSE VFDRFFTYDI KYQKNVLNLL  1200
QNILLRHNVI VEPILESGFK TIGEQTKPGA KLSIRSIKSD TFQYKVKGGT LITDAKDERY  1260
LETIRKILYY AENEEDNLKK SVVVTNADKY EKNKESDDQN KQKEKKNKDN KGKKNEETKS  1320
DAEKNNNERL SYNPFANLNF KLSN                                         1344

SEQ ID NO: 305          moltype = AA  length = 1285
FEATURE                 Location/Qualifiers
source                  1..1285
                        mol_type = protein
                        organism = Herbinix hemicellulosilytica
SEQUENCE: 305
MKLTRRRISG NSVDQKITAA FYRDMSQGLL YYDSEDNDCT DKVIESMDFE RSWRGRILKN  60
GEDDKNPFYM FVKGLVGSND KIVCEPIDVD SDPDNLDILI NKNLTGFGRN LKAPDSNDTL  120
```

```
ENLIRKIQAG IPEEEVLPEL KKIKEMIQKD IVNRKEQLLK SIKNNRIPFS LEGSKLVPST  180
KKMKWLFKLI DVPNKTFNEK MLEKYWEIYD YDKLKANITN RLDKTDKKAR SISRAVSEEL  240
REYHKNLRTN YNRFVSGDRP AAGLDNGGSA KYNPDKEEFL LFLKEVEQYF KKYFPVKSKH  300
SNKSKDKSLV DKYKNYCSYK VVKKEVNRSI INQLVAGLIQ QGKLLYYFYY NDTWQEDFLN  360
SYGLSYIQVE EAFKKSVMTS LSWGINRLTS FFIDDSNTVK FDDITTKKAK EAIESNYFNK  420
LRTCSRMQDH FKEKLAFFYP VYVKDKKDRP DDDIENLIVL VKNAIESVSY LRNRTFHFKE  480
SSLLELLKEL DDKNSGQNKI DYSVAAEFIK RDIENLYDVF REQIRSLGIA EYYKADMISD  540
CFKTCGLEFA LYSPKNSLMP AFKNVYKRGA NLNKAYIRDK GPKETGDQGQ NSYKALEEYR  600
ELTWYIEVKN NDQSYNAYKN LLQLIYYHAF LPEVRENEAL ITDFINRTKE WNRKETEERL  660
NTKNNKKHKN FDENDDITVN TYRYESIPDY QGESLDDYLK VLQRKQMARA KEVNEKEEGN  720
NNYIQFIRDV VVWAFGAYLE NKLKNYKNEL QPPLSKENIG LNDTLKELFP EEKVKSPFNI  780
KCRFSISTFI DNKGKSTDNT SAEAVKTDGK EDEKDKKNIK RKDLLCFYLF LRLLDENEIC  840
KLQHQFIKYR CSLKERRFPG NRTKLEKETE LLAELEELME LVRFTMPSIP EISAKAESGY  900
DTMIKKYFKD FIEKKVFKNP KTSNLYYHSD SKTPVTRKYM ALLMRSAPLH LYKDIFKGYY  960
LITKKECLEY IKLSNIIKDY QNSLNELHEQ LERIKLKSEK QNGKDSLYLD KKDFYKVKEY  1020
VENLEQVARY KHLQHKINFE SLYRIFRIHV DIAARMVGYT QDWERDMHFL FKALVYNGVL  1080
EERRFEAIFN NNDDNNDGRI VKKIQNNLNN KNRELVSMLC WNKKLNKNEF GAIIWKRNPI  1140
AHLNHFTQTE QNSKSSLESL INSLRILLAY DRKRQNAVTK TINDLLLNDY HIRIKWEGRV  1200
DEGQIYFNIK EKEDIENEPI IHLKHLHKKD CYIYKNSYMF DKQKEWICNG IKEEVYDKSI  1260
LKCIGNLFKF DYEDKNKSSA NPKHT                                      1285

SEQ ID NO: 306         moltype = AA  length = 1120
FEATURE                Location/Qualifiers
source                 1..1120
                       mol_type = protein
                       organism = Listeria seeligeri
SEQUENCE: 306
MWISIKTLIH HLGVLFFCDY MYNRREKKII EVKTMRITKV EVDRKKVLIS RDKNGGKLVY  60
ENEMQDNTEQ IMHHKKSSFY KSVVNKTICR PEQKQMKKLV HGLLQENSQE KIKVSDVTKL  120
NISNFLNHRF KKSLYYFPEN SPDKSEEYRI EINLSQLLED SLKKQQGTFI CWESFSKDME  180
LYINWAENYI SSKTKLIKKS IRNNRIQSTE SRSGQLMDRY MKDILNKNKP FDIQSVSEKY  240
QLEKLTSALK ATFKEAKKND KEINYKLKST LQNHERQIIE ELKENSELNQ FNIEIRKHLE  300
TYFPIKKTNR KVGDIRNLEI GEIQKIVNHR LKNKIVQRIL QEGKLASYEI ESTVNSNSLQ  360
KIKIEEAFAL KFINACLFAS NNLRNMVYPV CKKDILMIGE FKNSFKEIKH KKFIRQWSQF  420
FSQEITVDDI ELASWGLRGA IAPIRNEIIH LKKHSWKKFF NNPTFKVKKS KIINGKTKDV  480
TSEFLYKETL FKDYFYSELD SVPELIINKM ESSKILDYYS SDQLNQVFTI PNFELSLLTS  540
AVPFAPSFKR VYLKGFDYQN QDEAQPDYNL KLNIYNEKAF NSEAFQAQYS LFKMVYYQVF  600
LPQFTTNNDL FKSSVDFILT LNKERKGYAK AFQDIRKMNK DEKPSEYMSY IQSQLMLYQK  660
KQEEKEKINH FEKFINQVFI KGFNSFIEKN RLTYICHPTK NTVPENDNIE IPFHTDMDDS  720
NIAFWLMCKL LDAKQLSELR NEMIKFSCSL QSTEEISTFT KAREVIGLAL LNGEKGCNDW  780
KELFDDKEAW KKNMSLYVSE ELLQSLPYTQ EDGQTPVINR SIDLVKKYGT ETILEKLFSS  840
SDDYKVSAKD IAKLHEYDVT EKIAQQESLH KQWIEKPGLA RDSAWTKKYQ NVINDISNYQ  900
WAKTKVELTQ VRHLHQLTID LLSRLAGYMS IADRDFQFSS NYILERENSE YRVTSWILLS  960
ENKNKNKYND YELYNLKNAS IKVSSKNDPQ LKVDLKQLRL TLEYLELFDN RLKEKRNNIS  1020
HFNYLNGQLG NSILELFDDA RDVLSYDRKL KNAVSKSLKE ILSSHGMEVT FKPLYQTNHH  1080
LKIDKLQPKK IHHLGEKSTV SSNQVSNEYC QLVRTLLTMK                       1120

SEQ ID NO: 307         moltype = AA  length = 1154
FEATURE                Location/Qualifiers
source                 1..1154
                       mol_type = protein
                       organism = Paludibacter propionicigenes
SEQUENCE: 307
MRVSKVKVKD GGKDKMVLVH RKTTGAQLVY SGQPVSNETS NILPEKKRQS FDLSTLNKTI  60
IKFDTAKKQK LNVDQYKIVE KIFKYPKQEL PKQIKAEEIL PFLNHKFQEP VKYWKNGKEE  120
SFNLTLLIVE AVQAQDKRKL QPYYDWKTWY IQTKSDLLKK SIENNRIDLT ENLSKRKKAL  180
LAWETEFTAS GSIDLTHYHK VYMTDVLCKM LQDVKPLTDD KGKINTNAYH RGLKKALQNH  240
QPAIFGTREV PNEANRADNQ LSIYHLEVVK YLEHYFPIKT SKRRNTADDI AHYLKAQTLK  300
TTIEKQLVNA IRANIIQQGK TNHHELKADT TSNDLIRIKT NEAFVLNLTG TCAFAANNIR  360
NMVDNEQTND ILGKGDFIKS LLKDNTNSQL YSFFFGEGLS TNKAEKETQL WGIRGAVQQI  420
RNNVNHYKKD ALKTVFNISN FENPTITDPK QQTNYADTIY KARFINELEK IPEAFAQQLK  480
TGGAVSYYTI ENLKSLLTTF QFSLCRSTIP FAPGFKKVFN GGINYQNAKQ DESFYELMLE  540
QYLRKENFAE ESYNARYFML KLIYNNLFLP GFTTDRKAFA DSVGFVQMQN KKQAEKVNPR  600
KKEAYAFEAV RPMTAADSIA DYMAYVQSEL MQEQNKKEEK VAEETRINFE KFVLQVFIKG  660
FDSFLRAKEF DFVQMPQPQL TATASNQQKA DKLNQLEASI TADCKLTPQY AKADDATHIA  720
FYVFCKLLDA AHLSNLRNEL IKFRESVNEF KFHHLLEIIE ICLLSADVVP TDYRDLYSSE  780
ADCLARLRPF IEQGADITNW SDLFVQSDKH SPVIHANIEL SVKYGTTKLL EQIINKDTQF  840
KTTEANFTAW NTAQKSIEQL IKQREDHHEQ WVKAKNADDK EKQERKREKS NFAQKFIEKH  900
GDDYLDICDY INTYNWLDNK MHFVHLNRLH GLTIELLGRM AGFVALFDRD FQFFDEQQIA  960
DEFKLHGFVN LHSIDKKLNE VPTKKIKEIY DIRNKIIQIN GNKINESVRA NLIQFISSKR  1020
NYYNNAFLHV SNDEIKEKQM YDIRNHIAHF NYLTKDAADF SLIDLINELR ELLHYDRKLK  1080
NAVSKAFIDL FDKHGMILKL KLNADHKLKV ESLEPKKIYH LGSSAKDKPE YQYCTNQVMM  1140
AYCNMCRSLL EMKK                                                  1154

SEQ ID NO: 308         moltype = AA  length = 1159
FEATURE                Location/Qualifiers
source                 1..1159
                       mol_type = protein
                       organism = Leptotrichia buccalis
```

```
SEQUENCE: 308
MKVTKVGGIS HKKYTSEGRL VKSESEENRT DERLSALLNM RLDMYIKNPS STETKENQKR  60
IGKLKKFFSN KMVYLKDNTL SLKNGKKENI DREYSETDIL ESDVRDKKNF AVLKKIYLNE  120
NVNSEELEVF RNDIKKKLNK INSLKYSFEK NKANYQKINE NNIEKVEGKS KRNIIYDYYR  180
ESAKRDAYVS NVKEAFDKLY KEEDIAKLVL EIENLTKLEK YKIREFYHEI IGRKNDKENF  240
AKIIYEEIQN VNNMKELIEK VPDMSELKKS QVFYKYYLDK EELNDKNIKY AFCHFVEIEM  300
SQLLKNYVYK RLSNISNDKI KRIFEYQNLK KLIENKLLNK LDTYVRNCGK YNYYLQDGEI  360
ATSDFIARNR QNEAFLRNII GVSSVAYFSL RNILETENEN DITGRMRGKT VKNNKGEEKY  420
VSGEVDKIYN ENKKNEVKEN LKMFYSYDFN MDNKNEIEDF FANIDEAISS IRHGIVHFNL  480
ELEGKDIFAF KNIAPSEISK KMFQNEINEK KLKLKIFRQL NSANVFRYLE KYKILNYLKR  540
TRFEFVNKNI PFVPSFTKLY SRIDDLKNSL GIYWKTPKTN DDNKTKEIID AQIYLLKNIY  600
YGEFLNYFMS NNGNFFEISK EIIELNKNDK RNLKTGFYKL QKFEDIQEKI PKEYLANIQS  660
LYMINAGNQD EEEKDTYIDF IQKIFLKGFM TYLANNGRLS LIYIGSDEET NTSLAEKKQE  720
FDKFLKKYEQ NNNIKIPYEI NEFLREIKLG NILKYTERLN MFYLILKLLN HKELTNLKGS  780
LEKYQSANKE EAFSDQLELI NLLNLDNNRV TEDFELEADE IGKFLDFNGN KVKDNKELKK  840
FDTNKIYFDG ENIIKHRAFY NIKKYGMLNL LEKIADKAGY KISIEELKKY SNKKNEIEKN  900
HKMQENLHRK YARPRKDEKF TDEDYESYKQ AIENIEEYTH LKNKVEFNEL NLLQGLLLRI  960
LHRLVGYTSI WERDLRFRLK GEFPENQYIE EIFNFENKKN VKYKGGQIVE KYIKFYKELH  1020
QNDEVKINKY SSANIKVLKQ EKKDLYIRNY IAHFNYIPHA EISLLEVLEN LRKLLSYDRK  1080
LKNAVMKSVV DILKEYGFVA TFKIGADKKI GIQTLESEKI VHLKNLKKKK LMTDRNSEEL  1140
CKLVKIMFEY KMEEKKSEN                                                1159

SEQ ID NO: 309          moltype = AA  length = 1389
FEATURE                 Location/Qualifiers
source                  1..1389
                        mol_type = protein
                        organism = Leptotrichia shahii
SEQUENCE: 309
MGNLFGHKRW YEVRDKKDFK IKRKVKVKRN YDGNKYILNI NENNNKEKID NNKFIRKYIN  60
YKKNDNILKE FTRKFHAGNI LFKLKGKEGI IRIENNDDFL ETEEVVLYIE AYGKSEKLKA  120
LGITKKKIID EAIRQGITKD DKKIEIKRQE NEEEIEIDIR DEYTNKTLND CSIILRIIEN  180
DELETKKSIY EIFKNINMSL YKIIEKIIEN ETEKVFENRY YEEHLREKLL KDDKIDVILT  240
NFMEIREKIK SNLEILGFVK FYLNVGGDKK KSKNKKMLVE KILNINVDLT VEDIADFVIK  300
ELEFWNITKR IEKVKKVNNE FLEKRRNRTY IKSYVLLDKH EKFKIERENK KDKIVKFFVE  360
NIKNNSIKEK IEKILAEFKI DELIKKLEKE LKKGNCDTEI FGIFKKHYKV NFDSKKFSKK  420
SDEEKELYKI IYRYLKGRIE KILVNEQKVR LKKMEKIEIE KILNESILSE KILKRVKQYT  480
LEHIMYLGKL RHNDIDMTTV NTDDFSRLHA KEELDLELIT FFASTNMELN KIFSRENINN  540
DENIDFFGGD REKNYVLDKK ILNSKIKIIR DLDFIDNKNN ITNNFIRKFT KIGTNERNRI  600
LHAISKERDL QGTQDDYNKV INIIQNLKIS DEEVSKALNL DVVFKDKKNI ITKINDIKIS  660
EENNNDIKYL PSFSKVLPEI LNLYRNNPKN EPFDTIETEK IVLNALIYVN KELYKKLILE  720
DDLEENESKN IFLQELKKTL GNIDEIDENI IENYYKNAQI SASKGNNKAI KKYQKKVIEC  780
YIGYLRKNYE ELFDFSDFKM NIQEIKKQIK DINDNKTYER ITVKTSDKTI VINDDFEYII  840
SIFALLNSNA VINKIRNRFF ATSVWLNTSE YQNIIDILDE IMQLNTLRNE CITENWNLNL  900
EEFIQKMKEI EKDFDDFKIQ TKKEIFNNYY EDIKNNILTE FKDDINGCDV LEKKLEKIVI  960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNLFLNIGNP NFDKIYGLIS  1080
NDIKMADAKF LFNIDGKNIR KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VFEVFKKDVN LDYDELKKKF KLIGNNDILE RLMKPKKVSV LELESYNSDY IKNLIIELLT  1380
KIENTNDTL                                                           1389

SEQ ID NO: 310          moltype = AA  length = 1182
FEATURE                 Location/Qualifiers
source                  1..1182
                        mol_type = protein
                        organism = Leptotrichia wadei
SEQUENCE: 310
MYMKITKIDG VSHYKKQDKG ILKKKWKDLD ERKQREKIEA RYNKQIESKI YKEFFRLKNK  60
KRIEKEEDQN IKSLYFFIKE LYLNEKNEEW ELKNINLEIL DDKERVIKGY KFKEDVYFFK  120
EGYKEYYLRI LFNNLIEKVQ NENREKVRKN KEFLDLKEIF KKYKNRKIDL LLKSINNNKI  180
NLEYKKENVN EEIYGINPTN DREMTFYELL KEIIEKKDEQ KSILEEKLDN FDITNFLENI  240
EKIFNEETEI NIIKGKVLNE LREYIKEKEE NNSDNKLKQI YNLELKKYIE NNFSYKKQKS  300
KSKNGKNDYL YLNFLKKIMF IEEVDEKKEI NKEKFKNKIN SNFKNLFVQH ILDYGKLLYY  360
KENDEYIKNT GQLETKDLEY IKTKETLIRK MAVLVSFAAN SYYNLFGRVS GDILGTEVVK  420
SSKTNVIKVG SHIFKEKMLN YFFDFEIFDA NKIVEILESI SYSIYNVRNG VGHFNKLILG  480
KYKKKDINTN KRIEEDLNNN EEIKGYFIKK RGEIERKVKE KFLSNNLQYY YSKEKIENYF  540
EVYEFEILKR KIPFAPNFKR IIKKGEDLFN NKNNKKYEYF KNFDKNSAEE KKEFLKTRNF  600
LLKELYYNNF YKEFLSKKEE FEKIVLEVKE EKKSRGNINN KKSGVSFQSI DDYDTKINIS  660
DYIASIHKKE MERVEKYNEE KQKDTAKYIR DFVEEIFLTG FINYLEKDKR LHFLKEEFSI  720
LCNNNNNVVD FNININEEKI KEFLKENDSK TLNLYLFFNM IDSKRISEFR NELVKYKQFT  780
KKRLDEEKEF LGIKIELYET LIEFVILTRE KLDTKKSEEI DAWLVDKLYV KDSNEYKEYE  840
EILKLFVDEK ILSSKEAPYY ATDNKTPILL SNFEKTRKYG TQSFLSEIQS NYKYSKVEKE  900
NIEDYNKKEE IEQKKKSNIE KLQDLKVELH KKWEQNKITE KEIEKYNNTT RKINEYNYLK  960
NKEELQNVYL LHEMLSDLLA RNVAFFNKWE RDFKFIVIAI KQFLRENDKE KVNEFLNPPD  1020
NSKGKKVYFS VSKYKNTVEN IDGIHKNFMN LIFLNNKFMN RKIDKMNCAI WVYFRNYIAH  1080
FLHLHTKNEK ISLISQMNLL IKLFSYDKKV QNHILKSTKT LLEKYNIQIN FEISNDKNEV  1140
FKYKIKNRLY SKKGKMLGKN NKFEILENEF LENVKAMLEY SE                      1182
```

```
SEQ ID NO: 311          moltype = AA  length = 1385
FEATURE                 Location/Qualifiers
REGION                  1..1385
                        note = Leptotrichia sp. oral taxon 879
source                  1..1385
                        mol_type = protein
                        organism = unidentified
SEQUENCE: 311
MGNLFGHKRW YEVRDKKDFK IKRKVKVKRN YDGNKYILNI NENNNKEKID NNKFIGEFVN  60
YKKNNNVLKE FKRKFHAGNI LFKLKGKEEI IRIENNDDFL ETEEVVLYIE VYGKSEKLKA  120
LEITKKKIID EAIRQGITKD DKKIEIKRQE NEEEIEIDIR DEYTNKTLND CSIILRIIEN  180
DELETKKSIY EIFKNINMSL YKIIEKIIEN ETEKVFENRY YEEHLREKLL KDNKIDVILT  240
NFMEIREKIK SNLEIMGFVK FYLNVSGDKK KSENKKMFVE KILNTNVDLT VEDIVDFIVK  300
ELKFWNITKR IEKVKKFNNE FLENRRNRTY IKSYVLLDKH EKFKIERENK KDKIVKFFVE  360
NIKNNSIKEK IEKILAEFKI NELIKKLEKE LKKGNCDTEI FGIFKKHYKV NFDSKKFSNK  420
SDEEKELYKI IYRYLKGRIE KILVNEQKVR LKKMEKIEIE KILNESILSE KILKRVKQYT  480
LEHIMYLGKL RHNDIVKMTV NTDDFSRLHA KEELDLELIT FFASTNMELN KIFNGKEKVT  540
DFFGFNLNGQ KITLKEKVPS FKLNILKKLN FINNENNIDE KLSHFYSFQK EGYLLRNKIL  600
HNSYGNIQET KNLKGEYENV EKLIKELKVS DEEISKSLSL DVIFEGKVDI INKINSLKIG  660
EYKDKKYLPS FSKIVLEITR KFREINKDKL FDIESEKIIL NAVKYVNKIL YEKITSNEEN  720
EFLKTLPDKL VKKSNNKKEN KNLLSIEEYY KNAQVSSSKG DKKAIKKYQN KVTNAYLEYL  780
ENTFTEIIDF SKFNLNYDEI KTKIEERKDN KSKIIIDSIS TNINITNDIE YIISIFALLN  840
SNTYINKIRN RFFATSVWLE KQNGTKEYDY ENIISILDEV LLINLLRENN ITDILDLKNA  900
IIDAKIVEND ETYIKNYIFE SNEEKLKKRL FCEELVDKED IRKIFEDENF KFKSFIKKNE  960
IGNFKINFGI LSNLECNSEV EAKKIIGKNS KKLESFIQNI IDEYKSNIRT LFSSEFLEKY  1020
KEEIDNLVED TESENKNKFE KIYYPKEHKN ELYIYKKNLF LNIGNPNFDK IYGLISKDIK  1080
NVDTKILFDD DIKKNKISEI DAILKNLNDK LNGYSNDYKA KYVNKLKEND DFFAKNIQNE  1140
NYSSFGEFEK DYNKVSEYKK IRDLVEFNYL NKIESYLIDI NWKLAIQMAR FERDMHYIVN  1200
GLRELGIIKL SGYNTGISRA YPKRNGSDGF YTTTAYYKFF DEESYKKFEK ICYGFGIDLS  1260
ENSEINKPEN ESIRNYISHF YIVRNPFADY SIAEQIDRVS NLLSYSTRYN NSTYASVFEV  1320
FKKDVNLDYD ELKKKFRLIG NNDILERLMK PKKVSVLELE SYNSDYIKNL IIELLTKIEN  1380
TNDTL                                                        1385

SEQ ID NO: 312          moltype = AA  length = 1152
FEATURE                 Location/Qualifiers
source                  1..1152
                        mol_type = protein
                        organism = Leptotrichia wadei
SEQUENCE: 312
MKVTKVDGIS HKKYIEEGKL VKSTSEENRT SERLSELLSI RLDIYIKNPD NASEEENRIR  60
RENLKKFFSN KVLHLKDSVL YLKNRKEKNA VQDKNYSEED ISEYDLKNKN SFSVLKKILL  120
NEDVNSEELE IFRKDVEAKL NKINSLKYSF EENKANYQKI NENNVEKVGG KSKRNIIYDY  180
YRESAKRNDY INNVQEAFDK LYKKEDIEKL FFLIENSKKH EKYKIREYYH KIIGRKNDKE  240
NFAKIIYEEI QNVNNIKELI EKIPDMSELK KSQVFYKYYL DKEELNDKNI KYAFCHFVEI  300
EMSQLLKNYV YKRLSNISND KIKRIFEYQN LKKLIENKLL NKLDTYVRNC GKYNYYLQVG  360
EIATSDFIAR NRQNEAFLRN IIGVSSVAYF SLRNILETEN ENDITGRMRG KTVKNNKGEE  420
KYVSGEVDKI YNENKQNEVK ENLKMFYSYD FNMDNKNEIE DFFANIDEAI SSIRHGIVHF  480
NLELEGKDIF AFKNIAPSEI SKKMFQNEIN EKKLKLKIFK QLNSANVFNY YEKDVIIKYL  540
KNTKFNFVNK NIPFVPSFTK LYNKIEDLRN TLKFFWSVPK DKEEKDAQIY LLKNIYYGEF  600
LNKFVKNSKV FFKITNEVIK INKQRNQKTG HYKYQKFENI EKTVPVEYLA IIQSREMINN  660
QDKEEKNTYI DFIQQIFLKG FIDYLNKNNL KYIESNNNND NNDIFSKIKI KKDNKEKYDK  720
ILKNYEKHNR NKEIPHEINE FVREIKLGKI LKYTENLNMF YLILKLLNHK ELTNLKGSLE  780
KYQSANKEET FSDELELINL LNLDNNRVTE DFELEANEIG KFLDFNENKI KDRKELKKFD  840
TNKIYFDGEN IIKHRAFYNI KKYGMLNLLE KIADKAKYKI SLKELKEYSN KKNEIEKNYT  900
MQQNLHRKYA RPKKDEKFND EDYKEYEKAI GNIQKYTHLK NKVEFNELNL LQGLLLKILH  960
RLVGYTSIWE RDLRFRLKGE FPENHYIEEI FNFDNSKNVK YKSGQIVEKY INFYKELYKD  1020
NVEKRSIYSD KKVKKLKQEK KDLYIRNYIA HFNYIPHAEI SLLEVLENLR KLLSYDRKLK  1080
NAIMKSIVDI LKEYGFVATF KIGADKKIEI QTLESEKIVH LKNLKKKKLM TDRNSEELCE  1140
LVKVMFEYKA LE                                                1152

SEQ ID NO: 313          moltype = AA  length = 1197
FEATURE                 Location/Qualifiers
source                  1..1197
                        mol_type = protein
                        organism = Leptotrichia wadei
SEQUENCE: 313
MKVTKIDGLS HKKFEDEGKL VKFRNNKNIN EIKERLKKLK ELKLDNYIKN PENVKNKDKD  60
AEKETKIRRT NLKKYFSEII LRKEDEKYIL KKTKKFKDIN QEIDYYDVKS KKNQQEIFDV  120
LKEILELKIK ETEKEEIITF DSEKLKKVFG EDFVKKEAKI KAIEKSLKIN KANYKKDSIK  180
IGDDKYSNVK GENKRSRIYE YYKKSENLKK FEENIREAFE KLYTEENIKE LYSKIEEILK  240
KTHLKSIVRE FYQNEIIGES EFSKKNGDGI SILYNQIKDS IKKEENFIEF IENTGNLELK  300
ELTKSQIFYK YFLENEELND ENIKFAFCYF VEIEVNNLLK ENVYKIKRFN ESNKKRIENI  360
FEYGKLKKLI VYKLENKLNN YVRNCGKYNY HMENGDIATS DINMRNRQTE AFLRSIIGVS  420
SFGYFSLRNI LGVNDDDFYE TEEDLTKKER RNLEKAKEDI TIKNTFDEVV VKSFQKKGIY  480
NIKENLKMFY GDSFDNADKD ELKQFFVNML NAITSIRHRV VHYNMNTNSE NIFNFSGIEV  540
SKLLKSIFEK ETDKRELKLK IFRQLNSAGV FDYWENRKID KYLENIEFKF VNKNIPFVPS  600
FTKLYNRIDN LKGNNALNLG YINIPKRKEA RDSQIYLLKN IYYGEFVEKF VNNNDNFEKI  660
FREIIEINKK DGTNTKTKFY KLEKFETLKA NAPIEYLEKL QSLHQINYNR EKVEEDKDIY  720
```

-continued

```
VDFVQKIFLK GFINYLQGSD LLKSLNLLNL KKDEAIANKK SFYDEKLKLW QNNGSNLSKM  780
PEEIYDYIKK IKINKINYSD RMSIFYLLLK LIDHKELTNL RGNLEKYVSM NKNKIYSEEL  840
NIVNLVSLDN NKVRANFNLK PEDIGKFLKT ETSIRNINQL NNFSEIFADG ENVIKHRSFY  900
NIKKYGILDL LEKIVDKADL KITKEEIKKY ENLQNELKRN DFYKIQERIH RNYNQKPFLI  960
KNNEKDFNDY KKAIENIQNY TQLKNKIEFN DLNLLQSLLF RILHRLAGYT SLWERDLQFK  1020
LKGEYPENKY IDEIFNFDNS KNKIYNEKNE RGGSVVSKYG YFLVEKDGEI QRKNARDKKK  1080
NKIIKKEGLE IRNYIAHFNY IPDATKSILE ILEELRNLLK YDRKLKNAVM KSIKDIFKEY  1140
GLIIEFKISH VNNSEKIEVL NVDSEKIKHL KNNGLVTTRN SEDLCELIKM MLEYKKS      1197

SEQ ID NO: 314         moltype = AA  length = 1437
FEATURE                Location/Qualifiers
REGION                 1..1437
                       note = Lachnospiraceae bacterium NK4A179
source                 1..1437
                       mol_type = protein
                       organism = unidentified
SEQUENCE: 314
MKISKVREEN RGAKLTVNAK TAVVSENRSQ EGILYNDPSR YGKSRKNDED RDRYIESRLK  60
SSGKLYRIFN EDKNKRETDE LQWFLSEIVK KINRRNGLVL SDMLSVDDRA FEKAFEKYAE  120
LSYTNRRNKV SGSPAFETCG VDAATAERLK GIISETNFIN RIKNNIDNKV SEDIIDRIIA  180
KYLKKSLCRE RVKRGLKKLL MNAFDLPYSD PDIDVQRDFI DYVLEDFYHV RAKSQVSRSI  240
KNMNMPVQPE GDGKFAITVS KGGTESGNKR SAEKEAFKKF LSDYASLDER VRDDMLRRMR  300
RLVVLYFYGS DDSKLSDVNE KFDVWEDHAA RRVDNREFIK LPLENKLANG KTDKDAERIR  360
KNTVKELYRN QNIGCYRQAV KAVEEDNNGR YFDDKMLNMF FIHRIEYGVE KIYANLKQVT  420
EFKARTGYLS EKIWKDLINY ISIKYIAMGK AVYNYAMDEL NASDKKEIEL GKISEEYLSG  480
ISSFDYELIK AEEMLQRETA VYVAFAARHL SSQTVELDSE NSDFLLLKPK GTMDKNDKNK  540
LASNNILNFL KDKETLRDTI LQYFGGHSLW TDFPFDKYLA GGKDDVDFLT DLKDVIYSMR  600
NDSFHYATEN HNNGKWNKEL ISAMFEHETE RMTVVMKDKF YSNNLPMFYK NDDLKKLLID  660
LYKDNVERAS QVPSFNKVFV RKNFPALVRD KDNLGIELDL KADADKGENE LKFYNALYYM  720
FKEIYYNAFL NDKNVRERFI TKATKVADNY DRNKERNLKD RIKSAGSDEK KKLREQLQNY  780
IAENDFGQRI KNIVQVNPDY TLAQICQLIM TEYNQQNNGC MQKKSAARKD INKDSYQHYK  840
MLLLVNLRKA FLEFIKENYA FVLKPYKHDL CDKADFVPDF AKYVKPYAGL ISRVAGSSEL  900
QKWYIVSRFL SPAQANHMLG FLHSYKQYVW DIYRRASETG TEINHSIAED KIAGVDITDV  960
DAVIDLSVKL CGTISSEISD YFKDDEVYAE YISSYLDFEY DGGNYKDSLN RFCNSDAVND  1020
QKVALYYDGE HPKLNRNIIL SKLYGERRFL EKITDRVSRS DIVEYYKLKK ETSQYQTKGI  1080
FDSEDEQKNI KKFQEMKNIV EFRDLMDYSE IADELQGQLI NWIYLRERDL MNFQLGYHYA  1140
CLNNDSNKQA TYVTLDYQGK KNRKINGAIL YQICAMYING LPLYYVDKDS SEWTVSDGKE  1200
STGAKIGEFY RYAKSFENTS DCYASGLEIF ENISEHDNIT ELRNYIEHFR YYSSFDRSFL  1260
GIYSEVFDRF FTYDLKYRKN VPTILYNILL QHFVNVRFEF VSGKKMIGID KKDRKIAKEK  1320
ECARITIREK NGVYSEQFTY KLKNGTVYVD ARDKRYLQSI IRLLFYPEKV NMDEMIEVKE  1380
KKKPSDNNTG KGYSKRDRQQ DRKEYDKYKE KKKKEGNFLS GMGGNINWDE INAQLKN      1437

SEQ ID NO: 315         moltype = AA  length = 1285
FEATURE                Location/Qualifiers
source                 1..1285
                       mol_type = protein
                       organism = Rhodobacter capsulatus
SEQUENCE: 315
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA AALYEHLHVD EKRIDGQPKR  180
NPKTDKFAPG LVVARALGIE SSVLPRGMAR LARNWGEEEI QTYFVVDVAA SVKEVAKAAV  240
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRSSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTDARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FRVEIYVPPK SNTSKLNAAD LVRID                                    1285

SEQ ID NO: 316         moltype = AA  length = 1334
FEATURE                Location/Qualifiers
REGION                 1..1334
                       note = Lachnospiraceae bacterium NK4A144
source                 1..1334
                       mol_type = protein
                       organism = unidentified
SEQUENCE: 316
```

-continued

```
MKISKVDHTR MAVAKGNQHR RDEISGILYK DPTKTGSIDF DERFKKLNCS AKILYHVFNG  60
IAEGSNKYKN IVDKVNNNLD RVLFTGKSYD RKSIIDIDTV LRNVEKINAF DRISTEEREQ  120
IIDDLLEIQL RKGLRKGKAG LREVLLIGAG VIVRTDKKQE IADFLEILDE DFNKTNQAKN  180
IKLSIENQGL VVSPVSRGEE RIFDVSGAQK GKSSKKAQEK EALSAFLLDY ADLDKNVRFE  240
YLRKIRRLIN LYFYVKNDDV MSLTEIPAEV NLEKDFDIWR DHEQRKEENG DFVGCPDILL  300
ADRDVKKSNS KQVKIAERQL RESIREKNIK RYRFSIKTIE KDDGTYFFAN KQISVFWIHR  360
IENAVERILG SINDKKLYRL RLGYLGEKVW KDILNFLSIK YIAVGKAVFN FAMDDLQEKD  420
RDIEPGKISE NAVNGLTSFD YEQIKADEML QREVAVNVAF AANNLARVTV DIPQNGEKED  480
ILLWNKSDIK KYKKNSKKGI LKSILQFFGG ASTWNMKMFE IAYHDQPGDY EENYLYDIIQ  540
IIYSLRNKSF HFKTYDHGDK NWNRELIGKM IEHDAERVIS VEREKFHSNN LPMFYKDADL  600
KKILDLLYSD YAGRASQVPA FNTVLVRKNF PEFLRKDMGY KVHFNNPEVE NQWHSAVYYL  660
YKEIYYNLFL RDKEVKNLFY TSLKNIRSEV SDKKQKLASD DFASRCEEIE DRSLPEICQI  720
IMTEYNAQNF GNRKVKSQRV IEKNKDIFRH YKMLLIKTLA GAFSLYLKQE RFAFIGKATP  780
IPYETTDVKN FLPEWKSGMY ASFVEEIKNN LDLQEWYIVG RFLNGRMLNQ LAGSLRSYIQ  840
YAEDIERRAA ENRNKLFSKP DEKIEACKKA VRVLDLCIKI STRISAEFTD YFDSEDDYAD  900
YLEKYLKYQD DAIKELSGSS YAALDHFCNK DDLKFDIYVN AGQKPILQRN IVMAKLFGPD  960
NILSEVMEKV TESAIREYYD YLKKVSGYRV RGKCSTEKEQ EDLLKFQRLK NAVEFRDVTE  1020
YAEVINELLG QLISWSYLRE RDLLYFQLGF HYMCLKNKSF KPAEYVDIRR NNGTIIHNAI  1080
LYQIVSMYIN GLDFYSCDKE GKTLKPIETG KGVGSKIGQF IKYSQYLYND PSYKLEIYNA  1140
GLEVFENIDE HDNITDLRKY VDHFKYYAYG NKMSLLDLYS EFFDRFFTYD MKYQKNVVNV  1200
LENILLRHFV IFYPKFGSGK KDVGIRDCKK ERAQIEISEQ SLTSEDFMFK LDDKAGEEAK  1260
KFPARDERYL QTIAKLLYYP NEIEDMNRFM KKGETINKKV QFNRKKKITR KQKNNSSNEV  1320
LSSTMGYLFK NIKL                                                  1334

SEQ ID NO: 317          moltype = AA  length = 1385
FEATURE                 Location/Qualifiers
source                  1..1385
                        mol_type = protein
                        organism = Clostridium aminophilum
SEQUENCE: 317
MKFSKVDHTR SAVGIQKATD SVHGMLYTDP KKQEVNDLDK RFDQLNVKAK RLYNVFNQSK  60
AEEDDDEKRF GKVVKKLNRE LKDLLFHREV SRYNSIGNAK YNYYGIKSNP EEIVSNLGMV  120
ESLKGERDPQ KVISKLLLYY LRKGLKPGTD GLRMILEASC GLRKLSGDEK ELKVFLQTLD  180
EDFEKKTFKK NLIRSIENQN MAVQPSNEGD PIIGITQGRF NSQKNEEKSA IERMMSMYAD  240
LNEDHREDVL RKLRRLNVLY FNVDTEKTEE PTLPGEVDTN PVFEVWHDHE KGKENDRQFA  300
TFAKILTEDR ETRKKEKLAV KEALNDLKSA IRDHNIMAYR CSIKVTEQDK DGLFFEDQRI  360
NRFWIHHIES AVERILASIN PEKLYKLRIG YLGEKVWKDL LNYLSIKYIA VGKAVFHFAM  420
EDLGKTGQDI ELGKLSNSVS GGLTSFDYEQ IRADETLQRQ LSVEVAFAAN NLFRAVVGQT  480
GKKIEQSKSE ENEEDFLLWK AEKIAESIKK EGEGNTLKSI LQFFGGASSW DLNHFCAAYG  540
NESSALGYET KFADDLRKAI YSLRNETFHF TTLNKGSFDW NAKLIGDMFS HEAATGIAVE  600
RTRFYSNNLP MFYRESDLKR IMDHLYNTYH PRASQVPSFN SVFVRKNFRL FLSNTLNTNT  660
SFDTEVYQKW ESGVYYLFKE IYYNSFLPSG DAHHLFFEGL RRIRKEADNL PIVGKEAKKR  720
NAVQDFGRRC DELKNLSLSA ICQMIMTEYN EQNNGNRKVK STREDKRKPD IFQHYKMLLL  780
RTLQEAFAIY IRREEFKFIF DLPKTLYVMK PVEEFLPNWK SGMFDSLVER VKQSPDLQRW  840
YVLCKFLNGR LLNQLSGVIR SYIQFAGDIQ RRAKANHNRL YMDNTQRVEY YSNVLEVVDF  900
CIKGTSRFSN VFSDYFRDED AYADYLDNYL QFKDEKIAEV SSFAALKTFC NEEEVKAGIY  960
MDGENPVMQR NIVMAKLFGP DEVLKNVVPK VTREEIEEYY QLEKQIAPYR QNGYCKSEED  1020
QKKLLRFQRI KNRVEFQTIT EFSEIINELL GQLISWSFLR ERDLLYFQLG FHYLCLHNDT  1080
EKPAEYKEIS REDGTVIRNA ILHQVAAMYV GGLPVYTLAD KKLAAFEKGE ADCKLSISKD  1140
TAGAGKKIKD FFRYSKYVLI KDRMLTDQNQ KYTIYLAGLE LFENTDEHDN ITDVRKYVDH  1200
FKYYATSDEN AMSILDLYSE IHDRFFTYDM KYQKNVANML ENILLRHFVL IRPEFFTGSK  1260
KVGEGKKITC KARAQIEIAE NGMRSEDFTY KLSDGKKNIS TCMIAARDQK YLNTVARLLY  1320
YPHEAKKSIV DTREKKNNKK TNRGDGTFNK QKGTARKEKD NGPREFNDTG FSNTPFAGFD  1380
PFRNS                                                            1385

SEQ ID NO: 318          moltype = AA  length = 1175
FEATURE                 Location/Qualifiers
source                  1..1175
                        mol_type = protein
                        organism = Carnobacterium gallinarum
SEQUENCE: 318
MRITKVKIKL DNKLYQVTMQ KEEKYGTLKL NEESRKSTAE ILRLKKASFN KSFHSKTINS  60
QKENKNATIK KNGDYISQIF EKLVGVDTNK NIRKPKMSLT DLKDLPKKDL ALFIKRKFKN  120
DDIVEIKNLD LISLFYNALQ KVPGEHFTDE SWADFCQEMM PYREYKNKFI ERKIILLANS  180
IEQNKGFSIN PETFSKRKRV LHQWAIEVQE RGDFSILDEK LSKLAEIYNF KKMCKRVQDE  240
LNDLEKSMKK GKNPEKEKEA YKKQKNFKIK TIWKDYPYKT HIGLIEKIKE NEELNQFNIE  300
IGKYFEHYFP IKKERCTEDE PYYLNSETIA TTVNYQLKNA LISYLMQIGK YKQFGLENQV  360
LDSKKLQEIG IYEGFQTKFM DACVFATSSL KNIIEPMRSG DILGKREFKE AIATSSFVNY  420
HHFFPYFPFE LKGMKDRESE LIPFGEQTEA KQMQNIWALR GSVQQIRNEI FHSFDKNQKF  480
NLPQLDKSNF EFDASENSTG KSQSYIETDY KFLFEAEKNQ LEQFFIERIK SSGALEYYPL  540
KSLEKLFAKK EMKFSLGSQV VAFAPSYKKL VKKGHSYQTA TEGTANYLGL SYYNRYELKE  600
ESFQAQYYLL KLIYQYVFLP NFSQGNSPAF RETVKAILRI NKDEARKKMK KNKKFLRKYA  660
FEQVREMEFK ETPDQYMSYL QSEMREEKVR KAEKNDKGFE KNITMNFEKL LMQIFVKGFD  720
VFLTTFAGKE LLLSSEEKVI KETEISLSKK INEREKTLKA SIQVEHQLVA TNSAISYWLF  780
CKLLDSRHLN ELRNEMIKFK QSRIKFNHTQ HAELIQNLLP IVELTILSND YDEKNDSQNV  840
DVSAYFEDKS LYETAPYVQT DDRTRVSFRP ILKLEKYHTK SLIEALLKDN PQFRVAATDI  900
QEWMHKREEI GELVEKRKNL HTEWAEGQQT LGAEKREEYR DYCKKIDRFN WKANKVTLTY  960
LSQLHYLITD LLGRMVGFSA LFERDLVYFS RSFSELGGET YHISDYKNLS GVLRLNAEVK  1020
PIKIKNIKVI DNEENPYKGN EPEVKPFLDR LHAYLENVIG IKAVHGKIRN QTAHLSVLQL  1080
```

-continued

```
ELSMIESMNN LRDLMAYDRK LKNAVTKSMI KILDKHGMIL KLKIDENHKN FEIESLIPKE  1140
IIHLKDKAIK TNQVSEEYCQ LVLALLTTNP GNQLN                             1175

SEQ ID NO: 319          moltype = AA  length = 1164
FEATURE                 Location/Qualifiers
source                  1..1164
                        mol_type = protein
                        organism = Carnobacterium gallinarum
SEQUENCE: 319
MRMTKVKING SPVSMNRSKL NGHLVWNGTT NTVNILTKKE QSFAASFLNK TLVKADQVKG  60
YKVLAENIFI IFEQLEKSNS EKPSVYLNNI RRLKEAGLKR FFKSKYHEEI KYTSEKNQSV  120
PTKLNLIPLF FNAVDRIQED KFDEKNWSYF CKEMSPYLDY KKSYLNRKKE ILANSIQQNR  180
GFSMPTAEEP NLLSKRKQLF QQWAMKFQES PLIQQNNFAV EQFNKEFANK INELAAVYNV  240
DELCTAITEK LMNFDKDKSN KTRNFEIKKL WKQHPHNKDK ALIKLFNQEG NEALNQFNIE  300
LGKYFEHYFP KTGKKESAES YYLNPQTIIK TVGYQLRNAF VQYLLQVGKL HQYNKGVLDS  360
QTLQEIGMYE GFQTKFMDAC VFASSSLRNI IQATTNEDIL TREKFKKELE KNVELKHDLF  420
FKTEIVEERD ENPAKKIAMT PNELDLWAIR GAVQRVRNQI FHQQINKRHE PNQLKVGSFE  480
NGDLGNVSYQ KTIYQKLFDA EIKDIEIYFA EKIKSSGALE QYSMKDLEKL FSNKELTLSL  540
GGQVVAFAPS YKKLYKQGYF YQNEKTIELE QFTDYDFSND VFKANYYLIK LIYHYVFLPQ  600
FSQANNKLFK DTVHYVIQQN KELNTTEKDK KNNKKIRKYA FEQVKLMKNE SPEKYMQYLQ  660
REMQEERTIK EAKKTNEEKP NYNFEKLLIQ IFIKGFDTFL RNFDLNLNPA EELVGTVKEK  720
AEGLRKRKER IAKILNVDEQ IKTGDEEIAF WIFAKLLDAR HLSELRNEMI KFKQSSVKKG  780
LIKNGDLIEQ MQPILELCIL SNDSESMEKE SFDKIEVFLE KVELAKNEPY MQEDKLTPVK  840
FRFMKQLEKY QTRNFIENLV IENPEFKVSE KIVLNWHEEK EKIADLVDKR TKLHEEWASK  900
AREIEEYNEK IKKNKSKKLD KPAEFAKFAE YKIICEAIEN FNRLDHKVRL TYLKNLHYLM  960
IDLMGRMVGF SVLFERDFVY MGRSYSALKK QSIYLNDYDT FANIRDWEVN ENKHLFGTSS  1020
SDLTFQETAE FKNLKKPMEN QLKALLGVTN HSFEIRNNIA HLHVLRNDGK GEGVSLLSCM  1080
NDLRKLMSYD RKLKNAVTKA IIKILDKHGM ILKLTNNDHT KPFEIESLKP KKIIHLEKSN  1140
HSFPMDQVSQ EYCDLVKKML VFTN                                         1164

SEQ ID NO: 320          moltype = AA  length = 1051
FEATURE                 Location/Qualifiers
source                  1..1051
                        mol_type = protein
                        organism = Listeria newyorkensis
SEQUENCE: 320
MKITKMRVDG RTIVMERTSK EGQLGYEGID GNKTTEIIFD KKKESFYKSI LNKTVRKPDE  60
KEKNRRKQAI NKAINKEITE LMLAVLHQEV PSQKLHNLKS LNTESLTKLF KPKFQNMISY  120
PPSKGAEHVQ FCLTDIAVPA IRDLDEIKPD WGIFFEKLKP YTDWAESYIH YKQTTIQKSI  180
EQNKIQSPDS PRKLVLQKYV TAFLNGEPLG LDLVAKKYKL ADLAESFKLV DLNEDKSANY  240
KIKACLQQHQ RNILDELKED PELNQYGIEV KKYIQRYFPI KRAPNRSKHA RADFLKKELI  300
ESTVEQQFKN AVYHYVLEQG KMEAYELTDP KTKDLQDIRS GEAFSFKFIN ACAFASNNLK  360
MILNPECEKD ILGKGNFKKN LPNSTTRSDV VKKMIPFFSD ELQNVNFDEA IWAIRGSIQQ  420
IRNEVYHCKK HSWKSILKIK GFEFEPNNMK YADSDMQKLM DKDIAKIPEF IEEKLKSSGV  480
VRFYRHDELQ SIWEMKQGFS LLTTNAPFVP SFKRVYAKGH DYQTSKNRYY NLDLTTFDIL  540
EYGEEDFRAR YFLTKLVYYQ QFMPWFTADN NAFRDAANFV LRLNKNRQQD AKAFINIREV  600
EEGEMPRDYM GYVQGQIAIH EDSIEDTPNH FEKFISQVFI KGFDRHMRSA NLKFIKNPRN  660
QGLEQSEIEE MSFDIKVEPS FLKNKDDYIA FWIFCKMLDA RHLSELRNEM IKYDGHLTGE  720
QEIIGLALLG VDSRENDWKQ FFSSEREYEK IMKGYVVEEL YQREPYRQSD GKTPILFRGV  780
EQARKYGTET VIQRLFDANP EFKVSKCNLA EWERQKETIE ETIKRRKELH NEWAKNPKKP  840
QNNAFFKEYK ECCDAIDAYN WHKNKTTLAY VNELHHLLIE ILGRYVGYVA IADRDFQCMA  900
NQYFKHSGIT ERVEYWGDNR LKSIKKLDTF LKKEGLFVSE KNARNHIAHL NYLSLKSECT  960
LLYLSERLRE IFKYDRKLKN AVSKSLIDIL DRHGMSVVFA NLKENKHRLV IKSLEPKKLR  1020
HLGGKKIDGG YIETNQVSEE YCGIVKRLLE M                                 1051

SEQ ID NO: 321          moltype = AA  length = 1340
FEATURE                 Location/Qualifiers
REGION                  1..1340
                        note = Lachnospiraceae bacterium MA2020
source                  1..1340
                        mol_type = protein
                        organism = unidentified
SEQUENCE: 321
MQISKVNHKH VAVGQKDRER ITGFIYNDPV GDEKSLEDVV AKRANDTKVL FNVFNTKDLY  60
DSQESDKSEK DKEIISKGAK FVAKSFNSAI TILKKQNKIY STLTSQQVIK ELKDKFGGAR  120
IYDDDIEEAL TETLKKSFRK ENVRNSIKVL IENAAGIRSS LSKDEEELIQ EYFVKQLVEE  180
YTKTKLQKNV VKSIKNQNMV IQPDSDSQVL SLSESRREKQ SSAVSSDTLV NCKEKDVLKA  240
FLTDYAVLDE DERNSLLWKL RNLVNLYFYG SESIRDYSYT KEKSVWKEHD EQKANKTLFI  300
DEICHITKIG KNGKEQKVLD YEENRSRCRK QNINYYRSAL NYAKNNTSGI FENEDSNHFW  360
IHLIENEVER LYNGIENGEE FKFETGYISE KVWKAVINHL SIKYIALGKA VYNYAMKELS  420
SPGDIEPGKI DDSYINGITS FDYEIIKAEE SLQRDISMNV VFATNYLACA TVDTDKDFLL  480
FSKEDIRSCT KKDGNLCKNI MQFWGGYSTW KNFCEEYLKD DKDALELLYS LKSMLYSMRN  540
SSFHFSTENV DNGSWDTELI GKLFEEDCNR AARIEKEKFY NNNLHMFYSS SLLEKVLERL  600
YSSHHERASQ VPSFNRVFVR KNFPSSLSEQ RITPKFTDSK DEQIWQSAVY YLCKEIYYND  660
FLQSKEAYKL FREGVKNLDK NDINNQKAAD SFKQAVVYYG KAIGNATLSQ VCQAIMTEYN  720
RQNNDGLKKK SAYAEKQNSN KYKHYPLFLK QVLQSAFWEY LDENKEIYGF ISAQIHKSNV  780
EIKAEDFIAN YSSQQYKKLV DKVKKTPELQ KWYTLGRLIN PRQANQFLGS IRNYVQFVKD  840
IQRRAKENGN PIRNYYEVLE SDSIIKILEM CTKLNGTTSN DIHDYFRDED EYAEYISQFV  900
NFGDVHSGAA LNAFCNSESE GKKNGIYYDG INPIVNRNWV LCKLYGSPDL ISKIISRVNE  960
```

-continued

```
NMIHDFHKQE DLIREYQIKG ICSNKKEQQD LRTFQVLKNR VELRDIVEYS EIINELYGQL  1020
IKWCYLRERD LMYFQLGFHY LCLNNASSKE ADYIKINVDD RNISGAILYQ IAAMYINGLP  1080
VYYKKDDMYV ALKSGKKASD ELNSNEQTSK KINYFLKYGN NILGDKKDQL YLAGLELFEN  1140
VAEHENIIIF RNEIDHFHYF YDRDRSMLDL YSEVFDRFFT YDMKLRKNVV NMLYNILLDH  1200
NIVSSFVFET GEKKVGRGDS EVIKPSAKIR LRANNGVSSD VFTYKVGSKD ELKIATLPAK  1260
NEEFLLNVAR LIYYPDMEAV SENMVREGVV KVEKSNDKKG KISRGSNTRS SNQSKYNNKS  1320
KNRMNYSMGS IFEKMDLKFD                                              1340

SEQ ID NO: 322          moltype = AA  length = 913
FEATURE                 Location/Qualifiers
REGION                  1..913
                        note = Leptotrichia sp. oral taxon 225
source                  1..913
                        mol_type = protein
                        organism = unidentified
SEQUENCE: 322
MKELIEKVPN VSELKKSQVF YKYYLNKEKL NDENIKYVFC HFVEIEMSKL LKNYVYKKPS  60
NISNDKVKRI FEYQSLKKLI ENKLLNKLDT YIRNCGKYSF YLQDGEIATS DFIVGNRQNE  120
AFLRNIIGVS SAAYFSLRNI LETENENDIT GKMRGKTVKN KKGEEKYISG EIDKLYDNNK  180
QNEVKKNLKM FYSYDFNMNS KKEIEDFFSN IDEAISSIRH GIVHFNLELE GKDIFTFKNI  240
VPSQISKKMF HDEINEKKLK LKIFKQLNSA NVFRYLEKYK ILNYLNRTRF EFVNKNIPFV  300
PSFTKLYSRI DDLKNSLCIY WKIPKANDNN KTKEITDAQI YLLKNIYYSE FLNYFMSNNG  360
NFFEIIKEII ELNKNDKRNL KTGFYKLQKF ENLQEKTPKE YLANIQSFYM IDAGNKDEEE  420
KDAYIDFIQK IFLKGFMTYL ANNGRLSLMY IGNDEQINTS LAEKKQEFDK FLKKYEQNNN  480
IKIPYEINEF LREIKLGNIL KYTERLNMFY LILKLLNHKE LTNLKGSLEK YQSANKEEAF  540
SDQLELINLL NLDNNRVTED FELEADEIGK FLDFNGNKVK DNKELKKFDT NKIYFDGENI  600
IKHRAFYNIK KYGMLNLLEK ISDEAKYKIS IEELKNYSNK KNEIEKNHTN QENLHRKYAR  660
PRKDEKFNDE DYKKYEKAIR NIQQYTHLKN KVEFNELNLL QSLLLRILHR LVGYTSIWER  720
DLRFRLKGEF PENQYIEEIF NFNNSKNVKY KNGQIVEKYI SFYKELYKDD TEKISIYSDK  780
KVKELKKEKK DLYIRNYIAH FNYIPNAEIS LLEVLENLRK LLSYDRKLKN AIMKSIVDIL  840
KEYGFVVTFK IEKDKKIRIE SLKSEEVVHL KKLKLKDNDK KKEPIKTYRN SKELCELVKV  900
MFEYKMKEKK SEN                                                     913
```

METHODS AND COMPOSITIONS FOR DETECTING A TARGET RNA

CROSS-REFERENCE

This application is a continuation of U.S. patent application Ser. No. 16/281,939, filed Feb. 21, 2019, which application is a continuation of Ser. No. 15/920,222, filed Mar. 13, 2018, issued as U.S. Pat. No. 10,494,664, which application is a divisional of U.S. patent application Ser. No. 15/467,922, filed Mar. 23, 2017, issued as U.S. Pat. No. 10,337,051, which application claims the benefit of U.S. Provisional Patent Application No. 62/351,172, filed Jun. 16, 2016, and U.S. Provisional Patent Application No. 62/378,156, filed Aug. 22, 2016, which applications are incorporated herein by reference in their entirety.

STATEMENT REGARDING FEDERALLY SPONSORED RE SEARCH

This invention was made with government support under Grant No. GM102706 awarded by the National Institutes of Health and under Grant No. 1244557 awarded by the National Science Foundation. The government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, "BERK-337CON5_SEQ_LIST.xml", created on Oct. 23, 2023 and having a size of 330,277 bytes. The contents of the Sequence Listing XML are incorporated herein by reference in their entirety.

INTRODUCTION

Bacterial adaptive immune systems employ CRISPRs (clustered regularly interspaced short palindromic repeats) and CRISPR-associated (Cas) proteins for RNA-guided nucleic acid cleavage. Although generally targeted to DNA substrates, the Type III and Type VI CRISPR systems direct interference complexes against single-stranded RNA (ssRNA) substrates. In Type VI CRISPR systems, the single-subunit C2c2 protein functions as an RNA-guided RNA endonuclease.

CRISPR-Cas systems confer adaptive immunity in bacteria and archaea via RNA-guided nucleic acid interference. Among the diverse CRISPR types, only the relatively rare Type VI CRISPR systems are believed to target single-stranded RNA substrates exclusively, an activity conferred by the large effector protein C2c2. The Type VI operons share common features of other CRISPR-Cas genomic loci, including CRISPR sequence arrays that serve as repositories of short viral DNA segments. To provide anti-viral immunity, processed CRISPR array transcripts (crRNAs) assemble with Cas protein-containing surveillance complexes that recognize nucleic acids bearing sequence complementarity to the virus derived segment of the crRNAs, known as the spacer.

The first step of immune surveillance requires processing of precursor crRNAs (pre-crRNAs), consisting of repeat sequences flanking viral spacer sequences, into individual functional crRNAs that each contain a single virally-derived sequence segment. CRISPR systems employ a variety of mechanisms to produce mature crRNAs, including the use of dedicated endonucleases (e.g., Cas6 or Cas5d in Type I and III systems), coupling of a host endonuclease (e.g., RNase III) with a trans-activating crRNA (tracrRNA, Type II systems), or a ribonuclease activity endogenous to the effector enzyme itself (e.g., Cpf1, from Type V systems).

SUMMARY

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample.

Provided are compositions and methods for detecting a single stranded target RNA, where the methods include (i) contacting a sample having a plurality of RNAs with (a) a C2c2 guide RNA that hybridizes with the single stranded target RNA, and (b) a C2c2 protein that cleaves RNAs of the sample; and (ii) measuring a detectable signal produced by the cleavage. Once a subject C2c2 protein is activated by a C2c2 guide RNA, which occurs when the sample includes a single stranded target RNA to which the guide RNA hybridizes (i.e., the sample includes the targeted single stranded target RNA), the C2c2 protein becomes an endoribonuclease that cleaves RNAs of the sample. Thus, when the targeted single stranded target RNA is present in the sample (e.g., in some cases above a threshold amount), the result is cleavage of RNA in the sample, which can be detected using any convenient detection method (e.g., using a labeled detector RNA).

In some cases, two or more C2c2 guide RNAs can be provided by using a precursor C2c2 guide RNA array, which can be cleaved by the C2c2 protein into individual guide RNAs, and this is independent of whether the C2c2 protein has intact HEPN1 and/or HEPN2 domains. Thus, also provided are methods of cleaving a precursor C2c2 guide RNA array into two or more C2c2 guide RNAs. In some cases, the C2c2 protein lacks a catalytically active HEPN1 domain and/or lacks a catalytically active HEPN2 domain.

BRIEF DESCRIPTION OF THE DRAWINGS

FIG. 7A: Top is SEQ ID NO: 27, Bottom is SEQ ID NO: 28. FIG. 7B: Top to bottom: SEQ ID NOs: 29-34.

FIG. 8A-8F provides amino acid sequences of various C2c2 polypeptides.

FIG. 9A-9C depict C2c2 family processing of precursor crRNA transcripts to generate mature crRNAs. FIG. 9C: left to right: SEQ ID NOs: 35-37.

FIG. 10A-10C depict the effect of structure and sequence of CRISPR repeats on LbuC2c2 mediated crRNA biogenesis. FIG. 10B: SEQ ID NO: 38.

FIG. 12A-12D depict two distinct ribonuclease activities of LbuC2c2.

FIG. 13A-13D depict C2c2-mediated sensitive visual detection of transcripts in complex mixtures.

FIG. 14 provides Table 2: various DNA substrates used in the studies described in Examples 8-12 and shown in FIG. 12A-12D. Top to bottom: SEQ ID NOs: 39-44.

FIG. 15 provides Table 3: various RNA substrates used in the studies described in Examples 8-12. Top to bottom: SEQ ID NOs: 45-102.

FIG. 16E: top to bottom: SEQ ID NOs: 103-106.

FIG. 18A: A.1 (SEQ ID NO: 125); A.4 (SEQ ID NO: 126); A.0 (SEQ ID NO: 127); B.0 (SEQ ID NO: 128); A.2 (SEQ ID NO: 129); and A.3 (SEQ ID NO: 130). FIG. 18B: SEQ ID NO: 131.

FIG. 19B, top to bottom: SEQ ID NOs: 132-135.

FIG. 30A-30I depict mapping of pre-crRNA processing by C2c2 in vitro and in vivo. a, Cleavage site mapping of LseC2c2 and LshCc2c2 cleavage of a single cognate pre-crRNA array. OH: alkaline hydrolysis ladder; T1: T1 RNase hydrolysis ladder. Cleavage reactions were performed with 100 nM C2c2 and <1 nM pre-crRNA. left (SEQ ID NO: 137); right (SEQ ID NO: 138) b-i, Re-analysis of LshC2c2 (b-f) and LseC2c2 (g-i) CRISPR array RNA sequencing experiments from Shmakov et al.[10] (FIG. S7 and FIG. 5, respectively). All reads (b,g) and filtered reads (55 nt or less; as per original Shmakov et al. analysis; c,h) were stringently aligned to each CRISPR array using Bowtie2 (see Methods). Detailed views of individual CRISPR repeat-spacers are shown for Lsh (d-f) and Lse (i). Differences in 5' end pre-crRNA processing are indicated by arrows below each sequence. BAM alignment files of the analysis are available. This mapping clearly indicates that the 5' ends of small RNA sequencing reads generated from Lsh pre-crRNAs map to a position 2 nts from the base of the predicted hairpin, in agreement with the in vitro processing data (a). This pattern holds for all mature crRNAs detected from both native expression in *L. shahii* and heterologous expression in *E. coli*. Unfortunately, the LseC2c2 crRNA sequencing data (used in g-i) is less informative due to low read depth, and each aligned crRNA exhibits a slightly different 5' end with little obvious uniformity. The mapping for one of the processed repeats (repeat-spacer 2; i) is in agreement with the data but only with low confidence due to the insufficient read depth. d: SEQ ID NO: 139; e: SEQ ID NO: 140; f: SEQ ID NO: 141 and i: SEQ ID NO: 142.

FIG. 38B: Flank-stem, top-bottom: SEQ ID NOs: 150-160.

FIG. 39A-39C depict CRISPR loci and crRNA repeat architecture for Cas13a homologs. FIG. 39B: top to bottom: SEQ ID NOs: 161-172.

FIG. 40A-40F depict residues important for pre-crRNA cleavage by LbuCas13a. FIG. 40B: top to bottom: SEQ ID NOs: 173-183. FIG. 40C: top to bottom: SEQ ID NOs: 184-194.

FIG. 42A-42D depict efficiencies of ssRNA by members of the Cas13a family.

FIG. 43B: top to bottom: SEQ ID NOs: 233-234.

FIG. 44A-44F depict crRNA exchangeability within the Cas13a family.

FIG. 46A-46D depict crRNA array processing by wild-type (WT) LbuCas13a and LbuCas13a R1079A/K1080A double mutant.

FIG. 48A-48B depict features of the LbuCas13a R1079A/K1080A double mutant relative to wild-type LbuCas13a.

FIG. 49 provides Table 4. "CRISPR Repeat Consensus": top to bottom: SEQ ID NOs: 235-250. "Mature crRNA handle": top to bottom: SEQ ID NOs: 251-262.

FIG. 50 provides Table 5. Top to bottom: SEQ ID NOs: 253-298.

FIG. 51 provides Table 6.

FIG. 52 provides Table 7.

FIG. 53 provides Table 8.

FIG. 54 provides Table 9.

FIG. 56A-56K provide amino acid sequences of various Cas13a polypeptides. *Listeria seeligeri* (SEQ ID NO: 1); *Paludibacter propionicigenes* (SEQ ID NO: 299); *Leptotrichia buccalis* (SEQ ID NO: 2); *Leptotrichia shahii* (SEQ ID NO: 3); *Leptotrichia wadei* F0279 (SEQ ID NO: 300); *Lachnospiraceae bacterium* NK4A179 (SEQ ID NO: 301); *Rhodobacter capsulatus* R121 (SEQ ID NO: 4); *Clostridium aminophilum* (SEQ ID NO: 302); *Listeria newyorkensis* (SEQ ID NO: 303); *Eubacterium rectale* genome assembly T1815 (SEQ ID NO: 304); *Herbinix hemicellulosilytica* (SEQ ID NO: 6).

FIG. 57A-57H provides an alignment of amino acid sequences of various Cas13a polypeptides. Sequences labeled 1-19 are SEQ ID NOs: 304-322, respectively.

DEFINITIONS

Figure 1A:
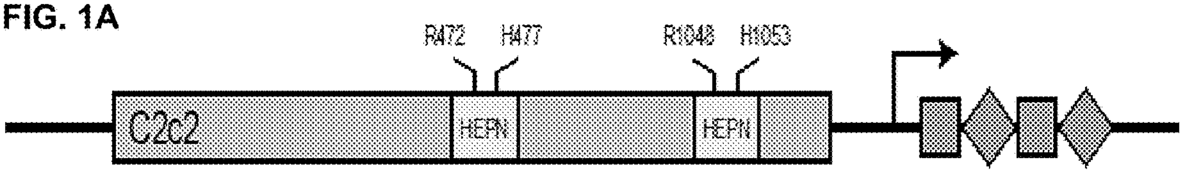
FIG. 1A-1E present schematics related to an endogenous C2c2 locus and experiments demonstrating heterologous expression and purification of recombinant C2c2 protein.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 3 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a C2c2 guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (dsRNA duplex) of a C2c2 guide RNA molecule; of a target nucleic acid base pairing with a C2c2 guide RNA) is considered complementary to both a U and to C. For example, when a G/U base-pair can be made at a given nucleotide position of a protein-binding segment (e.g., dsRNA duplex) of a C2c2 guide RNA molecule, the position is not considered to be non-complementary, but is instead considered to be complementary.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., *J. Mol. Biol.,* 1990, 215, 403-410; Zhang and Madden, *Genome Res.,* 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a C2c2 guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi.nlm.followed by nili.gov/ followed by BLAST, ebi.ac followed by .uk followed by /Tools/followed by msa followed by /tcoffee/, ebi. followed by ac.uk followed by /Tools/followed by msa/followed by muscle/, mafft. followed by cbrc. followed by jp/followed by alignment followed by /software/, http followed by:// followed by www followed by.sbg. followed by bio. followed by ic. followed by ac. followed by uk/followed by ~phyre2/. See, e.g., Altschul et al. (1990), *J. Mol. Biol.* 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a C2c2 guide RNA, etc.).

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., Cas9 guide RNA) or a coding sequence (e.g., Cas9 protein) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., C2c2 guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked"

refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as *Molecular Cloning: A Laboratory Manual,* 3rd Ed. (Sambrook et al., HaRBor Laboratory Press 2001); *Short Protocols in Molecular Biology,* 4th Ed. (Ausubel et al. eds., John Wiley & Sons 1999); *Protein Methods* (Bollag et al., John Wiley & Sons 1996); Nonviral Vectors for Gene Therapy (Wagner et al. eds., *Academic Press* 1999); Viral Vectors (Kaplift & Loewy eds., *Academic Press* 1995); Immunology Methods Manual (I. Lefkovits ed., *Academic Press* 1997); and *Cell and Tissue Culture: Laboratory Procedures in Biotechnology* (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the guide RNA" includes reference to one or more such guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample. The term "C2c2 guide RNA" is used herein interchangeably with "Cas13a guide RNA" and in some cases a guide RNA is referred to as a crRNA (e.g., "Cas13a crRNA"); the term "C2c2 protein" (or "C2c2 polypeptide") is used herein interchangeably with "Cas13a protein" (or "Cas13a polypeptide").

Methods of Detecting a Single-Stranded RNA

Provided are compositions and methods for detecting a single stranded target RNA, where the methods include (i) contacting a sample having a plurality of RNAs with (a) a C2c2 guide RNA that hybridizes with the single stranded target RNA, and (b) a C2c2 protein that cleaves RNAs present in the sample; and (ii) measuring a detectable signal produced by the cleavage. Once a subject C2c2 protein is activated by a C2c2 guide RNA, which occurs when the sample includes a single stranded target RNA to which the guide RNA hybridizes (i.e., the sample includes the targeted single stranded target RNA), the C2c2 protein is activated and functions as an endoribonuclease that non-specifically cleaves RNAs (including non-target RNAs) present in the sample. Thus, when the targeted single stranded target RNA is present in the sample (e.g., in some cases above a threshold amount), the result is cleavage of RNA (including non-target RNA) in the sample, which can be detected using any convenient detection method (e.g., using a labeled detector RNA). The contacting step is generally carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo. In some cases, the C2c2 guide RNA is provided as RNA; and the C2c2 protein is provided as protein per se. In some cases, the C2c2 guide RNA is provided as DNA encoding the guide RNA; and the C2c2 protein is provided as protein per se. In some cases, the C2c2 guide RNA is provided as RNA; and the C2c2 protein is provided as RNA encoding the C2c2 protein. In some cases, the C2c2 guide RNA is provided as DNA encoding the guide RNA; and C2c2 protein is provided as RNA encoding the C2c2 protein. In some cases, the C2c2 guide RNA is provided as RNA; and the C2c2 protein is provided as DNA comprising a nucleotide sequence encoding the C2c2 protein. In some cases, the C2c2 guide RNA is provided as DNA encoding the guide RNA; and the C2c2 protein is provided as DNA comprising a nucleotide sequence encoding the C2c2 protein. In some cases, a method of the present disclosure provides for substantially simultaneous detection of two different target RNAs (a first single-stranded target RNA and a second single-stranded target RNA) in a sample.

In some cases, two or more (e.g., 3 or more, 4 or more, 5 or more, or 6 or more) C2c2 guide RNAs can be provided by using a precursor C2c2 guide RNA array, which can be cleaved by the C2c2 protein into individual ("mature") guide RNAs; cleavage of a precursor C2c2 guide RNA is independent of whether the C2c2 protein has intact HEPN1 and/or HEPN2 domains. Thus, also provided are methods of cleaving a precursor C2c2 guide RNA array into two or more C2c2 guide RNAs. Thus a C2c2 guide RNA array can include more than one guide sequence. In some cases, a subject C2c2 guide RNA can include a handle from a precursor crRNA but does not necessarily have to include multiple guide sequences. In some cases, the C2c2 protein lacks a catalytically active HEPN1 domain and/or lacks a catalytically active HEPN2 domain. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

In some cases (e.g., when contacting with a C2c2 guide RNA and a C2c2 protein, when contacting with a precursor C2c2 guide RNA array and a C2c2 protein, and the like), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases the sample is contacted for 20 minutes or less prior to the measuring step. In some cases the sample is contacted for 10 minutes or less prior to the measuring step. In some cases the sample is contacted for 5 minutes or less prior to the measuring step. In some cases the sample is contacted for 1 minute or less prior to the measuring step. In some cases the sample is contacted for from 50 seconds to 60 seconds prior to the measuring step. In some cases the sample is contacted for from 40 seconds to 50 seconds prior to the measuring step. In some cases the sample is contacted for from 30 seconds to 40 seconds prior to the measuring step. In some cases the sample is contacted for from 20 seconds to 30 seconds prior to the measuring step. In some cases the sample is contacted for from 10 seconds to 20 seconds prior to the measuring step.

The present disclosure provides methods of detecting a single-stranded RNA in a sample comprising a plurality of RNAs (e.g., comprising a target RNA and a plurality of non-target RNAs). In some cases, the methods comprise: a) contacting the sample with: (i) a C2c2 guide RNA that hybridizes with the single stranded target RNA, and (ii) a C2c2 protein that cleaves RNAs present in the sample; and b) measuring a detectable signal produced by C2c2 protein-mediated RNA cleavage. In some cases, the methods comprise: a) contacting the sample with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and b) measuring a detectable signal produced by C2c2 protein-mediated RNA cleavage. In some cases, a method of the present disclosure provides for substantially simultaneous detection of two different target RNAs (a first single-stranded target RNA and a second single-stranded target RNA) in a sample.

A method of the present disclosure for detecting a single-stranded RNA (a single-stranded target RNA) in a sample comprising a plurality of RNAs (including the single stranded target RNA and a plurality of non-target RNAs) can detect a single-stranded target RNA with a high degree of sensitivity. In some cases, a method of the present disclosure can be used to detect a target single-stranded RNA present in a sample comprising a plurality of RNAs (including the single stranded target RNA and a plurality of non-target RNAs), where the target single-stranded RNA is present at one or more copies per $10^7$ non-target RNAs (e.g., one or more copies per $10^6$ non-target RNAs, one or more copies per $10^5$ non-target RNAs, one or more copies per $10^4$ non-target RNAs, one or more copies per $10^3$ non-target RNAs, one or more copies per $10^2$ non-target RNAs, one or more copies per 50 non-target RNAs, one or more copies per 20 non-target RNAs, one or more copies per 10 non-target RNAs, or one or more copies per 5 non-target RNAs).

In some cases, a method of the present disclosure can detect a target single-stranded RNA present in a sample comprising a plurality of RNAs (including the single stranded target RNA and a plurality of non-target RNAs), where the target single-stranded RNA is present at from one copy per $10^7$ non-target RNAs to one copy per 10 non-target RNAs (e.g., from 1 copy per $10^7$ non-target RNAs to 1 copy per $10^2$ non-target RNAs, from 1 copy per $10^7$ non-target RNAs to 1 copy per $10^3$ non-target RNAs, from 1 copy per $10^7$ non-target RNAs to 1 copy per $10^4$ non-target RNAs, from 1 copy per $10^7$ non-target RNAs to 1 copy per $10^5$ non-target RNAs, from 1 copy per $10^7$ non-target RNAs to 1 copy per $10^6$ non-target RNAs, from 1 copy per $10^6$ non-target RNAs to 1 copy per 10 non-target RNAs, from 1 copy per $10^6$ non-target RNAs to 1 copy per $10^2$ non-target RNAs, from 1 copy per $10^6$ non-target RNAs to 1 copy per $10^3$ non-target RNAs, from 1 copy per $10^6$ non-target RNAs to 1 copy per $10^4$ non-target RNAs, from 1 copy per $10^6$ non-target RNAs to 1 copy per $10^5$ non-target RNAs, from 1 copy per $10^5$ non-target RNAs to 1 copy per 10 non-target RNAs, from 1 copy per $10^5$ non-target RNAs to 1 copy per $10^2$ non-target RNAs, from 1 copy per $10^5$ non-target RNAs to 1 copy per $10^3$ non-target RNAs, or from 1 copy per $10^5$ non-target RNAs to 1 copy per $10^4$ non-target RNAs).

In some cases, a method of the present disclosure can detect a target single-stranded RNA present in a sample comprising a plurality of RNAs (including the single stranded target RNA and a plurality of non-target RNAs), where the target single-stranded RNA is present at from one copy per $10^7$ non-target RNAs to one copy per 100 non-target RNAs (e.g., from 1 copy per $10^7$ non-target RNAs to 1 copy per $10^2$ non-target RNAs, from 1 copy per $10^7$ non-target RNAs to 1 copy per $10^3$ non-target RNAs, from 1 copy per $10^7$ non-target RNAs to 1 copy per $10^4$ non-target RNAs, from 1 copy per $10^7$ non-target RNAs to 1 copy per $10^5$ non-target RNAs, from 1 copy per $10^7$ non-target RNAs to 1 copy per $10^6$ non-target RNAs, from 1 copy per $10^6$ non-target RNAs to 1 copy per 100 non-target RNAs, from 1 copy per $10^6$ non-target RNAs to 1 copy per $10^2$ non-target RNAs, from 1 copy per $10^6$ non-target RNAs to 1 copy per $10^3$ non-target RNAs, from 1 copy per $10^6$ non-target RNAs to 1 copy per $10^4$ non-target RNAs, from 1 copy per $10^6$ non-target RNAs to 1 copy per $10^5$ non-target RNAs, from 1 copy per $10^5$ non-target RNAs to 1 copy per 100 non-target RNAs, from 1 copy per $10^5$ non-target RNAs to 1 copy per $10^2$ non-target RNAs, from 1 copy per $10^5$ non-target RNAs to 1 copy per $10^3$ non-target RNAs, or from 1 copy per $10^5$ non-target RNAs to 1 copy per $10^4$ non-target RNAs).

In some cases, the threshold of detection, for a subject method of detecting a single stranded target RNA in a sample, is 10 nM or less. The term "threshold of detection" is used herein to describe the minimal amount of target RNA that must be present in a sample in order for detection to occur. Thus, as an illustrative example, when a threshold of detection is 10 nM, then a signal can be detected when a target RNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less.

In some cases, the threshold of detection (for detecting the single stranded target RNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target RNA at which the target RNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a single stranded target RNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a single stranded target RNA can be detected in a sample is in a range of from 800 fM to 100 pM. In some cases, the minimum concentration at which a single stranded target RNA can be detected in a sample is in a range of from 1 pM to 10 pM.

In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 500 fM (e.g., as low as 800 fM, as low as 1 pM, as low as 10 pM or as low as 100 pM). In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 1 pM.

In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 500 fM (e.g., as low as 800 fM, as low as 1 pM, as low as 10 pM or as low as 100 pM), and where the sample is contacted for 60 minutes or less prior to the measuring step (e.g., in some cases 40 minutes or less). In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 1 pM, and where the sample is contacted for 60 minutes or less prior to the measuring step (e.g., in some cases 40 minutes or less).

For example, in some cases, a method of the present disclosure provides for detection of a target RNA present in a sample at a concentration of 500 fM or more (e.g., 800 fM or more, 1 pM or more, 5 pM or more, 10 pM or more). In some cases, a method of the present disclosure provides for detection of a target RNA present in a sample at a concentration of 1 pM or more (e.g., 2 pM or more 5 pM or more, or 8 pM or more). In some cases, a method of the present disclosure provides for detection of a target RNA present in a sample at a concentration of 500 fM or more (e.g., 1 pM or more, 5 pM or more, 10 pM or more), where the sample is contacted for 60 minutes or less prior to the measuring step (e.g., in some cases 40 minutes or less). In some cases, a method of the present disclosure provides for detection of a target RNA present in a sample at a concentration of 1 pM or more (e.g., 2 pM or more 5 pM or more, or 8 pM or more) where the sample is contacted for 60 minutes or less prior to the measuring step (e.g., in some cases 40 minutes or less).

In some cases, a method of the present disclosure provides for detection of a target RNA present in a sample at a concentration of 10 nM or less. In some cases, a method of the present disclosure provides for detection of a target RNA present in a sample at a concentration of 5 nM or less. In some cases, a method of the present disclosure provides for detection of a target RNA present in a sample at a concentration of 1 nM or less. In some cases, a method of the present disclosure provides for detection of a target RNA present in a sample at a concentration of 0.5 nM or less. In some cases, a method of the present disclosure provides for detection of a target RNA present in a sample at a concentration of 0.1 nM or less. In some cases, a method of the present disclosure provides for detection of a target RNA present in a sample at a concentration of 0.05 nM or less. In some cases, a method of the present disclosure provides for detection of a target RNA present in a sample at a concentration of 0.01 nM or less. In some cases, a method of the present disclosure provides for detection of a target RNA present in a sample at a concentration of 0.005 nM or less. In some cases, a method of the present disclosure provides for detection of a target RNA present in a sample at a concentration of 0.001 nM or less. In some cases, a method of the present disclosure provides for detection of a target RNA present in a sample at a concentration of 0.0005 nM or less. In some cases, a method of the present disclosure provides for detection of a target RNA present in a sample at a concentration of 0.0001 nM or less. In some cases, a method of the present disclosure provides for detection of a target RNA present in a sample at a concentration of 0.00005 nM or less. In some cases, a method of the present disclosure provides for detection of a target RNA present in a sample at a concentration of 0.00001 nM or less.

In some cases, a method of the present disclosure provides for detection of a target RNA present in a sample at a concentration of from $10^{-6}$ nM to 1 nM, e.g., from $10^{-6}$ nM to $5\times10^{-6}$ nM, from $5\times10^{-6}$ nM to $10^{-5}$ nM, from $10^{-5}$ nM to $5\times10^{-5}$ nM, from $5\times10^{-5}$ nM to $10^{-4}$ nM, from $10^{-4}$ nM to $5\times10^{-4}$ nM, from $5\times10^{-4}$ nM to $10^{-3}$ nM, from $10^{-3}$ nM to $5\times10^{-3}$ nM, from $5\times10^{-3}$ nM to $10^{-2}$ nM, from $10^{-2}$ nM to $5\times10^{-2}$ nM, from $5\times10^{-2}$ nM to 0.1 nM, from 0.1 nM to 0.5 nM, from 0.5 nM to 1 nM, from 1 nM to 5 nM, or from 5 nM to 10 nM.

In some cases, a method of the present disclosure provides for detection of a target RNA present in a sample at a concentration of less than 10 nM. In some cases, a method of the present disclosure provides for detection of a target RNA present in a sample at a concentration of less than 5 nM. In some cases, a method of the present disclosure provides for detection of a target RNA present in a sample at a concentration of less than 1 nM. In some cases, a method of the present disclosure provides for detection of a target RNA present in a sample at a concentration of less than 0.5 nM. In some cases, a method of the present disclosure provides for detection of a target RNA present in a sample at a concentration of less than 0.1 nM. In some cases, a method of the present disclosure provides for detection of a target RNA present in a sample at a concentration of less than 0.05 nM. In some cases, a method of the present disclosure provides for detection of a target RNA present in a sample at a concentration of less than 0.01 nM. In some cases, a method of the present disclosure provides for detection of a target RNA present in a sample at a concentration of less than 0.005 nM. In some cases, a method of the present disclosure provides for detection of a target RNA present in a sample at a concentration of less than 0.001 nM. In some cases, a method of the present disclosure provides for detection of a target RNA present in a sample at a concentration of less than 0.0005 nM. In some cases, a method of the present disclosure provides for detection of a target RNA present in a sample at a concentration of less than 0.0001 nM. In some cases, a method of the present disclosure provides for detection of a target RNA present in a sample at a concentration of less than 0.00005 nM. In some cases, a method of the present disclosure provides for detection of a target RNA present in a sample at a concentration of less than 0.00001 nM.

In some cases, a method of the present disclosure can be used to determine the amount of a target RNA in a sample (e.g., a sample comprising the target RNA and a plurality of non-target RNAs). Determining the amount of a target RNA in a sample can comprise comparing the amount of detectable signal generated from a test sample to the amount of detectable signal generated from a reference sample. Determining the amount of a target RNA in a sample can comprise: measuring the detectable signal to generate a test measurement; measuring a detectable signal produced by a reference sample to generate a reference measurement; and comparing the test measurement to the reference measurement to determine an amount of target RNA present in the sample.

For example, in some cases, a method of the present disclosure for determining the amount of a target RNA in a sample comprises: a) contacting the sample (e.g., a sample comprising the target RNA and a plurality of non-target RNAs) with: (i) a C2c2 guide RNA that hybridizes with the single stranded target RNA, and (ii) a C2c2 protein that cleaves RNAs present in the sample; b) measuring a detectable signal produced by C2c2 protein-mediated RNA cleavage, generating a test measurement; c) measuring a detectable signal produced by a reference sample to generate a reference measurement; and d) comparing the test measurement to the reference measurement to determine an amount of target RNA present in the sample.

As another example, in some cases, a method of the present disclosure for determining the amount of a target RNA in a sample comprises: a) contacting the sample (e.g., a sample comprising the target RNA and a plurality of non-target RNAs) with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; b) measuring a detectable signal produced by C2c2 protein-mediated RNA cleavage, generating a test measurement; c) measuring a detectable signal produced by each of two or more reference samples to generate two or more reference measurements; and d) comparing the test measurement to the reference measurements to determine an amount of target RNA present in the sample.

Samples

A subject sample includes a plurality of target RNAs. The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) RNAs. A subject method can be used as a very sensitive way to detect a single stranded target RNA present in a complex mixture of RNAs. Thus, in some cases the sample includes 5 or more RNAs (e.g., 10 or more, 20 or more, 50 or more, 100 or more, 500 or more, 1,000 or more, or 5,000 or more RNAs) that differ from one another in sequence. In some cases, the sample includes 10 or more, 20 or more, 50 or more, 100 or more, 500 or more, 10' or more, $5\times10^3$ or more, $10^4$ or more, $5\times10^4$ or more, $10^5$ or more, $5\times10^5$ or more, $10^6$ or more $5\times10^6$ or more, or $10^7$ or more, RNAs that differ from one another in sequence. In some cases, the sample comprises from 10 to 20, from 20 to 50, from 50 to 100, from 100 to 500, from 500 to $10^3$, from $10^3$ to $5\times10^3$, from $5\times10^4$ to $10^4$, from $10^4$ to $5\times10^4$, from $5\times10^4$ to $10^5$, from $10^5$ to $5\times10^5$, from $5\times10^5$ to $10^6$, from $10^6$ to $5\times10^6$, or from $5\times10^6$ to $10^7$, or more than $10^7$, RNAs that differ from one another in sequence. In some cases, the sample comprises from 5 to $10^7$ RNAs that differ from one another in sequence (e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 RNAs that differ from one another in sequence). In some cases, the sample comprises from 5 to 50,000 RNAs that differ from one another in sequence (e.g., from 5 to 30,000, from 10 to 50,000, or from 10 to 30,000) RNAs that differ from one another in sequence). In some cases the sample includes 20 or more RNAs that differ from one another in sequence. In some cases, the sample includes RNAs from a cell lysate (e.g., a eukaryotic cell lysate, a mammalian cell lysate, a human cell lysate, a prokaryotic cell lysate, a plant cell lysate, and the like). For example, in some cases the sample includes expressed RNAs from a cell such as a eukaryotic cell, e.g., a mammalian cell such as a human cell.

The term "sample" is used herein to mean any sample that includes single stranded RNA. The sample can be derived from any source, e.g., the sample can be a synthetic combination of purified RNAs; the sample can be a cell lysate, an RNA-enriched cell lysate, or RNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., *Development* (2016) 143, 2862-2867 doi:10.1242/dev.138560.

A "sample" can include a single stranded target RNA and a plurality of non-target RNAs. In some cases, the target single-stranded RNA is present in the sample at one copy per 10 non-target RNAs, one copy per 20 non-target RNAs, one copy per 25 non-target RNAs, one copy per 50 non-target RNAs, one copy per 100 non-target RNAs, one copy per 500 non-target RNAs, one copy per $10^3$ non-target RNAs, one copy per $5\times10^3$ non-target RNAs, one copy per $10^4$ non-target RNAs, one copy per $5\times10^4$ non-target RNAs, one copy per $10^5$ non-target RNAs, one copy per $5\times10^5$ non-target RNAs, one copy per $10^6$ non-target RNAs, or less than one copy per $10^6$ non-target RNAs. In some cases, the target single-stranded RNA is present in the sample at from one copy per 10 non-target RNAs to 1 copy per 20 non-target RNAs, from 1 copy per 20 non-target RNAs to 1 copy per 50 non-target RNAs, from 1 copy per 50 non-target RNAs to 1 copy per 100 non-target RNAs, from 1 copy per 100 non-target RNAs to 1 copy per 500 non-target RNAs, from 1 copy per 500 non-target RNAs to 1 copy per $10^3$ non-target RNAs, from 1 copy per $10^3$ non-target RNAs to 1 copy per $5\times10^3$ non-target RNAs, from 1 copy per $5\times10^3$ non-target RNAs to 1 copy per $10^4$ non-target RNAs, from 1 copy per $10^4$ non-target RNAs to 1 copy per $10^5$ non-target RNAs, from 1 copy per $10^5$ non-target RNAs to 1 copy per $10^6$ non-target RNAs, or from 1 copy per $10^6$ non-target RNAs to 1 copy per $10^7$ non-target RNAs.

Suitable samples include but are not limited to blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., RNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising RNAs that is obtained from such cells (e.g., a cell lysate or other cell extract comprising RNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. Agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., *flagellates* (e.g., *Euglena*), amoeboids (e.g., amoeba), sporozoans (e.g, Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a diseased cell, fluid, tissue, or organ. In some cases, the source of the sample is a normal (non-diseased) cell, fluid, tissue, or organ. In some cases, the source of the sample is a pathogen-infected cell, tissue, or organ. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis*, and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogens include, e.g., HIV virus, *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium and M. pneumoniae.*

Target RNA

A target RNA can be any single stranded RNA (ssRNA). Examples include but are not limited to mRNA, rRNA, tRNA, non-coding RNA (ncRNA), long non-coding RNA (lncRNA), and microRNA (miRNA). In some cases, the target ssRNA is mRNA. In some cases, the single stranded target nucleic acid is ssRNA from a virus (e.g., Zika virus, human immunodeficiency virus, influenza virus, and the like). In some cases, the single-stranded target nucleic acid is ssRNA of a parasite. In some cases, the single-stranded target nucleic acid is ssRNA of a bacterium, e.g., a pathogenic bacterium. The source of the target RNA can be the same as the source of the RNA sample, as described above.

Measuring a Detectable Signal

In some cases, a subject method includes a step of measuring (e.g., measuring a detectable signal produced by C2c2 protein-mediated RNA cleavage). Because a C2c2 protein cleaves non-targeted RNA once activated, which occurs when a C2c2 guide RNA hybridizes with a target RNA in the presence of a C2c2 protein, a detectable signal can be any signal that is produced when RNA is cleaved. For example, in some cases the step of measuring can include one or more of: gold nanoparticle based detection (e.g., see Xu et al., *Angew Chem Int Ed Engl.* 2007; 46(19):3468-70; and Xia et. al., *Proc Natl Acad Sci USA.* 2010 Jun. 15; 107(24):10837-41), fluorescence polarization, colloid phase transition/dispersion (e.g., Baksh et. al., *Nature.* 2004 Jan. 8;

427(6970):139-41), electrochemical detection, semiconductor-based sensing (e.g., Rothberg et. al., *Nature.* 2011 Jul. 20; 475(7356):348-52; e.g., one could use a phosphatase to generate a pH change after RNA cleavage reactions, by opening 2'-3' cyclic phosphates, and by releasing inorganic phosphate into solution), and detection of a labeled detector RNA (see below for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target RNA present in the sample. The measuring can in some cases be qualitative, e.g., in the sense that the presence or absence of detectable signal can indicate the presence or absence of targeted RNA. In some cases, a detectable signal will not be present (e.g., above a given threshold level) unless the targeted RNA(s) is present above a particular threshold concentration (e.g., see FIG. 5). In some cases, the threshold of detection can be titrated by modifying the amount of C2c2 protein, guide RNA, sample volume, and/or detector RNA (if one is used). As such, for example, as would be understood by one of ordinary skill in the art, a number of controls can be used if desired in order to set up one or more reactions, each set up to detect a different threshold level of target RNA, and thus such a series of reactions could be used to determine the amount of target RNA present in a sample (e.g., one could use such a series of reactions to determine that a target RNA is present in the sample 'at a concentration of at least X').

Labeled Detector RNA

In some cases, a subject method includes contacting a sample (e.g., a sample comprising a target RNA and a plurality of non-target RNAs) with: i) a labeled detector RNA; ii) a C2c2 protein; and iii) a C2c2 guide RNA (or precursor C2c2 guide RNA array). For example, in some cases, a subject method includes contacting a sample with a labeled detector RNA comprising a fluorescence-emitting dye pair; the C2c2 protein cleaves the labeled detector RNA after it is activated (by binding to the C2c2 guide RNA in the context of the guide RNA hybridizing to a target RNA); and the detectable signal that is measured is produced by the fluorescence-emitting dye pair. For example, in some cases, a subject method includes contacting a sample with a labeled detector RNA comprising a fluorescence resonance energy transfer (FRET) pair or a quencher/fluor pair, or both. In some cases, a subject method includes contacting a sample with a labeled detector RNA comprising a FRET pair. In some cases, a subject method includes contacting a sample with a labeled detector RNA comprising a fluor/quencher pair. Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector RNA includes a FRET pair) the labeled detector RNA produces an amount of detectable signal prior to being cleaved, and the amount of detectable signal that is measured is reduced when the labeled detector RNA is cleaved. In some cases, the labeled detector RNA produces a first detectable signal prior to being cleaved (e.g., from a FRET pair) and a second detectable signal when the labeled detector RNA is cleaved (e.g., from a quencher/fluor pair). As such, in some cases, the labeled detector RNA comprises a FRET pair and a quencher/fluor pair.

In some cases, the labeled detector RNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector RNA includes two signal partners (a signal pair), when one signal partner is a FRET donor moiety and the other signal partner is a FRET acceptor moiety. A subject labeled detector RNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a C2c2 protein).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. *PLoS One.* 2015 Aug. 3; 10(8):e0134436.

TABLE 1

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |

TABLE 1-continued

| Examples of FRET pairs (donor and acceptor FRET moieties) | |
|---|---|
| Donor | Acceptor |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector RNA is cleaved (e.g., in some cases, the labeled detector RNA comprises a quencher/fluor pair. One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector RNA is cleaved. For example, in some cases, the signal exhibited by one signal partner (a signal moiety) is quenched by the other signal partner (a quencher signal moiety), e.g., when both are present on the same RNA molecule prior to cleavage by a C2c2 protein. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector RNA by a C2c2 protein), but the signal will be quenched when the partners are in close proximity (e.g., prior to cleavage of the detector RNA by a C2c2 protein).

A quencher moiety can quench a signal from the signal moiety (e.g., prior to cleave of the detector RNA by a C2c2 protein) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., *Annu Rev Biomed Eng.* 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector RNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector RNA can be detected by a color-shift. Such a shift can be expressed as a loss of an amount of signal of one color (wavelength), a gain in the amount of another color, a change in the ration of one color to another, and the like.

Nucleic Acid Modifications

In some cases, a labeled detector RNA comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a labeled detector RNA comprises one or more phosphorothioate and/or heteroatom internucleoside linkages, in particular —$CH_2$—NH—O—$CH_2$—, —$CH_2$—N($CH_3$)—O—$CH_2$-(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a labeled detector RNA comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A labeled detector RNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., *Chem. Commun.,* 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., *Proc. Natl. Acad. Sci. U.S.A.,* 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). LNAs and preparation thereof are also described in WO 98/39352 and WO 99/14226.

Modified Sugar Moieties

A labeled detector RNA can also include one or more substituted sugar moieties. Suitable polynucleotides comprise a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2$ $CH_2$ $CH_2NH_2$), allyl (—$CH_2$—CH═$CH_2$), —O-allyl (—O—$CH_2$—CH═$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled detector RNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, Antisense Research and Applications, pages 289-302, Crooke, S. T. and Lebleu, B., ed., *CRC Press,* 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, *CRC Press*, Boca Raton, 1993, pp. 276-278) and are suitable base substitutions, e.g., when combined with 2'-O-methoxyethyl sugar modifications.

Detection of Two Different Target RNAs

As noted above, in some cases, a method of the present disclosure provides for substantially simultaneous detection of two different target RNAs (a first single-stranded target RNA and a second single-stranded target RNA) in a sample. In some cases, the method comprises: a) contacting a sample (e.g., a sample comprising the two different target RNAs and a plurality of non-target RNAs) with: (i) a first C2c2 protein that cleaves adenine$^+$ RNAs (i.e., RNAs that include A, but not RNAs that lack A such as a polyU RNA) present in the sample; (ii); a second C2c2 protein that cleaves uracil$^+$ RNAs (i.e., RNAs that include U, but not RNAs that lack U such as a polyA RNA); (iii) a first C2c2 guide RNA that comprises a first nucleotide sequence that hybridizes with the first single stranded target RNA and a second nucleotide sequence that binds to the first C2c2 protein; and (iv) a second C2c2 guide RNA that comprises a first nucleotide sequence that hybridizes with the second single stranded target RNA and a second nucleotide sequence that binds to the second C2c2 protein; and b) measuring a detectable signal produced by RNA cleavage mediated by the first and the second C2c2 proteins, wherein a first detectable signal is produced by the first C2c2 protein and a second detectable signal is produced by the second C2c2 protein, where the first detectable signal and the second detectable signal are distinguishable from one another. In some cases, the first C2c2 protein is not activated by the second C2c2 guide RNA, and the first C2c2 protein cleaves ssRNA that includes A (e.g., does not cleave ssRNA that lacks A); and the second C2c2 protein is not activated by the first C2c2 guide RNA, and the second C2c2 protein cleaves ssRNA that includes U (e.g., does not cleave ssRNA that lacks U). In some cases, the first C2c2 protein is not activated by the second C2c2 guide RNA, and the first C2c2 protein cleaves ssRNA that includes U (e.g., does not cleave ssRNA that lacks U); and the second C2c2 protein is not activated by the first C2c2 guide RNA, and the second C2c2 protein cleaves ssRNA that includes A (e.g., does not cleave ssRNA that lacks A).

In some cases, the method also comprises contacting the sample with: i) a first labeled detector RNA comprising a first FRET pair and/or a first quencher/fluor pair (example FRET pairs and quencher/fluor pairs are described above); and ii) a second labeled detector RNA comprising a second FRET pair and/or a second quencher/fluor pair (example FRET pairs and quencher/fluor pairs are described above). In some cases, the first labelled detector RNA comprises at least one A and does not comprise U; while the second labelled detector RNA comprises at least one U and does not comprise A. In some cases, the first labelled detector RNA comprises at least one U and does not comprise A; while the second labelled detector RNA comprises at least one A and does not comprise U. The first C2c2 protein cleaves the first labelled detector RNA, and the first detectable signal is produced by the first FRET pair and/or the first quencher/fluor pair, and the second C2c2 protein cleaves the second labelled detector RNA, and the second detectable signal is produced by the second FRET pair and/or the second quencher/fluor pair. Detection of the first detectable signal indicates the presence in the sample of the first target RNA; and detection of the second detectable signal indicates the presence in the sample of the second target RNA. In some cases, the relative amounts of detected first and second signal indicate the ratio of the first target RNA to the second target RNA in the sample.

In some cases, the first labelled detector RNA comprises a label that is distinguishable from the label of the second labelled detector RNA. For example, the first labelled detector RNA can comprise a first FRET pair and/or a first quencher/fluor pair; and the second labelled detector RNA can comprise a second FRET pair and/or a second quencher/fluor pair. As one non-limiting example, the first labelled detector RNA can comprise a donor comprising tryptophan and an acceptor comprising dansyl; and the second labelled detector RNA can comprise a donor comprising IAEDANS and an acceptor comprising DDPM. As another non-limiting example, the first labelled detector RNA comprises a donor comprising dansyl and an acceptor comprising FITC; and the second labelled detector RNA comprises a donor comprising Cy3 and an acceptor comprising Cy5. In some cases, the first labelled detector RNA comprises a 5' FAM (Fluorescein)-3' IBFQ (Iowa Black® FQ) quencher/fluor pair, and in some cases the second labelled detector RNA comprises a 5'FAM (Fluorescein)-3' IBFQ (Iowa Black® FQ) quencher/fluor pair.

In some cases, the first and second labelled detector RNAs are added to the sample at the same time (substantially simultaneous contact). In some such cases, the signals produced by the first and second labelled detector RNAs are detected at the same time (substantially simultaneous contact), e.g., because in such cases the first and second labelled detector RNAs can be distinguishably labeled.

"Substantially simultaneous" refers to within about 5 minutes, within about 3 minutes, within about 2 minutes, within about 1 minute, within about 30 seconds, within about 15 seconds, within about 10 seconds, within about 5 seconds, or within about 1 second.

However, in some cases, the signals produced by the first and second labelled detector RNAs are not detected at the same time and are instead detected sequentially (one before the other). For example, in some cases, the first and second labelled detector RNAs are not added to the sample at the same time and are instead added seqeuntially (e.g., the second labelled detector RNA can be added after the first labelled detector RNA is added), and in some such cases the second labelled detector RNA is not added until after the signal produced by the first labelled detector RNA is detected. Thus, in some cases, the first and second labelled detector RNAs do not need to be distinguishably labeled (e.g, they can in some cases produce the same detectable signal, e.g., can flouresce at the same wavelength) because the signals are to be detected sequentially.

As an illustrative example, in some cases: (i) the first and second labelled detector RNAs are not distinguishably labeled; (ii) the sample is contacted with one labelled detector RNA and the signal produced by that labelled detector RNA is detected (e.g., measured); and (iii) the sample is then contacted with the other labelled detector RNA and the signal produced by the second added labelled detector RNA is detected—thus, when both target ssRNAs are present in the sample, addition of the second labelled detector RNA can result in a boost of signal (e.g, if the signal increases with increased cleavage, e.g., Flour/Quencher pair) or can result in a detectable decrease in signal following addition of the second labelled detector RNA (e.g., if the signal decreases with increased cleavage, e.g., FRET pair).

The first and the second C2c2 proteins can be orthogonal to one another with respect to C2c2 guide RNA binding. In such cases, the first C2c2 protein does not bind to the second C2c2 guide RNA; and the second C2c2 protein does not bind to the first guide RNA. The first C2c2 protein and the second C2c2 protein can also differ from one another in their ssRNA cleavage preference, such that one of the C2c2 proteins cleaves ssRNA at As and the other C2c2 protein cleaves ssRNA at Us.

Guidance for orthogonal pairs of C2c2 proteins can be found in FIG. 44E.

Non-limiting examples of orthogonal pairs of C2c2 proteins suitable for use in a method of the present disclosure include those depicted below in Table 10. The cleavage preference is presented in parenthesis following the name of the Cas13a protein. For example, "Lba (A)" refers to an Lba Cas13a protein, which cleaves ssRNA at A; and "Lbu (U)" refers to an Lbu Cas13a protein, which cleaves ssRNA at U.

TABLE 10

| C2c2 protein #1 | C2c2 protein #2 |
|---|---|
| Lba (A) | Hhe (U) |
| Lba (A) | Rca (U) |
| Lba (A) | Ppr (U) |
| Lba (A) | Lne (U) |
| Lba (A) | Lbu (U) |
| Lba (A) | Lwa (U) |
| Lba (A) | Lsh (U) |
| Ere (A) | Hhe (U) |
| Ere (A) | Rca (U) |
| Ere (A) | Ppr (U) |
| Ere (A) | Lne (U) |
| Ere (A) | Lbu (U) |
| Ere (A) | Lwa (U) |
| Ere (A) | Lsh (U) |
| Ere (A) | Lse (U) |
| Cam (A) | Hhe (U) |
| Cam (A) | Rca (U) |
| Cam (A) | Ppr (U) |
| Cam (A) | Lne (U) |
| Cam (A) | Lbu (U) |
| Cam (A) | Lwa (U) |
| Cam (A) | Lsh (U) |
| Cam (A) | Lse (U) |

The first and the second labelled detector RNAs can each independently have a length of from 2 to 100 ribonucleotides (e.g., from 2 to 80, 2 to 60, 2 to 50, 2 to 40, 2 to 30, 2 to 20, 2 to 15, or 2 to 10 ribonucleotides). The first and the second labelled detector RNAs can each independently have a length of from 2 ribonucleotides to 100 ribonucleotides, e.g., from 2 ribonucleotides to 5 ribonucleotides, from 5 ribonucleotides to 7 ribonucleotides, from 7 ribonucleotides to 10 ribonucleotides, from 10 ribonucleotides to 15 ribonucleotides, from 15 ribonucleotides to 20 ribonucleotides, from 20 ribonucleotides to 25 ribonucleotides, from 25 ribonucleotides to 30 ribonucleotides, from 30 ribonucleotides to 35 ribonucleotides, from 35 ribonucleotides to 40 ribonucleotides, from 40 ribonucleotides to 45 ribonucleotides, or from 45 ribonucleotides to 50 ribonucleotides.

In some cases, the first labelled detector RNA comprises at least one A (e.g., at least 2, at least 3, or at least 4 As) and lacks U; and the second labelled detector RNA comprises at least one U (e.g., at least 2, at least 3, or at least 4 Us) and lacks A.

In some cases, the first labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the first labelled detector RNA lacks U and includes a stretch of at least 2 consecutive As (e.g., at least 3, at least 4, or at least 5 consecutive As). In some cases, the second labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the second labelled detector RNA lacks A and includes a stretch of at least 2 consecutive Us (e.g., at least 3, at least 4, or at least 5 consecutive Us).

In some cases, the first labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the first labelled detector RNA lacks A and includes a stretch of at least 2 consecutive Us (e.g., at least 3, at least 4, or at least 5 consecutive Us). In some cases, the second labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the second labelled detector RNA lacks U and includes a stretch of at least 2 consecutive As (e.g., at least 3, at least 4, or at least 5 consecutive As).

In some cases, the first labelled detector RNA comprises at least one U and lacks A; and the second labelled detector RNA comprises at least one A and lacks U.

In some cases, the first labelled detector RNA comprises at least one A and lacks U. For example, in some cases, the first labelled detector RNA is a homoadenosine polymer (a polyA RNA). As another example, the first labelled detector RNA: i) comprises at least one A; ii) lacks U; and iii) comprises one or more C and/or Gs. In some cases, the second labelled detector RNA comprises at least one U and lacks A. For example, in some cases, the second labelled detector RNA is a homouridine polymer (a polyU RNA). As another example, the second labelled detector RNA: i) comprises at least one U; ii) lacks A; and iii) comprises one or more C and/or Gs.

In some cases, the first labelled detector RNA comprises at least one U and lacks A. For example, in some cases, the first labelled detector RNA is a homouridine polymer (polyU RNA). As another example, the second labelled detector RNA: i) comprises at least one U; ii) lacks A; and iii) comprises one or more Cs and/or Gs. In some cases, the second labelled detector RNA comprises at least one A and lacks U. For example, in some cases, the second labelled detector RNA is a homoadenosine polymer (polyA RNA). As another example, the second labelled detector RNA: i) comprises at least one A; ii) lacks U; and iii) comprises one or more Cs and/or Gs.

As noted above, a method of the present disclosure can comprise contacting a sample with: a first C2c2 protein; a second C2c2 protein; a first C2c2 guide RNA that comprises a first nucleotide sequence that hybridizes with the first single stranded target RNA and a second nucleotide sequence also referred to herein as a 'constant region' or 'handle' that binds to the first C2c2 protein; and a second C2c2 guide RNA that comprises a first nucleotide sequence that hybridizes with the second single stranded target RNA and a second nucleotide sequence (a handle) that binds to the second C2c2 protein.

For example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the first C2c2 guide RNA comprises a constant region (a 'handle'—a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AGAUAGCCCAAGAAAGAGGGCAAUAAC (SEQ ID NO: 16), where the crRNA has a length of about 25 nt, 26 nt, 27 nt, 28 nt, 29 nt, or 30 nt. In some cases, the crRNA has the nucleotide sequence AGAUAGCCCAAGAAAGAGGGCAAUAAC (SEQ ID NO: 16); and has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUAGACAGGGGAACUGCAAC (SEQ ID NO: 17). In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CAUCACCGCCAAGACGACGGCGGACUGAACC (SEQ ID NO: 18). In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCCCAAAAUUGAAGGGAACUACAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGGGAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCUCAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCUCAAAACAAAAGAGGACUAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCUCAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGACUAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCCCAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGACUAAAACUU (SEQ ID NO: 21); where the handle has a length of about 28 nt, 29 nt, 30 nt, 31 nt, or 32 nt. In some cases, the second guide RNA comprises a handle comprising the nucleotide sequence GACCACCCCAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCCCAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt.

As another example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAGUAGCCCGAUAUAGAGGGCAAUAAC (SEQ ID NO: 23), where the handle has a length of about 25 nt, 26 nt, 27 nt, 28 nt, 29 nt, or 30 nt. In some cases, the handle has the nucleotide sequence AAGUAGCCCGAUAUAGAGGGCAAUAAC (SEQ ID NO: 23); and has a length of 27 nt. in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AUACAGCUCGAUAUAGUGAGCAAUAAG (SEQ ID NO: 24), where the handle has a length of about 25 nt, 26 nt, 27 nt, 28 nt, 29 nt, or 30 nt. In some cases, the handle has the nucleotide sequence AUACAGCUCGAUAUAGUGAGCAAUAAG (SEQ ID NO: 24); and has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUAGACAGGGGAACUGCAAC (SEQ ID NO: 17); where the handle has a length of about 30 nt, 31 nt, 32 nt, 33 nt, 34 nt, or 35 nt. In some cases, the second C2c2 guide RNA comprises a handle comprising the nucleotide sequence GUAACAAUCCCCGUAGACAGGGGAACUGCAAC (SEQ ID NO: 17); and the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence UCACAUCACCGCCAAGACGACGGCGGACUGAACC (SEQ ID NO: 25); where the handle has a length of about 32 nt, 33 nt, 34 nt, 35 nt, 36 nt, or 37 nt. In some cases, the second C2c2 guide RNA comprises a handle comprising the nucleotide sequence UCACAUCACCGCCAAGACGACGGCGGACUGAACC (SEQ ID NO: 25); and the handle has a length of 34 nt. In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCCCAAAAUUGAAGGGAACUACAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGGGAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCUCAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCUCAAAACAAAAGAGGACUAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCUCAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGACUAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCCCAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGACUAAAACUU (SEQ ID NO: 21); where the handle has a length of about 28 nt, 29 nt, 30 nt, 31 nt, or 32 nt. In some cases, the second guide RNA comprises a handle comprising the nucleotide sequence GACCACCCCAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCCCAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACUACCUCUAUAUGAAAGAGGACUAAAAC (SEQ ID NO: 7); where the handle has a length of about 28 nt, 29 nt, 30 nt, 31 nt, or 32 nt. In some cases, the second C2c2 guide RNA comprises a handle comprising the nucleotide sequence GACUACCUCUAUAUGAAAGAGGACUAAAAC (SEQ ID NO: 7); and the handle has a length of 30 nt.

As another example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAACAGCCCGAUAUAGAGGGCAAUAGAC (SEQ ID NO: 26), where the handle has a length of about 26 nt, 27 nt, 28 nt, 29 nt, or 30 nt. In some cases, the handle has the nucleotide sequence GAACAGCCCGAUAUA-GAGGGCAAUAGAC (SEQ ID NO: 26); and has a length of 28 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUAGACAGGG-GAACUGCAAC (SEQ ID NO: 17); where the handle has a length of about 30 nt, 31 nt, 32 nt, 33 nt, 34 nt, or 35 nt. In some cases, the second C2c2 guide RNA comprises a handle comprising the nucleotide sequence GUAACAAUCCCCGUAGACAGGGGAACUGCAAC (SEQ ID NO: 17); and the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence UCACAUCACCGCCAAGACGACGGCGGACUGAACC (SEQ ID NO: 25); where the handle has a length of about 32 nt, 33 nt, 34 nt, 35 nt, 36 nt, or 37 nt. In some cases, the second C2c2 guide RNA comprises a handle comprising the nucleotide sequence UCACAUCACCGCCAA-GACGACGGCGGACUGAACC (SEQ ID NO: 25); and the handle has a length of 34 nt. In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCC-CAAAAUUGAAGGGAACUACAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGGGAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCUCAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCU-CAAAACAAAAGAGGACUAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCUCAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAC-CACCCCAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGAC-UAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCC-CAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCC-CAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGAC-UAAAACUU (SEQ ID NO: 21); where the handle has a length of about 28 nt, 29 nt, 30 nt, 31 nt, or 32 nt. In some cases, the second guide RNA comprises a handle comprising the nucleotide sequence GACCACCC-CAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCC-CAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACUACCUCUAUAUGAAAGAGGACUAAAAC (SEQ ID NO: 7); where the handle has a length of about 28 nt, 29 nt, 30 nt, 31 nt, or 32 nt. In some cases, the second C2c2 guide RNA comprises a handle comprising the nucleotide sequence GACUACCUCUAUAUGAAAGAGGAC-UAAAAC (SEQ ID NO: 7); and the handle has a length of 30 nt.

Multiplexing

As noted above, in some cases, a method of the present disclosure comprises: a) contacting a sample (e.g., a sample comprising a target RNA and a plurality of non-target RNAs) with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and b) measuring a detectable signal produced by C2c2 protein-mediated RNA cleavage.

In some cases, two or more C2c2 guide RNAs can be present on an array (a precursor C2c2 guide RNA array). A C2c2 protein can cleave the precursor C2c2 guide RNA array into individual C2c2 guide RNAs (e.g., see FIG. 4 and FIG. 6).

In some cases a subject C2c2 guide RNA array includes 2 or more C2c2 guide RNAs (e.g., 3 or more, 4 or more, 5 or more, 6 or more, or 7 or more, C2c2 guide RNAs). The C2c2 guide RNAs of a given array can target (i.e., can include guide sequences that hybridize to) different target sites of the same target RNA (e.g., which can increase sensitivity of detection) and/or can target different target RNA molecules (e.g., a family of transcripts, e.g., based on variation such as single-nucleotide polymorphisms, single nucleotide polymorphisms (SNPs), etc., and such could be used for example to detect multiple strains of a virus such as influenza virus variants, Zika virus variants, HIV variants, and the like).

C2c2 Protein

A C2c2 protein binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

Example naturally existing C2c2 proteins are depicted in FIG. 8 and are set forth as SEQ ID NOs: 1-6. In some cases, a subject C2c2 protein includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a suitable C2c2 polypeptide comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a suitable C2c2 polypeptide comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a suitable C2c2 polypeptide comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a suitable C2c2 polypeptide comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a suitable C2c2 polypeptide comprises an amino acid sequence having at least 80%, at least 85%, at least 90%, at least 95%, at least 98%, at least 99%, or 100%, amino acid sequence identity to the *Herbinix hemicellulosilytica* C2c2 amino acid sequence set forth in SEQ ID NO:6. In some cases, the C2c2 protein includes an amino acid sequence having 80% or more amino acid sequence identity with the *Leptotrichia buccalis* (Lbu) C2c2 amino acid sequence set forth in SEQ ID NO: 2. In some cases, the C2c2 protein is a *Leptotrichia buccalis* (Lbu) C2c2 protein (e.g., see SEQ ID NO: 2). In some cases, the C2c2 protein includes the amino acid sequence set forth in any one of SEQ ID NOs: 1-2 and 4-6.

In some cases, a C2c2 protein used in a method of the present disclosure is not a *Leptotrichia shahii* (Lsh) C2c2 protein. In some cases, a C2c2 protein used in a method of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, the C2c2 protein is more efficient, by a factor of 1.2-fold or more, than a *Leptotrichia shahii* (Lsh) C2c2 protein at cleaving RNA that is not targeted by a C2c2 guide RNA of the method. In some cases, the C2c2 protein is more efficient, by a factor of 1.5-fold or more, than a *Leptotrichia shahii* (Lsh) C2c2 protein at cleaving RNA that is not targeted by a C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

In some cases, the C2c2 protein exhibits at least a 50% RNA cleavage efficiency within 1 hour of said contacting (e.g., 55% or more, 60% or more, 65% or more, 70% or more, or 75% or more cleavage efficiency). In some cases, the C2c2 protein exhibits at least a 50% RNA cleavage efficiency within 40 minutes of said contacting (e.g., 55% or more, 60% or more, 65% or more, 70% or more, or 75% or more cleavage efficiency). In some cases, the C2c2 protein exhibits at least a 50% RNA cleavage efficiency within 30 minutes of said contacting (e.g., 55% or more, 60% or more, 65% or more, 70% or more, or 75% or more cleavage efficiency).

In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 60 minutes, e.g., from 1 minute to 60 minutes, from 30 seconds to 5 minutes, from 1 minute to 5 minutes, from 1 minute to 10 minutes, from 5 minutes to 10 minutes, from 10 minutes to 15 minutes, from 15 minutes to 20 minutes, from 20 minutes to 25 minutes, from 25 minutes to 30 minutes, from 30 minutes to 35 minutes, from 35 minutes to 40 minutes, from 40 minutes to 45 minutes, from 45 minutes to 50 minutes, from 50 minutes to 55 minutes, or from 55 minutes to 60 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 5 minutes (e.g., from 1 minute to 5 minutes, e.g., in a time period of 1 minute, 2 minutes, 3 minutes, 4 minutes, or 5 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 5 minutes to 10 minutes (e.g., in a time period of 5 minutes, 6 minutes, 7 minutes, 8 minutes, 9 minutes, or 10 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 10 minutes to 15 minutes (e.g., 10 minutes, 11 minutes, 12 minutes, 13 minutes, 14 minutes, or 15 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 15 minutes to 20 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 20 minutes to 25 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 25 minutes to 30 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 minutes to 35 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 35 minutes to 40 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 40 minutes to 45 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 45 minutes to 50 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 50 minutes to 55 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 55 minutes to 60 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of less than 1 minute, e.g., in a time period of from 50 seconds to 59 seconds, from 40 seconds to 49 seconds, from 30 seconds to 39 seconds, or from 20 seconds to 29 seconds. In some cases, the cleavage takes place under physiological conditions. In some cases, the cleavage takes place at a temperature of from 15° C. to 20° C., from 20° C. to 25° C., from 25° C. to 30° C., from 30° C. to 35° C., or from 35° C. to 40° C. In some cases, the cleavage takes place at about 37° C. In some cases, the cleavage takes place at about 37° C. and the reaction conditions include divalent metal ions. In some cases, the divalent metal ion is $Mg^{2+}$. In some cases, the divalent metal ion is $Mn^{2+}$. In some cases the pH of the reaction conditions is between pH 5 and pH 6. In some cases the pH of the reaction conditions is between pH 6 and pH 7. In some cases the pH of the reaction conditions is between pH 6.5 and pH 7.5. In some cases the pH of reaction conditions is above pH 7.5.

The term "cleavage efficiency" is used herein to refer to the ability of the C2c2 protein to rapidly cleave RNA in sample once the C2c2 protein has been activated by an appropriate C2c2 guide RNA/target RNA hybridization. "Cleavage efficiency" refers to the amount of RNA the protein can cleave within a given period of time. For example, 50% cleavage efficiency would indicate that 50% of a given RNA is cleaved within a specified period of time. For example, if an RNA is present in a sample at a starting concentration of 100 μM, 50% cleavage has been achieved when 50 μM of the RNA has been cleaved. As another example, if a plurality of RNA molecules is present in the sample, 50% cleavage has been achieved when 50% of the RNA molecules have been cleaved; efficiency is an expression of the amount of time that is required for a certain percent of the total RNA to be cleaved. This can be measured by any convenient method and many such methods will be known to one of ordinary skill in the art. For example, a labeled detector RNA can be used. In some cases, the RNA species (cleaved versus uncleaved) can be separated on a gel and the amount of cleaved RNA can be compared to the amount of uncleaved RNA, e.g., see FIG. 3.

When the phrase "wherein the C2c2 protein cleaves at least X % of the RNAs present in the sample" (e.g., within a specified time period) is used, it is meant that X % of the 'signal-producing' RNAs present in the sample is cleaved within the specified time period. Which RNAs are 'signal-producing' RNAs can depend on the detection method used. For example, when a labeled detector RNA is used, the labeled detector RNA might be the only 'signal-producing RNA.' However, the labeled detector RNA is used to represent the RNAs of the sample and thus, what one observes for the labeled detector RNA is assumed to be representative of what is happening to the non-target RNAs of the sample. As such, when 50% of the labeled detector RNA is cleaved, this will generally be assumed to represent when 50% of the 'RNAs present in the sample' are cleaved. In some cases, RNA cleavage in general is being measured and as such, all cleavable RNAs of the sample are 'signal-producing RNAs'. Thus, when referring to the % of RNAs present in the sample being cleaved, this value can be measured using any convenient method, and whatever the method being used, the value is generally meant herein to mean when the enzyme has cleaved half of the cleavable targets in the sample.

In some cases, the C2c2 protein is not a *Leptotrichia shahii* (Lsh) C2c2 protein. In some cases, the C2c2 protein is more efficient than a *Leptotrichia shahii* (Lsh) C2c2 protein (e.g., at cleaving non-target RNA) by a factor of 1.2-fold or more (e.g., 1.5-fold or more, 1.7-fold or more, or 2-fold or more). As such, in some cases, a subject C2c2 protein is more efficient, by a factor of 1.2-fold or more (e.g., 1.5-fold or more, 1.7-fold or more, or 2-fold or more), than a *Leptotrichia shahii* (Lsh) C2c2 protein at cleaving RNA that is not targeted by the C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

Variant C2c2 Polypeptides

Variant C2c2 polypeptides include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (*Leptotrichia buccalis* C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (*Listeria seeligeri* C2c2) that correspond to R472, H477, R1048, and H1053 of SEQ ID NO:2 are R445, H450, R1016, and H1021, respectively. As another example, amino acid positions in SEQ ID NO:4 (*Rhodobacter capsulatus* C2c2) that correspond to R472, H477, R1048, and H1053 of SEQ ID NO:2 are R464, H469, R1052, and H1057, respectively. As another example, amino acid positions in SEQ ID NO:5 (*Carnobacterium gallinarum* C2c2) that correspond to R472, H477, R1048, and H1053 of SEQ ID NO:2 are R467, H472, R1069, and H1074, respectively. As another example, amino acid positions in SEQ ID NO:6 (*Herbinix hemicellulosilytica* C2c2) that correspond to R472, H477, R1048, and H1053 of SEQ ID NO:2 are R472, H477, R1044, and H1049, respectively.

In some cases, a variant C2c2 polypeptide comprises amino acid substitutions of amino acids R472 and H477 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His.

In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (*Herbinix hemicellulosilytica* C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of 1, 2, 3, or 4 of amino acids R472, H477, R1048, and H1053, such that the variant C2c2 polypeptide has reduced or undetectable cleavage of ss RNA (e.g., RNA-guided cleavage activity), and retains the ability to bind C2c2 guide RNA and ss RNA.

In some cases, the variant C2c2 polypeptide retains the ability to cleave precursor C2c2 guide RNA. For example, in some cases, the variant C2c2 polypeptide exhibits less than 50%, less than 40%, less than 30%, less than 20%, less than 10%, less than 5%, less than 1%, or less than 0.1%, of the RNA-guided cleavage of a non-target RNA exhibited by a C2c2 polypeptide having the amino acid sequence set forth in SEQ ID NO:2. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Any of the above variant C2c2 polypeptides can also include a mutation (e.g., at any one of positions R1079, R1072, and K1082, as described in further detail below) that results in reduced ability (e.g., loss of ability) to cleave precursor C2c2 guide RNA.

In some cases, a variant C2c2 polypeptide has reduced ability to cleave precursor C2c2 guide RNA (e.g., see examples below and related FIGS. 26C-26D, 35D, and 37). For example, in some cases, a variant C2c2 polypeptide comprises amino acid substitutions of 1, 2, or 3 of amino acids R1079, R1072, and K1082 of the amino acid sequence set forth in SEQ ID NO:2 (*Leptotrichia buccalis* C2c2), or a corresponding amino acid of any C2c2 amino acid sequence (e.g., the C2c2 amino acid sequence depicted in SEQ ID NO:1, SEQ ID NO:4, SEQ ID NO:5, or SEQ ID NO:6). Corresponding amino acids in SEQ ID NO:1, SEQ ID NO:4, SEQ ID NO:5, and SEQ ID NO:6 are readily identified. For example, amino positions in SEQ ID NO:1 (*Listeria seeligeri* C2c2) that correspond to R1079, R1072, and K1082 of SEQ ID NO:2 are R1048, R1041, and K1051, respectively. As another example, amino acid positions in SEQ ID NO:4 (*Rhodobacter capsulatus* C2c2) that correspond to R1079, R1072, and K1082 of SEQ ID NO:2 are R1085, R1078, and K1088, respectively. As another example, amino acid positions in SEQ ID NO:5 (*Carnobacterium gallinarum* C2c2) that correspond to R1079, R1072, and K1082 of SEQ ID NO:2 are R1099, R1092, and K1102, respectively. As another example, amino acid positions in SEQ ID NO:6 (*Herbinix hemicellulosilytica* C2c2) that correspond to R1079 and R1072 of SEQ ID NO:2 are R1172 and R1165, respectively.

In some cases, a variant C2c2 polypeptide comprises an amino acid substitution of amino acid R1079 (e.g., R1079A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid substitution of amino acid R1072 (e.g., R1072A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid substitution of amino acid K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises one or more (e.g, two or more, or all three) amino acid substitutions at positions selected from R1079 (e.g., R1079A). R1072 (e.g., R1072A), and K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid R1079 (e.g., R1079A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid R1072 (e.g., R1072A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises one or more (e.g, two or more, or all three) amino acid substitutions at positions selected from R1079 (e.g., R1079A). R1072 (e.g., R1072A), and K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid R1041 (e.g., R1041A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid R1048 (e.g., R1048A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid K1051 (e.g., K1051A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises one or more (e.g, two or more, or all three) amino acid substitutions at positions selected from R1048 (e.g., R1048A). R1041 (e.g., R1041A), and K1051 (e.g., K1051A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid R1085 (e.g., R1085A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid R1078 (e.g., R1078A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid K1088 (e.g., K1088A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises one or more (e.g, two or more, or all three) amino acid substitutions at positions selected from R1085 (e.g., R1085A). R1078 (e.g., R1078A), and K1088 (e.g., K1088A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid R1099 (e.g., R1099A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid R1092 (e.g., R1092A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid K1102 (e.g., K1102A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises one or more (e.g, two or more, or all three) amino acid substitutions at positions selected from R1099 (e.g., R1099A). R1092 (e.g., R1092A), and K1102 (e.g., K1102A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises an amino acid substitution of amino acid R1172 (e.g., R1172A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises an amino acid substitution of amino acid R1165 (e.g., R1165A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises one or more (e.g, both) amino acid substitutions at positions selected from R1172 (e.g., R1172A) and R1165 (e.g., R1165A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2).

C2c2 Guide RNA

A subject C2c2 guide RNA (e.g., a C2c2 crRNA) includes a guide sequence and a constant region (e.g., a region that is 5' of the guide sequence). The region that is 5' of the guide sequence binds to the C2c2 protein (and can be considered a protein-binding region) while the guide sequence hybridizes to a target sequence of the target RNA.

Guide Sequence

The guide sequence has complementarity with (hybridizes to) a target sequence of the single stranded target RNA. In some cases, the base of the target RNA that is immediately 3' of the target sequence (protospacer) is not a G. In some cases, the guide sequence is 16-28 nucleotides (nt) in length (e.g., 16-26, 16-24, 16-22, 16-20, 16-18, 17-26, 17-24, 17-22, 17-20, 17-18, 18-26, 18-24, or 18-22 nt in length). In some cases, the guide sequence is 18-24 nucleotides (nt) in length. In some cases, the guide sequence is at least 16 nt long (e.g., at least 18, 20, or 22 nt long). In some cases, the guide sequence is at least 17 nt long. In some cases, the guide sequence is at least 18 nt long. In some cases, the guide sequence is at least 20 nt long.

In some cases, the guide sequence has 80% or more (e.g., 85% or more, 90% or more, 95% or more, or 100% complementarity) with the target sequence of the single stranded target RNA. In some cases, the guide sequence is 100% complementary to the target sequence of the single stranded target RNA.

Constant Region

The following 3 sequences are each an example of a constant region of a naturally existing C2c2 guide RNA (e.g., a region that is 5' of the guide sequence):

```
                                (SEQ ID NO: 7)
GACUACCUCUAUAUGAAAGAGGACUAAAAC
(Listeria seeligeri) ("Lse")

                                (SEQ ID NO: 8)
CCACCCCAAUAUCGAAGGGGACUAAAACA
(Leptotrichia shahii) ("Lsh")

                                (SEQ ID NO: 9)
GACCACCCCAAAAAUGAAGGGGACUAAAACA
(Leptotrichia buccalis) ("Lbu")
```

In some embodiments, a subject C2c2 guide RNA includes a nucleotide sequence having 70% or more identity (e.g., 80% or more, 85% or more, 90% or more, 95% or more, 98% or more, 99% or more, or 100% identity) with the sequence set forth in any one of SEQ ID NOs: 7-9. In some embodiments, a subject C2c2 guide RNA includes a nucleotide sequence having 90% or more identity (e.g., 95% or more, 98% or more, 99% or more, or 100% identity) with the sequence set forth in any one of SEQ ID NOs: 7-9. In some embodiments, a subject C2c2 guide RNA includes the nucleotide sequence set forth in any one of SEQ ID NOs: 7-9.

In some embodiments, a subject C2c2 guide RNA includes a nucleotide sequence having 70% or more identity (e.g., 80% or more, 85% or more, 90% or more, 95% or more, 98% or more, 99% or more, or 100% identity) with the sequence set forth in SEQ ID NO: 9. In some embodiments, a subject C2c2 guide RNA includes a nucleotide sequence having 90% or more identity (e.g., 95% or more, 98% or more, 99% or more, or 100% identity) with the sequence set forth in SEQ ID NO: 9. In some embodiments, a subject C2c2 guide RNA includes the nucleotide sequence set forth in SEQ ID NO: 9.

In some embodiments, a subject C2c2 guide RNA does not include a nucleotide sequence of a *Leptotrichia shahii* (LsH) C2c2 guide RNA. For example, in some cases, the C2c2 protein that is used is not a C2c2 from *Leptotrichia shahii* (e.g., is not an Lsh C2c2 protein), and in some such cases the C2c2 guide RNA that is used is also not from *Leptotrichia shahii* (e.g., the guide RNA used does not include the constant region of an Lsh C2c2 guide RNA). Therefore, in some cases a subject C2c2 guide RNA does not include the sequence set forth in SEQ ID NO: 8.

Figure 7A:
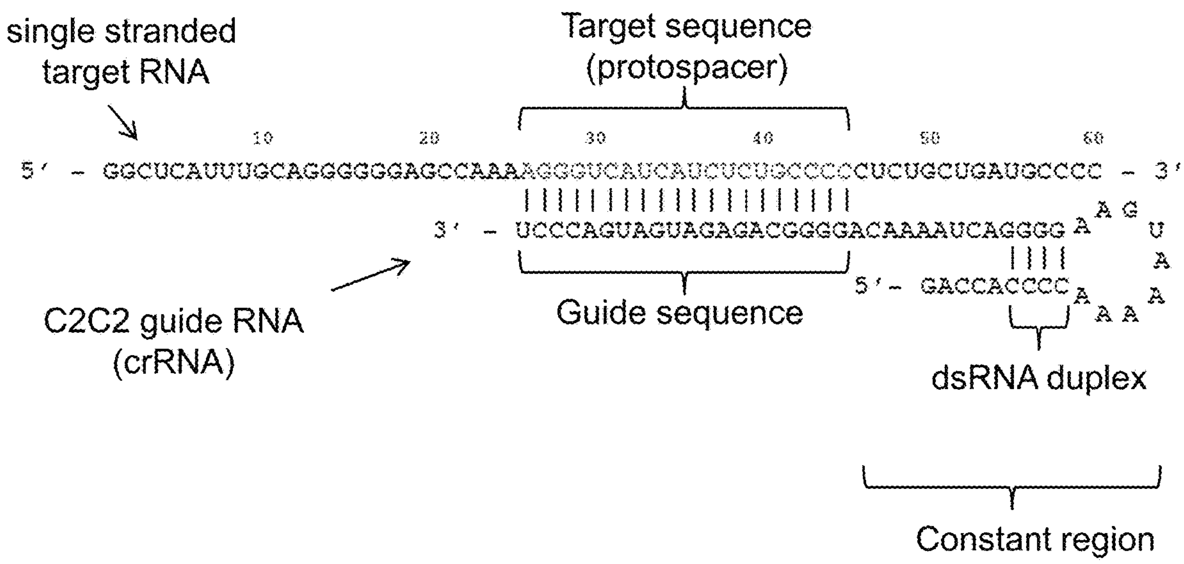
FIG. 7A-7B depict a schematic and sequences of example C2c2 guide RNAs.
Figure 7B:
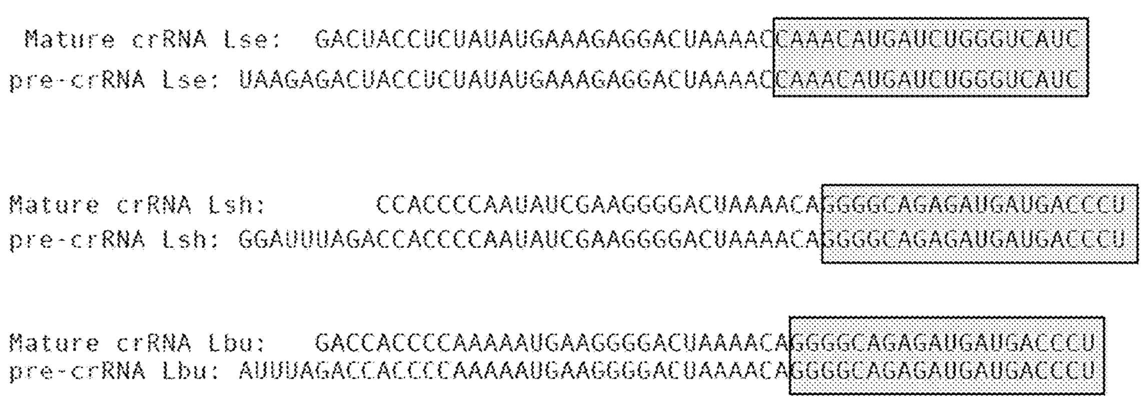

In some cases, the C2c2 guide RNA includes a double stranded RNA duplex (dsRNA duplex). For example, see FIG. 7A which illustrates a C2c2 guide RNA from Lbu hybridized to a single stranded target RNA, where the C2c2 guide RNA includes a dsRNA duplex that is 4 base pairs (bp) in length. In some cases, a C2c2 guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In some cases, a C2c2 guide RNA includes a dsRNA duplex that is 2 or more bp in length (e.g., 3 or more, 4 or more, 5 or more, 6 or more, or 7 or more bp in length). In some cases, a C2c2 guide RNA includes a dsRNA duplex that is longer than the dsRNA duplex of a corresponding wild type C2c2 guide RNA. For example, see FIG. 7A, which illustrates a C2c2 guide RNA from Lbu hybridized to a single stranded target RNA, where the C2c2 guide RNA includes a dsRNA duplex that is 4 base pairs (bp) in length. As such, a C2c2 guide RNA can in some cases include a dsRNA duplex that is 5 or more bp in length (e.g., 6 or more, 7 or more, or 8 or more bp in length). In some cases, a C2c2 guide RNA includes a dsRNA duplex that is shorter than the dsRNA duplex of a corresponding wild type C2c2 guide RNA. As such in some cases, a C2c2 guide RNA includes a dsRNA duplex that is less than 4 bp in length. In some cases, a C2c2 guide RNA includes a dsRNA duplex having a length of 2 or 3 bp in length.

In some cases, the region of a C2c2 guide RNA that is 5' of the guide sequence is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In some cases, the region of a C2c2 guide RNA that is 5' of the guide sequence is 29 or more nt in length.

In some cases, the region of a C2c2 guide RNA that is 5' of the guide sequence has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In some cases, the region of a C2c2 guide RNA that is 5' of the guide sequence has a length in a range of from 28 to 100 nt. In some cases, the region of a C2c2 guide RNA that is 5' of the guide sequence has a length in a range of from 28 to 40 nt.

In some cases, the region of the C2c2 guide RNA that is 5' of the guide sequence is truncated relative to (shorter than) the corresponding region of a corresponding wild type C2c2 guide RNA. For example, the mature Lse C2c2 guide RNA includes a region 5' of the guide sequence that is 30 nucleotides (nt) in length, and a subject truncated C2c2 guide RNA (relative to the Lse C2c2 guide RNA) can therefore have a region 5' of the guide sequence that is less than 30 nt in length (e.g., less than 29, 28, 27, 26, 25, 22, or 20 nt in length). In some cases, a truncated C2c2 guide RNA includes a region 5' of the guide sequence that has a length in a range of from 12 to 29 nt (e.g., from 12 to 28, 12 to 27, 12 to 26, 12 to 25, 12 to 22, 12 to 20, 12 to 18 nt). In some cases, the truncated C2c2 guide RNA is truncated by one or more nt (e.g., 2 or more, 3 or more, 4 or more, 5 or more, or 10 or more nt), e.g., relative to a corresponding wild type C2c2 guide).

In some cases, the region of the C2c2 guide RNA that is 5' of the guide sequence is extended relative to (longer than) the corresponding region of a corresponding wild type C2c2 guide RNA. For example, the mature Lse C2c2 guide RNA includes a region 5' of the guide sequence that is 30 nucleotides (nt) in length, and an extended C2c2 guide RNA (relative to the Lse C2c2 guide RNA) can therefore have a region 5' of the guide sequence that is longer than 30 nt (e.g., longer than 31, longer than 32, longer than 33, longer than 34, or longer than 35 nt). In some cases, an extended C2c2 guide RNA includes a region 5' of the guide sequence that has a length in a range of from 30 to 100 nt (e.g., from 30 to 90, 30 to 80, 30 to 70, 30 to 60, 30 to 50, or 30 to 40 nt). In some cases, the extended C2c2 guide RNA includes a region 5' of the guide sequence that is extended (e.g., relative to the corresponding region of a corresponding wild type C2c2 guide RNA) by one or more nt (e.g., 2 or more, 3 or more, 4 or more, 5 or more, or 10 or more nt).

In some cases, a subject C2c2 guide RNA is 30 or more nucleotides (nt) in length (e.g., 34 or more, 40 or more, 45 or more, 50 or more, 55 or more, 60 or more, 65 or more, 70 or more, or 80 or more nt in length). In some cases, the C2c2 guide RNA is 35 or more nt in length.

In some cases, a subject C2c2 guide RNA has a length in a range of from 30 to 120 nt (e.g., from 30 to 110, 30 to 100, 30 to 90, 30 to 80, 30 to 70, 30 to 60, 35 to 120, 35 to 110, 35 to 100, 35 to 90, 35 to 80, 35 to 70, 35 to 60, 40 to 120, 40 to 110, 40 to 100, 40 to 90, 40 to 80, 40 to 70, 40 to 60, 50 to 120, 50 to 110, 50 to 100, 50 to 90, 50 to 80, or 50 to 70 nt). In some cases, the C2c2 guide RNA has a length in a range of from 33 to 80 nt. In some cases, the C2c2 guide RNA has a length in a range of from 35 to 60 nt.

In some cases, a subject C2c2 guide RNA is truncated relative to (shorter than) a corresponding wild type C2c2 guide RNA. For example, a mature Lse C2c2 guide RNA can be 50 nucleotides (nt) in length, and a truncated C2c2 guide RNA (relative to the Lse C2c2 guide RNA) can therefore in some cases be less than 50 nt in length (e.g., less than 49, 48, 47, 46, 45, 42, or 40 nt in length). In some cases, a truncated C2c2 guide RNA has a length in a range of from 30 to 49 nt (e.g., from 30 to 48, 30 to 47, 30 to 46, 30 to 45, 30 to 42, 30 to 40, 35 to 49, 35 to 48, 35 to 47, 35 to 46, 35 to 45, 35 to 42, or 35 to 40 nt). In some cases, the truncated C2c2 guide RNA is truncated by one or more nt (e.g., 2 or more, 3 or more, 4 or more, 5 or more, or 10 or more nt), e.g., relative to a corresponding wild type C2c2 guide).

In some cases, a subject C2c2 guide RNA is extended relative to (longer than) a corresponding wild type C2c2 guide RNA. For example, a mature Lse C2c2 guide RNA can be 50 nucleotides (nt) in length, and an extended C2c2 guide RNA (relative to the Lse C2c2 guide RNA) can therefore in some cases be longer than 50 nt (e.g., longer than 51, longer than 52, longer than 53, longer than 54, or longer than 55 nt). In some cases, an extended C2c2 guide RNA has a length in a range of from 51 to 100 nt (e.g., from 51 to 90, 51 to 80, 51 to 70, 51 to 60, 53 to 100, 53 to 90, 53 to 80, 53 to 70, 53 to 60, 55 to 100, 55 to 90, 55 to 80, 55 to 70, or 55 to 60 nt). In some cases, the extended C2c2 guide RNA is extended (e.g., relative to a corresponding wild type C2c2 guide RNA) by one or more nt (e.g., 2 or more, 3 or more, 4 or more, 5 or more, or 10 or more nt).

Methods of Cleaving a Precursor C2c2 Guide RNA Array

The present disclosure provides a method of cleaving a precursor C2c2 guide RNA array into two or more C2c2 guide RNAs. The method comprises contacting a precursor C2c2 guide RNA array with a C2c2 protein. The precursor C2c2 guide RNA array comprises two or more (e.g., 2, 3, 4, 5, or more) C2c2 guide RNAs, each of which can have a different guide sequence. The C2c2 protein cleaves the precursor C2c2 guide RNA array into individual C2c2 guide RNAs. In some cases, the constant region (also referred to as a 'handle') of a C2c2 guide RNA includes nucleotide sequence from the precursor guide RNA (e.g., sequence that is normally present prior to cleavage of the guide RNA array). In other words, in some cases the constant region of a subject C2c2 guide RNA includes a precursor crRNA handle.

In some cases, the contacting step does not take place inside a cell, e.g., inside a living cell. In some cases, the contacting step takes place inside of a cell (e.g., a cell in vitro (in culture), a cell ex vivo, a cell in vivo). Any cell is suitable. Examples of cells in which contacting can take place include but are not limited to: a eukaryotic cell; a prokaryotic cell (e.g., a bacterial cell, an archaeal cell); a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens*, C. *agardh*, and the like; a fungal cell (e.g., a yeast cell); an animal cell; an invertebrate cell (e.g. fruit fly, cnidarian, echinoderm, nematode, an insect, an arachnid, etc.); a vertebrate cell (e.g., fish, amphibian, reptile, bird, mammal); a mammal cell (e.g., a human; a non-human primate; an ungulate; a feline; a bovine; an ovine; a caprine; a rat; a mouse; a rodent; a pig; a sheep; a cow; etc.); a parasite cell (e.g., helminths, malarial parasites, etc.).

C2c2 Protein

When a C2c2 protein has intact HEPN domains, it can cleave RNA (target RNA as well as non-target RNA) after it is 'activated'. However, C2c2 protein can also cleave precursor C2c2 guide RNAs into mature C2c2 guide RNAs in a HEPN-independent fashion. For example, when a C2c2 protein lacks a catalytically active HEPN1 domain and also lacks a catalytically active HEPN2 domain, it can still cleave precursor guide RNA into mature guide RNA. As such, when used in a method that includes a precursor C2c2 guide RNA and/or a precursor C2c2 guide RNA array, the C2c2 protein can (and will in some cases) lack a catalytically active HEPN1 domain and/or catalytically active HEPN2 domain. In some cases, the C2c2 protein lacks a catalytically active HEPN1 domain and lacks a catalytically active HEPN2 domain.

A C2c2 protein that lacks a catalytically active HEPN1 domain and lacks a catalytically active HEPN2 domain can in some cases be used in methods of binding (e.g. imaging methods). For example, in some cases, a method of binding (and/or imaging) includes contacting a sample with a precursor C2c2 guide RNA array and a C2c2 protein that lacks a catalytically active HEPN1 domain and lacks a catalytically active HEPN2 domain. In such cases, the C2c2 protein can be detectably labeled (e.g., fused an epitope tag, fused to a fluorophore, fused to a fluorescent protein such as a green fluorescent protein, etc.).

A C2c2 protein suitable for use in a method of the present disclosure for cleaving a precursor C2c2 guide RNA array can have intact HEPN1 and HEPN2 domains. However, in some cases, the C2c2 protein lacks a catalytically active HEPN1 domain and/or lacks a catalytically active HEPN2 domain.

In some cases, a C2c2 protein suitable for use in a method of the present disclosure for cleaving a precursor C2c2 guide RNA array includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Herbinix hemicellulosilytica* C2c2 amino acid sequence set forth in SEQ ID NO:6. In some cases, a C2c2 protein suitable for use in a method of the present disclosure for cleaving a precursor C2c2 guide RNA array includes an amino acid sequence having 80% or more amino acid sequence identity with the *Leptotrichia buccalis* (Lbu) C2c2 amino acid sequence set forth in SEQ ID NO: 2. In some cases, a C2c2 protein suitable for inclusion in a kit of the present disclosure is a *Leptotrichia buccalis* (Lbu) C2c2 protein (e.g., see SEQ ID NO: 2). In some cases, a C2c2 protein suitable for use in a method of the present disclosure for cleaving a precursor C2c2 guide RNA array includes the amino acid sequence set forth in any one of SEQ ID NOs: 1-2 and 4-6.

In some cases, a C2c2 protein used in a method of the present disclosure for cleaving a precursor C2c2 guide RNA array is not a *Leptotrichia shahii* (Lsh) C2c2 protein. In some cases, a C2c2 protein used in a method of the present disclosure for cleaving a precursor C2c2 guide RNA array is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 polypeptide suitable for use in a method of the present disclosure for cleaving a precursor C2c2 guide RNA array is a variant C2c2 polypeptide. Variant C2c2 polypeptides suitable for use in a method of the present disclosure for cleaving a precursor C2c2 guide RNA array include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (*Leptotrichia buccalis* C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (*Listeria seeligeri* C2c2) that correspond to R472, H477, R1048, and H1053 of SEQ ID NO:2 are R445, H450, R1016, and H1021, respectively.

In some cases, a variant C2c2 polypeptide comprises amino acid substitutions of amino acids R472 and H477 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (*Herbinix hemicellulosilytica* C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Precursor C2c2 Guide RNA Array

As demonstrated in the working examples below, a C2c2 protein can cleave a precursor C2c2 guide RNA into a mature guide RNA, e.g., by endoribonucleolytic cleavage of the precursor. Also as demonstrated in the working examples below, a C2c2 protein can cleave a precursor C2c2 guide RNA array (that includes more than one C2c2 guide RNA arrayed in tandem) into two or more individual C2c2 guide RNAs. Thus, in some cases a precursor C2c2 guide RNA array comprises two or more (e.g., 3 or more, 4 or more, 5 or more, 2, 3, 4, or 5) C2c2 guide RNAs (e.g., arrayed in tandem as precursor molecules). In some cases, each guide RNA of a precursor C2c2 guide RNA array has a different guide sequence. In some cases, two or more guide RNAs of a precursor C2c2 guide RNA array have the same guide sequence.

In some cases, the precursor C2c2 guide RNA array comprises two or more C2c2 guide RNAs that target different target sites within the same target RNA molecule. For example, such a scenario can in some cases increase sensitivity of detection by activating C2c2 protein when either one hybridizes to the target RNA molecule.

In some cases, the precursor C2c2 guide RNA array comprises two or more C2c2 guide RNAs that target different target RNA molecules. For example, such a scenario can result in a positive signal when any one of a family of potential target RNAs is present. Such an array could be used for targeting a family of transcripts, e.g., based on variation such as single nucleotide polymorphisms (SNPs) (e.g., for diagnostic purposes). Such could also be useful for detecting whether any one of a number of different strains of virus is present (e.g., influenza virus variants, Zika virus variants, HIV variants, and the like). Such could also be useful for detecting whether any one of a number of different species, strains, isolates, or variants of a bacterium is present (e.g., different species, strains, isolates, or variants of *Mycobacterium*, different species, strains, isolates, or variants of *Neisseria*, different species, strains, isolates, or variants of *Staphylococcus aureus*; different species, strains, isolates, or variants of *E. coli*; etc.)

Variant C2c2 Polypeptides

The present disclosure provides a variant C2c2 polypeptide, as well as a nucleic acid (e.g., a recombinant expression vector) comprising a nucleotide sequence encoding the variant C2c2 polypeptide.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (*Herbinix hemicellulosilytica* C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of 1, 2, 3, or 4 of amino acids R472, H477, R1048, and H1053, such that the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. For example, in some cases, the variant C2c2 polypeptide exhibits less than 50%, less than 40%, less than 30%, less than 20%, less than 10%, less than 5%, less than 1%, or less than 0.1%, of the RNA-guided cleavage of a non-target RNA exhibited by a C2c2 polypeptide having the amino acid sequence set forth in SEQ ID NO:2. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

The present disclosure provides a nucleic acid (e.g., an isolated nucleic acid) comprising a nucleotide sequence encoding a variant C2c2 polypeptide of the present disclosure. In some cases, the nucleotide sequence is operably linked to a transcriptional control element, e.g., a promoter. In some cases, the promoter is a constitutive promoter. In some cases, the promoter is a regulatable promoter. In some cases, the promoter is an inducible promoter. In some cases, the promoter is functional in a eukaryotic cell. In some cases, the promoter is functional in a prokaryotic cell.

The present disclosure provides a recombinant expression vector comprising a nucleic acid of the present disclosure, e.g., a nucleic acid comprising a nucleotide sequence encoding a variant C2c2 polypeptide of the present disclosure.

The present disclosure provides a host cell that is genetically modified with a nucleic acid of the present disclosure, e.g., a nucleic acid comprising a nucleotide sequence encoding a variant C2c2 polypeptide of the present disclosure. The present disclosure provides a host cell that is genetically modified with a recombinant expression vector comprising a nucleic acid of the present disclosure, e.g., a nucleic acid comprising a nucleotide sequence encoding a variant C2c2 polypeptide of the present disclosure. In some cases, the host cell is a prokaryotic cell. In some cases, the host cell is a eukaryotic cell. In some cases, the host cell is in vitro. In some cases, the host cell is ex vivo. In some cases, the host cell is in vivo. In some cases, the host cell is a bacterial cell. In some cases, the host cell is a yeast cell. In some cases, the host cell is a plant cell. In some cases, the host cell is a mammalian cell. In some cases, the host cell is human cell. In some cases, the host cell is a non-human mammalian cell. In some cases, the host cell is an insect cell. In some cases, the host cell is an arthropod cell. In some cases, the host cell is a fungal cell. In some cases, the host cell is an algal cell.

Kits

The present disclosure provides a kit for detecting a target RNA in a sample comprising a plurality of RNAs. In some cases, the kit comprises: (a) a precursor C2c2 guide RNA array comprising two or more C2c2 guide RNAs each of which has a different guide sequence; and (b) a C2c2 protein, and/or a nucleic acid encoding said C2c2 protein. In some cases, such a kit further includes a labeled detector RNA (e.g., a labeled detector RNA comprising a fluorescence-emitting dye pair, i.e., a FRET pair and/or a quencher/fluor pair). In some cases, two or more C2c2 guide RNAs (e.g., in some cases each of the C2c2 guide RNAs) of a given precursor C2c2 guide RNA array include the same guide sequence.

In some cases, a subject kit comprises: (a) a labeled detector RNA comprising a fluorescence-emitting dye pair, i.e., a FRET pair and/or a quencher/fluor pair; and (b) a C2c2 protein, and/or a nucleic acid encoding said C2c2 protein. In some cases, such a kit further includes (c) a C2c2 guide RNA (and/or a nucleic acid encoding a C2c2 guide RNA), and/or (d) a precursor C2c2 guide RNA (and/or a nucleic acid encoding a precursor C2c2 guide RNA) and/or (e) a precursor C2c2 guide RNA array (and/or a nucleic acid encoding a precursor C2c2 guide RNA array, e.g., a nucleic acid encoding a precursor C2c2 guide RNA array that includes sequence insertion sites for the insertion of guide sequences by a user).

1) Kit Comprising a Precursor C2c2 Guide RNA Array and a C2c2 Protein

In some cases, the kit comprises: (a) a precursor C2c2 guide RNA array comprising two or more C2c2 guide RNAs each of which has a different guide sequence; and (b) a C2c2 protein, and/or a nucleic acid encoding said C2c2 protein. As noted above, in some cases such a kit further includes a labeled detector RNA (e.g., a labeled detector RNA comprising a fluorescence-emitting dye pair, i.e., a FRET pair and/or a quencher/fluor pair).

C2c2 Protein

A C2c2 protein suitable for inclusion in a kit of the present disclosure binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

In some cases, a C2c2 protein suitable for inclusion in a kit of the present disclosure includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Herbinix hemicellulosilytica* C2c2 amino acid sequence set forth in SEQ ID NO:6. In some cases, a C2c2 protein suitable for inclusion in a kit of the present disclosure includes an amino acid sequence having 80% or more amino acid sequence identity with the *Leptotrichia buccalis* (Lbu) C2c2 amino acid sequence set forth in SEQ ID NO: 2. In some cases, a C2c2 protein suitable for inclusion in a kit of the present disclosure is a *Leptotrichia buccalis* (Lbu) C2c2 protein (e.g., see SEQ ID NO: 2). In some cases, a C2c2 protein suitable for inclusion in a kit of the present disclosure includes the amino acid sequence set forth in any one of SEQ ID NOs: 1-2 and 4-6.

In some cases, a C2c2 protein included in a kit of the present disclosure is not a *Leptotrichia shahii* (Lsh) C2c2 protein. In some cases, a C2c2 protein included in a kit of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 polypeptide included in a kit of the present disclosure is a variant C2c2 polypeptide. Variant C2c2 polypeptides suitable for inclusion in a kit of the present disclosure include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (*Leptotrichia buccalis* C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (*Listeria seeligeri* C2c2) that correspond to R472, H477, R1048, and H1053 of SEQ ID NO:2 are R445, H450, R1016, and H1021, respectively.

In some cases, a variant C2c2 polypeptide comprises amino acid substitutions of amino acids R472 and H477 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (*Herbinix hemicellulosilytica* C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

2) Kit Comprising a Labeled Detector RNA and a C2c2 Protein

In some cases, the kit comprises: (a) a labeled detector RNA comprising a fluorescence-emitting dye pair, i.e., a FRET pair and/or a quencher/fluor pair; and (b) a C2c2 protein, and/or a nucleic acid encoding said C2c2 protein. In some cases, a kit further includes a C2c2 guide RNA, precursor C2c2 guide RNA array, and/or a nucleic acid encoding a constant region of a C2c2 guide RNA. As noted above, in some cases such a kit further includes (c) a C2c2 guide RNA (and/or a nucleic acid encoding a C2c2 guide RNA), and/or (d) a precursor C2c2 guide RNA (and/or a nucleic acid encoding a precursor C2c2 guide RNA), and/or (e) a precursor C2c2 guide RNA array (and/or a nucleic acid encoding a precursor C2c2 guide RNA array, e.g., a nucleic acid encoding a precursor C2c2 guide RNA array that includes sequence insertion sites for the insertion of guide sequences by a user).

Labeled Detector RNA

In some cases, a kit of the present disclosure comprises a labeled detector RNA comprising a fluorescence-emitting dye pair, i.e., a FRET pair and/or a quencher/fluor pair. The labeled detector RNA produces an amount of detectable signal prior to being cleaved, and the amount of detectable signal that is measured is reduced when the labeled detector RNA is cleaved. In some cases, the labeled detector RNA produces a first detectable signal prior to being cleaved (e.g., from a FRET pair) and a second detectable signal when the labeled detector RNA is cleaved (e.g., from a quencher/fluor pair). As such, in some cases, the labeled detector RNA comprises a FRET pair and a quencher/fluor pair.

In some cases, the labeled detector RNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. The donor-acceptor pair (a FRET donor moiety and a FRET acceptor moiety) is referred to herein as a "FRET pair" or a "signal FRET pair." Thus, in some cases, a subject labeled detector RNA includes two signal partners (a signal pair), when one signal partner is a FRET donor moiety and the other signal partner is a FRET acceptor moiety. A subject labeled detector RNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a C2c2 protein).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1, above.

In some cases, a detectable signal is produced when the labeled detector RNA is cleaved (e.g., in some cases, the labeled detector RNA comprises a quencher/fluor pair. One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector RNA is cleaved. For example, in some cases, the signal exhibited by one signal partner (a signal moiety) is quenched by the other signal partner (a quencher signal moiety), e.g., when both are present on the same RNA molecule prior to cleavage by a C2c2 protein. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector RNA by a C2c2 protein), but the signal will be quenched when the partners are in close proximity (e.g., prior to cleavage of the detector RNA by a C2c2 protein).

A quencher moiety can quench a signal from the signal moiety (e.g., prior to cleave of the detector RNA by a C2c2 protein) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., *Annu Rev Biomed Eng.* 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

Nucleic Acid Modifications

In some cases, a labeled detector RNA comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids (having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a labeled detector RNA comprises one or more phosphorothioate and/or heteroatom internucleoside linkages, in particular $-CH_2-NH-O-CH_2-$, $-CH_2-N(CH_3)-O-CH_2-$(known as a methylene (methylimino) or MMI backbone), $-CH_2-O-N(CH_3)-CH_2-$, $-CH_2-N(CH_3)-N(CH_3)-CH_2-$ and $-O-N(CH_3)-CH_2-CH_2-$ (wherein the native phosphodiester internucleotide linkage is represented as $-O-P(=O)(OH)-O-CH_2-$). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a labeled detector RNA comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A labeled detector RNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.,* 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., *Proc. Natl. Acad. Sci. U.S.A.,* 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). LNAs and preparation thereof are also described in WO 98/39352 and WO 99/14226.

Modified Sugar Moieties

A labeled detector RNA can also include one or more substituted sugar moieties. Suitable polynucleotides comprise a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2$ $CH_2$ $CH_2NH_2$), allyl (—$CH_2$—CH═$CH_2$), —O-allyl (—O—$CH_2$—CH═$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled detector RNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, Antisense Research and Applications, pages 289-302, Crooke, S. T. and Lebleu, B., ed., *CRC Press,* 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, *CRC Press*, Boca Raton, 1993, pp. 276-278) and are suitable base substitutions, e.g., when combined with 2'-O-methoxyethyl sugar modifications.

3) Kit Comprising Two Different C2c2 Proteins, and Two Different Labeled Detector RNAs In some cases, a subject kit comprises: (a) a first labeled detector RNA that lacks U but comprises at least one A (e.g., at least 2, at least 3, or at least 4 As) and comprises a first FRET pair and/or a first quencher/fluor pair; (b) a second labeled detector RNA that lacks A but comprises at least one U (e.g., at least 2, at least 3, or at least 4 Us) and comprises a second FRET pair and/or a second quencher/fluor pair; (c) a first C2c2 protein, and/or a nucleic acid encoding said first C2c2 protein, wherein the first C2c2 protein cleaves adenine⁺ RNAs (RNAs that include A) when activated but does not cleave RNAs that lack A (e.g., polyU RNAs) [e.g., the first C2c2 protein can cleave the first labeled detector RNA but not the second labeled detector RNA]; and (d) a second C2c2 protein, and/or a nucleic acid encoding said second C2c2 protein, wherein the second C2c2 protein cleaves uracil⁺ RNAs (RNAs that include U) when activated but does not cleave RNAs that lack U (e.g., polyA RNAs) (e.g., the second C2c2 protein can cleave the second labeled detector RNA but not the first labeled detector RNA).

In some cases, the first labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the first labelled detector RNA lacks U and includes a stretch of at least 2 consecutive As (e.g., at least 3, at least 4, or at least 5 consecutive As). In some cases, the second labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the second labelled detector RNA lacks A and includes a stretch of at least 2 consecutive Us (e.g., at least 3, at least 4, or at least 5 consecutive Us).

In some cases, such a kit further includes: (e) a first C2c2 guide RNA (and/or a nucleic acid encoding the first C2c2 guide RNA), e.g., a nucleic acid comprising a nucleotide sequence encoding the first C2c2 guide RNA, where the nucleic acid includes a sequence insertion site for the insertion of a guide sequence (e.g., a nucleotide sequence that hybridizes to a target RNA) by a user); and (f) a second C2c2 guide RNA (and/or a nucleic acid encoding the second C2c2 guide RNA), e.g., a nucleic acid comprising a nucleotide sequence encoding the second C2c2 guide RNA, where the nucleic acid includes a sequence insertion site for the insertion of a guide sequence (e.g., a nucleotide sequence that hybridizes to a target RNA) by a user). The first C2c2 guide RNA comprises a first nucleotide sequence that hybridizes with a first single stranded target RNA and a second nucleotide sequence that binds to the first C2c2 protein. The second C2c2 guide RNA comprises a first nucleotide sequence that hybridizes with a second single stranded target RNA and a second nucleotide sequence that binds to the second C2c2 protein. The first C2c2 protein is not activated by the second C2c2 guide RNA, and the first C2c2 protein cleaves ssRNA that includes at least one A (e.g., does not cleave ssRNA that lacks A). The second C2c2 protein is not activated by the first C2c2 guide RNA, and the second C2c2 protein cleaves ssRNA that includes at least one U (e.g., does not cleave ssRNA that lacks U).

The following are non-limiting examples (listed as a) through w), below) of first and second C2c2 proteins suitable for inclusion in a kit of the present disclosure:

a) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

b) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

c) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

d) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

e) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

f) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

g) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

h) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

i) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

j) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

k) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

l) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

m) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

n) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

o) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A;

p) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

q) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

r) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

s) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

t) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

u) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

v) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56F; or w) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A.

C2c2 Protein

A C2c2 protein suitable for inclusion in a kit of the present disclosure binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

In some cases, a C2c2 protein suitable for inclusion in a kit of the present disclosure includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Herbinix hemicellulosilytica* C2c2 amino acid sequence set forth in SEQ ID NO:6. In some cases, a C2c2 protein suitable for inclusion in a kit of the present disclosure includes an amino acid sequence having 80% or more amino acid sequence identity with the *Leptotrichia buccalis* (Lbu) C2c2 amino acid sequence set forth in SEQ ID NO: 2. In some cases, a C2c2 protein suitable for inclusion in a kit of the present disclosure is a *Leptotrichia buccalis* (Lbu) C2c2 protein (e.g., see SEQ ID NO: 2). In some cases, a C2c2 protein suitable for inclusion in a kit of the present disclosure includes the amino acid sequence set forth in any one of SEQ ID NOs: 1-2 and 4-6.

In some cases, a C2c2 protein included in a kit of the present disclosure is not a *Leptotrichia shahii* (Lsh) C2c2 protein. In some cases, a C2c2 protein included in a kit of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 protein suitable for inclusion in a kit of the present disclosure is more efficient, by a factor of 1.2-fold or more, than a *Leptotrichia shahii* (Lsh) C2c2 protein at cleaving RNA that is not targeted by a C2c2 guide RNA of the method. In some cases, the C2c2 protein is more efficient, by a factor of 1.5-fold or more, than a *Leptotrichia shahii* (Lsh) C2c2 protein at cleaving RNA that is not targeted by a C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

In some cases, a C2c2 protein suitable for inclusion in a kit of the present disclosure exhibits at least a 50% RNA cleavage efficiency within 1 hour of said contacting (e.g., 55% or more, 60% or more, 65% or more, 70% or more, or 75% or more cleavage efficiency). In some cases, a C2c2 protein suitable for inclusion in a kit of the present disclosure exhibits at least a 50% RNA cleavage efficiency within 40 minutes of said contacting (e.g., 55% or more, 60% or more, 65% or more, 70% or more, or 75% or more cleavage efficiency). In some cases, a C2c2 protein suitable for inclusion in a kit of the present disclosure exhibits at least a 50% RNA cleavage efficiency within 30 minutes of said contacting (e.g., 55% or more, 60% or more, 65% or more, 70% or more, or 75% or more cleavage efficiency).

In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 60 minutes, e.g., from 1 minute to 60 minutes, from 30 seconds to 5 minutes, from 1 minute to 5 minutes, from 1 minute to 10 minutes, from 5 minutes to 10 minutes, from 10 minutes to 15 minutes, from 15 minutes to 20 minutes, from 20 minutes to 25 minutes, from 25 minutes to 30 minutes, from 30 minutes to 35 minutes, from 35 minutes to 40 minutes, from 40 minutes to 45 minutes, from 45 minutes to 50 minutes, from 50 minutes to 55 minutes, or from 55 minutes to 60 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 5 minutes (e.g., from 1 minute to 5 minutes, e.g., in a time period of 1 minute, 2 minutes, 3 minutes, 4 minutes, or 5 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 5 minutes to 10 minutes (e.g., in a time period of 5 minutes, 6 minutes, 7 minutes, 8 minutes, 9 minutes, or 10 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 10 minutes to 15 minutes (e.g., 10 minutes, 11 minutes, 12 minutes, 13 minutes, 14 minutes, or 15 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 15 minutes to 20 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 20 minutes to 25 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 25 minutes to 30 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 minutes to 35 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 35 minutes to 40 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 40 minutes to 45 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 45 minutes to 50 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 50 minutes to 55 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 55 minutes to 60 minutes.

In some cases, the C2c2 protein included in a kit of the present disclosure is not a *Leptotrichia shahii* (Lsh) C2c2 protein. In some cases, the C2c2 protein is more efficient than a *Leptotrichia shahii* (Lsh) C2c2 protein (e.g., at cleaving non-target RNA) by a factor of 1.2-fold or more (e.g., 1.5-fold or more, 1.7-fold or more, or 2-fold or more). As such, in some cases, a C2c2 protein suitable for inclusion in a kit of the present disclosure is more efficient, by a factor of 1.2-fold or more (e.g., 1.5-fold or more, 1.7-fold or more, or 2-fold or more), than a *Leptotrichia shahii* (Lsh) C2c2 protein at cleaving RNA that is not targeted by the C2c2 guide RNA of the method. In some cases, a C2c2 protein suitable for inclusion in a kit of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

Positive Controls

A kit of the present disclosure that comprises a labeled detector RNA and a C2c2 polypeptide can also include a positive control target RNA. In some cases, the kit also includes a positive control guide RNA that comprises a nucleotide sequence that hybridizes to the control target RNA. In some cases, the positive control target RNA is provided in various amounts, in separate containers. In some cases, the positive control target RNA is provided in various known concentrations, in separate containers, along with control non-target RNAs.

Nucleic Acid Encoding a C2c2 Guide RNA and/or a Precursor C2c2 Guide RNA Array and/or a C2c2 Protein While the RNAs of the disclosure (e.g., C2c2 guide RNAs and precursor C2c2 guide RNA arrays) can be synthesized using any convenient method (e.g., chemical synthesis, in vitro using an RNA polymerase enzyme, e.g., T7 polymerase, T3 polymerase, SP6 polymerase, etc.), nucleic acids encoding 2c2 guide RNAs and/or precursor C2c2 guide RNA arrays are also envisioned. Additionally, while C2c2 proteins of the disclosure can be provided (e.g., as part of a kit) in protein form, nucleic acids (such as mRNA and/or DNA) encoding the C2c2 protein(s) can also be provided.

For example, in some embodiments, a kit of the present disclosure comprises a nucleic acid (e.g., a DNA, e.g., a recombinant expression vector) that comprises a nucleotide sequence encoding a C2c2 guide RNA. In some cases, the nucleotide sequence encodes a C2c2 guide RNA without a guide sequence. For example, in some cases, the nucleic acid comprises a nucleotide sequence encoding a constant region of a C2c2 guide RNA (a C2c2 guide RNA without a guide sequence), and comprises an insertion site for a nucleic acid encoding a guide sequence. In some embodiments, a kit of the present disclosure comprises a nucleic acid (e.g., an mRNA, a DNA, e.g., a recombinant expression vector) that comprises a nucleotide sequence encoding a C2c2 protein.

In some embodiments, a kit of the present disclosure comprises a nucleic acid (e.g., a DNA, e.g., a recombinant expression vector) that comprises a nucleotide sequence encoding a precursor C2c2 guide RNA array (e.g., in some cases where each guide RNA of the array has a different guide sequence). In some cases, one or more of the encoded guide RNAs of the array does not have a guide sequence, e.g., the nucleic acid can include insertion site(s) for the guide sequence(s) of one or more of the guide RNAs of the array. In some cases, a subject C2c2 guide RNA can include a handle from a precursor crRNA but does not necessarily have to include multiple guide sequences.

In some cases, the C2c2 guide RNA-encoding nucleotide sequence (and/or the precursor C2c2 guide RNA array-encoding nucleotide sequence) is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a C2c2 protein is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-90 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method of detecting a single stranded target RNA in a sample comprising a plurality of RNAs, the method comprising:

a) contacting the sample with: (i) a C2c2 guide RNA that hybridizes with the single stranded target RNA; and (ii) a C2c2 protein that cleaves RNAs present in the sample; and b) measuring a detectable signal produced by C2c2 protein-mediated RNA cleavage.

Aspect 2. A method of detecting a single stranded target RNA in a sample comprising a plurality of RNAs, the method comprising:

(a) contacting the sample with: (i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and (b) measuring a detectable signal produced by C2c2 protein-mediated RNA cleavage.

Aspect 3. The method according to aspect 1 or 2 aspect, wherein the C2c2 protein cleaves at least 50% of the RNAs present in the sample within 1 hour of said contacting.

Aspect 4. The method according to aspect 3, wherein the C2c2 protein cleaves at least 50% of the RNAs present in the sample within 40 minutes of said contacting.

Aspect 5. The method according to aspect 4, wherein the C2c2 protein cleaves at least 50% of the RNAs present in the sample within 5 minutes of said contacting.

Aspect 6. The method according to aspect 5, wherein the C2c2 protein cleaves at least 50% of the RNAs present in the sample within 1 minute of said contacting.

Aspect 7. The method according to aspect 1, wherein the C2c2 protein cleaves from 50% to more than 90% of the RNAs present in the sample within 1 minute of said contacting.

Aspect 8. The method according to any one of aspects 1-7, wherein the minimum concentration at which the single stranded target RNA can be detected is in a range of from 500 fM to 1 nM.

Aspect 9. The method according to any one of aspects 1-7, wherein the single stranded target RNA can be detected at a concentration as low as 800 fM.

Aspect 10. The method according to any of aspects 1-9, wherein the C2c2 protein is not a *Leptotrichia shahii* (Lsh) C2c2 protein comprising an amino acid sequence having at least 80%, at least 85%, at least 90%, at least 95%, at least 98%, at least 99%, or 100%, amino acid sequence identity to the amino acid sequence set forth in SEQ ID NO:3.

Aspect 11. The method according to aspect 10, wherein the C2c2 protein cleaves non-target RNA at least 1.2-fold efficiently than a *Leptotrichia shahii* (Lsh) C2c2 protein comprising at least 80%, at least 85%, at least 90%, at least 95%, at least 98%, at least 99%, or 100%, amino acid sequence identity to the amino acid sequence set forth in SEQ ID NO:3.

Aspect 12. The method according to aspect 11, wherein the C2c2 protein cleaves non-target RNA at least 1.5-fold efficiently than a *Leptotrichia shahii* (Lsh) C2c2 protein comprising the amino acid sequence set forth in SEQ ID NO:3.

Aspect 13. The method according to any of aspects 1-9, wherein the C2c2 protein comprises an amino acid sequence having 80% or more amino acid sequence identity with the amino acid sequence set forth in any one of SEQ ID NOs:1, 2, or 4-6.

Aspect 14. The method according to any of aspects 1-9, wherein the C2c2 protein comprises an amino acid sequence having 80% or more amino acid sequence identity with the *Leptotrichia buccalis* (Lbu) C2c2 amino acid sequence set forth in SEQ ID NO: 2.

Aspect 15. The method according to any of aspects 1-9, wherein the C2c2 protein comprises an amino acid sequence having 80% or more amino acid sequence identity with the *Listeria seeligeri* C2c2 amino acid sequence set forth in SEQ ID NO: 1.

Aspect 16. The method according to any of aspects 1-9, wherein the C2c2 protein comprises the amino acid sequence set forth in any one of SEQ ID NOs: 1-2 and 4-6.

Aspect 17. The method according to aspect 1, wherein the C2c2 protein comprises an amino acid sequence having at least 80% amino acid sequence identity to the C2c2 amino acid sequence set forth in SEQ ID NO:2, and comprises a substitution of one or more of R472, H477, R1048, and H1053.

Aspect 18. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R472 and H477.

Aspect 19. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R1048 and H1053.

Aspect 20. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R472, H477, R1048, and H1053.

Aspect 21. The method according to any one of aspects 1-20, wherein the sample is contacted for 2 hours or less prior to said measuring.

Aspect 22. The method according to aspect 21, wherein the sample is contacted for 60 minutes or less prior to said measuring.

Aspect 23. The method according to aspect 22, wherein the sample is contacted for 30 minutes or less prior to said measuring.

Aspect 24. The method according to aspect 23, wherein the sample is contacted for 10 minutes or less prior to said measuring.

Aspect 25. The method according to aspect 24, wherein the sample is contacted for 1 minute or less prior to said measuring.

Aspect 26. The method according to any one of aspects 1-25, comprising determining an amount of target RNA present in the sample.

Aspect 27. The method according to aspect 26, wherein said determining comprises:

measuring the detectable signal to generate a test measurement;

measuring a detectable signal produced by a reference sample to generate a reference measurement; and comparing the test measurement to the reference measurement to determine an amount of target RNA present in the sample.

Aspect 28. The method according to aspect 26, comprising:

measuring the detectable signal to generate a test measurement, measuring a detectable signal produced by each of two or more reference samples, wherein the two or more reference samples each include a different amount of a positive control RNA, to generate two or more reference measurements, and comparing the test measurement to the two or more reference measurements to determine an amount of target RNA present in the sample.

Aspect 29. The method according to any one of aspects 1-28, wherein the sample comprises from 5 to $10^7$ RNAs that differ from one another in sequence.

Aspect 30. The method according to any one of aspects 1-28, wherein the sample comprises from 10 to $10^6$ RNAs that differ from one another in sequence.

Aspect 31. The method according to any one of aspects 1-30, wherein the sample comprises RNAs from a cell lysate.

Aspect 32. The method according to any one of aspects 1-31, wherein measuring a detectable signal comprises one or more of: gold nanoparticle based detection, fluorescence polarization, colloid phase transition/dispersion, electrochemical detection, and semiconductor-based sensing.

Aspect 33. The method according to any one of aspects 1-32, wherein (i) the method comprises contacting the sample with a labeled detector RNA comprising a fluorescence-emitting dye pair (i.e., a fluorescence resonance energy transfer (FRET) pair and/or a quencher/fluor pair), (ii) the C2c2 protein cleaves the labeled detector RNA, and (iii) the detectable signal is produced by the FRET pair and/or the quencher/fluor pair.

Aspect 34. The method according to aspect 33, wherein the labeled detector RNA produces an amount of detectable signal prior to being cleaved, and the amount of detectable signal is reduced when the labeled detector RNA is cleaved.

Aspect 35. The method according to aspect 33, wherein the labeled detector RNA produces a first detectable signal prior to being cleaved and a second detectable signal when the labeled detector RNA is cleaved.

Aspect 36. The method according to aspect 35, wherein the labeled detector RNA comprises a FRET pair and a quencher/fluor pair.

Aspect 37. The method according to any one of aspects 33-36, wherein the labeled detector RNA comprises a FRET pair.

Aspect 38. The method according to aspect 33, wherein a detectable signal is produced when the labeled detector RNA is cleaved.

Aspect 39. The method according to aspect 33, wherein an amount of detectable signal increases when the labeled detector RNA is cleaved.

Aspect 40. The method according to aspect 38 or 3 aspect 9, wherein the labeled detector RNA comprises a quencher/fluor pair.

Aspect 41. The method according to any of aspects 33-40, wherein the labeled detector RNA comprises a modified nucleobase, a modified sugar moiety, and/or a modified nucleic acid linkage.

Aspect 42. The method according to any one of aspects 1-41, wherein said contacting is carried out in an acellular sample.

Aspect 43. The method according to any one of aspects 1-41, wherein said contacting is carried out in a cell in vitro, ex vivo, or in vitro.

Aspect 44. A method of cleaving a precursor C2c2 guide RNA array into two or more C2c2 guide RNAs, the method comprising:

contacting a precursor C2c2 guide RNA array comprising two or more C2c2 guide RNAs each of which has a different guide sequence, with a C2c2 protein, wherein the C2c2 protein cleaves the precursor C2c2 guide RNA array into individual C2c2 guide RNAs.

Aspect 45. The method according to aspect 44, wherein the C2c2 protein lacks a catalytically active HEPN1 domain and/or lacks a catalytically active HEPN2 domain.

Aspect 46. The method according to aspect 44 or aspect 45, wherein the precursor C2c2 guide RNA array comprises two or more C2c2 guide RNAs that target different target sequences within the same target RNA molecule.

Aspect 47. The method according to any one of aspects 44-46, wherein the precursor C2c2 guide RNA array comprises two or more C2c2 guide RNAs that target different target RNA molecules.

Aspect 48. The method according to any one of aspects 44-47, wherein said contacting does not take place inside of a cell.

Aspect 49. The method according to any one of aspects 44-48, wherein at least one of the guide RNAs and/or the precursor C2c2 guide RNA array is detectably labeled.

Aspect 50. A kit for detecting a target RNA in a sample comprising a plurality of RNAs, the kit comprising:

(a) a precursor C2c2 guide RNA array, and/or a nucleic acid encoding said precursor C2c2 guide RNA array, wherein the precursor C2c2 guide RNA array comprises two or more C2c2 guide RNAs each of which has a different guide sequence and/or an insertion site for a guide sequence of choice; and (b) a C2c2 protein.

Aspect 51. The kit of aspect 50, wherein the C2c2 protein lacks a catalytically active HEPN1 domain and/or lacks a catalytically active HEPN2 domain.

Aspect 52. The kit of aspect 50 or aspect 51, wherein the precursor C2c2 guide RNA array comprises two or more C2c2 guide RNAs that target different target sequences within the same target RNA molecule.

Aspect 53. The kit of any one of aspects 50-52, wherein the precursor C2c2 guide RNA array comprises two or more C2c2 guide RNAs that target different target RNA molecules.

Aspect 54. The kit of any one of 5 aspects 0-53, wherein at least one of the guide RNAs and/or the precursor C2c2 guide RNA array is detectably labeled.

Aspect 55. The kit of any one of aspects 50-54, further comprising a labeled detector RNA comprising a fluorescence-emitting dye pair (i.e., a FRET pair and/or a quencher/fluor pair).

Aspect 56. A kit for detecting a target RNA in a sample comprising a plurality of RNAs, the kit comprising:

(a) a labeled detector RNA comprising a fluorescence-emitting dye pair (i.e., a FRET pair and/or a quencher/fluor pair); and (b) a C2c2 protein.

Aspect 57. The kit of aspect 56, comprising a positive control target RNA.

Aspect 58. The kit of aspect 57, where in the positive control target RNA is present in different amounts in each of two or more containers.

Aspect 59. The kit of any one of aspects 56-58, comprising at least one of:

(c) a C2c2 guide RNA and/or a nucleic acid encoding said C2c2 guide RNA;

(d) a precursor C2c2 guide RNA and/or a nucleic acid encoding said precursor C2c2 guide RNA; and (e) a precursor C2c2 guide RNA array, and/or a nucleic acid encoding said precursor C2c2 guide RNA array, wherein the precursor C2c2 guide RNA array comprises two or more C2c2 guide RNAs each of which has a different guide sequence and/or an insertion site for a guide sequence of choice.

Aspect 60. The kit of any one of aspects 56-59, comprising a DNA comprising a nucleotide sequence that encodes a C2c2 guide RNA with or without a guide sequence.

Aspect 61. The kit of aspect 60, wherein the DNA comprises an insertion sequence for the insertion of a guide sequence.

Aspect 62. The kit of aspect 60 or aspect 61, wherein the DNA is an expression vector and the C2c2 guide RNA is operably linked to a promoter.

Aspect 63. The kit of aspect 62, wherein the promoter is a T7 promoter.

Aspect 64. The kit of any one of aspects 56-63, comprising a C2c2 endoribonuclease variant that lacks nuclease activity.

Aspect 65. The kit of any one of aspects 56-64, wherein the labeled detector RNA comprises a FRET pair.

Aspect 66. The kit of any one of aspects 56-65, wherein the labeled detector RNA comprises a quencher/fluor pair.

Aspect 67. The kit of any one of aspects 56-66, wherein the labeled detector RNA comprises a FRET pair that produces a first detectable signal and a quencher/fluor pair that produces a second detectable signal.

Aspect 68. A variant C2c2 polypeptide comprising:

a) an amino acid sequence having at least 80%, at least 85%, at least 90%, at least 95%, at least 98%, or at least 99%, amino acid sequence identity to the amino acid sequence set forth in SEQ ID NO:2, and comprises substitution of: i) amino acids R472 and H477; ii) amino acids R1048 and H1053; or iii) amino acids R472, H477, R1048, and H1053;

b) an amino acid sequence having at least 80%, at least 85%, at least 90%, at least 95%, at least 98%, or at least 99%, amino acid sequence identity to the amino acid sequence set forth in SEQ ID NO:1, and comprises substitution of: i) amino acids R445 and H450; ii) amino acids R1016 and H1021; or iii) amino acids R445, H450, R1016, and H1021;

c) an amino acid sequence having at least 80%, at least 85%, at least 90%, at least 95%, at least 98%, or at least 99%, amino acid sequence identity to the amino acid sequence set forth in SEQ ID NO:4, and comprises substitution of: i) amino acids R464 and H469; ii) amino acids R1052, and H1057; or iii) amino acids R464, H469, R1052, and H1057;

d) an amino acid sequence having at least 80%, at least 85%, at least 90%, at least 95%, at least 98%, or at least 99%, amino acid sequence identity to the amino acid sequence set forth in SEQ ID NO:5, and comprises substitution of: i) amino acids R467 and H472; ii) amino acids R1069, and H1074; or iii) amino acids R467, H472, R1069, and H1074; or e) an amino acid sequence having at least 80%, at least 85%, at least 90%, at least 95%, at least 98%, or at least 99%, amino acid sequence identity to the amino acid sequence set forth in SEQ ID NO:6, and comprises substitution of: i) amino acids R472 and H477; ii) amino acids R1044 and H1049; iii) or amino acids R472, H477, R1044, and H1049.

Aspect 69. A variant C2c2 polypeptide of 68, wherein the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Aspect 70. A nucleic acid comprising a nucleotide sequence encoding a variant C2c2 polypeptide of aspect 68 or aspect 69.

Aspect 71. The nucleic acid of aspect 70, wherein the nucleotide sequence is operably linked to a constitutive promoter or a regulatable promoter.

Aspect 72. A recombinant expression vector comprising the nucleic acid of aspect 70 or aspect 71.

Aspect 73. A host cell genetically modified with the nucleic acid of aspect 70 or aspect 71, or with the recombinant expression vector of aspect 72.

Aspect 74. The host cell of aspect 73, wherein the host cell is a eukaryotic cell.

Aspect 75. The host cell of aspect 73, wherein the host cell is a prokaryotic cell.

Aspect 76. The host cell of any one of aspects 73-75, wherein the host cell is in vitro, ex vivo, or in vivo.

Aspect 77. A method of detecting at least two different single stranded target RNAs in a sample comprising a plurality of RNAs, the method comprising:

a) contacting the sample with:

(i) a first C2c2 protein that cleaves single stranded RNAs (ssRNAs) that include at least one A;

(ii) a second C2c2 protein that cleaves ssRNAs that include at least one U;

(iii) a first C2c2 guide RNA that comprises a first nucleotide sequence that hybridizes with the first single stranded target RNA and a second nucleotide sequence that binds to the first C2c2 protein; and (iv) a second C2c2 guide RNA that comprises a first nucleotide sequence that hybridizes with the second single stranded target RNA and a second nucleotide sequence that binds to the second C2c2 protein;

wherein the first C2c2 protein is not activated by the second C2c2 guide RNA, and wherein the first C2c2 protein cleaves ssRNA that includes at least one A, and wherein the second C2c2 protein is not activated by the first C2c2 guide RNA, and wherein the second C2c2 protein cleaves ssRNA that includes at least one U; and b) measuring a detectable signal produced by RNA cleavage mediated by the first and the second C2c2 proteins, wherein a first detectable signal is produced upon activation of the first C2c2 protein and a second detectable signal is produced upon activation of the second C2c2 protein, wherein detection of the first signal indicates the presence in the sample of the first target ssRNA, and wherein detection of the second signal indicates the presence in the sample of the second target ssRNA.

Aspect 78. The method of aspect 77, wherein:

a) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

b) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

c) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

d) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

e) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

f) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

g) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

h) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

i) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

j) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

k) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

l) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

m) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

n) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

o) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A;

p) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

q) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

r) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

s) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

t) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

u) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

v) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56F; or w) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A.

Aspect 79. The method according to aspect 77 or aspect 78, wherein the method comprises contacting the sample with:

i) a first labeled detector RNA comprising a first fluorescence resonance energy transfer (FRET) pair and/or first a quencher/fluor pair, where the first labeled detector RNA comprises at least one A and does not comprise U; and ii) a second labeled detector RNA comprising a second FRET pair and/or a second quencher/fluor pair, where the second labeled detector RNA comprises at least one U and does not comprise A, wherein the first C2c2 protein cleaves the first labelled detector RNA, and the first detectable signal is produced by the first FRET pair and/or the first quencher/fluor pair, and wherein the first C2c2 protein cleaves the second labelled detector RNA, and the second detectable signal is produced by the second FRET pair and/or the second quencher/fluor pair.

Aspect 80. The method according to 7 aspect 9, wherein the first labeled detector RNA comprises a stretch of from 2 to 15 consecutive As and/or the second labeled detector RNA comprises a stretch of from 2 to 15 consecutive Us.

Aspect 81. The method according to aspect 79, wherein the first labeled detector RNA comprises a stretch of from 4 to 15 consecutive As and/or the second labeled detector RNA comprises a stretch of from 4 to 15 consecutive Us.

Aspect 82. The method according to aspect 79, wherein the first labeled detector RNA comprises a stretch of at least 3 consecutive As and/or the second labeled detector RNA comprises a stretch of at least 3 consecutive Us.

Aspect 83. The method according to aspect 79, wherein the first labeled detector RNA comprises a stretch of at least 4 consecutive As and/or the second labeled detector RNA comprises a stretch of at least 4 consecutive Us.

Aspect 84. A kit comprising:

(a) a first labeled detector RNA that lacks U and comprises at least one A and comprises a first fluorescence-emitting dye pair;

(b) a second labeled detector RNA that lacks A and comprises at least one U and comprises a second fluorescence-emitting dye pair;

(c) a first C2c2 protein, and/or a nucleic acid encoding said first C2c2 protein, wherein the first C2c2 protein can cleave the first labeled detector RNA but not the second labeled detector RNA (e.g., the first C2c2 protein cleaves adenine+ RNAs when activated and does not cleave RNAs that lack A); and (d) a second C2c2 protein, and/or a nucleic acid encoding said second C2c2 protein, wherein the second C2c2 protein can cleave the second labeled detector RNA but not the first labeled detector RNA (e.g., the second C2c2 protein cleaves uracil$^+$ RNAs when activated but does not cleave RNAs that lack U).

Aspect 85. The kit of aspect 84, comprising at least one of:

(e) a first C2c2 guide RNA and/or a nucleic acid encoding said first C2c2 guide RNA, wherein the first C2c2 guide RNA comprises a constant region sequence that binds to the first C2c2 protein;

(f) a second C2c2 guide RNA and/or a nucleic acid encoding said second C2c2 guide RNA, wherein the second C2c2 guide RNA comprises a constant region sequence that binds to the second C2c2 protein;

(g) a nucleic acid comprising a nucleotide sequence encoding a constant region sequence that binds to the first C2c2 protein and an insertion site for a guide sequence of choice;

(h) a nucleic acid comprising a nucleotide sequence encoding a constant region sequence that binds to the second C2c2 protein and an insertion site for a guide sequence of choice.

Aspect 86. The kit of aspect 84, comprising a nucleic acid comprising a nucleotide sequence encoding a first C2c2 guide RNA, wherein the first C2c2 guide RNA comprises a constant region sequence that binds to the first C2c2 protein.

Aspect 87. The kit of aspect 84, comprising a nucleic acid comprising a nucleotide sequence encoding a second C2c2 guide RNA, wherein the second C2c2 guide RNA comprises a constant region sequence that binds to the second C2c2 protein.

Aspect 88. The kit of aspect 84, comprising a nucleic acid comprising a nucleotide sequence encoding a constant region sequence that binds to the first C2c2 protein and an insertion site for a guide sequence of choice.

Aspect 89. The kit of aspect 84, comprising a nucleic acid comprising a nucleotide sequence encoding a constant region sequence that binds to the second C2c2 protein and an insertion site for a guide sequence of choice.

Aspect 90. The kit of any one of aspects 86-89, wherein the nucleic acid is an expression vector and the nucleotide sequence is operably linked to a promoter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

The data described herein show that C2c2 possesses two distinct ribonuclease activities responsible for CRISPR RNA processing and ssRNA degradation. Maturation of precursor CRISPR RNAs (pre-crRNAs) is a relatively slow, highly specific catalytic event. In contrast, upon binding to target RNAs bearing sequence complementarity to the guide segment of the crRNA, C2c2 is activated as a robust general RNase that cleaves RNA in cis and in trans by initiating strand scission at uracil nucleotides. The data show that this trans cleavage activity can be harnessed for ultra-sensitive RNA detection within complex mixtures.

Example 1: C2c2 Recombinant Protein Purification

Figure 1B:
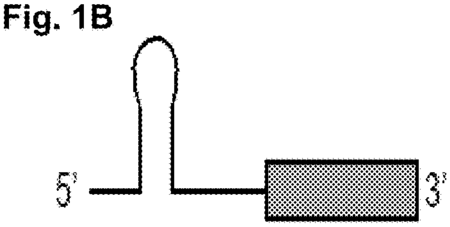
Figure 1C:
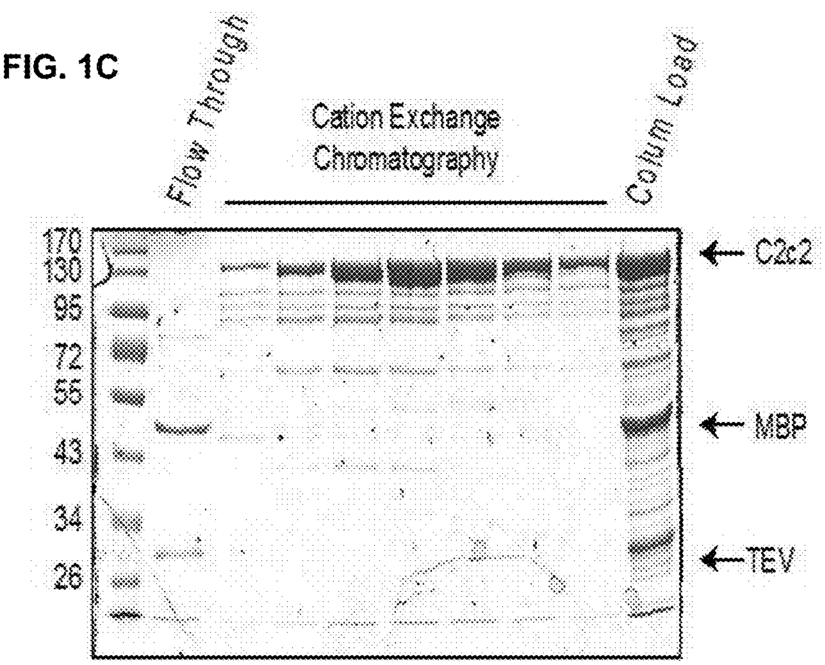
Figure 1D:
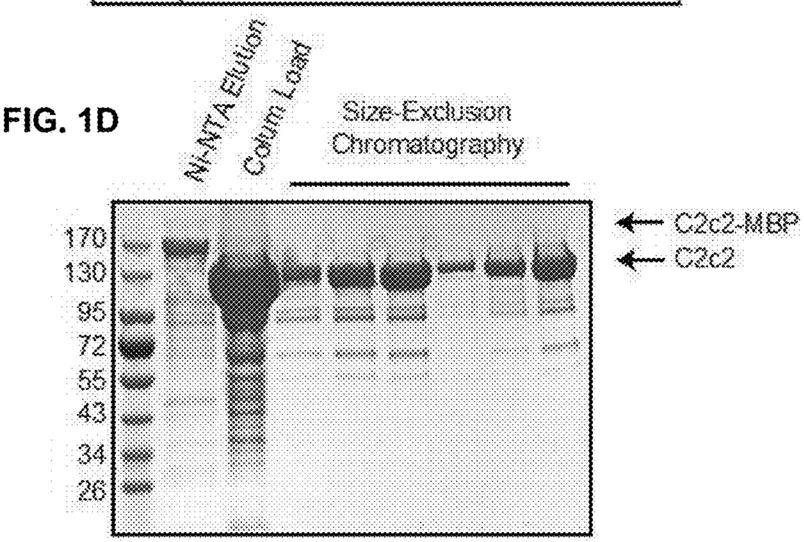
Figure 1E:
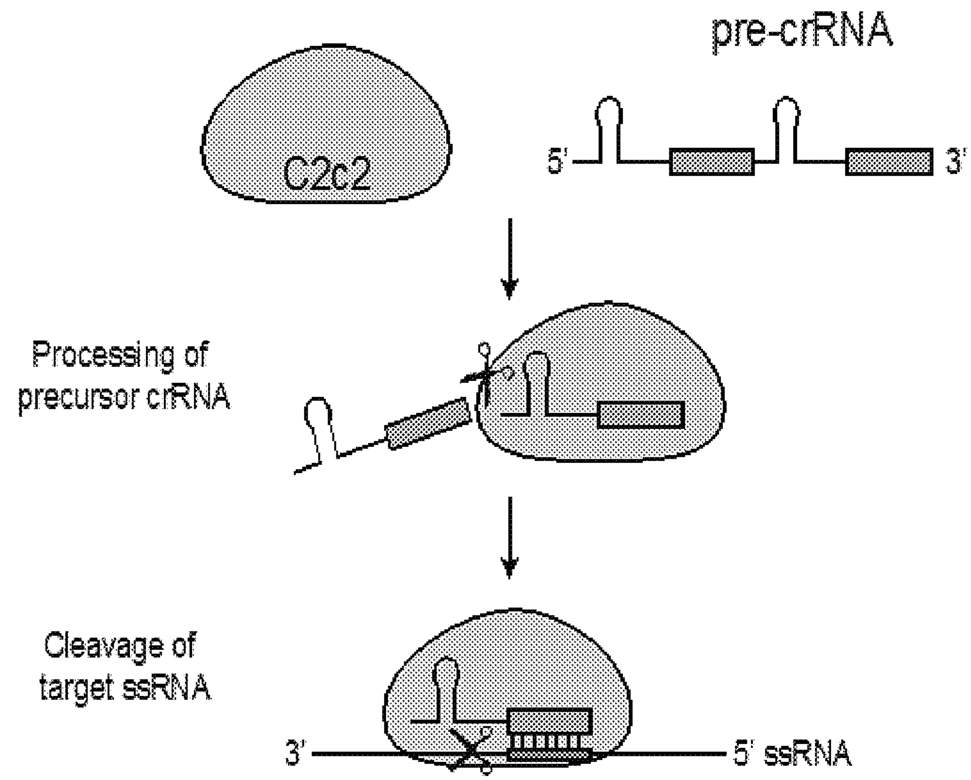

FIG. 1A-1E. Summary of endogenous C2c2 locus and heterologous expression and purification of recombinant C2c2 protein. FIG. 1A. Schematic diagram of *Leptotricia buccalis* C2c2 locus. Predicted HEPN active sites indicated in yellow with active site residues noted. FIG. 1B. Schematic diagram of mature crRNA from this Type VI CRISPR system. FIG. 1C. Sodium dodecyl sulfate-polyacrylamide gel electrophoresis (SDS-PAGE) analysis of cation exchange chromatography fractions. *E. coli* cells expressing His-maltose binding protein (MBP)-C2c2 were harvested and lysed by sonication. Lysates were cleared by centrifugation and then the His-MBP-C2c2 was isolated over metal ion affinity chromatography. Protein eluates were incubated with TEV protease to cleave off the His-MBP tag. Cleaved protein was loaded onto HiTrap heparin column and eluted over a linear KCl gradient. Elution fractions were loaded onto a 10% SDS-PAGE gel for analysis. FIG. 1D. Cation exchange chromatography fractions were pooled, concentrated and then loaded onto S200 size-exclusion chromatography column. Fractions from size exchange chromatography were analyzed via SDS-PAGE. FIG. 1E. Working model for C2c2 enzymatic activity.

Example 2: C2c2 is a Programmable Endoribonuclease

Figure 2:
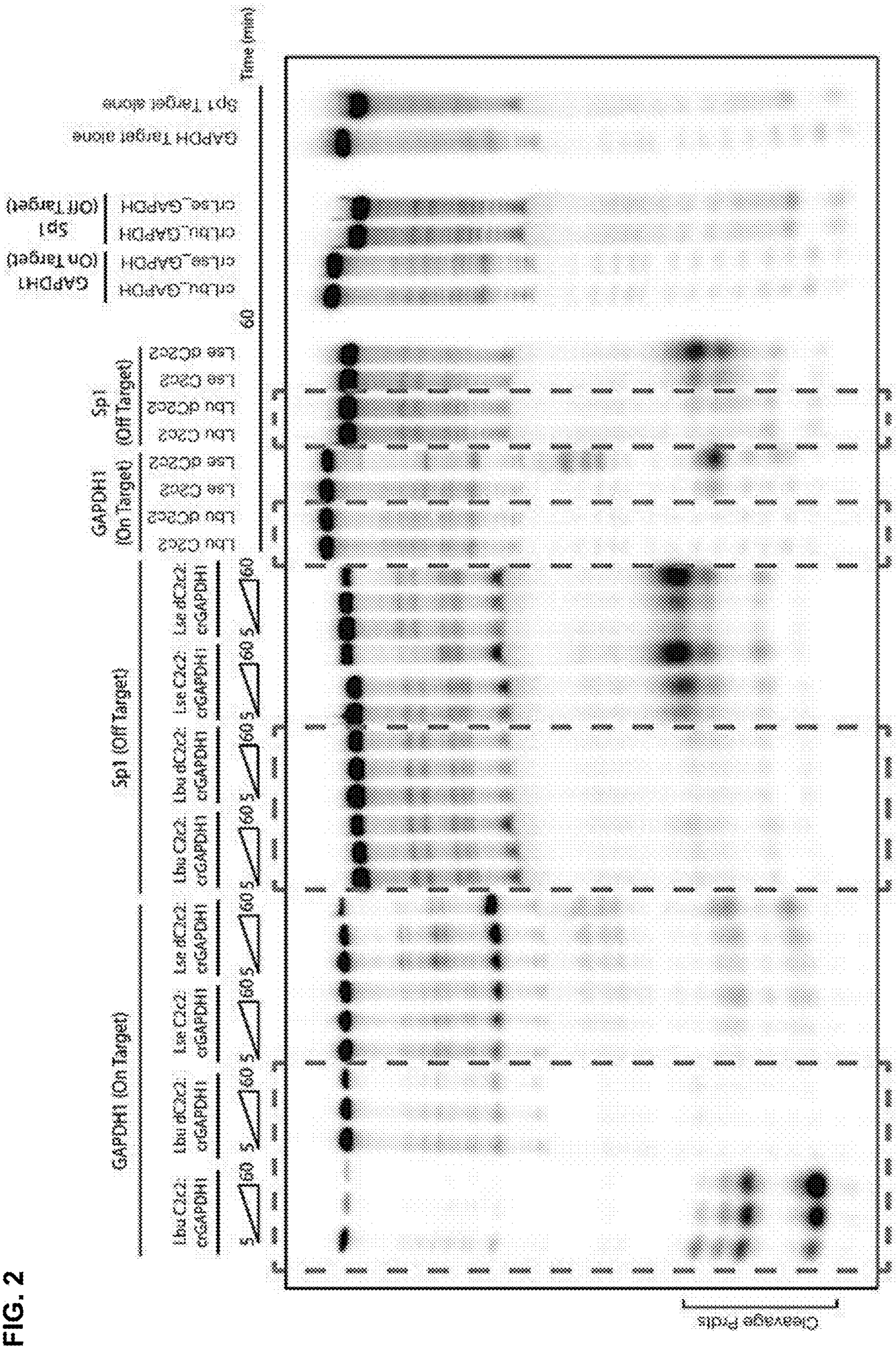
FIG. 2 depicts results from cleavage assays that were performed using C2c2 protein.

Purified C2c2 cleaved single-stranded RNA (ssRNA) in a crRNA-directed manner that was dependent on the presence of catalytically-active HEPN domains (FIG. 2)

FIG. 2. Cleavage assays were performed in 20 mM Tris-HCl pH 6.8, 50 mM KCl, 5 mM $MgCl_2$, 5% glycerol. 100 nM C2c2 protein was preincubated with crRNA at a ratio of 2:1 for 10 mins at 37° C. to promote complex assembly. Addition of ~1 nM 5' $^{32}P$ labeled ssRNA initiated the reaction and time-points were taken by quenching with formamide loading buffer. Cleavage product formation was resolved by 15% denaturing urea-PAGE and visualized using a phoshorimager. Inactivated protein (indicated by dC2c2 notation) is a quadruple point mutant (R472A, H477A, R1048A, H1053A) which eliminates both the arginine and histidine from the R—$X_{4-6}$—H HEPN motif in both predicted active sites. In this gel, lanes of interest are highlighted by the red boxes. No cleavage activity is detected with off-target ssRNA or when the HEPN domains are inactivated.

Example 3: C2c2 Cleavage Activity is Specific to Single Stranded RNA

Figure 3:
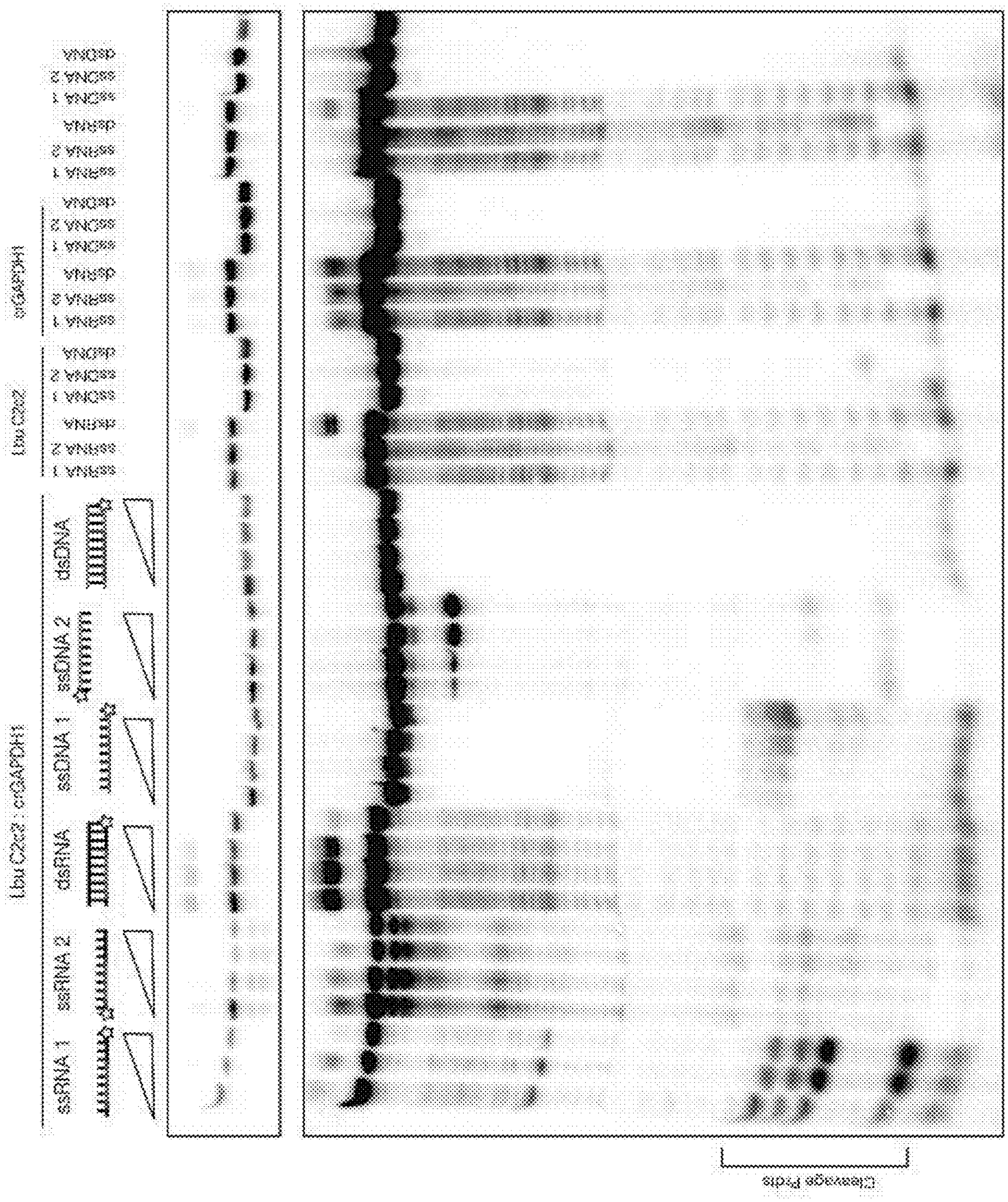
FIG. 3 depicts results showing that C2c2 robustly cleaved single stranded RNA.

C2c2 exhibited no cleavage of double-stranded RNA or DNA, with limited cleavage of single-stranded DNA at a much reduced rate as compared to ssRNA (FIG. 3).

FIG. 3. C2c2 robustly cleaved single stranded RNA and did not cleave double stranded substrates. Cleavage assay conditions as per FIG. 2. Cleavage products were resolved on a 15% denaturing urea-PAGE gel. Samples were taken at 5, 10, 30, 75 mins, with all controls lanes incubated in parallel for 75 mins. Cleavage products of the expected size range can be detected only in the ssRNA reactions and to a lesser extent in the single stranded DNA conditions. 3' end labeling of the single stranded RNA target demonstrates that cleavage is occurring outside of the target-spacer hybridization region. Labels to top of figure indicate whether protein ("Lbu C2c2") or C2c2 guide RNA ("crGAPDH1") were added. Controls included (i) protein but no guide RNA, (ii) guide RNA but no protein, and (iii) no protein and no guide RNA.

Example 4: C2c2 Processes Precursor crRNAs into Mature crRNAs

C2c2 processed precursor crRNAs to mature crRNAs in a HEPN-domain independent manner (FIG. 4A-4B), indicating the presence of an additional endonuclease domain.

Figure 4A:
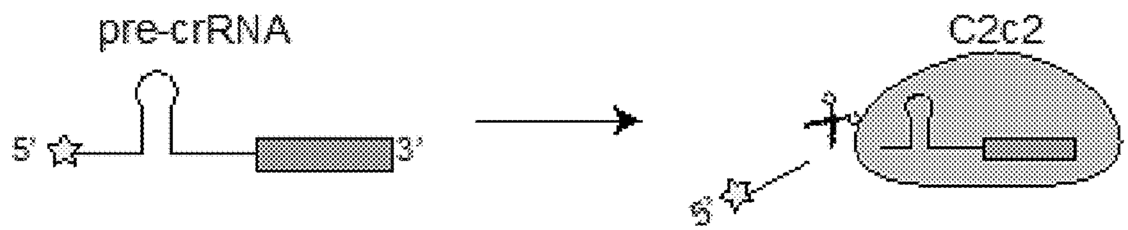
FIG. 4A-4B present a diagram and results from various cleavage assays using C2c2 protein.
Figure 4B:
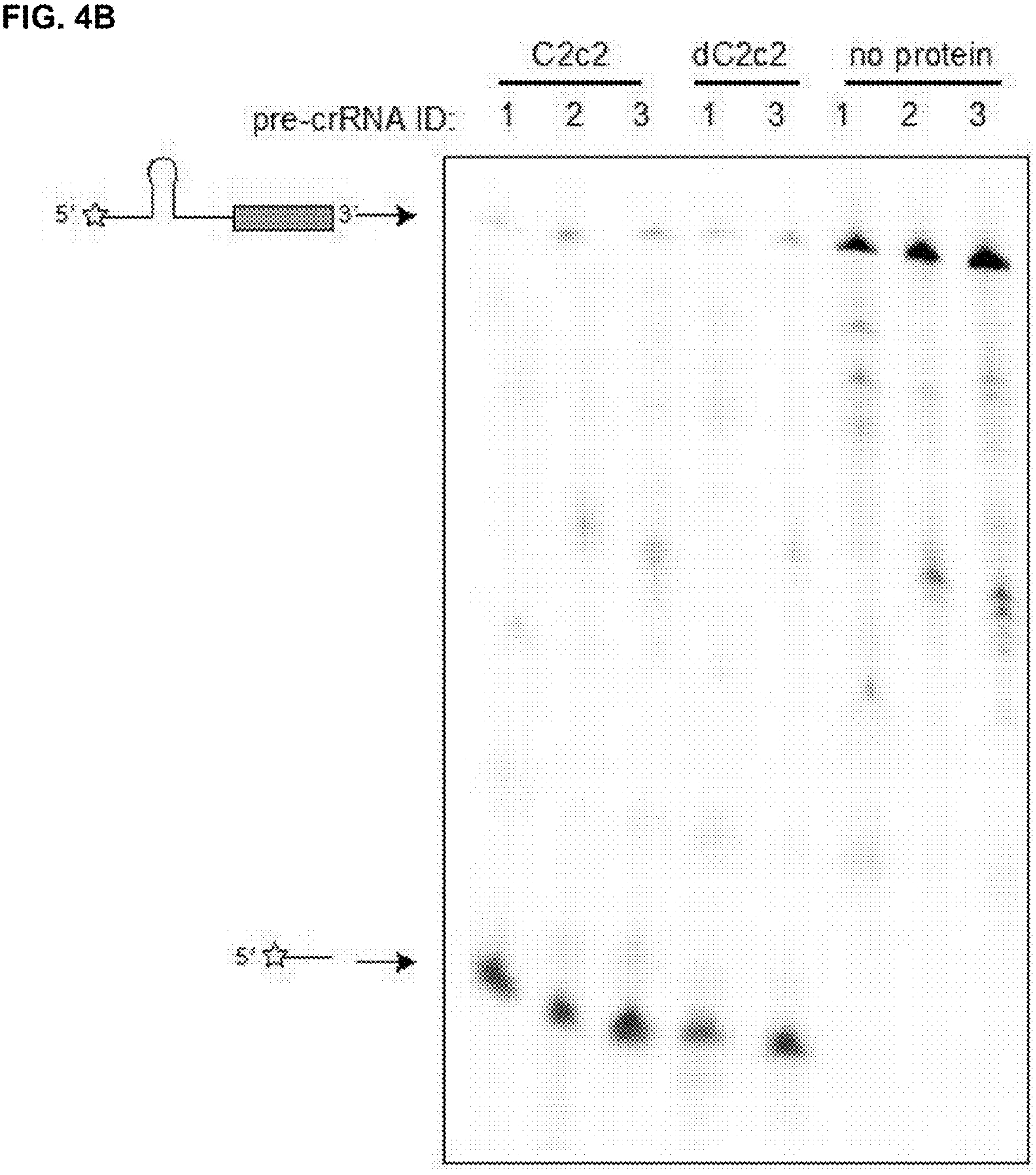

FIG. 4A. Diagram of pre-crRNA processing reaction catalyzed by C2c2. FIG. 4B. 100 nM Lbu C2c2 was incubated in 20 mM HEPES pH 6.8, 50 mM KCl, 5 mM $MgCl_2$, 5% glycerol with ~5 nM 5' $^{32}P$ labeled ssRNA for 60 min prior to quenching with formamide loading buffer. Reaction products were resolved on 15% denaturing urea-PAGE gel and visualized with a phosphoimager. Inactivated protein (indicated by dC2c2 notation) is a quadruple point mutant (R472A, H477A, R1048A, H1053A) which eliminates both the arginine and histidine from the R—$X_{4-6}$—H HEPN motif in both predicted active sites. Three different pre-crRNA with variable spacer sequences were tested for C2c2 processing capacity.

Example 5: Sensitive Detection of Transcripts in Complex Mixtures

Figure 5:
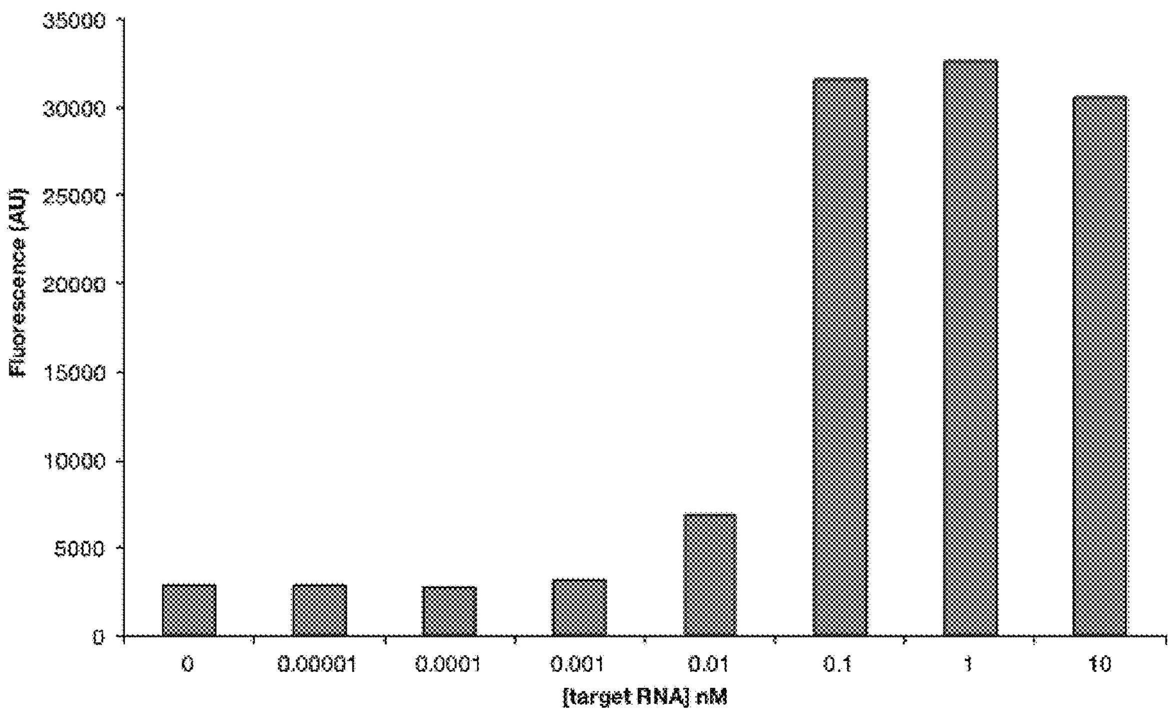
FIG. 5 depicts results from experiments performed using a labeled detector RNA (using a quencher/fluor pair) to detect RNA cleave by C2c2 protein.

C2c2 was used to detect target transcripts in complex mixtures (FIG. 5).

FIG. 5. 50 nM C2c2:crRNA targeting lambda2 ssRNA was incubated with 185 nM of RNAase-Alert substrate (A small Fluorescence-Quencher RNA oligonucleotide—a labeled detector RNA labeled with a quencher/fluor pair) and 100 ng of HEK293T total RNA in the presence of increasing amounts of lambda2 ssRNA (0-10 nM) for 30 minutes at 37 C. An increase in fluorescence was observed when 'activated' C2c2 (C2c2:crRNA:lamda2 ssRNA) cleaved the RNAse-Alert substrate releasing the fluor from the quencher moiety.

Example 6: Precursor crRNA (Pre-crRNA) Processing by C2c2 Protein

Figure 6:
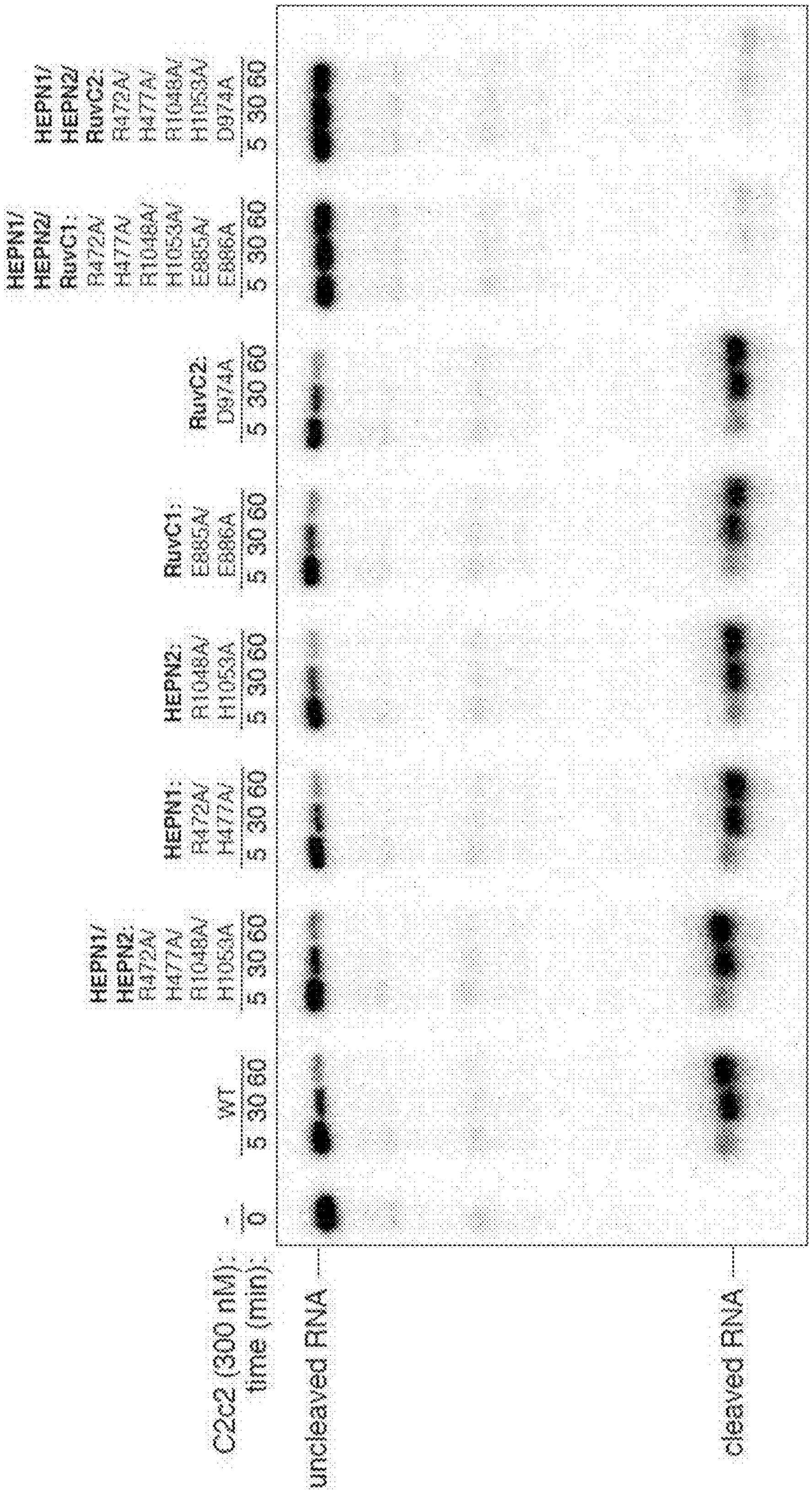
FIG. 6 depicts results from experiments that demonstrate pre-crRNA processing by C2c2 protein.

C2c2 cleaved (Processed) precursor crRNA (pre-crRNA), and this cleavage was independent of a HEPN-domain (FIG. 6).

FIG. 6. 300 nM of C2c2 was incubated with lnM 5'-$^{32}P$-labelled pre-crRNA for 0-60 minutes at 37 C. RNA products were separated on 15% urea-PAGE and imaged using a phosphorimager. Successful processing of the pre-crRNA is determined by the presence of smaller 'cleaved RNA' product.

Example 7

Materials and Methods

The following materials and methods were used, and are applicable to Examples 8-12.

C2c2 phylogenic and candidate selection. C2c2 maximum-likelihood phylogenies were computed using RAxML with the PROTGAMMALG evolutionary model and 100 bootstrap samplings. Sequences were aligned by MAFFT with the 'einsi' method. Niewoehner, 0. & Jinek, M. Structural basis for the endoribonuclease activity of the type III-A CRISPR-associated protein Csm6. RNA 22, 318-329 (2016). Candidate homologs were selected to sample main branches of the protein family.

C2c2 Protein production and purification. Expression vectors for protein purification were assembled using synthetic gBlocks ordered from Integrated DNA Technologies. The codon-optimized C2c2 genomic sequence was N-terminally tagged with a $His_6$-MBP-TEV cleavage site, with expression driven by a T7 promoter (map available upon request). Mutant proteins were cloned via round-the-horn, site-directed mutagenesis of wild-type C2c2 constructs. Expression vectors were transformed into Rosetta2 *E. coli* cells grown in 2×YT broth at 37° C. *E. coli* cells were induced during log phase with 0.5 M isopropyl β-D-1-thiogalatopyranoside (ITPG), and the temperature was reduced to 16° C. for overnight expression of His-MBP-C2c2. Cells were subsequently harvested, resuspended in lysis buffer (50 mM Tris-HCl pH 7.0, 500 mM NaCl, 5% glycerol, 1 mM tris(2-carboxyethyl)phosphine (TCEP), 0.5 mM phenylmethane sulfonyl fluoride (PMSF), and ethylenediaminetetraacetic acid (EDTA)-free protease inhibitor (Roche) and lysed by sonication, and the lysates were clarified by centrifugation. Soluble His-MBP-C2c2 was isolated over metal ion affinity chromatography, and protein-containing eluate was incubated with tobacco etch virus (TEV) protease at 4° C. overnight while dialyzing into ion exchange buffer (50 mM Tris-HCl pH 7.0, 250 mM KCl, 5% glycerol, 1 mM TCEP) in order to cleave off the $His_6$-MBP tag. Cleaved protein was loaded onto a HiTrap SP column and eluted over a linear KCl (0.25-1.5M) gradient. Cation exchange chromatography fractions were pooled and concentrated with 30 kD cutoff concentrators (Thermo Fisher). The C2c2 protein was further purified via size-exclusion chromatography on an 5200 column and stored in gel filtration buffer (20 mM Tris-HCl pH 7.0, 200 mM KCl, 5% glycerol, 1 mM TCEP) for subsequent enzymatic assays.

Generation of ssRNA. All RNAs used in this study were transcribed in vitro except for crRNA AES461 which was ordered synthetically (Integrated DNA Technologies) [see FIG. 15 and FIG. 19]. In vitro transcription reactions were performed as previously described with the following modifications: the T7 polymerase concentration was reduced to 10 μg/mL, and the UTP concentration was reduced to 2.5 mM. Transcriptions were incubated at 37° C. for 1-2 hrs to reduce non-template addition of nucleotides. All transcription reactions were purified using 15% denaturing PAGE gels. All RNAs were resuspended in cleavage buffer (20 mM HEPES pH 6.8, 50 mM KCl, 5 mM $MgCl_2$, and 5% glycerol). For radioactive experiments, 5' triphosphates were removed by calf intestinal phosphate (New England Biolabs) prior to radiolabeling and ssRNA substrates were then 5'-end labeled using T4 polynucleotide kinase (New England Biolabs) and [γ-$^{32}P$]-ATP (Perkin Elmer) as described previously. Sternberg, S. H., Haurwitz, R. E. & Doudna, J. A. Mechanism of substrate selection by a highly specific CRISPR endoribonuclease. RNA 18, 661-672 (2012).

DNA substrates used in this study are presented in Table 2, FIG. 14.

RNA substrates used in this study are presented in Table 3, FIG. 15.

Pre-crRNA processing assays. Pre-crRNA cleavage assays were performed at 37° C. in processing buffer (20 mM HEPES pH 6.8, 50 mM KCl, 5 mM $MgCl_2$, 10 pg/mL bovine serum albumin (BSA), 10 pg/mL tRNA, 0.05% Igepal CA-630 and 5% glycerol) with a 100-fold molar excess of C2c2 relative to 5'-labeled pre-crRNA (final concentrations of 100 nM and >1 nM, respectively). Unless otherwise indicated, reaction was quenched after 60 mins with 1.5×RNA loading dye (100% formamide, 0.025 w/v % bromophenol blue, and 200 μg $mL^{-1}$ heparin). After quenching, reactions were denatured at 95° C. for 5 min prior to resolving by 12% or 15% denaturing PAGE(0.5×TBE buffer). Metal dependence of the reaction was tested by addition of EDTA or EGTA to reaction buffer at concentrations varying from 10-100 mM. Bands were visualized by phosphorimaging and quantified with ImageQuant (GE Healthcare). The percent cleavage was determined as the ratio of the product band intensity to the total intensity of both the product and uncleaved pre-crRNA bands and normalized for background within each measured substrate using ImageQuant TL Software (GE Healthcare) and fit to a one phase exponential association using Prism (GraphPad).

Product Size Mapping. Cleavage product length was determined biochemically by comparing gel migration of product bands to alkaline hydrolysis and RNase T1 digestion ladders using the RNase T1 Kit from Ambion. For hydrolysis ladder, 15 nM full length RNA substrates were incubated at 95° C. in 1× alkaline hydrolysis buffer (Ambion) for 5 mins. Reactions were quenched with 1.5×RNA loading buffer, and cooled to −20° C. to immediately stop hydrolysis. For RNase T1 ladder, 15 nM full length RNA substrates were unfolded in 1×RNA sequencing buffer (Ambion) at 65° C. Reactions were cooled to ambient temperature, and then 1 μl of RNase T1 was added to reaction. After 15 mins, reactions were stopped by phenol-chlorofrom extraction and 1.5×RNA loading buffer was added for storage. Hydrolysis bands were resolved in parallel to cleavage samples on 15% denaturing PAGE and visualized by phosphorimaging.

Target cleavage assays. Target cleavages assays were performed at 25° C. and 37° C. in cleavage buffer (20 mM HEPES pH 6.8, 50 mM KCl, 5 mM $MgCl_2$, and 5% glycerol). crRNA guides were pre-folded by heating to 65° C. for 5 min and then slowly cooling to ambient temperature in cleavage buffer. RNP complex formation was performed in cleavage buffer, generally at a molar ratio of 2:1 protein to crRNA at 37° C. for 10 min, prior to adding 5'-end labeled target and/or other non-radiolabeled RNA target substrates. Unless otherwise indicated, final concentrations of protein, guide, and targets were 100 nM, 50 nM, and >1 nM respectively for all reactions. Reactions were quenched with 1.5×RNA loading dye and resolved by 15% denaturing PAGE(0.5×TBE buffer). Bands were visualized by phosphorimaging and quantified with ImageQuant (GE Healthcare). The percent cleavage was determined as the ratio of total banding intensity for all shorter products relative to the uncleaved band and normalized for background within each measured substrate using ImageQuant TL Software (GE Healthcare) and fit to a one phase exponential association using Prism (GraphPad).

crRNA filter-binding assays. Filter binding assays was carried out in RNA processing buffer (20 mM HEPES pH 6.8, 50 mM KCl, 5 mM $MgCl_2$, 10 pg/mL BSA, 10 pg/mL yeast tRNA, 0.01% Igepal CA-630 and 5% glycerol). LbuC2c2 was incubated with radiolabeled crRNA (<0.1 nM) for 1 hr at 37° C. Tufryn, Protran and Hybond-N+ were assembled onto a dot-blot apparatus in the order listed above. The membranes were washed twice with 50 μL Equilibration Buffer (20 mM HEPES pH 6.8, 50 mM KCl, 5 mM $MgCl_2$ and 5% glycerol) before the sample was applied to the membranes. Membranes were again washed with 50 μL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the figure legends.

Electrophoretic mobility-shift assays. In order to avoid the dissociation of the LbuC2c2-dHEPN1/dHEPN2: crRNA complex at low concentrations during ssRNA-binding experiments, binding reactions contained a constant excess of LbuC22c2-dHEPN1/dHEPN2 (200 nM), and increasing concentrations of crRNA-A and <0.1 nM target ssRNA. Assays were carried out in C2c2 electrophoretic mobility shift assay (EMSA) buffer (20 mM HEPES pH 6.8, 50 mM KCl, 10 pg/mL BSA, 100 pg/mL yeast tRNA, 0.01% Igepal CA-630 and 5% glycerol). LbuC2c2-crRNA-A complexes were pre-formed as described above for 10 min at 37° C. before the addition of 5'-radiolabelled ssRNA substrate and a further incubation for 45 mins at 37° C. Samples were then resolved by 8% native PAGE at 4° C. (0.5×TBE buffer). Gels were imaged by phosphorimaging, quantified using ImageQuant TL Software (GE Healthcare) and fit to a binding isotherm using Prism (GraphPad Software). All experiments were carried out in triplicate. Dissociation constants and associated errors are reported in the figure legends.

Fluorescent RNA detection assay. LbuC2c2:crRNA complexes were preassembled by incubating 1 μM of Lbu-C2c2: C2c2 with 500 nM of crRNA for 10 min at 37° C. These complexes were then diluted to 100 nM LbuC2c2: 50 nM crRNA-λ2 in RNA processing buffer (20 mM HEPES pH 6.8, 50 mM KCl, 5 mM $MgCl_2$, 10 pg/mL BSA, 10 pg/mL yeast tRNA, 0.01% Igepal CA-630 and 5% glycerol) in the presence of 185 nM of RNAase-Alert substrate (Thermo-Fisher), 100 ng of HeLa total RNA and increasing amounts of ssRNA (0-1 nM). These reactions were incubated in a fluorescence plate reader for up to 120 minutes at 37° C. with fluorescence measurements taken every 5 minutes ($\lambda_{ex}$: 485 nm; $\lambda_{em}$: 535 nm). Background-corrected fluorescence values were obtained by subtracting fluorescence values obtained from reactions carried out in the absence of target ssRNA. Maximal fluorescence was measured by incubating 50 nM RNaseA with 185 nM of RNAase-Alert substrate. For coupled pre-crRNA processing and RNA detection assays, LbuCas9-sgRNA complexes were preassembled by incubating 1 μM of Lbu-C2c2:C2c2 with 500 nM of pre-crRNA-A-λ2 for 20 min at 37° C. and reactions carried out as described above in the presence of increasing amounts of ssRNA A and ssRNA λ2 (0-1 nM each). In each case, error bars represent the standard deviation from three independent experiments.

Example 8: C2c2 Family Processes Precursor crRNA Transcripts to Generate Mature crRNAs Type VI CRISPR loci lack an obvious Cas6 or Cas5d-like endonuclease or tracrRNA. The question was asked whether C2c2 itself might possess pre-crRNA processing activity. To test this, recombinant C2c2 homologs from *Leptotrichia buccalis* (Lbu), *Leptotrichia shahii* (Lsh), and *Listeria seeligeri*(Lse), which originate from three distinct branches of the C2c2 protein family, were expressed in *Escherichia coli* and purified. FIG. 9A-9B.

All three proteins cleaved 5'-end radiolabeled pre-crRNA substrates consisting of a full-length consensus repeat sequence and a 20 nucleotide (nt) spacer sequence in 60 minutes. FIG. 9C. The cleavage site for all pre-crRNA homologs was mapped using T1 RNase and hydroxide hydrolysis ladders; it was shown that processing occurs at positions two or five nts upstream of the predicted hairpin structure depending on the homolog. FIG. 9C.

It is possible that cellular factors can further process the crRNA, as sequencing data from heterologous expression of LseC2c2 and LshC2c2 operons in *E. coli* found similar but not identical processing events. Cleavage assays with LbuC2c2 and a pre-crRNA containing a tandem hairpin-repeat array resulted in two products corresponding to two successive cleavage events (FIG. 16A-16F), consistent with a role for C2c2 in processing primary crRNA transcripts. These results demonstrate that within Type VI CRISPR systems C2c2 homologs catalyze maturation of their associated crRNAs.

FIG. 9A-9C. C2c2 family processes precursor crRNA transcripts to generate mature crRNAs. FIG. 9A, Maximum-likelihood phylogenetic tree of C2c2 proteins. Full details including accessions, organism names, and bootstrap values are provided in FIG. 22A. Homologs used in this study are highlighted in yellow. FIG. 9B, Diagram of the three different Type VI CRISPR loci. Black rectangles denote repeat elements, whereas yellow diamonds denote spacer sequences. Cas1 and Cas2 are only found in the genomic vicinity of Lsh C2c2. FIG. 9C, CC2c2-mediated cleavage of pre-crRNA derived from the LbuC2c2, LseC2c2 and LshC2c2. OH: alkaline hydrolysis ladder; T1: T1 RNase hydrolysis ladder; Processing cleavage reactions were performed with 100 nM C2c2 and >1 nM pre-crRNA. A schematic of cleavage is depicted on right, and the predicted pre-crRNA secondary structure is diagramed below, with arrows indicating the mapped C2c2 cleavage site.

Figure 22A:
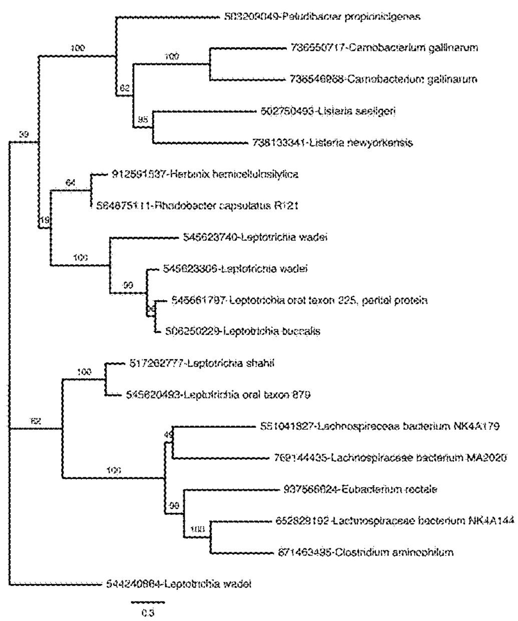
FIG. 22A-22B depict a phylogenetic tree of C2c2 family and C2c2 alignment. *Leptotrichia_buccalis* (SEQ ID NO: 2); *Listeria_seeligeri* (SEQ ID NO: 1); *Leptotrichia_shahii* (SEQ ID NO: 3).
Figure 22B:
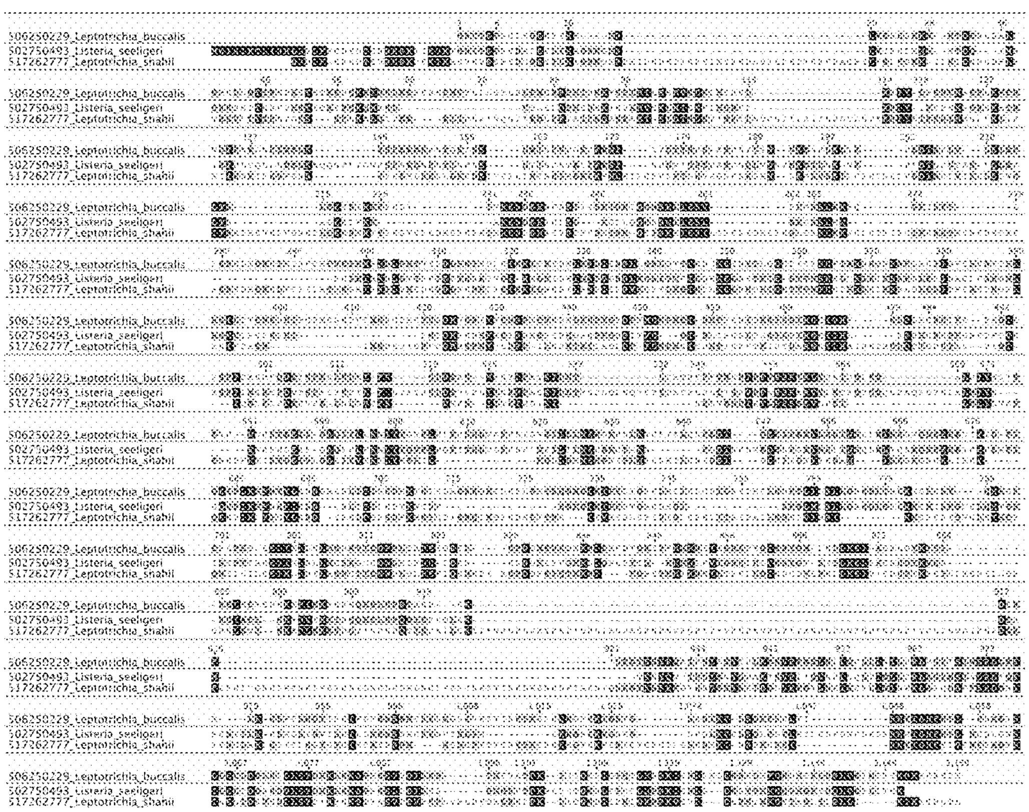

FIG. 22A-22B. Complete phylogenetic tree of C2c2 family and C2c2 alignment. FIG. 22A, Maximum-likelihood phylogenetic reconstruction of C2c2 proteins. Leaves include GI protein numbers and organism of origin; bootstrap support values, out of 100 resamplings, are presented for inner split. Scale is in substitutions per site. FIG. 22B, multiple sequence alignment of the three analyzed homologs of C2c2, coordinates are based on LbuC2c2.

Figure 23A:
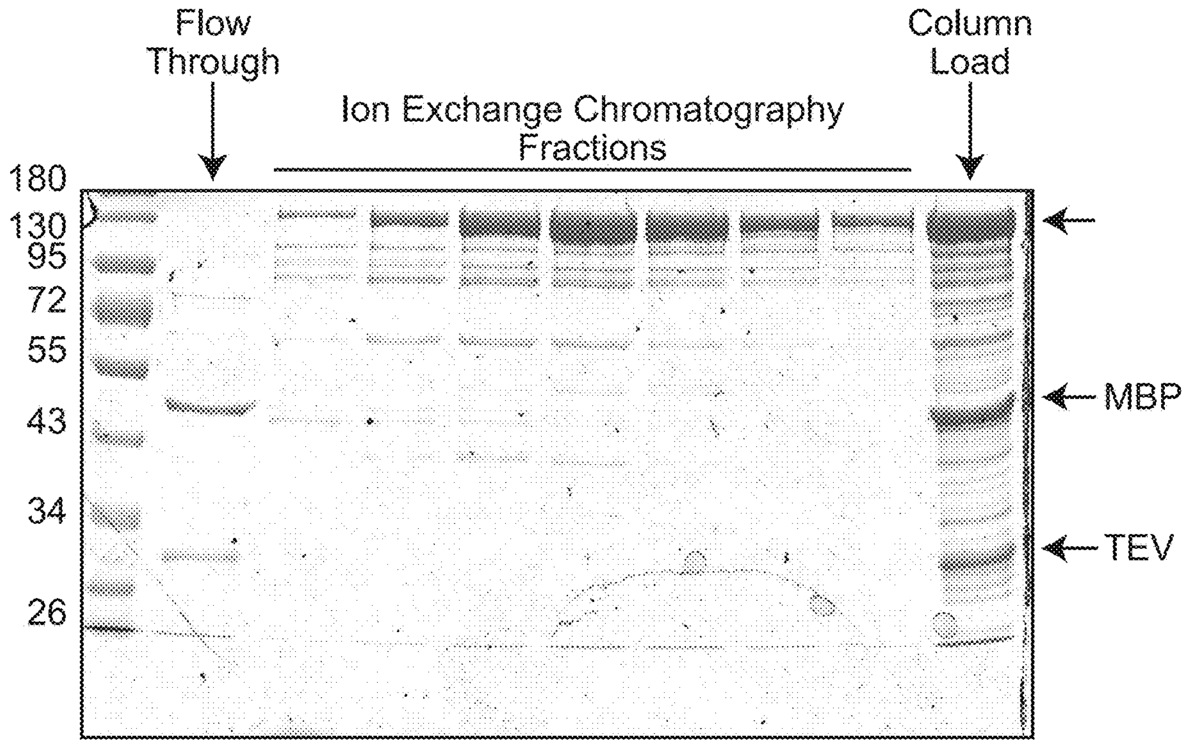
FIG. 23A-23D depict purification and production of C2c2.
Figure 23B:
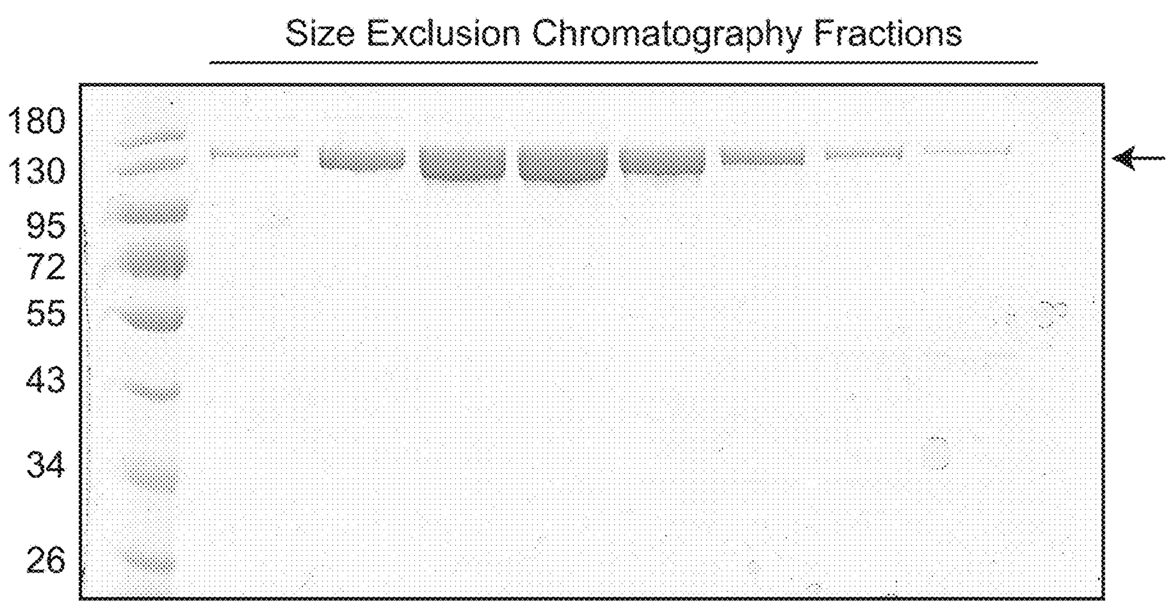
Figure 23C:
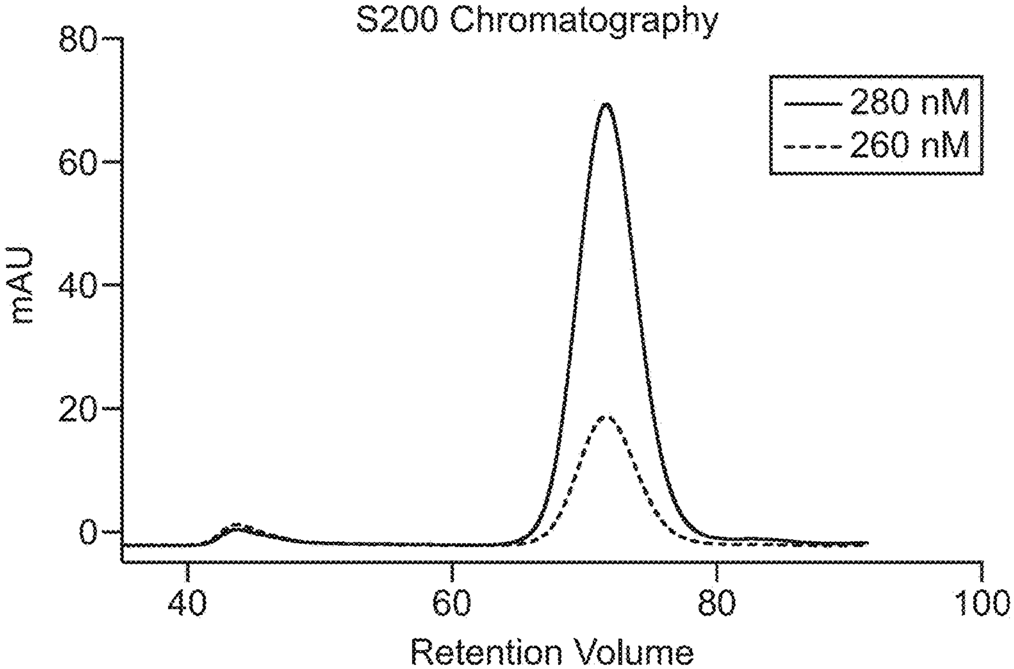
Figure 23D:
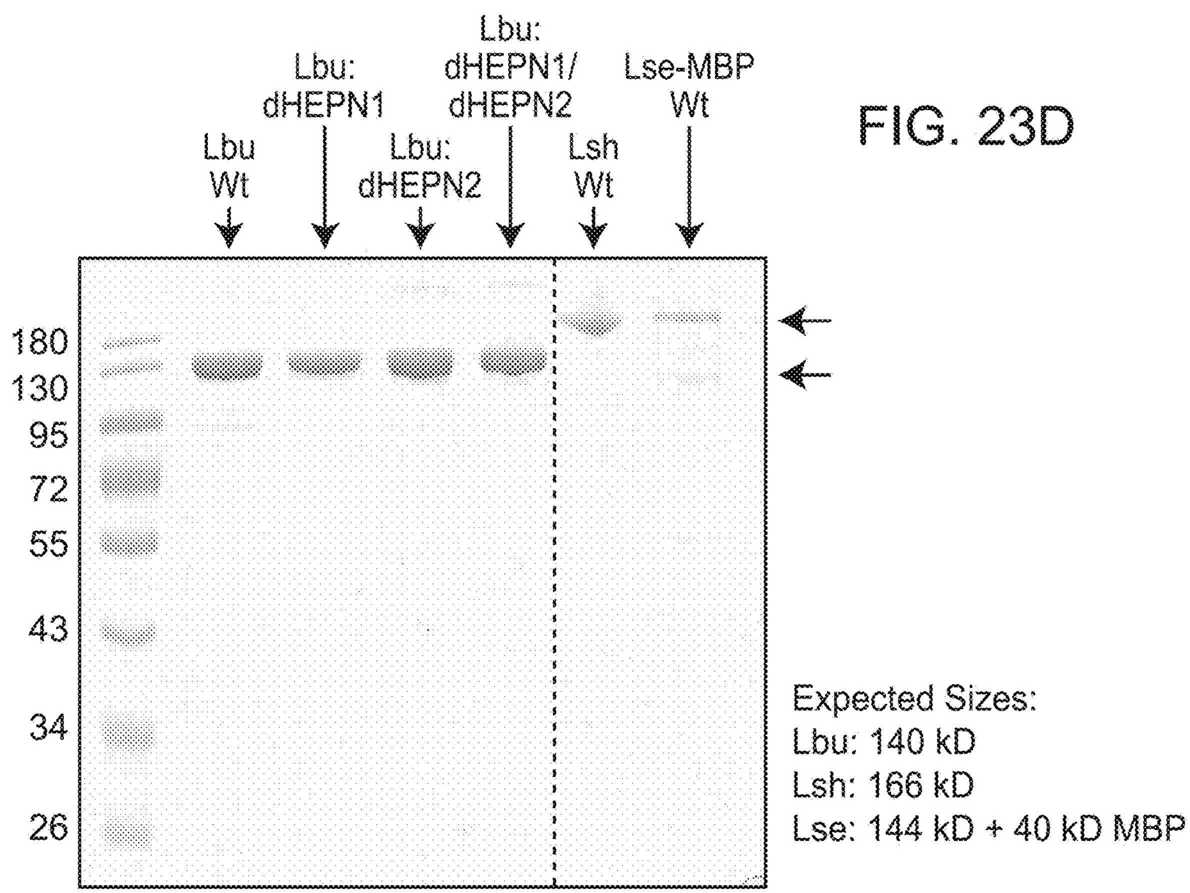

FIG. 23A-23D. Purification and Production of C2c2. All C2c2 homologs were expressed in *E. coli* as His-MBP fusions and purified by a combination of affinity, ion exchange and size exclusion chromatography. $Ni^{+}$ affinity tag was removed by incubation with TEV protease. Representative SDS-PAGE gels of chromatography fractions are shown above in (FIG. 23A-23B). FIG. 23C, The chromatograph from Superdex 200 (16/60) column demonstrating that C2c2 elutes off as a single peak, devoid of nucleic acid. FIG. 23D, SDS PAGE analysis of all purified proteins used in this manuscript.

Figure 16A:
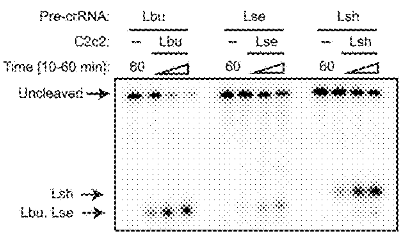
FIG. 16A-16F depict data showing that pre-crRNA processing by C2c2 is spacer sequence independent, can occur on tandem crRNA arrays, is affected by mutations in the 5' and/or 3' flanking region of the pre-cRNA, and is metal independent.
Figure 16B:
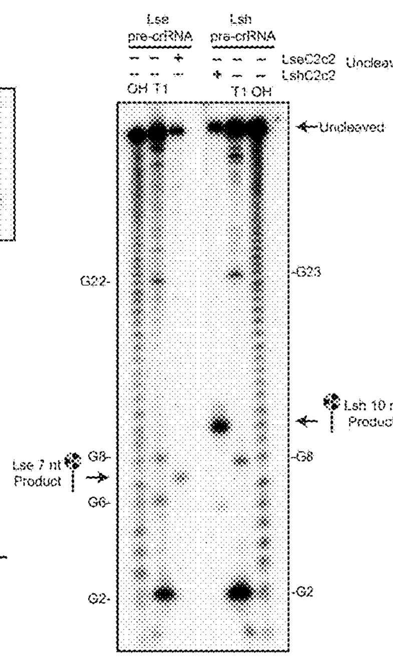
Figure 16C:
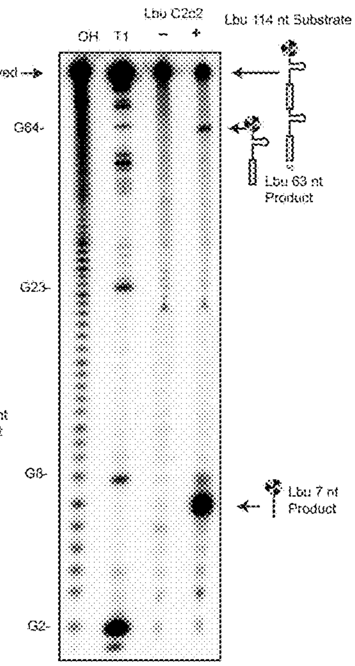
Figure 16D:
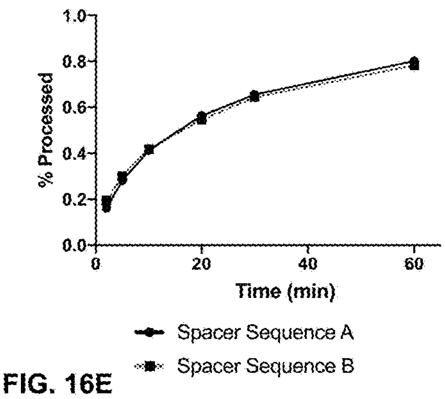
Figure 16E:
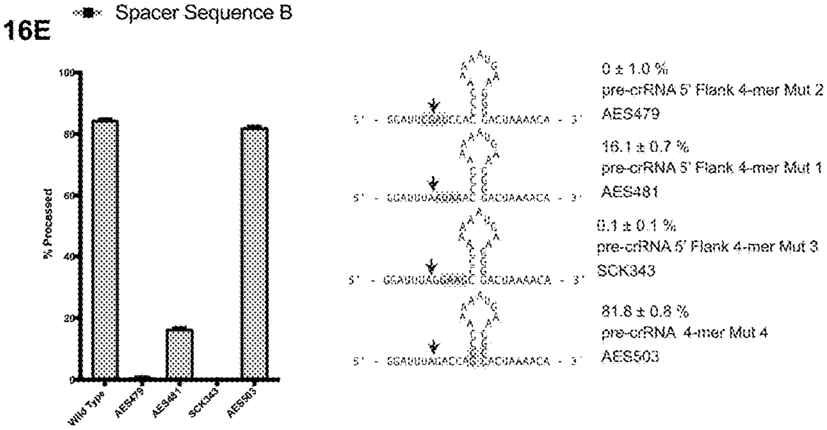
Figure 16F:
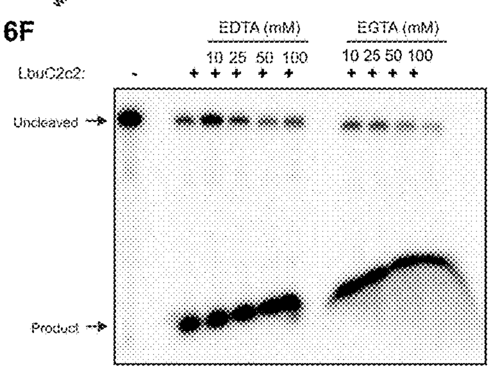
Figure 17:
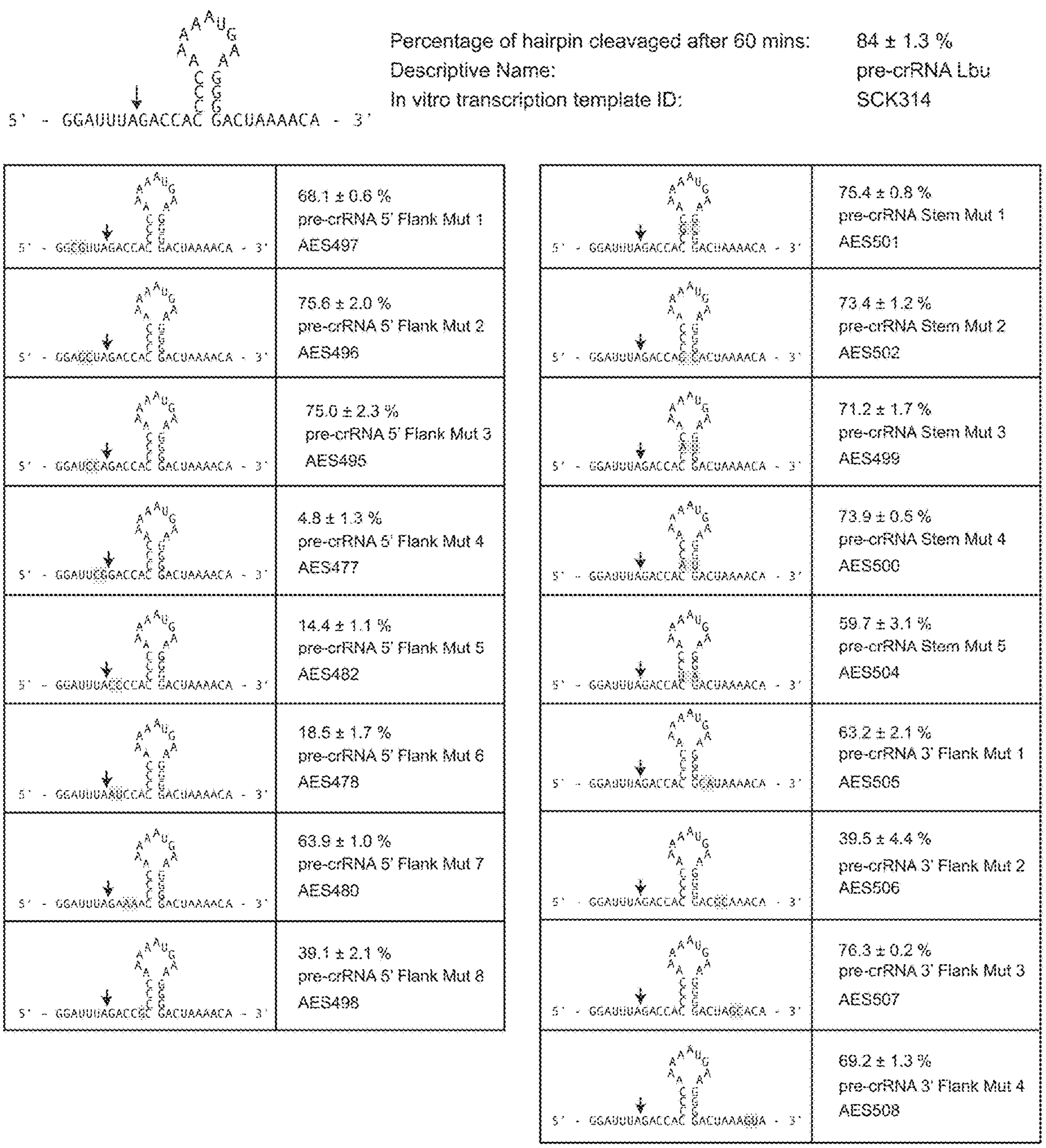
FIG. 17 provides a summary of the effect of pre-crRNA double mutations on pre-crRNA processing activity. top to bottom left: SEQ ID NOs: 107-115; top to bottom right: SEQ ID NOs: 116-124.

FIG. 16A-16F. pre-crRNA processing by C2c2 is spacer sequence independent, can occur on tandem crRNA arrays, affected by mutations in the 5'flanking region of the pre-cRNA and is metal independent. a, Representative time-course pre-crRNA cleavage assay demonstrating the similar rates of LbuC2c2, LshC2c2, and LseC2c2 pre-crRNA processing. b, Cleavage site mapping of LseC2c2 and LshCC2c2 cleavage of a single cognate pre-crRNA array. OH: alkaline hydrolysis ladder; T1: T1 RNase hydrolysis ladder. Cleavage reactions were performed with 100 nM Lbu C2c2 and <1 nM pre-crRNA. A schematic of cleavage products is depicted, with arrows indicating the mapped C2c2 cleavage products. c, Cleavage site mapping of LbuCC2c2 cleavage of a tandem pre-crRNA array. OH: alkaline hydrolysis ladder; T1: T1 RNase hydrolysis ladder. Cleavage reactions were performed with 100 nM Lbu C2c2 and <1 nM pre-crRNA. A schematic of cleavage products is depicted on right, with arrows indicating the mapped C2c2 cleavage products. d, Representative LbuC2c2 pre-crRNA cleavage time-course demonstrating that similar rates of pre-crRNA processing occur independent of crRNA spacer sequence. e, LbuC2c2 4-mer mutant pre-crRNA processing data demonstrating the importance of the 5' single-stranded flanking region for efficient pre-crRNA processing. Percentage of pre-crRNA processing was measured after 60 mins (mean±s.d., n=3). f, Denaturing gel illustrating processing activity at a range of different EDTA and EGTA concentrations. High concentrations of chelators change the expected migration pattern of products Example 9: LbuC2c2 Mediated crRNA Biogenesis Depends on Both Structure and Sequence of CRISPR Repeats Other pre-crRNA processing enzymes, such as Cas6 and Cas5d, recognize the hairpin of their respective CRISPR repeat sequence in a highly specific manner. The sequence and structural requirements for LbuC2c2 guide RNA processing were determined. Cleavage assays were performed with pre-crRNAs harboring mutations in either the stem loop or the single-stranded flanking regions of the consensus repeat sequence (FIG. 10A-10C). Pre-crRNA cleavage activity was significantly attenuated upon altering the length of the stem in the repeat region; while the repeat consensus 4-base pair (bp) stem resulted in 85±0.7% cleavage at after 60 min, −1 bp and +1 bp stems resulted in only 54±1.3% and 6±3.8% cleavage, respectively (FIG. 10*a*). Similarly, inversion of the stem loop or reduction of the loop length reduced processing activity. Initial studies with contiguous 4-nt mutations including or near the scissile bond completely abolished LbuC2c2's capacity to process the pre-crRNAs (FIG. 16D). A more extensive mutational analysis of the full crRNA repeat sequence revealed two distinct regions on either side of the hairpin with marked sensitivity to base changes (FIG. 10B; FIG. 17). Processing activity was completely unaffected by the presence of divalent metal ion chelators EDTA or EGTA (FIG. 10C; FIG. 16E). Collectively, these data indicate that C2c2 pre-crRNA cleavage is a divalent metal ion-independent process governed by a combination of structural- and sequence-specific recognition of repeat-derived hairpins within the precursor CRISPR transcript.

FIG. 10A-10C. LbuC2c2 mediated crRNA biogenesis depends on both structure and sequence of CRISPR repeats. FIG. 10A, Representative gel of LbuC2c2 processing of pre-crRNAs containing structural mutations within the stem and loop regions of hairpin. Processed percentages listed below are quantified at 60 min for each condition (mean±s.d., n=3). FIG. 10B, Graphical map showing the dependence of pre-crRNA processing on the CRISPR repeat sequence. The wild-type repeat sequence is shown below with individual bars representing 2 nucleotide mutations as noted in red above. The cleavage site is indicated by cartoon scissors. Percentage processed was measured after 60 mins (mean±s.d., n=3). Diagramed hairpins of tested mutants can be found in FIG. 16A-16F and FIG. 17. FIG. 2C, Diavalent metal dependence of processing reaction was challenged by addition of 10-100 mM EDTA to standard processing reaction conditions. Reaction end point at 60 min is shown.

FIG. 17. Detailed summary of the effect of pre-crRNA double mutations on pre-crRNA processing activity. Percentage of pre-crRNA processing was measured after 60 mins (mean±s.d., n=3), as per Methods. Mutated nucleotides are highlighted in yellow. See FIG. 10B for graphical representation.

Figure 11A:
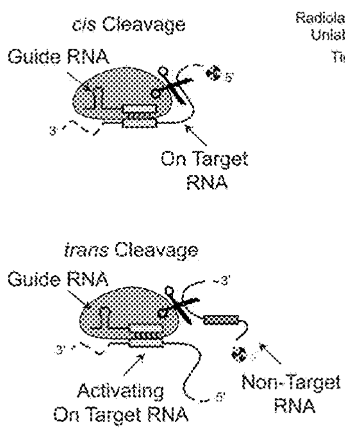
FIG. 11A-11C depict guide-dependent ssRNA degradation of cis and trans targets by LbuC2c2.
Figure 11B:
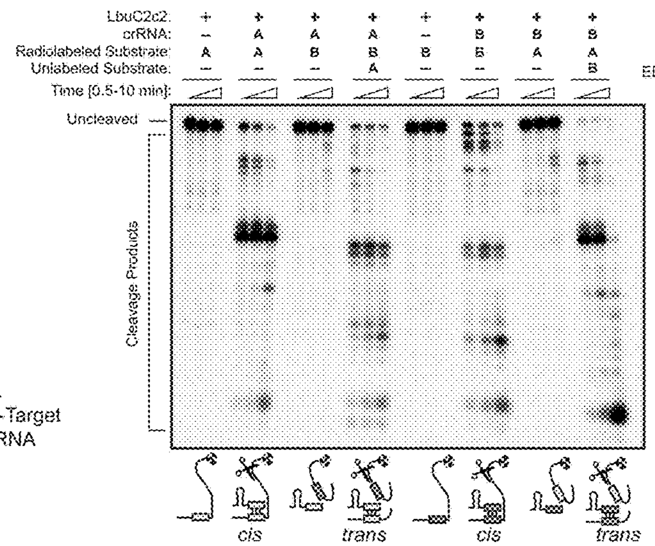

Example 10: LbuC2c2 Catalyzes Guide-Dependent ssRNA Degradation on Cis and Trans Targets Following maturation, crRNAs typically bind with high affinity to Cas effector protein(s) to create RNA-guided surveillance complexes capable of sequence-specific nucleic acid recognition. To test the functionality of the C2c2- processed crRNA, the LbuC2c2 protein, which demonstrated the most robust activity in initial cleavage experiments, was used. For multiple ssRNA substrates, it was observed that LbuC2c2 efficiently cleaved only when bound to the complementary crRNA, indicating that LbuC2c2: crRNA cleaves ssRNA in an RNA-guided fashion (FIG. 11*b*). This activity is hereafter referred to as on-target or cis-target cleavage (FIG. 11*a*). LbuC2c2-mediated cis cleavage resulted in a laddering of multiple products, with cleavage preferentially occurring before uracil residues, analogous to LshC2c2 (FIG. 18A-18B)[9], This activity is distinct from other class II CRISPR effectors (such as Cas9 and Cpf1) that catalyze target nucleic acid cleavage only within a defined region specified by base pairing to the crRNA. The ability of LbuC2c2 to act as a crRNA-activated non-specific RNA endonuclease in trans (i.e. C2c2-catalyzed cleavage of RNA molecules that are not targeted by the crRNA) was tested (FIG. 11A). This ability was investigated by repeating non-target cleavage reactions in the presence of unlabeled, on-target (crRNA-complementary) ssRNA. Rapid degradation of 5'-labeled non-target RNA under these trans cleavage conditions was observed (FIG. 11B). This result suggests that recognition of a target ssRNA complementary to the spacer segment of the crRNA activates C2c2 for rapid and non-specific degradation of RNA in trans. The similar RNA cleavage rates and near identical cleavage products observed for both cis on-target cleavage and trans non-target cleavage implicate the same nuclease center in both activities. Furthermore, these results suggest that what is observed as "cis" activity is simply trans activity that occurs when only one substrate is available (FIG. 18A-18B).

Figure 11C:
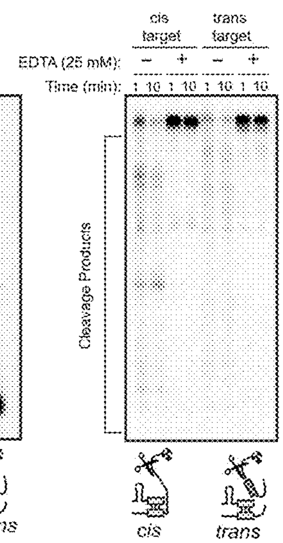

FIG. 11A-11C. LbuC2c2 catalyzes guide-dependent ssRNA degradation on cis and trans targets. FIG. 11A, Schematic of the two modes of C2c2, guide dependent ssRNA degradation. FIG. 11B, Cleavage of two distinct radiolabeled ssRNA substrates, A and B, by LbuC2c2. Complexes of 100 nM C2c2 and 50 nM crRNA were pre-formed at 37° C. and reaction was initiated upon addition of >1 nM 5'-labeled target RNA at 25° C. Trans cleavage reactions contained equal molar (>1 nM) concentrations of radiolabeled non-guide-complementary substrate, and unlabeled on target ssRNA. FIG. 11C, LbuC2c2 loaded with crRNA with spacer A was challenged for cleavage activity under both cis (target A labeled) and trans (target B labeled in the presence of unlabeled target A) cleavage conditions in the presence of EDTA.

Figure 18A:
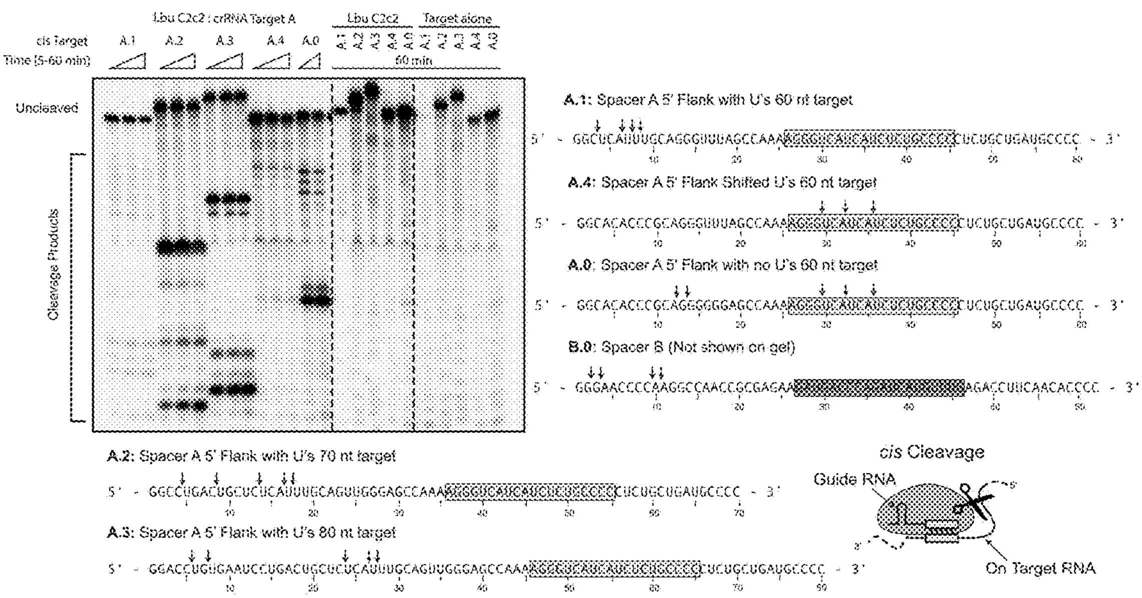
FIG. 18A-18B depict LbuC2c2 ssRNA target cleavage site mapping.
Figure 18B:
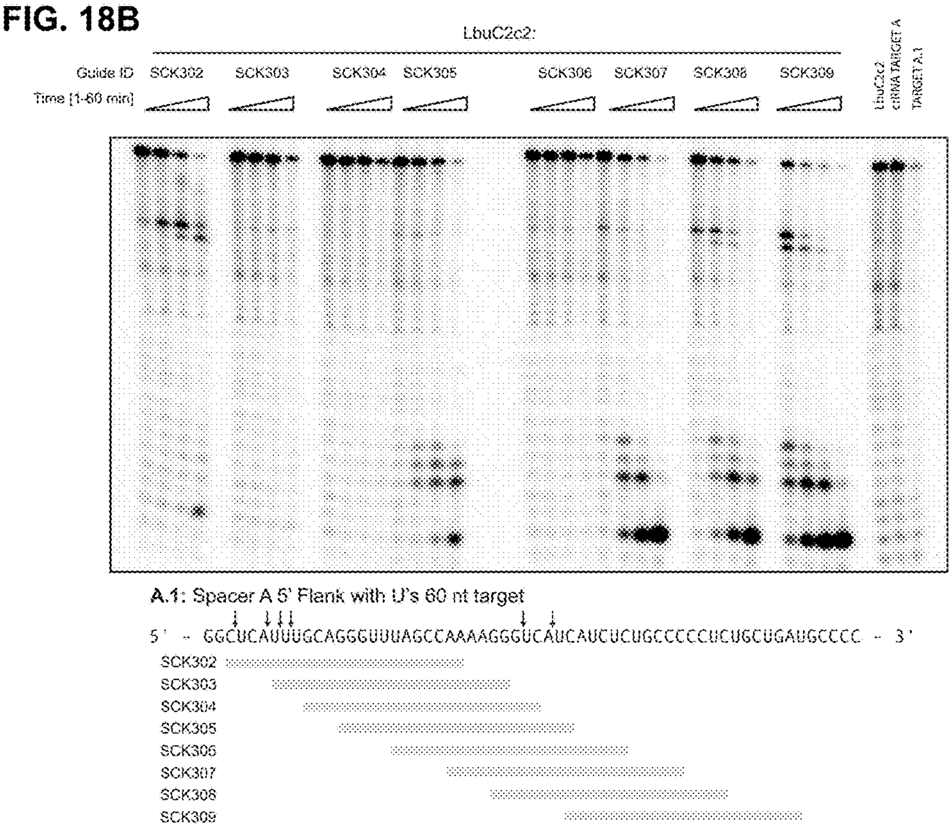

FIG. 18A-18B. LbuC2c2 ssRNA target cleavage site mapping a, ssRNA target cleavage assay carried as per Methods demonstrating LbuC2c2-mediated 'cis'-cleavage of several radiolabeled ssRNA substrates with identical spacer-complementary sequences but distinct 5' flanking sequences of variable length and nucleotide composition. Sequences of ssRNA substrates are shown to the right and bottom of the gel with spacer complementary sequences for crRNA-A and crRNA-B are highlighted in yellow and red, respectively. Arrows indicate predicted cleavage sites. Gel was cropped for clarity. It should be noted that the pattern of cleavage products produced on different substrates (e.g. A.1 vs. A.2 vs. A.3) indicates that the cleavage site choice is primarily driven by a uracil preference and exhibits an apparent lack of a 'crRNA-ruler-based' cleavage mechanism, which is in contrast to what is observed for other Class II CRISPR single effector complexes such as Cas9 and Cpf1 <ref?>. Interestingly, the cleavage pattern observed for substrate A.0 hints at a secondary preference for polyG sequences, that might conceivably form G-quadraplexes or similar secondary structures. b, LbuC2c2 ssRNA target cleavage assay as per Methods, using a range of crRNAs that tile the length of the ssRNA target. The sequence of the ssRNA substrates used in this experiment is shown below the gel with spacer complementary sequences for each crRNA highlighted in yellow. Arrows indicate predicted cleavage sites. Likewise, it should be noted that for every crRNA the cleavage product length distribution is very similar, again indicating an apparent lack of a 'crRNA-ruler-based' cleavage mechanism. The absence of a several cleavage products in a subset of the reactions might be explained by the presence of bound C2c2:crRNA on the ssRNA target sterically occluding access to uracils by any cis (intramolecular) or trans (intermolecular) LbuC2c2 active sites. While proper analysis for PFS preference for LbuC2c2 is beyond the scope of this study, minimal impact of 3' flanking sequence was observed. Expected PFS base is noted in diagram next to each guide tested in red.

Example 11: LbuC2c2 Contains Two Distinct Ribonuclease Activities

Figure 19A:
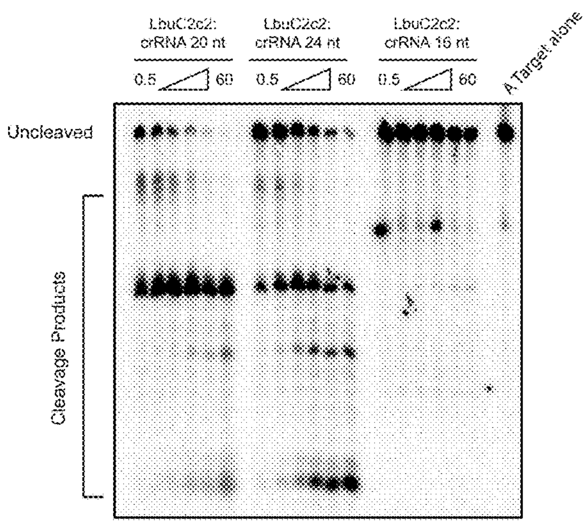
FIG. 19A-19C depict dependence of crRNA spacer length, reaction temperature, and 5'-end sequence of crRNA on target RNA cleavage efficiency.
Figure 19B:
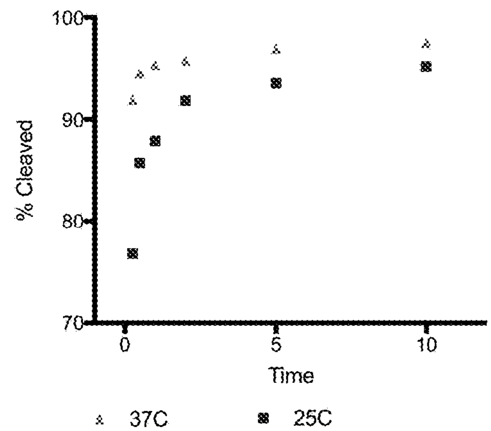
Figure 19C:
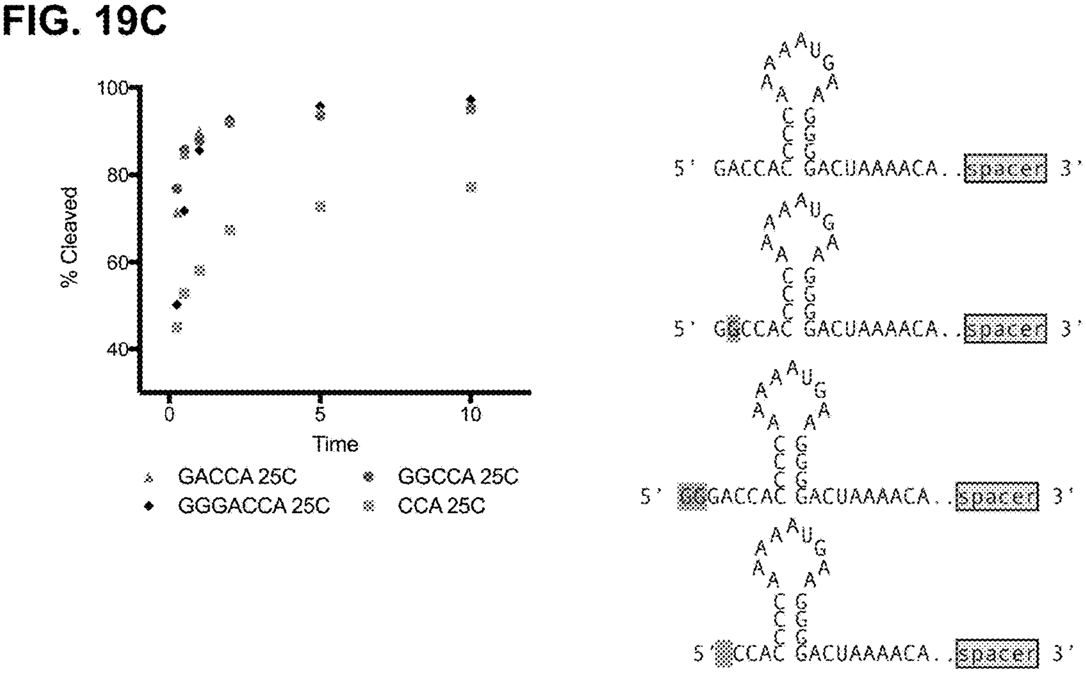
Figure 20A:
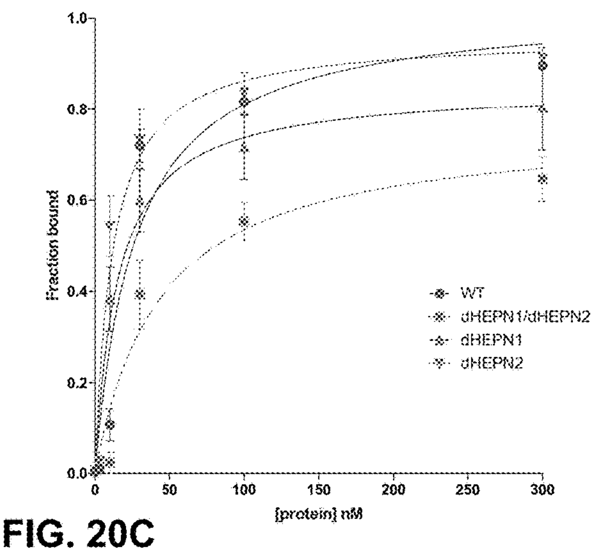
FIG. 20A-20C depict binding data for LbuC2c2 to mature crRNA and target ssRNA.
Figure 20B:
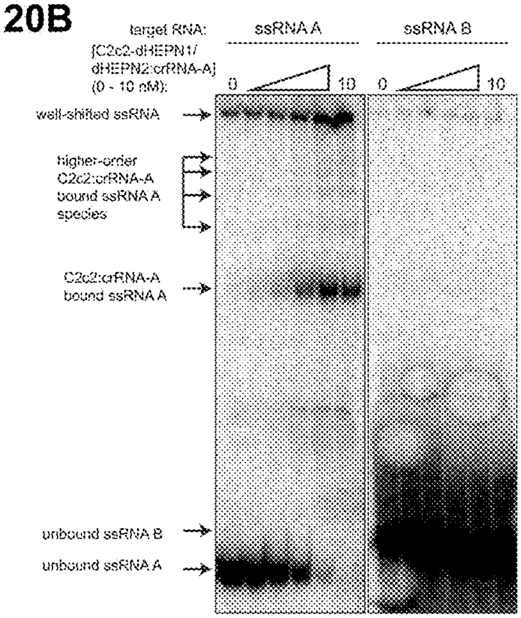
Figure 20C:
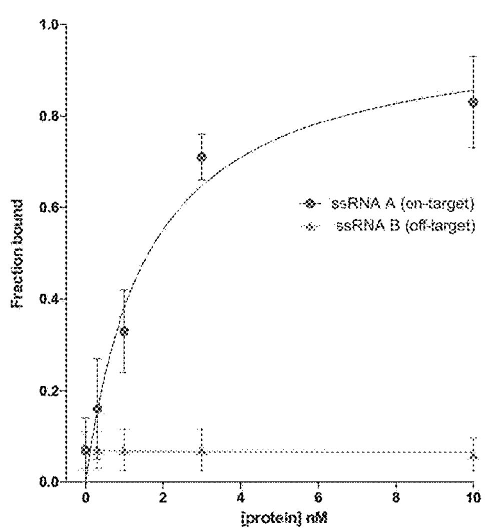

Pre-crRNA processing activity occurred at an apparent rate 80-fold slower than crRNA-mediated cleavage of either target RNA or a non-complementary trans-ssRNA (FIG. 12*a*). Under saturating enzyme conditions, pre-crRNA processing reached only ~85% after 1 h, while the rate of RNA-guided cleavage of trans substrates was nearly unmeasurable due to reaction completion within 1 min at 37° C. (FIG. 19A-19C). It was also found that in contrast to pre-crRNA processing, RNA-guided cleavage was completely abolished in the presence of EDTA, indicating that this activity is divalent metal ion-dependent (FIG. 11*c*). Given the clear differences in kinetics and metal ion dependence between pre-crRNA processing and RNA-guided cleavage, it was reasoned that C2c2 might represent a novel class of CRISPR effector proteins possessing two orthogonal RNA cleavage activities: one for crRNA maturation, and the other for crRNA-directed, non-specific RNA degradation. To test this hypothesis, several residues within the conserved HEPN domains of the LbuC2c2, which are predicted to contain RNA cleavage active sites, were systematically mutated; and pre-crRNA processing and RNA-guided RNase activity of the mutants was assessed (FIG. 12*b*). Double and quadruple mutants of conserved HEPN residues (R472A, R477A, R1048A and R1053) retained robust pre-crRNA cleavage activity (FIG. 12*c*). By contrast, all HEPN mutants abolished RNA-guided cleavage activity while not affecting crRNA or ssRNA-binding ability (FIG. 20A-20C). The discrepancies in cleavage rates and differential sensitivity to point mutations and EDTA show that pre-crRNA processing and RNA-directed RNA cleavage are mediated by distinct catalytic centers within the C2c2 protein, the former metal-independent and the latter requiring divalent metal-dependent HEPN domains.

FIG. 12A-12D. LbuC2c2 contains two distinct ribonuclease activities. FIG. 4A, Quantified time course data of cis ssRNA target (black) and pre-crRNA (teal) cleavage by LbuC2c2 performed at 37° C. Exponential fits are shown as solid lines (n=3) and calculated first order rate constants ($k_{obs}$) are 9.74±1.15 and 0.12±0.02 for cis target and pre-crRNA cleavage respectively. FIG. 12B, Domain architecture of LbuC2c2 depicting the location of HEPN mutations FIGS. 12C and 12D, Ribonuclease activity of double and quadruple HEPN domain mutants for pre-crRNA processing in FIG. 12C and ssRNA targeting in FIG. 12D. cis and trans cleavage reactions performed as in FIG. 11*c*, utilizing crRNA targeting spacer A for both activities.

FIG. 19A-19C Dependence of crRNA spacer length, reaction temperature, 5'-end sequence of crRNA on target RNA cleavage efficiency. FIG. 19A, LbuC2c2 ssRNA target cleavage assay carried out, as per Methods with crRNAs possessing 16-nt, 20-nt or 24-nt spacers. FIG. 19B, LbuC2c2 ssRNA target cleavage time-course carried out at either 25° C. or 37° C., as per Methods. FIG. 19C, LbuC2c2 ssRNA target cleavage time-course carried out as per Methods with crRNAs possessing different 5'-flanking nucleotide mutations. Mutations are highlighted in red. 1-2 nucleotide 5' extensions negligibly impacted cleavage efficiencies. In contrast shortening the flanking region to 3 nts slowed cleavage efficiencies. Exponential fits are shown as solid lines for representative replicates.

FIG. 20A-20C. Binding data for LbuC2c2 to mature crRNA and target ssRNA. FIG. 20A, Filter binding assays were conducted as described in the Methods to determine the binding affinity of mature crRNA-A to LbuC2c2-WT, LbuC2c2-dHEPN1, LbuC2c2-dHEPN2, or LbuC2c2-dHEPN1/dHEPN2. The quantified data were fitted to standard binding isoforms. Error bars represent the standard deviation from three independent experiments. Measured dissociation constants from three independent experiments (mean±sd) were 27.1±7.5 nM (LbuC2c2-WT), 15.2±3.2 nM (LbuC2c2-dHEPN1), 11.5±2.5 nM (LbuC2c2-dHEPN2), and 43.3±11.5 nM (LbuC2c2-dHEPN1/dHEPN2). FIG. 20B, Representative electrophoretic mobility shift assay for binding reactions between LbuC2c2-dHEPN1/dHEPN2: crRNA-A and either 'on-target' A ssRNA or 'off-target' B ssRNA, as indicated. Three independent experiments were conducted as described in the Methods. The gel was cropped for clarity. FIG. 20C, Quantified binding data from (b) were fitted to standard binding isoforms. Error bars represent the standard deviation from three independent experiments. Measured dissociation constants from three independent experiments (mean±sd) were 1.62±0.43 nM for ssRNA A and N.D (>>10 nM) for ssRNA B.

Figure 21:
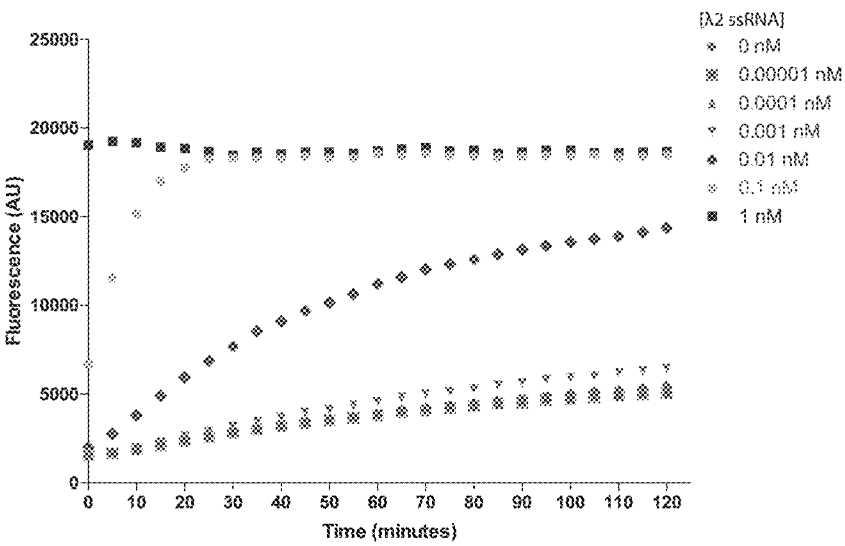
FIG. 21 depicts an RNase detection assay λ2-ssRNA time course.

Example 12: C2c2 Provides Sensitive Visual Detection of Transcripts in Complex Mixtures C2c2's robust RNA-stimulated cleavage of trans substrates can be employed as a means of detecting specific RNAs within a pool of transcripts. To date, the most sensitive RNA-detection strategies require multiple rounds of polymerase- and/or reverse-transcriptase-based amplification As an alternative, it was tested whether C2c2's RNA-guided trans endonuclease activity could be harnessed to cleave a fluorophore-quencher-labeled reporter RNA substrate, thereby resulting in an increase in fluorescence upon target RNA-triggered RNase activation (FIG. 13*a*). Briefly, LbuC2c2 was loaded with bacteriophage λ-targeting crRNAs and tested for its ability to detect the corresponding λ ssRNA targets spiked into HeLa cell total RNA. If LbuC2c2 were to successfully detect the complementary target, the trans cleavage activity would be activated to cleave the reporter, liberating the fluorophore from the quencher. Upon addition of as little as 1-10 pM of complementary λ target-RNA, a substantial crRNA-specific increase in fluorescence was observed after 30 minutes (FIG. 13*b* and FIG. 21). Control experiments with either C2c2:crRNA complex alone or in the presence of crRNA and a non-complementary target RNA resulted in negligible increases in fluorescence relative to an RNase A positive control (FIG. 13*b* and FIG. 21). At the 10 pM concentration of a λ target RNA, only ~0.02% of the C2c2:crRNA complex is predicted to be in the active state, yet the observed fluorescent signal reflected ~25-50% cleavage of the reporter RNA substrate, depending on the RNA target, suggesting robust multi-turnover enzymatic activity by LbuC2c2. Thus, crRNA-directed trans cleavage is potent and detectable even at extremely low levels of active protein.

Given that C2c2 processes its own pre-crRNA, it was tested whether pre-crRNA processing and RNA detection could be combined in a single reaction. To test this idea, tandem crRNA-repeat containing spacers complementary to target RNAs A and λ2 were designed, and their ability to detect decreasing amounts of A and λ2 RNA spiked into HeLa total RNA was tested. A significant increase in fluorescence, similar in magnitude and sensitivity to experiments using mature crRNAs, was observed (FIG. 13*b*, 13*c*), suggesting that a tandem pre-crRNA can be successfully processed and utilized by C2c2 for RNA targeting. These data highlight the potential for multiplexed RNA detection of single and/or multiple RNA molecules in one assay using a single tandem pre-crRNA transcript.

Without being bound to theory, it is proposed that when invasive transcripts are detected within the host cell via base pairing with crRNAs, C2c2 is activated for promiscuous cleavage of RNA in trans (FIG. 13*d*).

FIG. 13A-13D. C2c2 provides sensitive visual detection of transcripts in complex mixtures. FIG. 13A, Illustration of RNA detection approach by C2c2 using a quenched fluorescent RNA reporter. Upon complementary target RNA binding, C2c2 catalyzes the degradation of the reporter RNA resulting in accumulation of fluorescent signal. FIG. 13B, Quantification of fluorescence signal after 30 minutes for varying concentrations of target RNA by C2c2 in the presence of 100 ng total RNA. RNaseA shown as positive RNA degradation control. Data shown as mean±s.d. for n=3 independent experiments. FIG. 13C, Tandem pre-crRNA processing also enables RNA detection. Data shown as mean±s.d. for n=3 independent experiments. FIG. 13D, Model of the Type VI CRISPR pathway highlighting both of C2c2's ribonuclease activities.

FIG. 21. RNase detection assay λ2-ssRNA time course. LbuC2c2:crRNA-λ2 was incubated with RNAase-Alert substrate (Thermo-Fisher)) and 100 ng HeLa total RNA in the presence of increasing amounts of λ2 ssRNA (0-1 nM) for 120 minutes at 37° C. Fluorescence measurements were taken every 5 minutes. The 1 nM λ2 ssRNA reaction reached saturation before the first time point could be measured. Error bars represent the standard deviation from three independent experiments.

Example 13

Materials and Methods

MEC2c2 phylogenic and candidate selection. C2c2 maximum-likelihood phylogenies were computed using RAxML with the PROTGAMMALG evolutionary model and 100 bootstrap samplings. Sequences were aligned by MAFFT with the 'einsi' method.

C2c2 protein production and purification. Expression vectors for protein purification were assembled using synthetic gBlocks ordered from Integrated DNA Technologies. The codon-optimized C2c2 genomic sequence was N-terminally tagged with a $His_6$-MBP-TEV cleavage site, with expression driven by a T7 promoter. Mutant proteins were cloned via site-directed mutagenesis of wild-type C2c2 constructs. Expression vectors were transformed into Rosetta2 *E. coli* cells grown in 2×YT broth at 37° C. *E. coli* cells were induced during log phase with 0.5 M ITPG, and the temperature was reduced to 16° C. for overnight expression of His-MBP-C2c2. Cells were subsequently harvested, resuspended in lysis buffer (50 mM Tris-HCl pH 7.0, 500 mM NaCl, 5% glycerol, 1 mM TCEP, 0.5 mM PMSF, and EDTA-free protease inhibitor (Roche)) and lysed by sonication, and the lysates were clarified by centrifugation. Soluble His-MBP-C2c2 was isolated over metal ion affinity chromatography, and protein-containing eluate was incubated with TEV protease at 4° C. overnight while dialyzing into ion exchange buffer (50 mM Tris-HCl pH 7.0, 250 mM KCl, 5% glycerol, 1 mM TCEP) in order to cleave off the $His_6$-MBP tag. Cleaved protein was loaded onto a HiTrap SP column and eluted over a linear KCl (0.25-1.5M) gradient. Cation exchange chromatography fractions were pooled and concentrated with 30 kD cutoff concentrators (Thermo Fisher). The C2c2 protein was further purified via size-exclusion chromatography on an 5200 column and stored in gel filtration buffer (20 mM Tris-HCl pH 7.0, 200 mM KCl, 5% glycerol, 1 mM TCEP) for subsequent enzymatic assays. Expression plasmids are deposited with Addgene.

Generation of RNA. All RNAs used in this study were transcribed in vitro except for crRNA AES461 which was ordered synthetically (Integrated DNA Technologies) [see FIG. 33]. In vitro transcription reactions were performed as previously described with the following modifications: the T7 polymerase concentration was reduced to 10 μg/mL, and the UTP concentration was reduced to 2.5 mM. Transcriptions were incubated at 37° C. for 1-2 hr to reduce non-template addition of nucleotides and quenched via treatment with DNase I at 37° C. for 0.5-1 hr. Transcription reactions were purified by 15% denaturing polyacrylamide gel electrophoresis (PAGE), and all RNAs were resuspended in cleavage buffer (20 mM HEPES pH 6.8, 50 mM KCl, 5 mM $MgCl_2$, and 5% glycerol). For radioactive experiments, 5' triphosphates were removed by calf intestinal phosphate (New England Biolabs) prior to radiolabeling and ssRNA substrates were then 5'-end labeled using T4 polynucleotide kinase (New England Biolabs) and [$\gamma$-$^{32}$P]-ATP (Perkin Elmer) as described previously.

Pre-crRNA processing assays. Pre-crRNA cleavage assays were performed at 37° C. in RNA processing buffer (20 mM HEPES pH 6.8, 50 mM KCl, 5 mM $MgCl_2$, 10 pg/mL BSA, 10 pg/mL tRNA, 0.05% Igepal CA-630 and 5% glycerol) with a 100-fold molar excess of C2c2 relative to 5'-labeled pre-crRNA (final concentrations of 100 nM and <1 nM, respectively). Unless otherwise indicated, reaction was quenched after 60 min with 1.5×RNA loading dye (100% formamide, 0.025 w/v % bromophenol blue, and 200 μg $mL^{-1}$ heparin). After quenching, reactions were denatured at 95° C. for 5 min prior to resolving by 12% or 15% denaturing PAGE (0.5×TBE buffer). Metal dependence of the reaction was tested by addition of EDTA or EGTA to reaction buffer at concentrations varying from 10-100 mM. Bands were visualized by phosphorimaging and quantified with ImageQuant (GE Healthcare). The percent cleavage was determined as the ratio of the product band intensity to the total intensity of both the product and uncleaved pre-crRNA bands and normalized for background within each measured substrate using ImageQuant TL Software (GE Healthcare) and fit to a one phase exponential association using Prism (GraphPad).

Product Size Mapping and 3' end moiety identification. Cleavage product length was determined biochemically by comparing gel migration of product bands to alkaline hydrolysis and RNase T1 digestion ladders using the RNase T1 Kit from Ambion. For hydrolysis ladder, 15 nM full-length RNA substrates were incubated at 95° C. in 1× alkaline hydrolysis buffer (Ambion) for 5 min. Reactions were quenched with 1.5×RNA loading buffer, and cooled to −20° C. to immediately stop hydrolysis. For RNase T1 ladder, 15 nM full length RNA substrates were unfolded in 1×RNA sequencing buffer (Ambion) at 65° C. Reactions were cooled to ambient temperature, and then 1 U of RNase T1 (Ambion) was added to reaction. After 15 min, reactions were stopped by phenol-chlorofrom extraction and 1.5× RNA loading buffer was added for storage. Hydrolysis bands were resolved in parallel to cleavage samples on 15% denaturing PAGE and visualized by phosphorimaging. For 3' end moiety identification, products from the processing reaction were incubated with 10 U of T4 polynucleotide kinase (New England Biolabs) for 1 hr at 37° C. in processing buffer. Reactions were quenched with 1.5×RNA loading buffer, resolved on 20% denaturing PAGE and visualized by phosphorimaging.

Small RNA sequencing analysis. RNA reads from Smakov et al. were downloaded from SRA runs SRR3713697, SRR3713948, and SRR3713950. The paired-end reads were locally mapped to the reference sequences using Bowtie2 with the following options: "-reorder-very-fast-local-local". The mapping was then filtered to retain only alignments that contained no mismatch using mapped.py with the "-m 0-p both" options. BAM file of the resulting mapping available. Read coverage was visualized using Geneious and plotted using Prism (GraphPad).

Target cleavage assays. Target cleavages assays were performed at 25° C. or 37° C. in cleavage buffer (20 mM HEPES pH 6.8, 50 mM KCl, 5 mM $MgCl_2$, and 5% glycerol). crRNA guides were pre-folded by heating to 65° C. for 5 min and then slowly cooling to ambient temperature in cleavage buffer. C2c2:crRNA complex formation was performed in cleavage buffer, generally at a molar ratio of 2:1 protein to crRNA at 37° C. for 10 min, prior to adding 5'-end labeled target and/or other non-radiolabeled RNA target substrates. Unless otherwise indicated, final concentrations of protein, guide, and targets were 100 nM, 50 nM, and <1 nM respectively for all reactions. Reactions were quenched with 1.5×RNA loading dye and resolved by 15% denaturing PAGE (0.5×TBE buffer). Bands were visualized by phosphorimaging and quantified with ImageQuant (GE Healthcare). The percent cleavage was determined as the ratio of total banding intensity for all shorter products relative to the uncleaved band and normalized for background within each measured substrate using ImageQuant TL Software (GE Healthcare) and fit to a one phase exponential association using Prism (GraphPad).

crRNA filter-binding assays. Filter binding assays was carried out in RNA processing buffer (20 mM HEPES pH 6.8, 50 mM KCl, 5 mM $MgCl_2$, 10 pg/mL BSA, 10 pg/mL yeast tRNA, 0.01% Igepal CA-630 and 5% glycerol). LbuC2c2 was incubated with radiolabeled crRNA (<0.1 nM) for 1 hr at 37° C. Tufryn, Protran and Hybond-N+ were assembled onto a dot-blot apparatus in the order listed above. The membranes were washed twice with 50 μL Equilibration Buffer (20 mM HEPES pH 6.8, 50 mM KCl, 5 mM $MgCl_2$ and 5% glycerol) before the sample was applied to the membranes. Membranes were again washed with 50 μL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the figure legends.

Electrophoretic mobility-shift assays. In order to avoid the dissociation of the LbuC2c2-dHEPN1/dHEPN2: crRNA complex at low concentrations during ssRNA-binding experiments, binding reactions contained a constant excess of LbuC22c2-dHEPN1/dHEPN2 (200 nM), and increasing concentrations of crRNA-A and <0.1 nM target ssRNA. Assays were carried out in C2c2 EMSA buffer (20 mM HEPES pH 6.8, 50 mM KCl, 10 pg/mL BSA, 100 pg/mL yeast tRNA, 0.01% Igepal CA-630 and 5% glycerol). LbuC2c2-crRNA-A complexes were pre-formed as described above for 10 min at 37° C. before the addition of 5'-radiolabelled ssRNA substrate and a further incubation for 45 min at 37° C. Samples were then resolved by 8% native PAGE at 4° C. (0.5×TBE buffer). Gels were imaged by phosphorimaging, quantified using ImageQuant TL Software (GE Healthcare) and fit to a binding isotherm using Prism (GraphPad Software). All experiments were carried out in triplicate. Dissociation constants and associated errors are reported in the figure legends.

Fluorescent RNA detection assay. LbuC2c2:crRNA complexes were preassembled by incubating 1 μM of Lbu-C2c2: C2c2 with 500 nM of crRNA for 10 min at 37° C. These complexes were then diluted to 100 nM LbuC2c2: 50 nM crRNA-λ2 in RNA processing buffer (20 mM HEPES pH 6.8, 50 mM KCl, 5 mM $MgCl_2$, 10 pg/mL BSA, 10 pg/mL yeast tRNA, 0.01% Igepal CA-630 and 5% glycerol) in the presence of 185 nM of RNAase-Alert substrate (Thermo-Fisher), 100 ng of HeLa total RNA and increasing amounts of target 60 nt ssRNA (0-1 nM). These reactions were incubated in a fluorescence plate reader for up to 120 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA. Maximal fluorescence was measured by incubating 50 nM RNaseA with 185 nM of RNAase-Alert substrate. For measurement of crRNA-ACTB mediated LbuC2c2 activation by beta-actin mRNA in human total RNA, LbuCas9:crRNA complexes were preassembled by incubating 1 μM of LbuC2c2 with 500 nM of crRNA-ACTB for 10 min at 37° C. and reactions were carried out in the conditions above in the presence of increasing amounts (0-1 pg) of either HeLa cell total RNA or *E. Coli* total RNA (as a negative control). These reactions were incubated in a fluorescence plate reader for up to 180 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA. For coupled pre-crRNA processing and RNA detection assays, LbuCas9-crRNA complexes were preassembled by incubating 1 μM of LbuC2c2 with 500 nM of pre-crRNA-A-λ2 for 20 min at 37° C. and reactions carried out as described above in the presence of increasing amounts of ssRNA A and ssRNA λ2 (0-1 nM each). In each case, error bars represent the standard deviation from three independent experiments.

Background cleavage in total RNA. LbuC2c2:crRNAX4 complexes were assembled as previously described for fluorescence RNA detection assay. Complexes were incubated in RNA processing buffer in the presence of 3 ug total RNA with and without 10 nM λ4 ssRNA target. After 2 hr, RNA was isolated by trizol extraction and ethanol precipitation. The RNA fragment size distribution of resuspended samples was resolved using Small RNA Analysis Kit (Agilent) on a Bioanalyzer 2100 (Agilent) using the manufacturer's protocol. Fluorescent intensity curves were normalized in Prism for curve overlay (GraphPad Software).

Results

Figures 24A, 24B, 24C:
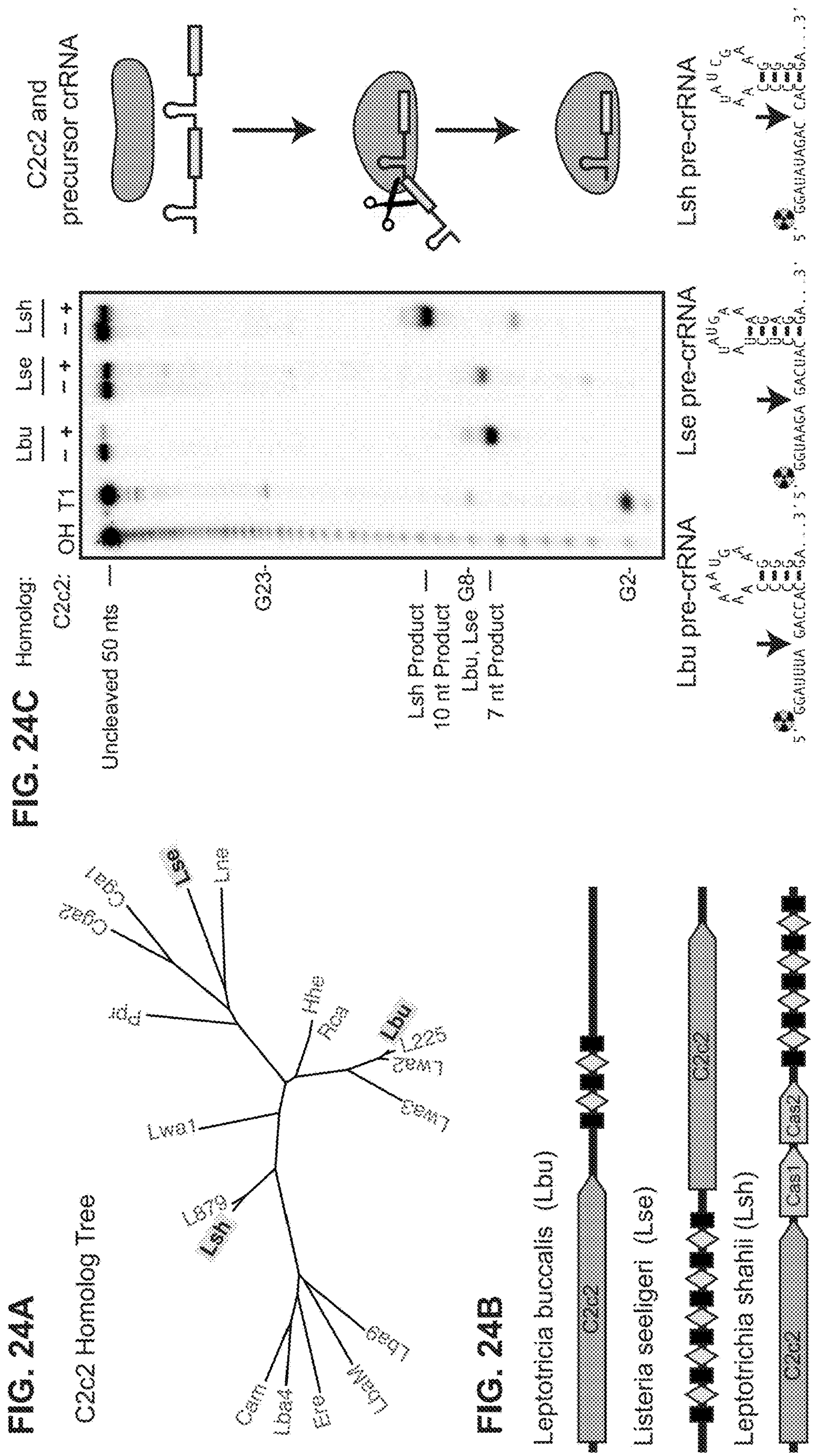
FIG. 24A-24C depict data showing that C2c2 proteins process precursor crRNA transcripts to generate mature crRNAs. a, Maximum-likelihood phylogenetic tree of C2c2 proteins. Homologs used in this study are highlighted in yellow. b, Diagram of the three Type VI CRISPR loci used in this study. Black rectangles denote repeat elements, yellow diamonds denote spacer sequences. Cas1 and Cas2 are only found in the genomic vicinity of LshC2c2. left to right: SEQ ID NOs: 136-138._c, C2c2-mediated cleavage of pre-crRNA derived from the LbuC2c2, LseC2c2 and LshC2c2 CRISPR repeat loci. OH: alkaline hydrolysis ladder; T1: RNase T1 hydrolysis ladder; processing cleavage reactions were performed with 100 nM C2c2 and <1 nM pre-crRNA. Schematic of cleavage is depicted on right, and predicted pre-crRNA secondary structures are diagrammed below, with arrows indicating the mapped C2c2 cleavage sites.
Figure 31A:
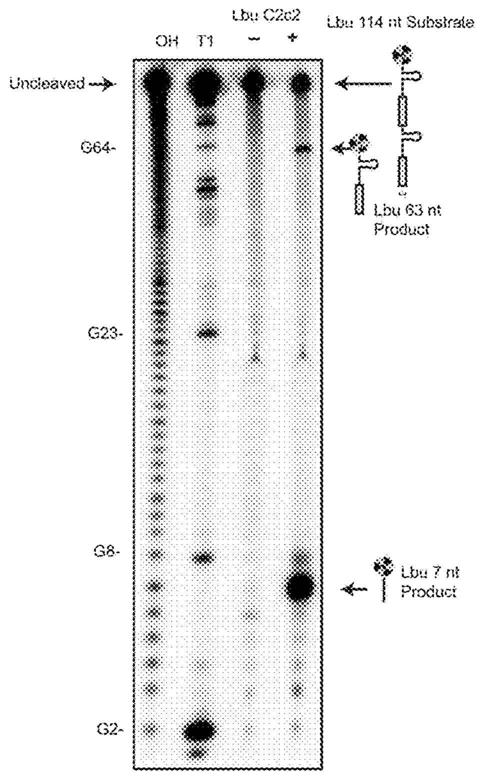
FIG. 31A-31D depict that pre-crRNA processing by C2c2 is spacer-sequence independent, can occur on tandem crRNA arrays, is affected by mutations in the 5' flanking region of the pre-cRNA and produces a 3' phosphate product. a, Cleavage site mapping of LbuCc2c2 cleavage of a tandem pre-crRNA array. OH: alkaline hydrolysis ladder; T1: T1 RNase hydrolysis ladder. Cleavage reactions were performed with 100 nM LbuC2c2 and <1 nM pre-crRNA. A schematic of cleavage products is depicted on right, with arrows indicating the mapped C2c2 cleavage products. b, LbuC2c2 4-mer mutant pre-crRNA processing data demonstrating the importance of the 5' single-stranded flanking region for efficient pre-crRNA processing. Percentage of pre-crRNA processing was measured after 60 min (mean±s.d., n=3). top to bottom (SEQ ID NOs: 143-146). c, Representative LbuC2c2 pre-crRNA cleavage time-course demonstrating that similar rates of pre-crRNA processing occur independent of crRNA spacer sequence pseudo-first-order rate constants ($k_{obs}$) (mean±s.d.) are 0.07±0.04 $min^{-1}$ and 0.08±0.04 $min^{-1}$ for spacer A and spacer λ2, respectively. d, End group analysis of cleaved RNA by T4 polynucleotide kinase (PNK) treatment. Standard processing assay conditions were used to generate cleavage product, which was then incubated with PNK for 1 hr to remove any 2', 3'-cyclic phosphates/3' monophosphates. Retarded migration of band indicates removal of the charged, monophosphate from the 3' end of radiolabeled 5' product.

Type VI CRISPR loci lack an obvious Cas6 or Cas5d-like endonuclease or tracrRNA. Using purified recombinant C2c2 protein homologs from three distinct branches of the C2c2 protein family (FIG. 24*a*-24*b* and FIG. 28 and FIG. 29), that data presented here show that all three C2c2 enzymes cleave 5'-end radiolabeled pre-crRNA substrates consisting of a full-length consensus repeat sequence and a 20 nucleotide (nt) spacer sequence (FIG. 24*c*). The cleavage site for each pre-crRNA:C2c2 homolog pair was mapped, revealing that processing occurs at a position either two or five nucleotides upstream of the predicted repeat-sequence hairpin structure, depending on the C2c2 homolog (FIG. 24*c*, FIG. 30A). Surprisingly, the biochemically mapped 5'-cleavage sites did not agree with previously reported cleavage sites for *Leptotrichia shahii* (LshC2c2) or *Listeria seeligeri* (LseC2c2) pre-crRNAs. Re-analysis of Shmakov et al.'s RNA sequencing data set indicated agreement of the in vivo cleavage site with the in vitro site reported here (FIG. 30*b*-*i*). Furthermore, cleavage assays using C2c2 from *Leptotricia buccalis* (LbuC2c2) and a larger pre-crRNA comprising a tandem hairpin-repeat array resulted in two products resulting from two separate cleavage events (FIG. 31*a*), consistent with a role for C2c2 in processing precursor crRNA transcripts generated from Type VI CRISPR loci.

Figure 25A:
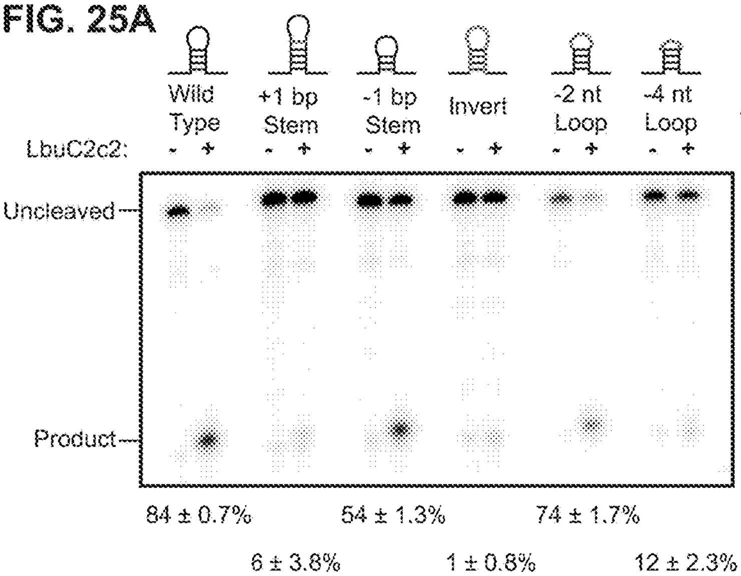
FIG. 25A-25C depict data showing that LbuC2c2 mediated crRNA biogenesis depends on both structure and sequence of CRISPR repeats. a, Representative cleavage assay by LbuC2c2 on pre-crRNAs containing structural mutations within the stem and loop regions of hairpin. Processed percentages listed below are quantified at 60 min (mean±s.d., n=3). b, Bar graph showing the dependence of pre-crRNA processing on the CRISPR repeat sequence. The wild-type repeat sequence is shown below (SEQ ID NO: 38) with individual bars representing tandem nucleotide mutations as noted in red. The cleavage site is indicated by cartoon scissors. Percentage processed was measured after 60 min (mean±s.d., n=3). Diagrammed hairpins of tested mutants can be found in Extended Data FIGS. 3-4 c, Divalent metal ion dependence of the crRNA processing reaction was tested by addition of 10-50 mM EDTA and EGTA to standard reaction conditions.
Figure 25C:
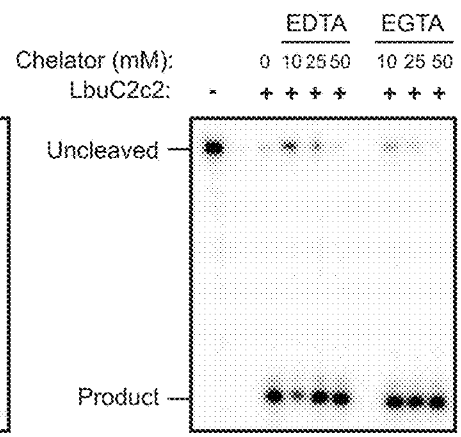
Figure 25B:
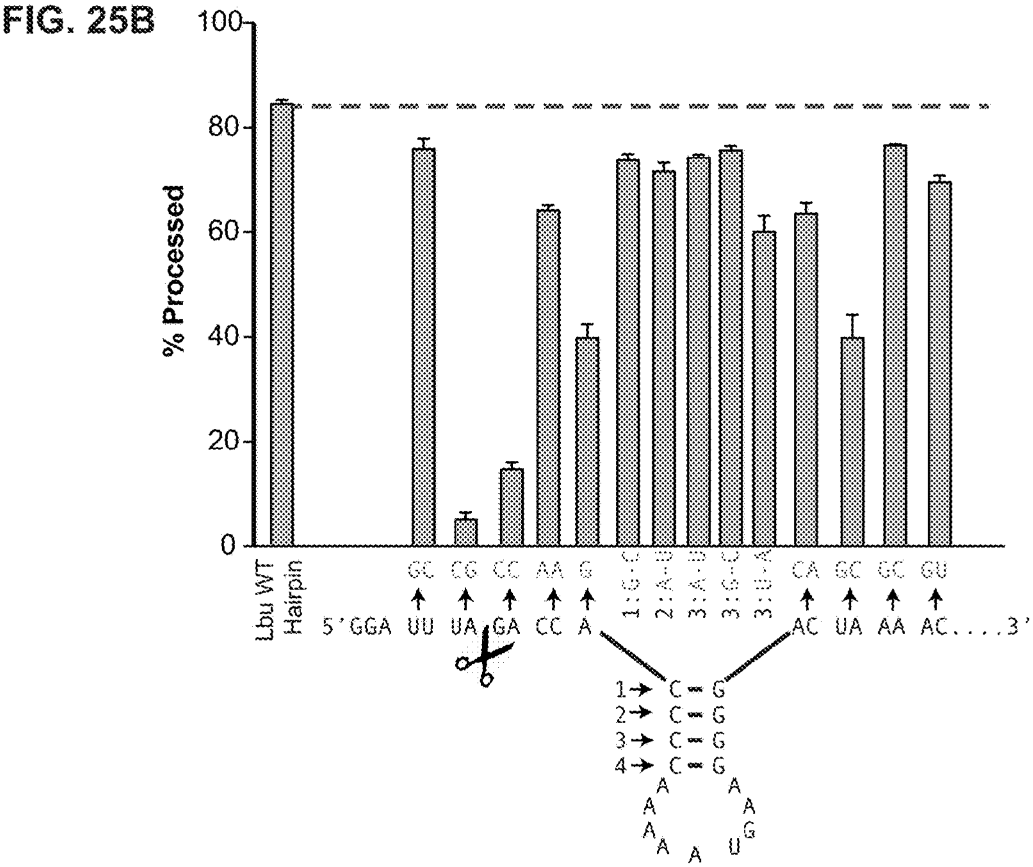
Figure 31B:
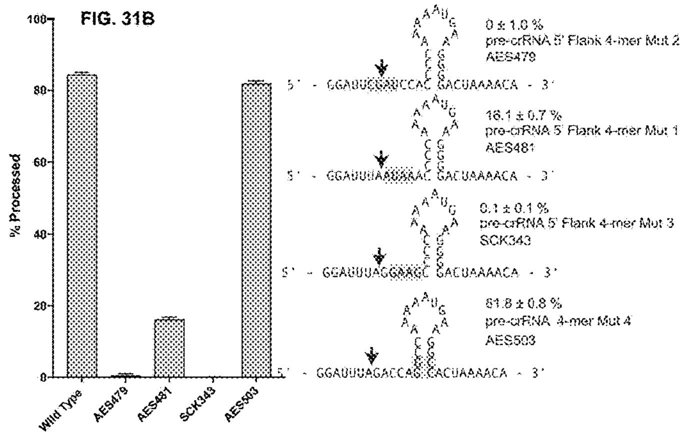
Figure 31C:
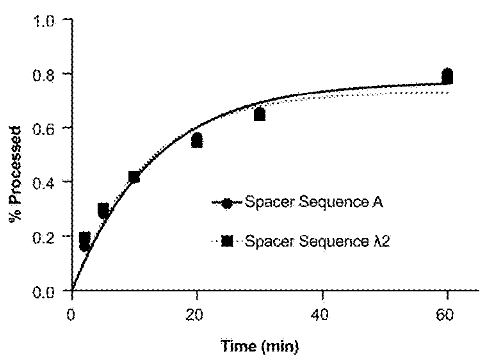
Figure 31D:
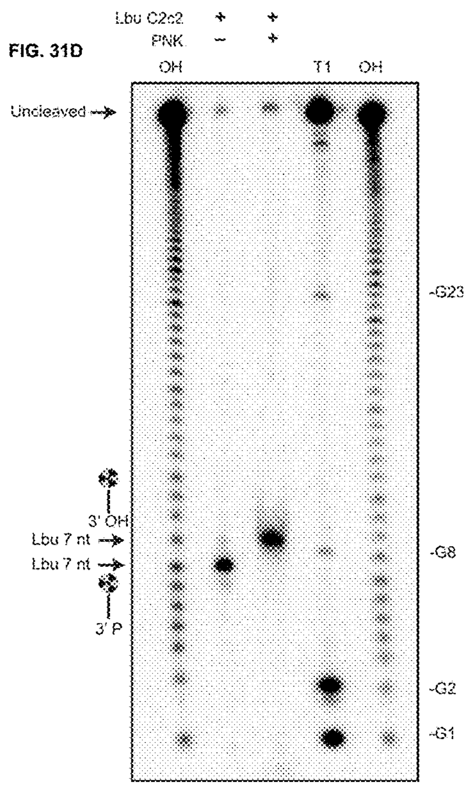

To understand the substrate requirements and mechanism of C2c2 guide RNA processing, pre-crRNAs harboring mutations in either the stem loop or the single-stranded flanking regions of the consensus repeat sequence were generated and their ability to be processed by LbuC2c2 was tested (FIG. 25). The data showed that C2c2-catalyzed cleavage was attenuated upon altering the length of the stem in the repeat region (FIG. 25*a*). Inversion of the stem loop or reduction of the loop length also reduced C2c2's processing activity, while contiguous 4-nt mutations including or near the scissile bond completely abolished it (FIG. 31*b*). A more extensive mutational analysis of the full crRNA repeat sequence revealed two distinct regions on either side of the hairpin with marked sensitivity to base changes (FIG. 25*b*). By contrast, there was no dependence on the spacer sequence for kinetics of processing (FIG. 31*c*). This sensitivity to both flanking regions of the hairpin is reminiscent of the sequence and structural motifs required by many Cas6 and Cas5d enzymes. In contrast, Cpf1 does not have any dependence on the 3' hairpin flanking region, as the variable spacer region abuts the hairpin stem.

Mechanistic studies of LbuC2c2 revealed that processing activity was unaffected by the presence of divalent metal ion chelators EDTA or EGTA (FIG. 25*c*), indicative of a metal ion-independent RNA hydrolytic mechanism. Metal ion-independent RNA hydrolysis is typified by the formation of a 2', 3-cyclic phosphate and 5'-hydroxide on the 5' and 3' halves of the crRNA cleavage products, respectively. To determine the end-group chemical identity of C2c2-processed substrates, the 5' flanking products were further incubated with T4 polynucleotide kinase, which removes 2'3'-cyclic phosphates to leave a 3'-hydroxyl. Altered denaturing-gel migration of the 5' flanking product was observed after kinase treatment, consistent with the removal of a 3' phosphate group (FIG. 31*c*). The divalent metal ion independence of C2c2's pre-crRNA processing activity is in stark contrast with the divalent metal ion dependency of Cpf1, the only other single-protein CRISPR effector shown to perform guide processing. Collectively, these data indicate that C2c2-catalyzed pre-crRNA cleavage is a divalent metal ion-independent process that likely uses a general acid-base catalysis mechanism.

Figures 32A, 32B, 32C:
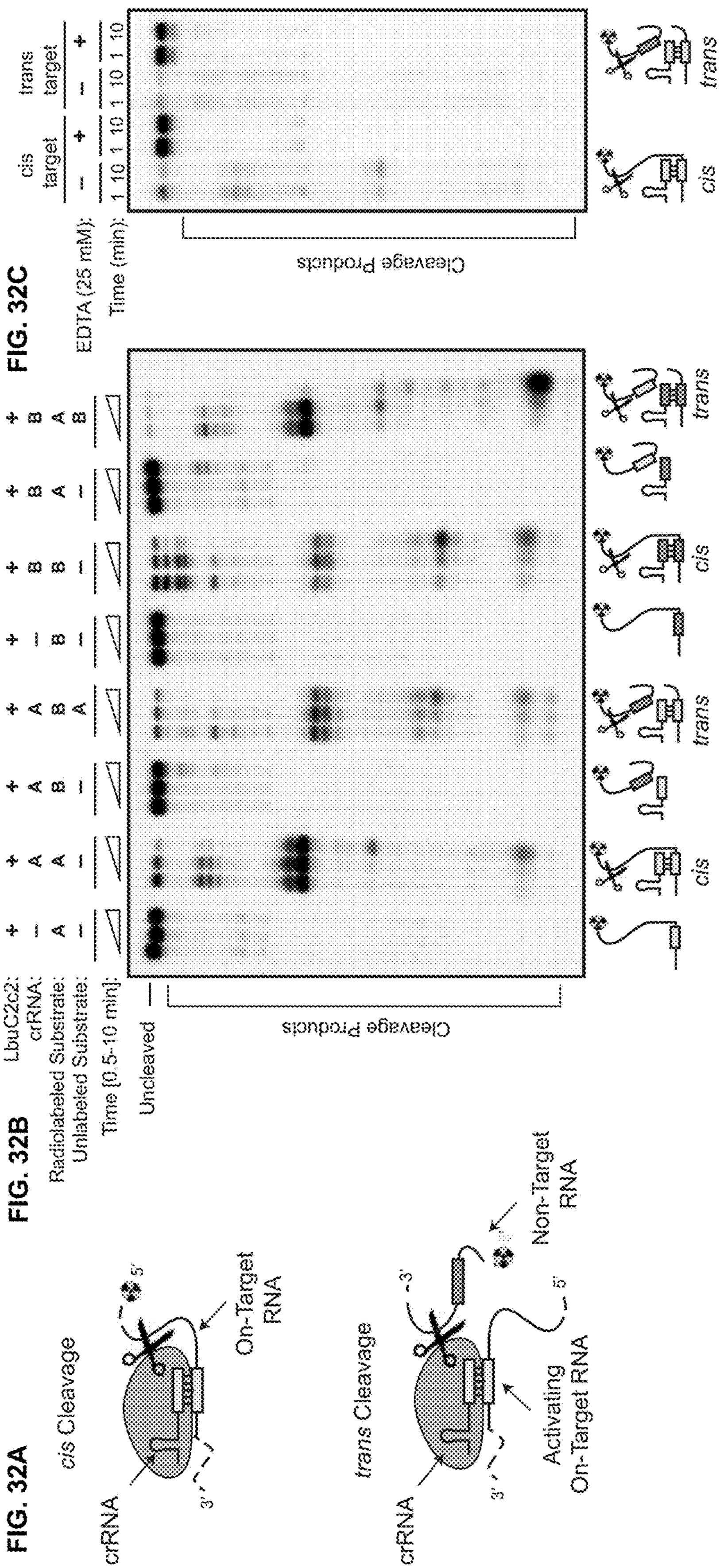
FIG. 32A-32C show that LbuC2c2 catalyzes guide-dependent ssRNA degradation on cis and trans targets. a, Schematic of the two modes of C2c2, guide-dependent ssRNA degradation. b, Cleavage of two distinct radiolabeled ssRNA substrates, A and B, by LbuC2c2. Complexes of 100 nM C2c2 and 50 nM crRNA were pre-formed at 37° C., and reaction was initiated upon addition of <1 nM 5'-labeled target RNA at 25° C. Trans cleavage reactions contained equimolar (<1 nM) concentrations of radiolabeled non-guide-complementary substrate, and unlabeled on-target ssRNA. For multiple ssRNA substrates, we observed that LbuC2c2 catalyzed efficient cleavage only when bound to the complementary crRNA, indicating that LbuC2c2:crRNA cleaves ssRNA in an RNA-guided fashion This activity is hereafter referred to as on-target or cis-target cleavage. LbuC2c2-mediated cis cleavage resulted in a laddering of multiple products, with cleavage preferentially occurring before uracil residues, analogous to LshC2c2[9]. We repeated non-target cleavage reactions in the presence of unlabeled, on-target (crRNA-complementary) ssRNA. In contrast to non-target cleavage experiments performed in cis, we observed rapid degradation of non-target RNA in trans. The similar RNA cleavage rates and near identical cleavage products observed for both cis on-target cleavage and trans non-target cleavage implicate the same nuclease center in both activities. c, LbuC2c2 loaded with crRNA targeting spacer A was tested for cleavage activity under both cis (target A labeled) and trans (target B labeled in the presence of unlabeled target A) cleavage conditions in the presence of 25 mM EDTA.
Figure 33A:
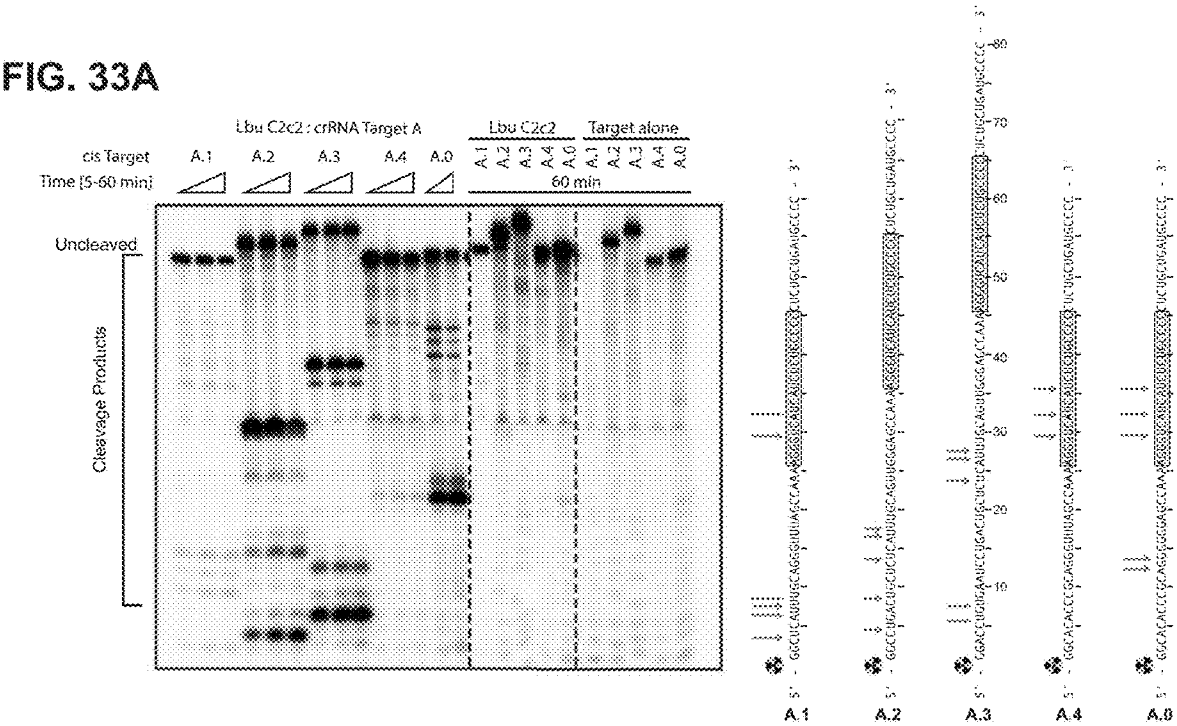
FIG. 33A-33B show LbuC2c2 ssRNA target cleavage site mapping a, ssRNA target cleavage assay conducted per Methods demonstrating LbuC2c2-mediated 'cis'-cleavage of several radiolabeled ssRNA substrates with identical spacer-complementary sequences but distinct 5' flanking sequences of variable length and nucleotide composition. Sequences of ssRNA substrates are shown to the right with spacer-complementary sequences for crRNA-A highlighted in yellow. Arrows indicate detected cleavage sites. Gel was cropped for clarity. It should be noted that the pattern of cleavage products produced on different substrates (e.g. A.1 vs. A.2 vs. A.3) indicates that the cleavage site choice is primarily driven by a uracil preference and exhibits an apparent lack of exclusive cleavage mechanism within the crRNA-complementary target sequence, which is in contrast to what is observed for other Class II CRISPR single effector complexes such as Cas9 and Cpf1[11,21]. Interestingly, the cleavage pattern observed for substrate A.0 hints at a secondary preference for polyG sequences. A.1 (SEQ ID NO: 125); A.2 (SEQ ID NO: 129); A.3 (SEQ ID NO: 130); A.4 (SEQ ID NO: 126); and A.0 (SEQ ID NO: 127). b, LbuC2c2 ssRNA target cleavage assay as per Methods, using a range of crRNAs that tile the length of the ssRNA target. The sequence of the ssRNA substrates used in this experiment is shown below the gel with spacer-complementary sequences for each crRNA highlighted in yellow. Arrows indicate predicted cleavage sites. Above each set of lanes, a small diagram indicates the location of the spacer sequence along the target (yellow box) and the cleavage products observed (red arrows) or absent (black arrows). Likewise, it should be noted that for every crRNA the cleavage product length distribution is very similar, again indicating an apparent lack of exclusive cleavage within the crRNA-bound sequence. The absence of a several cleavage products in a subset of the reactions might be explained by the presence of bound C2c2:crRNA on the ssRNA target, which could sterically occlude access to uracils by any cis (intramolecular) or trans (intermolecular) LbuC2c2 active sites. While proper analysis for protospacer flanking site (PFS) preference for LbuC2c2 is beyond the scope of this study, minimal impact of the 3' flanking nucleotide was observed. Expected PFS base is noted in diagram next to each guide tested in red. (SEQ ID NO: 131).
Figure 33B:
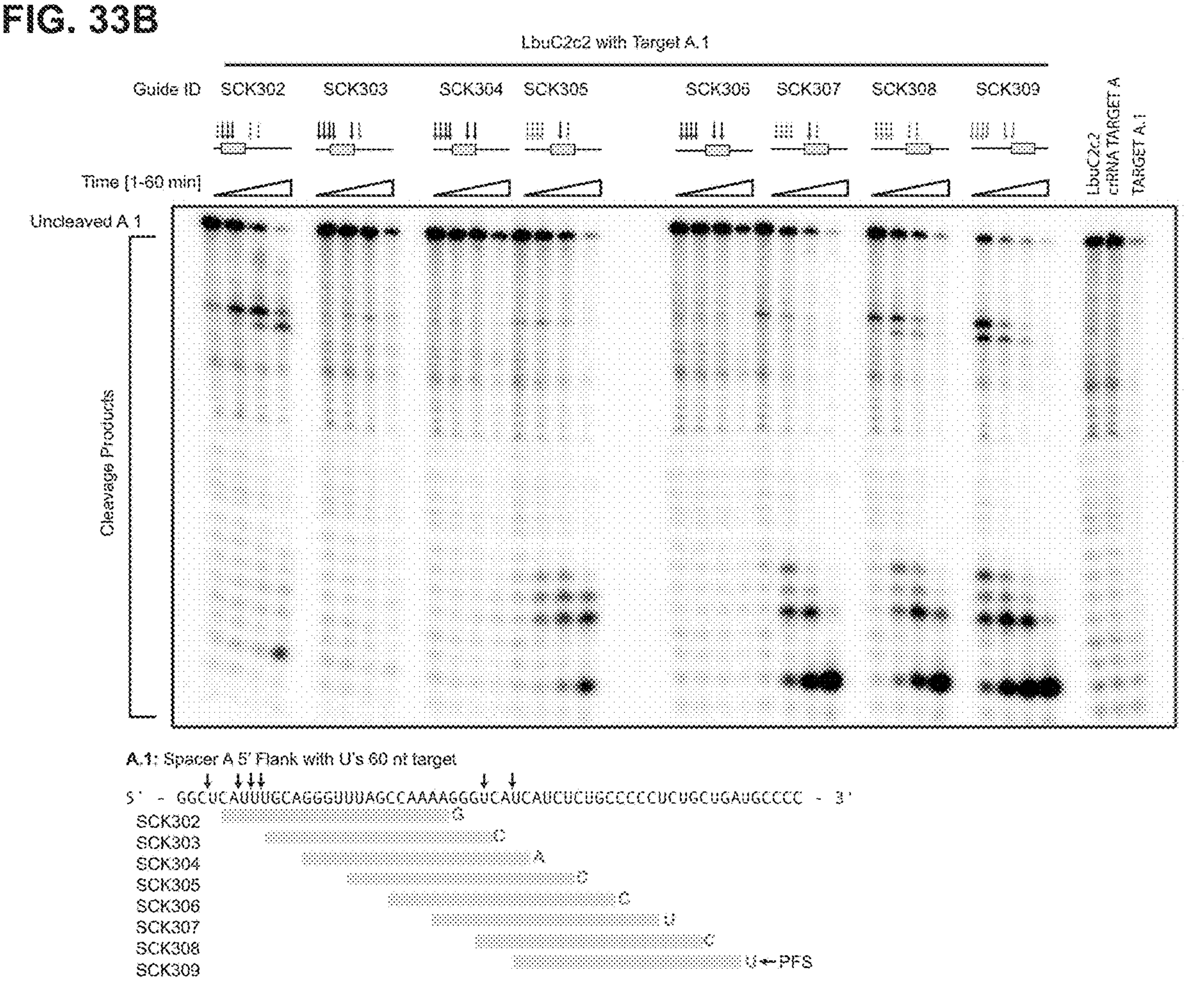
Figure 34A:
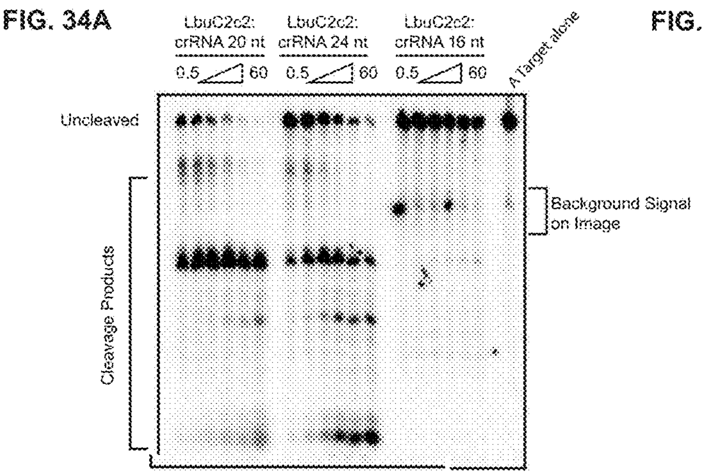
FIG. 34A-34D depict dependence of RNA targeting on crRNA variants, temperature and point mutations. a, LbuC2c2 ssRNA target cleavage assay carried out, as per Methods with crRNAs possessing 16-nt, 20-nt or 24-nt spacers. b, LbuC2c2 ssRNA target cleavage time-course carried out at either 25° C. and 37° C. as per methods. c, LbuC2c2 ssRNA target cleavage timecourse carried out as per Methods with crRNAs possessing different 5'-flanking nucleotide mutations. Mutations are highlighted in red. 1-2 nucleotide 5' extensions negligibly impacted cleavage efficiencies. In contrast, shortening the flanking region to 3 nts slowed cleavage rates. Triangle (SEQ ID NO: 9); Diamond (SEQ ID NO: 147); Circle (SEQ ID NO: 148); Square (SEQ ID NO: 149); d Impact of point mutations on ribonuclease activity of C2c2 in conserved residue mutants within HEPN motifs for ssRNA targeting.
Figure 34B:
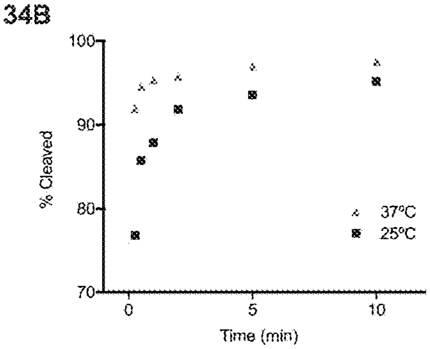
Figure 34C:
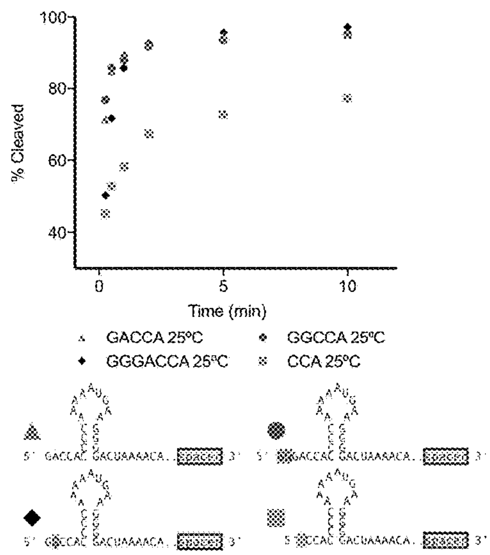
Figure 34D:
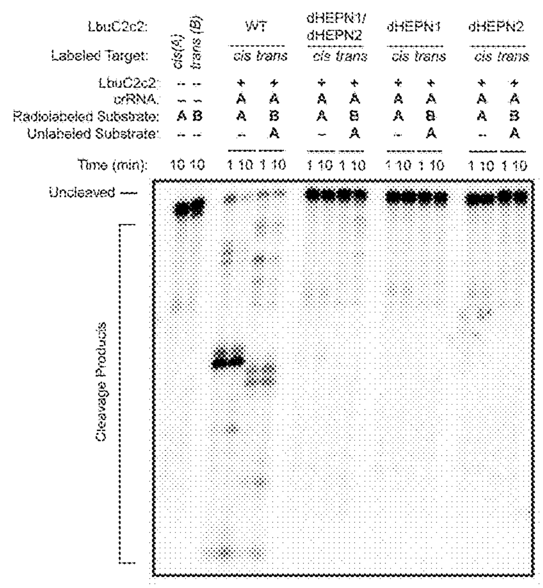

Following maturation, crRNAs typically bind with high affinity to Cas effector protein(s) to create RNA-guided surveillance complexes capable of sequence-specific nucleic acid recognition. In agreement with previous work using LshC2c2, LbuC2c2 catalyzed efficient target RNA cleavage only when such substrates could base pair with a complementary sequence in the crRNA (FIGS. 32-34). Given the promiscuous pattern of cleavage observed for C2c2 (FIG. 33), the ability of LbuC2c2 to act as a crRNA-activated non-specific RNA endonuclease in trans was tested (FIG. 32*b*). In striking contrast to non-target cleavage experiments performed in cis and consistent with previous observations for LshC2c2, rapid degradation of non-target RNA in trans was observed (FIG. 32*b*). This result shows that target recognition activates C2c2 for general non-specific degradation of RNA. Importantly, the similar RNA cleavage rates and near-identical cleavage products observed for both cis on-target cleavage and trans non-target cleavage of the same RNA substrate implicate the same nuclease center in both activities (FIG. 32*b*).

Figure 26A:
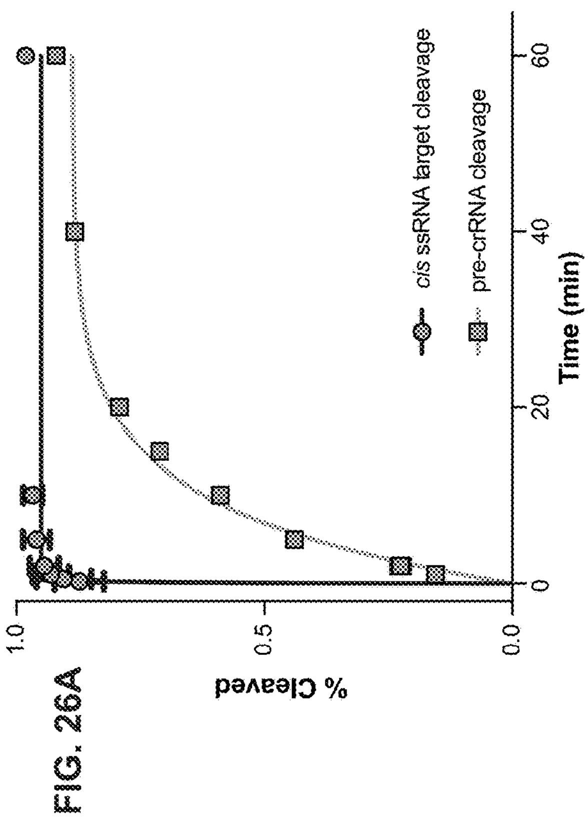
FIG. 26A-26D depict data showing that that LbuC2c2 contains two distinct ribonuclease activities. a, Quantified time-course data of cis ssRNA target (black) and pre-crRNA (teal) cleavage by LbuC2c2 performed at 37° C. Exponential fits are shown as solid lines (n=3), and the calculated pseudo-first-order rate constants ($k_{obs}$) (mean±s.d.) are 9.74±1.15 $min^{-1}$ and 0.12±0.02 $min^{-1}$ for cis ssRNA target and pre-crRNA cleavage, respectively. b, LbuC2c2 architecture depicting the location of HEPN motifs and processing deficient point mutant c,d Ribonuclease activity of LbuC2c2 mutants for pre-crRNA processing in c and ssRNA targeting in d and Extended Data FIG. 6d.
Figure 26B:
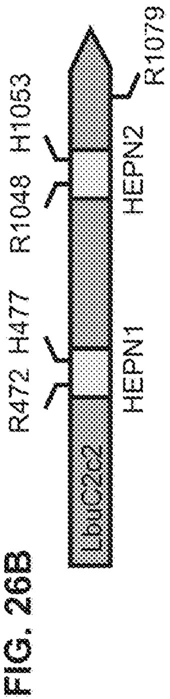
Figure 26C:
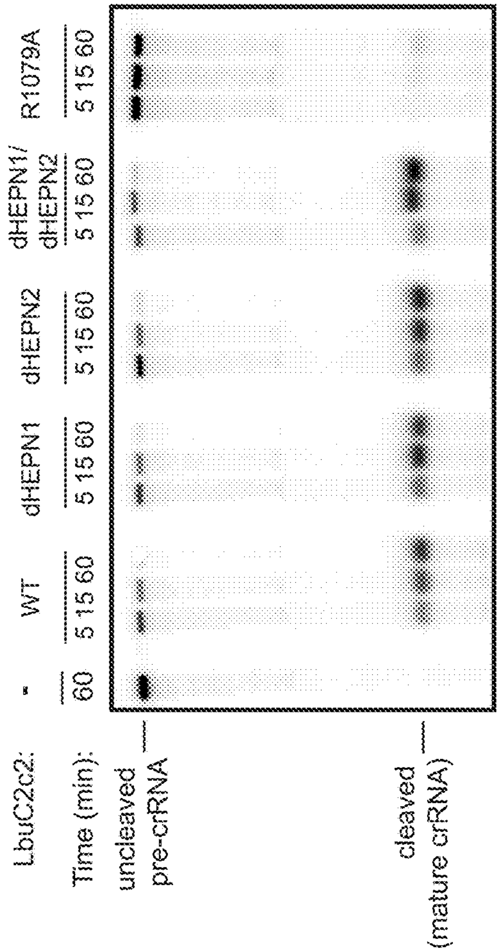

Notably, crRNA-mediated cleavage of target ssRNA occurred at an ~80-fold faster rate than pre-crRNA processing (FIG. 26*a*), and in contrast to pre-crRNA processing, RNA-guided target cleavage was severely reduced in the presence of EDTA, indicating that this activity is divalent metal ion-dependent (FIG. 26*a*, (FIG. 32*c*, FIG. 34). Given these clear differences, it was reasoned that C2c2 might possess two orthogonal RNA cleavage activities: one for crRNA maturation, and the other for crRNA-directed, non-specific RNA degradation. To test this hypothesis, several residues within the conserved HEPN motifs of LbuC2c2 were systematically mutated, and pre-crRNA processing and RNA-guided RNase activity of the mutants was assessed (FIG. 26, FIG. 34*d*). Double and quadruple mutants of conserved HEPN residues (R472A, R477A, R1048A and R1053) retained robust pre-crRNA cleavage activity (FIG. 26*c*). By contrast, all HEPN mutations abolished RNA-guided cleavage activity while not affecting crRNA or ssRNA-binding ability (FIG. 34*d*, 35).

Figure 26D:
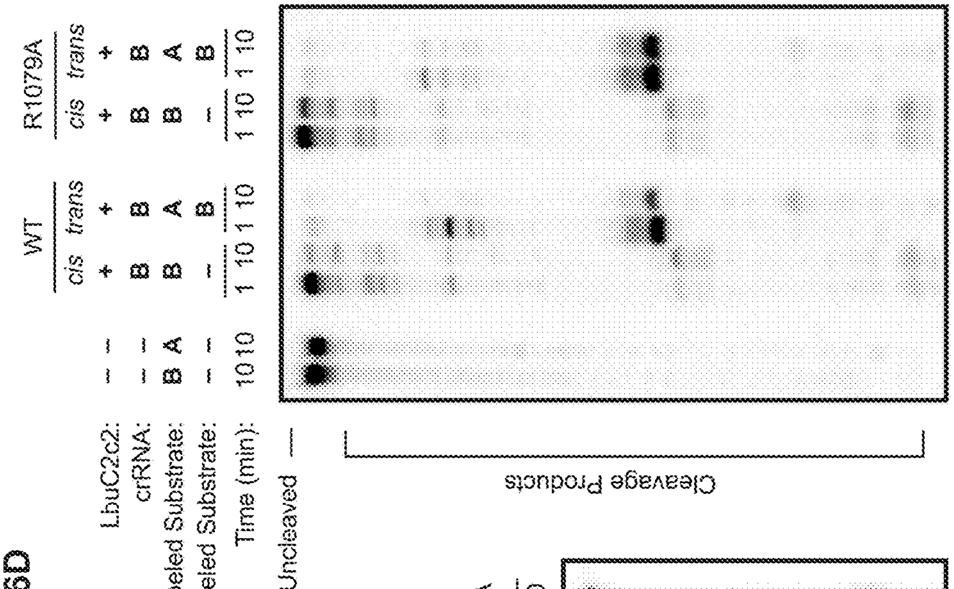
Figure 35A:
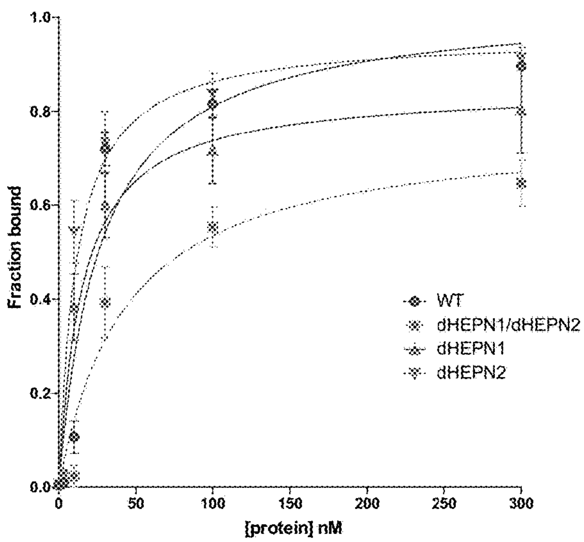
FIG. 35A-35D depict binding data for LbuC2c2 to mature crRNA and target ssRNA. a, Filter binding assays were conducted as described in the Methods to determine the binding affinity of mature crRNA-A_GG to LbuC2c2-WT, LbuC2c2-dHEPN1, LbuC2c2-dHEPN2, or LbuC2c2-dHEPN1/dHEPN2. The quantified data were fit to standard binding isotherms. Error bars represent the standard deviation from three independent experiments. Measured dissociation constants from three independent experiments (mean±sd) were 27.1±7.5 nM (LbuC2c2-WT), 15.2±3.2 nM (LbuC2c2-dHEPN1), 11.5±2.5 nM (LbuC2c2-dHEPN2), and 43.3±11.5 nM (LbuC2c2-dHEPN1/dHEPN2). b, Representative electrophoretic mobility shift assay for binding reactions between LbuC2c2-dHEPN1/dHEPN2: crRNA-A_GG and either 'on-target' A ssRNA or 'off-target' B ssRNA, as indicated. Three independent experiments were conducted as described in the Methods. The gel was cropped for clarity. c, Quantified binding data from (b) were fitted to standard binding isoforms. Error bars represent the standard deviation from three independent experiments. Measured dissociation constants from three independent experiments (mean±sd) were 1.62±0.43 nM for ssRNA A and N.D (>>10 nM) for ssRNA B. d, Filter binding assays were conducted as described in the Methods to determine the binding affinity of mature crRNA-A_GA to LbuC2c2-WT and LbuC2c2-R1079A. The quantified data were fit to standard binding isotherms. Error bars represent the standard deviation from three independent experiments. Measured dissociation constants from three independent experiments (mean±sd) were 4.65±0.6 nM (LbuC2c2-WT) and 2.52±0.5 nM (LbuC2c2-R1079A). It is of note that these binding affinities differ from panel a. This difference is accounted for in a slight difference in the 5' sequence of the guide with panel a guides beginning with a 5'-GGCCA . . . and panel d 5'-GACCA. While the native sequence guide (5'-GACCA) binds tighter to LbuC2c2, no difference is seen in the RNA targeting efficiencies of these guide variants (Extended Data FIG. 6c).
Figure 35B:
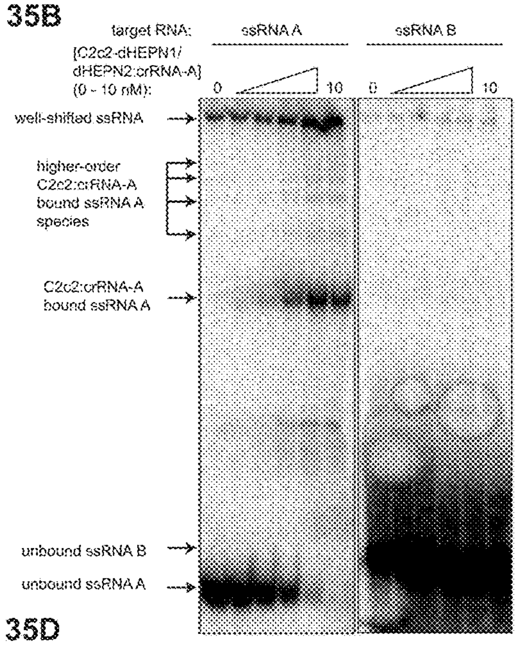
Figure 35C:
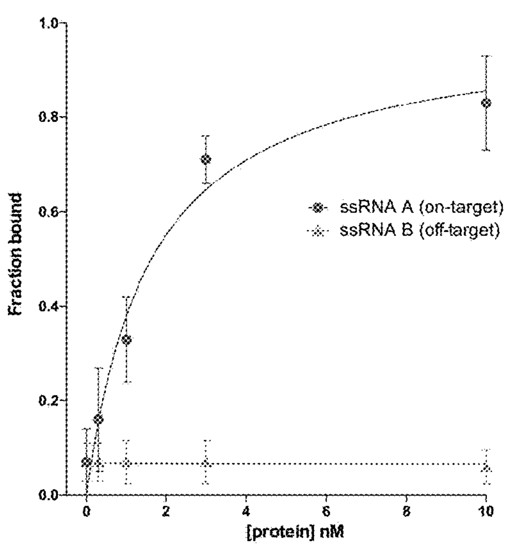
Figure 35D:
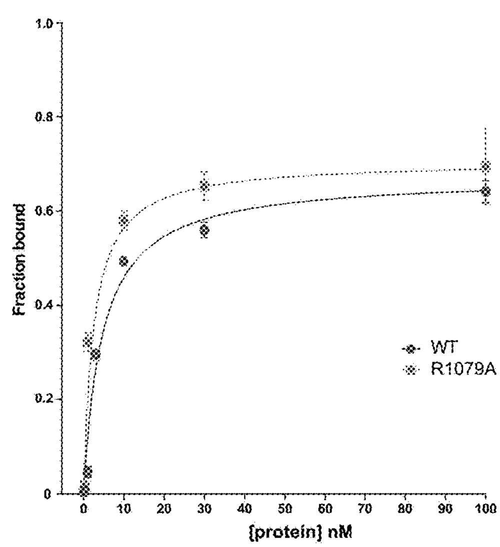

Next, mutations were sought that would abrogate pre-crRNA processing activity without disrupting target RNA cleavage. Given that we were unable to predict any other potential RNase motifs beyond the HEPN motifs, and that C2c2 proteins bear no homology to Cpf1, the charged residues throughout LbuC2c2 were systematically mutated. An arginine residue (R1079A) was identified that upon mutation resulted in severely attenuated pre-crRNA processing activity (FIG. 26*c*). This C2c2 mutant enzyme retained crRNA-binding ability as well as RNA target cleavage activity (FIG. 35*d*, FIG. 26*d*). Taken together, the results show that distinct active sites within the C2c2 protein catalyze pre-crRNA processing and RNA-directed RNA cleavage.

Figure 27A:
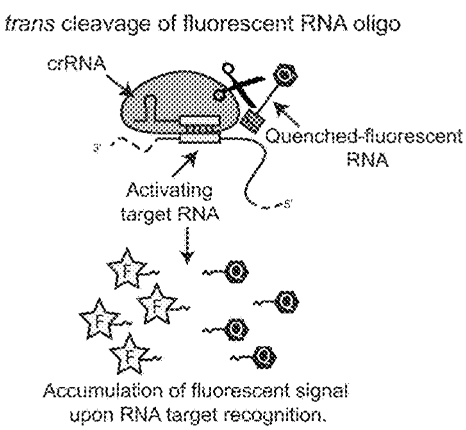
FIG. 27A-27E shows that C2c2 provides sensitive detection of transcripts in complex mixtures. a, Illustration of LbuC2c2 RNA detection approach using a quenched fluorescent RNA reporter. b, Quantification of fluorescence signal generated by LbuC2c2 after 30 min for varying concentrations of target RNA in the presence of human total RNA. RNase A shown as positive RNA degradation control. (mean±s.d., n=3) c, Quantification of fluorescence signal generated by LbuC2c2 loaded with a β-actin targeting crRNA after 3 h for varying amounts of human total RNA or bacterial total RNA (as a β-actin null negative control). (mean±s.d., n=3) d, Tandem pre-crRNA processing also enables RNA detection. (mean±s.d., n=3) e, Model of the Type VI CRISPR pathway highlighting both of C2c2's ribonuclease activities.
Figure 27B:
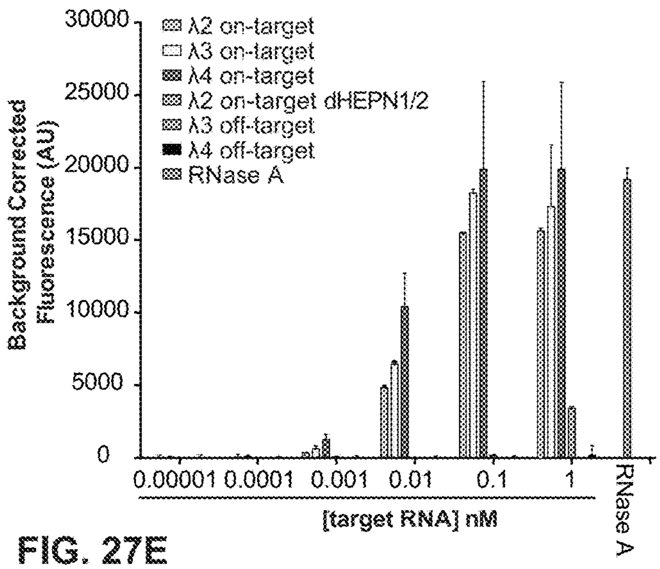
Figure 36A:
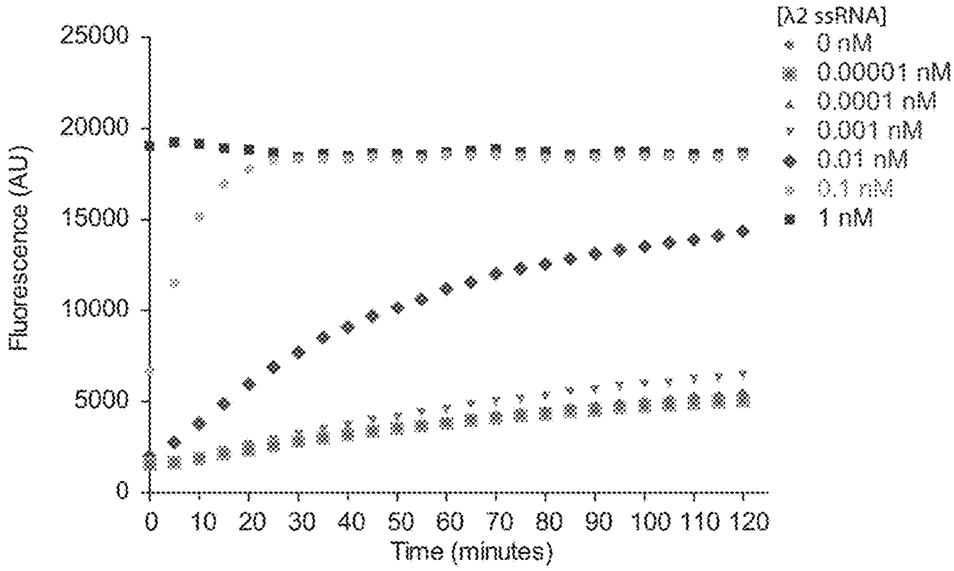
FIG. 36A-36B depict an RNase detection assay λ2-ssRNA time-course. a, LbuC2c2:crRNA-λ2 was incubated with RNAase-Alert substrate (Thermo-Fisher)) and 100 ng HeLa total RNA in the presence of increasing amounts of λ2 ssRNA (0-1 nM) for 120 min at 37° C. Fluorescence measurements were taken every 5 min. The 1 nM λ2 ssRNA reaction reached saturation before the first time point could be measured. Error bars represent the standard deviation from three independent experiments. b, LbuC2c2:crRNA-λ4 or apo LbuC2c2 was incubated in HeLa total RNA for 2 hours in the presence or absence of on-target activating λ4 ssRNA. Degradation of background small RNA was resolved on a small RNA chip in a Bioanalyzer 2100 as per Methods. Small differences are seen in the fragment profile of between apo LbuC2c2 and LbuC2c2: crRNA-λ4. In contrast, upon addition of the on-target ssRNA to the reaction, a drastic broadening and shifting of the tRNA peak reveals extensive degradation of other structured and nonstructured RNA's present in the reaction upon activation of LbuC2c2 trans activity.
Figure 36B:
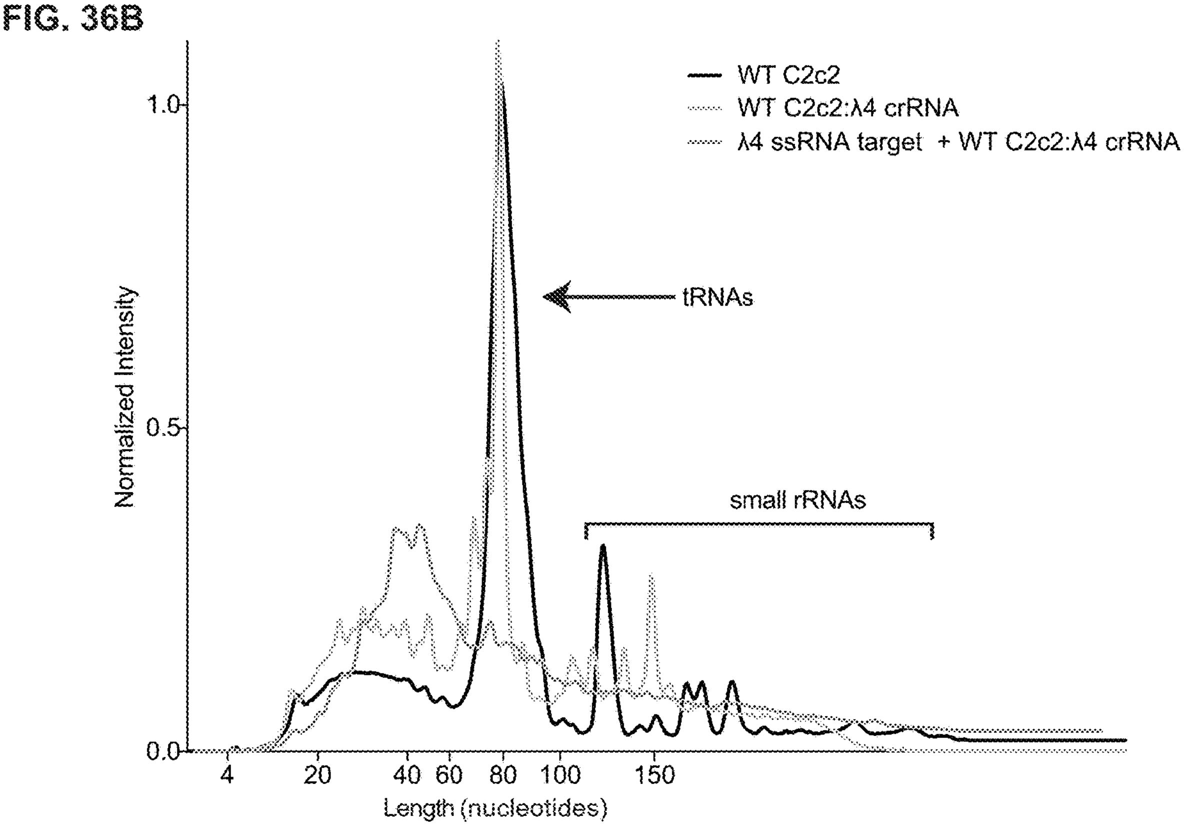

It was next tested whether C2c2's robust RNA-stimulated cleavage of trans substrates can be employed as a means of detecting specific RNAs within a pool of transcripts. While many polymerase-based methods have been developed for RNA amplification and subsequent detection, few approaches are able to directly detect the target RNA without significant engineering or stringent design constraints for each new RNA target. As a readily-programmable alternative, it was tested whether C2c2's RNA-guided trans endonuclease activity could be harnessed to cleave a fluorophore-quencher-labeled reporter RNA substrate, thereby resulting in increased fluorescence upon target RNA-triggered RNase activation (FIG. 27*a*). LbuC2c2 was loaded with bacteriophage λ-targeting crRNAs and tested for its ability to detect the corresponding λ ssRNA targets spiked into HeLa cell total RNA. Upon addition of as little as 1-10 pM complementary λ target-RNA, a substantial crRNA-specific increase in fluorescence occurred within 30 min (FIG. 27*b* and FIG. 36*a*). Control experiments with either C2c2:crRNA complex alone or in the presence of crRNA and a non-complementary target RNA resulted in negligible increases in fluorescence relative to an RNase A positive control (FIG. 27*b* and FIG. 36*a*). It was noted that at the 10 pM concentration of a λ target RNA, only ~0.02% of the C2c2:crRNA complex was predicted to be in the active state, yet the observed fluorescent signal reflected ~25-50% cleavage of the reporter RNA substrate, depending on the RNA target. Fragment size resolution of the background RNA in these reactions revealed significant degradation, even on highly structured tRNAs (FIG. 36*b*). Since reporter RNA cleavage occurred in the presence of a vast excess of unlabeled RNA, we conclude that LbuC2c2 is a robust multiple-turnover enzyme capable of at least $10^4$ turnovers per target RNA recognized. Thus, in contrast to previous observations, crRNA-directed trans cleavage is potent and detectable even at extremely low levels of activated protein.

Figure 27C:
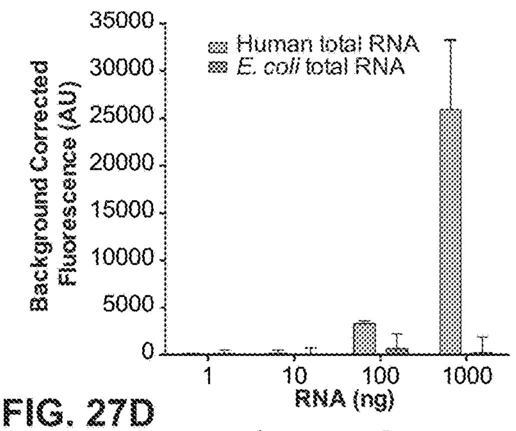
Figure 27D:
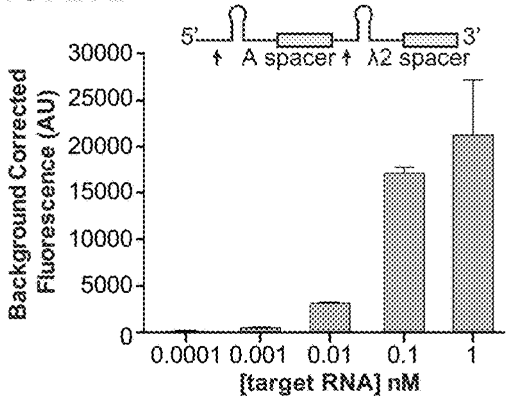
Figure 27E:
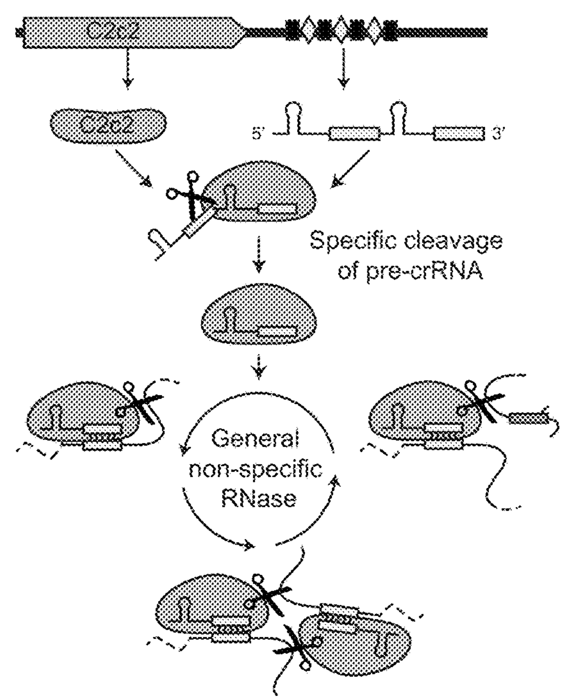
Figure 28A:
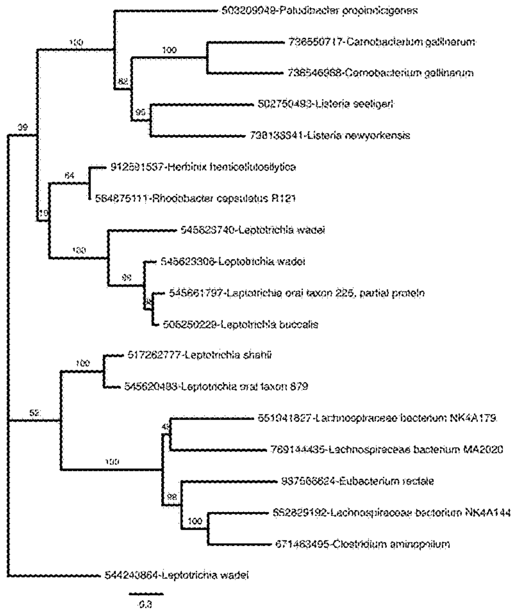
FIG. 28A-28B depict a complete phylogenetic tree of C2c2 family and C2c2 alignment. a, Maximum-likelihood phylogenetic reconstruction of C2c2 proteins. Leaves include GI protein numbers and organism of origin; bootstrap support values, out of 100 resamplings, are presented for inner split. Scale is in substitutions per site. b, Multiple sequence alignment of the three analyzed homologs of C2c2; coordinates are based on LbuC2c2. *Leptotrichia_buccalis* (SEQ ID NO: 2); *Listeria_seeligeri* (SEQ ID NO: 1); *Leptotrichia_shahii* (SEQ ID NO: 3).
Figure 28B:
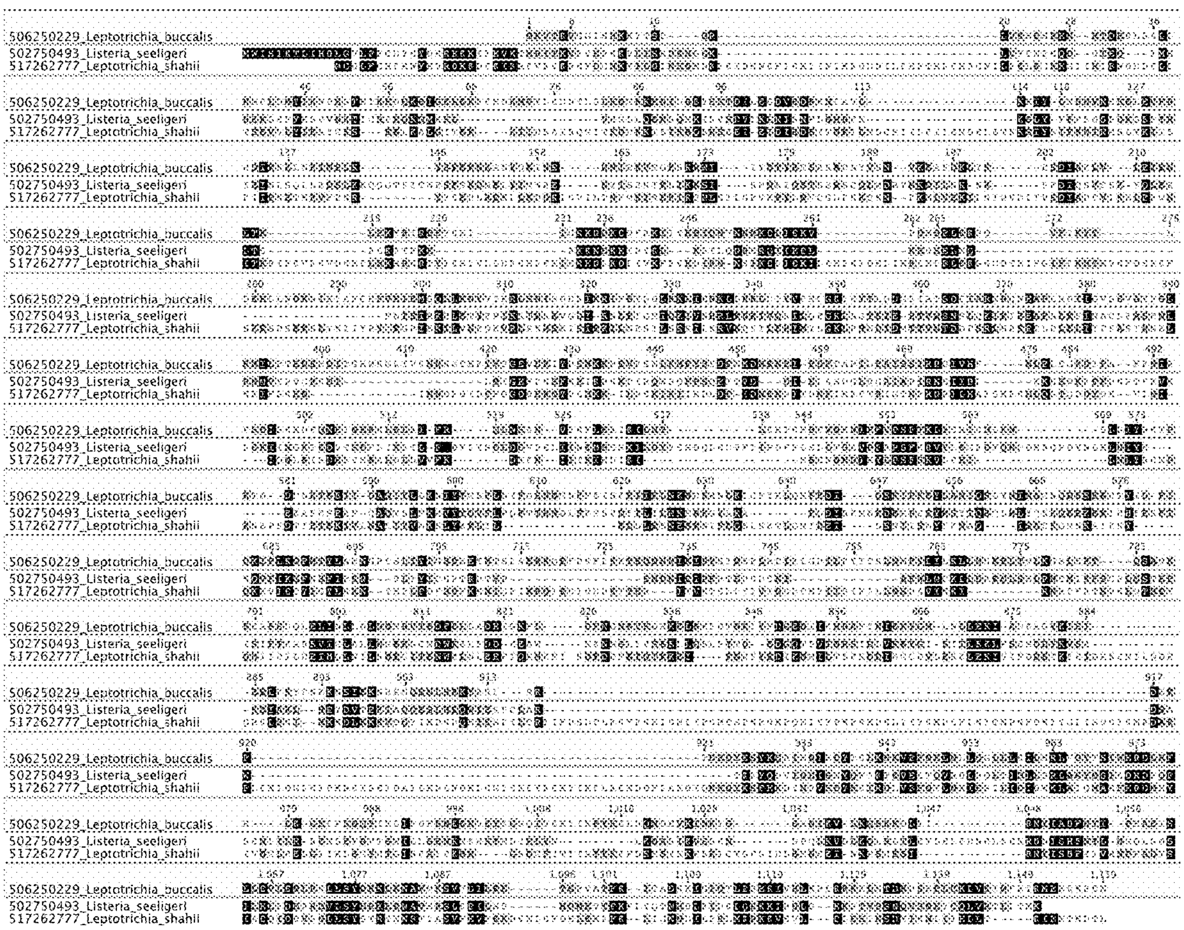
Figure 29A:
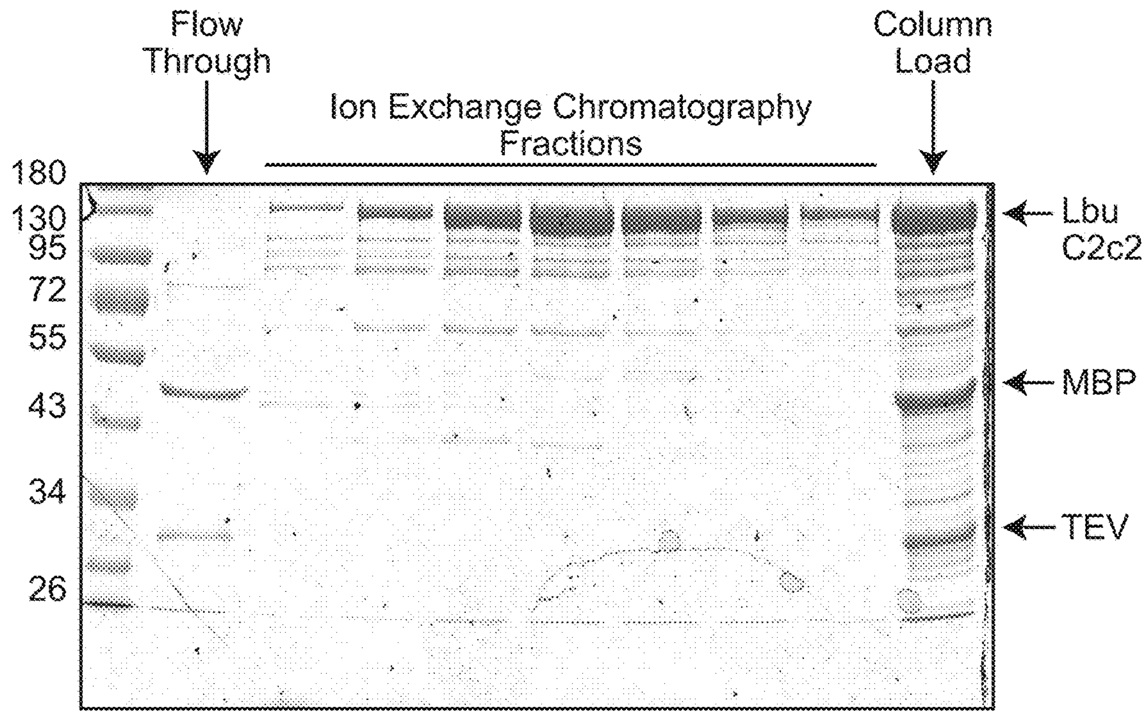
FIG. 29A-29D depict data related to purification and production of C2c2. All C2c2 homologs were expressed in *E. coli* as His-MBP fusions and purified by a combination of affinity, ion exchange and size exclusion chromatography. The $Ni^+$ affinity tag was removed by incubation with TEV protease. Representative SDS-PAGE gels of chromatography fractions are shown in (a, b). c, The chromatogram from Superdex 200 (16/60) column demonstrating that C2c2 elutes as a single peak, devoid of nucleic acid. d, SDS PAGE analysis of purified proteins used in this manuscript.
Figure 29B:
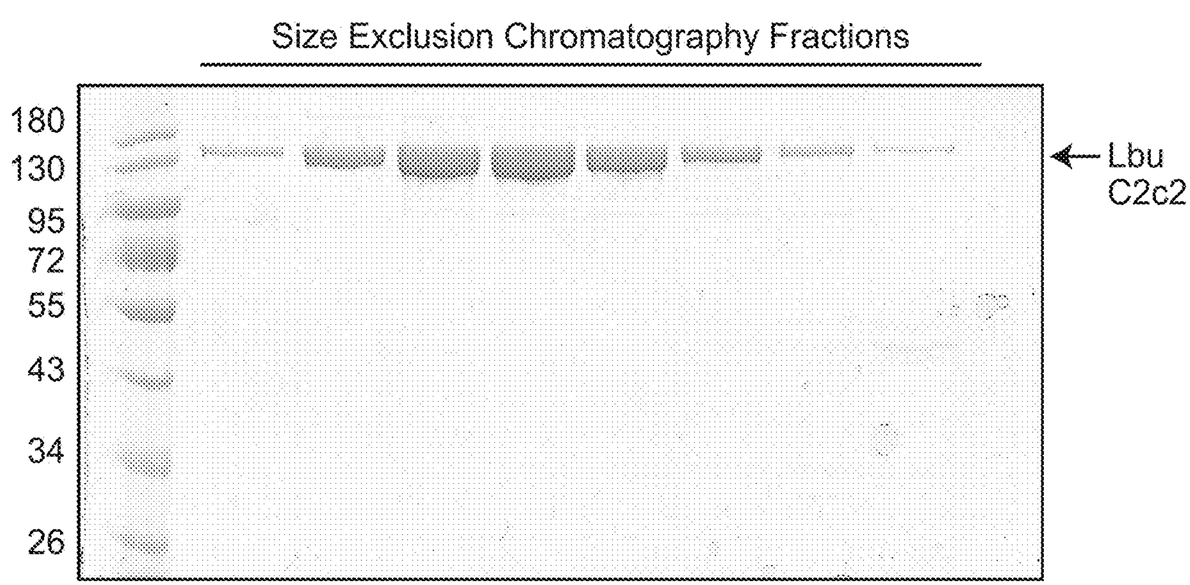
Figure 29C:
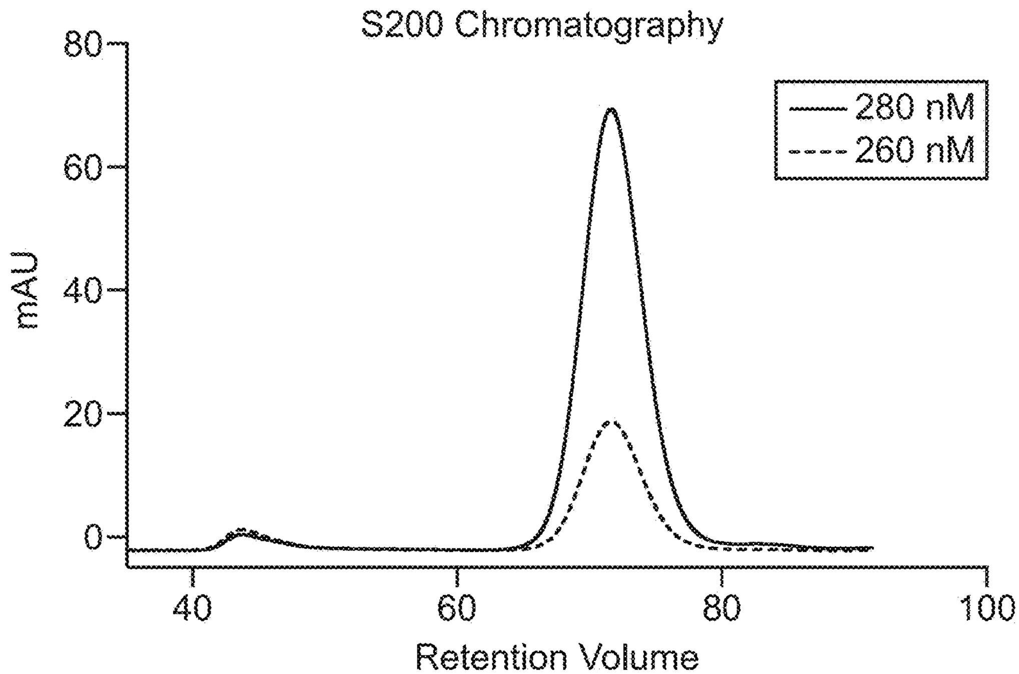
Figure 29D:
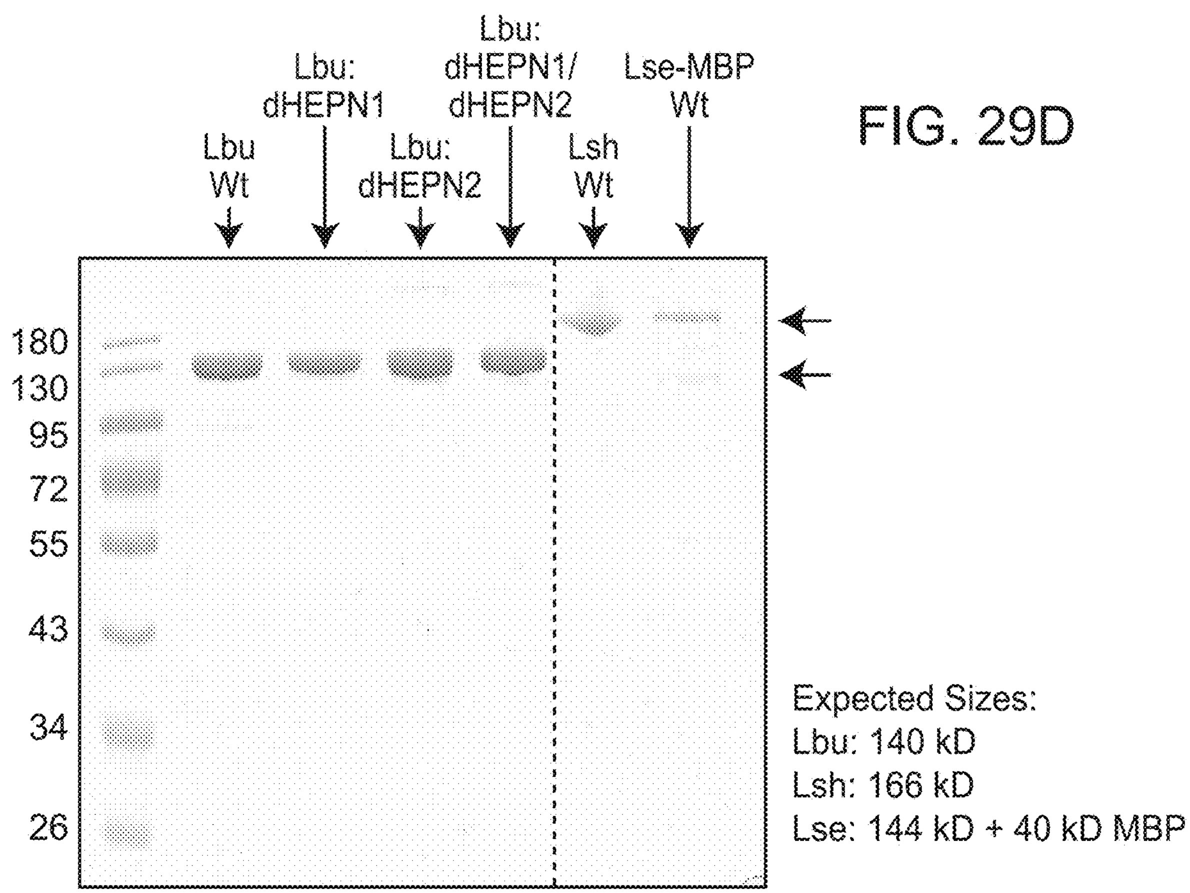

To extend this LbuC2c2 RNA detection system, a crRNA was designed to target endogenous beta-actin mRNA. A measurable increase in fluorescence was observed in the presence of human total RNA relative to *E. coli* total RNA, demonstrating the specificity of this method (FIG. 27*c*). Furthermore, given that C2c2 processes its own guide, pre-crRNA processing and RNA detection was combined in a single reaction by designing tandem crRNA-repeat containing spacers complementary to target RNAs A and λ2. LbuC2c2 incubated with this unprocessed tandem guide RNA in the detection assay generated a significant increase in fluorescence similar in magnitude and sensitivity to experiments using mature crRNAs (FIG. 27*b*, 27*d*). Taken together, these data highlight the exciting opportunity to take advantage of C2c2's two distinct RNase activities for a range of biotechnological applications (FIG. 27*e*).

In bacteria, C2c2 likely operates as a sentinel for viral RNAs. Without being bound by theory, we propose that when invasive transcripts are detected within the host cell via base pairing with crRNAs, C2c2 is activated for promiscuous cleavage of RNA in trans (FIG. 27*e*). As a defense mechanism, this bears striking similarity to RNase L and caspase systems in eukaryotes, whereby a cellular signal triggers promiscuous ribonucleolytic or proteolytic degradation within the host cell, respectively, leading to apoptosis. While the RNA targeting mechanisms of Type III CRISPR systems generally result in RNA cleavage within the protospacer-guide duplex, recent examples of associated nucleases Csx1 and Csm6 provide compelling parallels between the Type VI systems and the multi-component Type III inference complexes.

The data described herein show that CRISPR-C2c2 proteins represent a new class of enzyme capable of two separate RNA recognition and cleavage activities. Efficient pre-crRNA processing requires sequence and structural motifs within the CRISPR repeat which prevent non-endogenous crRNA loading and helps to reduce the potential toxicity of this potent RNase. The entirely different pre-crRNA processing mechanisms of C2c2 and the Type V CRISPR effector protein Cpf1 indicate that each protein family has converged upon independent activities encompassing both the processing and interference functions of their respective CRISPR pathways. Furthermore, the two distinct catalytic capabilities of C2c2 can be harnessed in concert for RNA detection, as the activation of C2c2 to cleave thousands of trans-RNAs for every target RNA detected enables potent signal amplification. The capacity of C2c2 to process its own guide RNAs from arrays allows the use of tissue-specific Pol II promoters for guide expression, in addition to target multiplexing for a wide range of applications. The C2c2 enzyme is unique within bacterial adaptive immunity for its dual RNase activities, and highlights the utility of harnessing CRISPR proteins for precise nucleic acid manipulation in cells and cell-free systems.

Example 14

Figure 37:
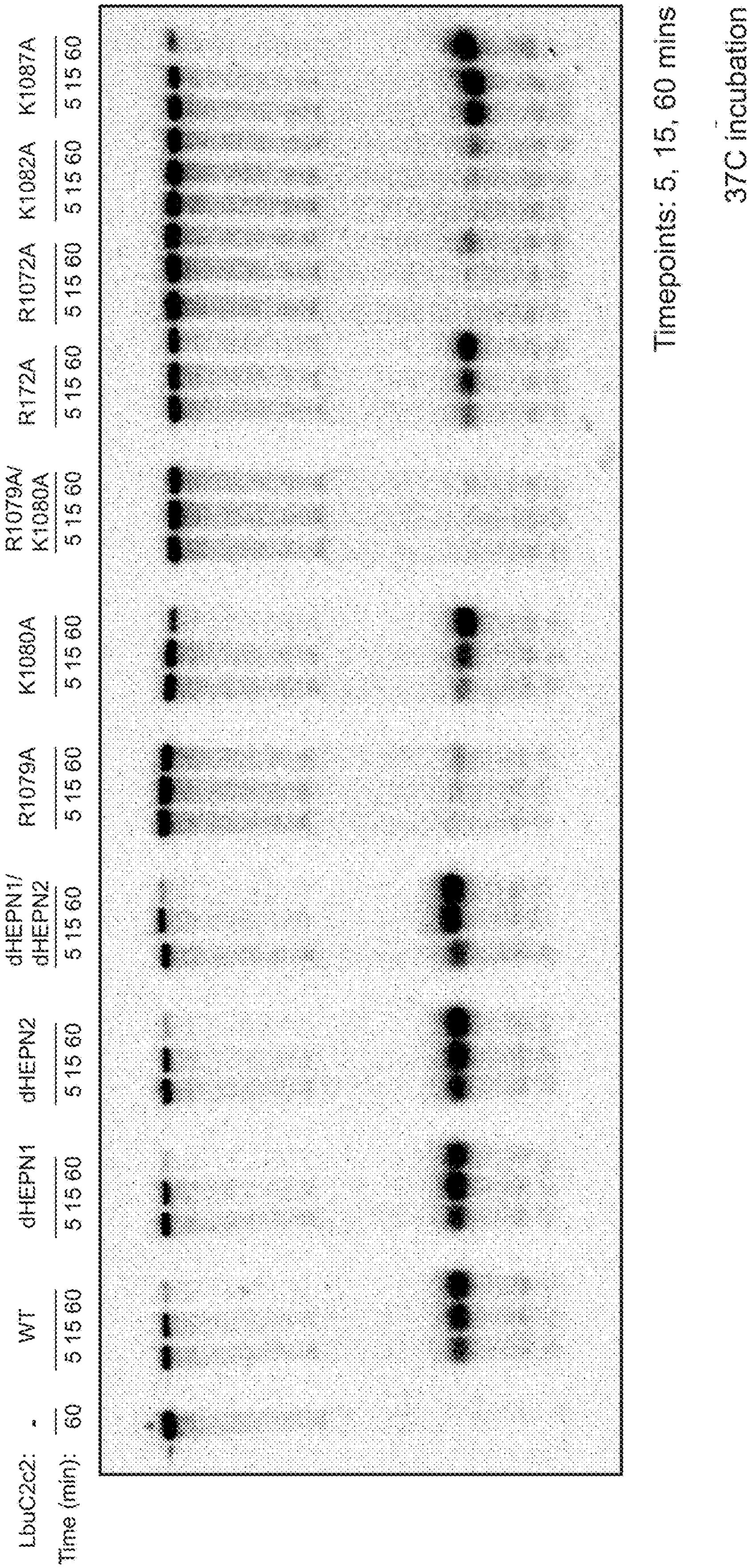
FIG. 37 depicts cleavage experiments demonstrating severely reduced cleavage of precursor guide RNA (guide RNA processing) by LbuC2c2 when the protein includes a mutation at any amino acid position selected from R1079 (e.g., R1079A), R1072 (e.g., R1072A), and K1082 (e.g., K1082A).

Additional amino acid positions were identified in LbuC2c2 that when mutated result in severely attenuated pre-crRNA processing activity (FIG. 37). The amino acid positions included R1079 (e.g., R1079A), R1072 (e.g., R1072A), and K1082 (e.g., K1082A).

Example 15

Cas13a enzymes comprise two distinct functional groups that recognize orthogonal sets of crRNAs and possess different ssRNA cleavage specificities. Cas13a pre-crRNA processing is not essential for ssRNA cleavage, although it enhances ssRNA targeting for crRNAs encoded internally within the CRISPR array. Two Cas13a protein subfamilies were defined, which subfamilies can operate in parallel for RNA detection and destruction both in bacteria and for diagnostic applications.

Materials and Methods

Cas13a phylogenic and repeat conservation analysis. Cas13a maximum-likelihood phylogenies were computed using RAxML (Stamatakis, *Bioinformatics*. 2014 May 1; 30(9):1312-3) with the PROTGAMMALG evolutionary model and 100 bootstraps. Protein clades alpha and beta were defined as branch points with bootstrap values greater than 90, suggesting high confidence in having a common ancestor. The remaining proteins were labeled as ambiguous ancestry, as the phylogenetic relationships between them were low confidence, reflected in bootstrap values less than 90. Sequences were aligned by MAFFT with the 'einsi' method (Katoh and Standley, *Mol Biol Evol*. 2013 April; 30(4):772-80). Candidates were selected to represent each of the major branches of the Cas13a protein tree. Alignments were performed for all non-redundant homologs (FIG. 41) and candidate proteins. Comparison of the CRISPR-RNA (crRNA) repeats was carried out by calculating pairwise similarity scores using the Needleman-Wunsch algorithm through the Needle tool on EMBL-EBI (McWilliam et al., *Nucleic Acids Res*. 2013 July; 41 (Web Server issue):W597-600). Hierarchical clustering of CRISPR crRNA was performed in R using the similarity score matrix.

Cas13a protein expression and purification. Expression vectors for protein purification were assembled using synthetic gBlocks ordered from Integrated DNA Technologies (IDT). The codon-optimized Cas13a genomic sequences were N-terminally tagged with a $His_6$-MBP-TEV cleavage site sequence, with expression driven by a T7 promoter. Mutant proteins were cloned via site-directed mutagenesis of wild-type Cas13a constructs. Purification of all homologs was carried out as described in Examples 7 and 13, above. Briefly, expression vectors were transformed into Rosetta2 DE3 or BL21 *E. coli* cells grown in 2×YT broth at 37° C., induced at mid-log phase with 0.5 mM IPTG, and then transferred to 16° C. for overnight expression. Cell pellets were resuspended in lysis buffer (50 mM Tris-Cl pH 7.0, 500 mM NaCl, 5% glycerol, 1 mM TCEP, 0.5 mM PMSF, and EDTA-free protease inhibitor (Roche)), lysed by sonication, and clarified by centrifugation at 15,000 g. Soluble $His_6$-MBP-TEV-Cas13a was isolated over metal ion affinity chromatography, and in order to cleave off the $His_6$-MBP tag, the protein-containing eluate was incubated with TEV protease at 4° C. overnight while dialyzing into ion exchange buffer (50 mM Tris-Cl pH 7.0, 250 mM KCl, 5% glycerol, 1 mM TCEP). Cleaved protein was loaded onto a HiTrap SP column (GE Healthcare) and eluted over a linear KCl (0.25-1.5M) gradient. Cas13a containing fractions were pooled, concentrated, and further purified via size-exclusion chromatography on a S200 column (GE Healthcare) in gel filtration buffer (20 mM Tris-Cl pH 7.0, 200 mM KCl, 5% glycerol, 1 mM TCEP) and were subsequently stored at −80° C. All homologs were purified using this protocol except LwaCas13a which was bound to a HiTrap Heparin column instead of a SP column, and the size-exclusion chromatography step was omitted due to sufficient purity of the sample post ion-exchange. All expression plasmids are deposited with Addgene.

In-vitro RNA transcription. All pre-crRNAs, mature crRNAs, and targets were transcribed in vitro using previously described methods (Sternberg et al., RNA. 2012 April; 18(4):661-72) and as described in the above Examples. Briefly, all substrates were transcribed off a single-stranded DNA oligonucleotide template (IDT), except for mature crRNAs requiring a non-GR 5' terminus. For these mature crRNAs, T7 polymerase templates containing a Hammerhead Ribozyme sequence immediately upstream of the mature crRNA sequence were generated using overlap PCR, and then purified for use as the template for T7 transcription (see FIG. 50 (Table 5) for sequences). Lbu six-mer CRISPR array in vitro transcription template was synthesized by GeneArt (Thermofisher) as a plasmid. The T7 promoter-CRISPR array region was PCR amplified and purified prior to use as the template for T7 transcription. All transcribed RNAs were purified using 15% Urea-PAGE, except for the array which was purified using 6% Urea-PAGE. All RNAs were subsequently treated with calf alkaline phosphatase to remove 5' phosphates. Radiolabeling was performed as previously described (Sternberg et al., RNA. 2012 April; 18(4):661-72), and as described in the above Examples. A, C, G and U homopolymers, and fluorescently-labeled RNA reporters for trans—ssRNA cleavage were synthesized by IDT. Homopolymers were purified using 25% Urea-PAGE after radiolabeling to reduce substrate heterogeneity.

Radiolabeled ssRNA nuclease assays. pre-crRNA processing assays were performed at 37° C. in RNA processing buffer (20 mM HEPES-Na pH 6.8, 50 mM KCl, 5 mM $MgCl_2$, 10 pg/mL BSA, 10 pg/mL tRNA, 0.05% Igepal CA-630 and 5% glycerol) with a 100-fold molar excess of Cas13a relative to 5'-labeled pre-crRNA (final concentrations of 100 nM and <1 nM, respectively). Unless otherwise indicated, reactions were quenched after 60 min with 1.5× RNA loading dye (100% formamide, 0.025% bromophenol blue, and 200 μg $mL^{-1}$ heparin). After quenching, reactions were denatured at 95° C. for 5 min prior to resolving by 15% denaturing PAGE (0.5×TBE buffer). Target cleavages assays were performed at 37° C. in cleavage buffer (20 mM HEPES-Na pH 6.8, 50 mM KCl, 5 mM $MgCl_2$, and 5% glycerol). Generally, Cas13a:crRNA complex formation was performed in cleavage buffer, at a molar ratio of 2:1 protein to crRNA at 37° C. for 60 min, prior to adding 5'-labeled target and/or other non-radiolabeled RNA target substrates. Unless otherwise indicated, final concentrations were 100 nM Cas13a, 50 nM crRNA or pre-crRNA, 50 nM crRNA-complementary target ssRNA (henceforth referred to as 'activator') and <1 nM trans-ssRNA target. All bands were visualized by phosphorimaging (Typhoon, GE Healthcare) and quantified with ImageQuant (GE Healthcare). For pre-crRNA processing, the percent cleavage was determined as the ratio of the product band intensity to the total intensity of both the product and uncleaved pre-crRNA bands and normalized for background within each measured substrate. For trans-ssRNA cleavage reactions, the percentage cleavage was determined as the ratio of all fragments smaller than the target to the total intensity within the lane and normalized for background within each substrate. These data were subsequently fit to a single-exponential decay using Prism7 (GraphPad) and cleavage rates are reported in figure legends.

Fluorescent ssRNA nuclease assays. Cas13a:crRNA complexes were assembled in cleavage buffer, as described above. 150 nM of RNase Alert reporter (IDT) and various final concentrations (0-1 μM) of ssRNA-activator were added to initiate the reaction. Notably these reactions are in the absence of competitor tRNA or total RNA, to more accurately measure trans-cleavage activity. These reactions were incubated in a fluorescence plate reader (Tecan Infinite Pro F2000) for up to 120 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA activator. For determining homolog sensitivities and array processing effects, background corrected values were fit to a single-exponential decay using Prism7 (GraphPad) and the calculated rates were plotted with their associated standard deviations from n=3. For comparing non-cognate crRNA directed trans-ssRNA cleavage, initial reaction rates were instead calculated due to discrepancies in fluorescence plateau values across the dataset. Rates were then scaled relative to the cognate crRNA to normalize rates across the homologs. See FIG. 52, FIG. 53, and FIG. 54, presenting Tables 7, 8, and 9, respectively, for normalized values. For fluorescent homopolymer ssRNA reporter studies, Cas13a: crRNA complexes were pre-incubated at 37° C. for 60 mins using standard conditions. Activator ssRNA and 200 nM fluorescent ssRNA reporter were added to initiate the reaction immediately before placing reaction in plate reader. For Lbu- and Lba-Cas13a containing samples with fluorescent homopolymer ssRNA reporters, 10 pM and 1 nM activator was used, respectively. For pre-crRNA array experiments, 300 nM Cas13a was first incubated with 50 nM pre-crRNA array for 1 hr in cleavage buffer to enable binding and processing of the array. 100 pM of each ssRNA activator was added along with 150 nM of RNase Alert reporter (IDT) to initiate the reaction, in biological triplicate for each spacer sequence. Apparent rates were calculated using one single-exponential decay using Prism7 (GraphPad) and calculated rates are plotted with their associated standard deviations.

crRNA filter-binding assays. Filter binding assays was carried out as described in the Examples above. Briefly, Cas13a and radiolabeled crRNA were incubated for 1 hr at 37° C. in RNA processing buffer (20 mM HEPES-Na pH 6.8, 50 mM KCl, 5 mM $MgCl_2$, 10 μg/mL BSA, 10 μg/mL yeast tRNA, 0.01% Igepal CA-630 and 5% glycerol). Tufryn, Protran and Hybond-N+ were assembled onto a dot-blot apparatus in the order listed above. The membranes were washed twice with 50 μL Equilibration Buffer (20 mM HEPES-Na pH 6.8, 50 mM KCl, 5 mM $MgCl_2$ and 5% glycerol) before the sample was applied to the membranes. Membranes were again washed with 50 μL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the Figure legends.

Results

Most Cas13a Homologs Possess Pre-crRNA Processing Activity

Figure 38A:
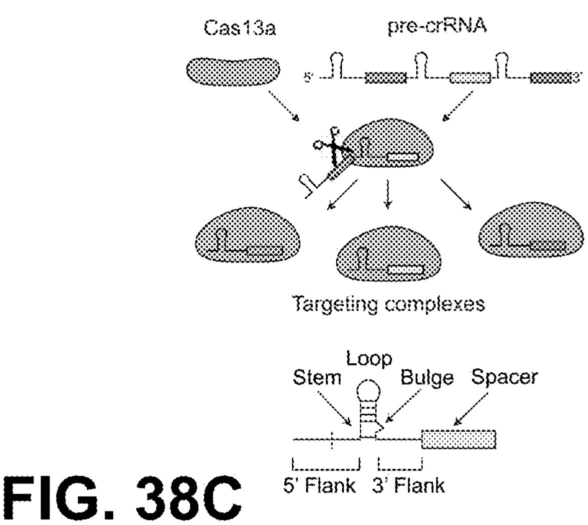
FIG. 38A-38C depict conservation of pre-crRNA processing within the Cas13a family.
Figure 38B:
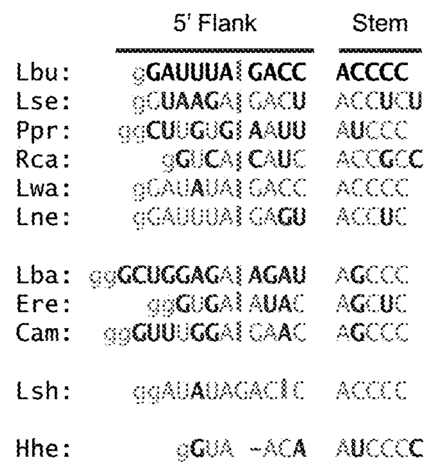
Figure 38C:
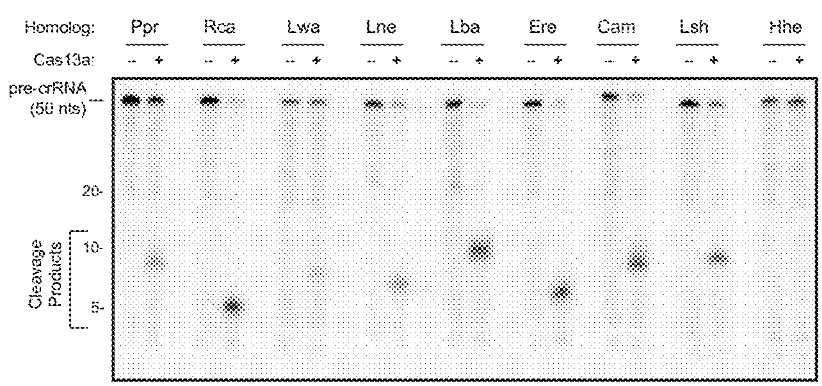

To explore the functional diversity of Cas13a proteins, the pre-crRNA processing activities of ten homologs from across the protein family tree were compared for their capacity to produce mature crRNAs from cognate pre-crRNAs (FIG. 38A; FIG. 39). Similar to the three homologs discussed above, seven additional Cas13a enzymes possess crRNA maturation activity (FIGS. 38B and 38C). Only one of the eleven Cas13a proteins tested to date exhibited no detectable cleavage of its cognate pre-crRNA across a wide range of assay conditions (HheCas13a) (FIG. 38; FIG. 39A). Of the homologs that processed their native crRNAs, all but LshCas13a cleaved at the phosphodiester bond four nucleotides upstream of the conserved crRNA-repeat hairpin (FIGS. 38B and 38C). These results show strong conservation of Cas13a-mediated crRNA biogenesis activity within Type VI-A CRISPR systems.

A Conserved crRNA Maturation Center within Most Cas13a Enzymes

Figure 40A:
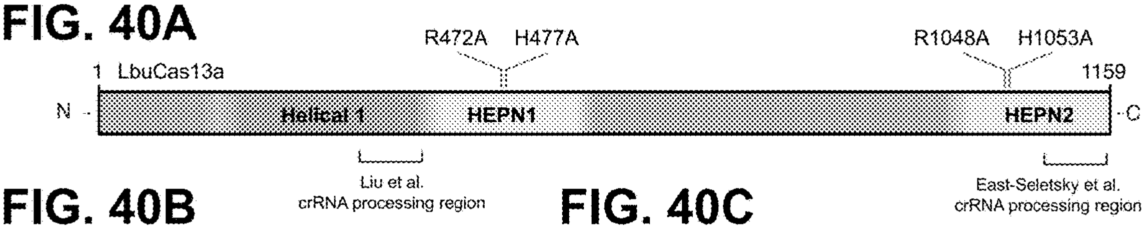

Previous studies have implicated two distinct regions of Cas13a as responsible for pre-crRNA processing. The general Cas13a protein architecture established by the LshCas13a crystal structure consists of an N-terminal domain and two HEPN (higher eukaryotes and prokaryotes nucleotide-binding) domains separated by two helical domains (FIG. 40A) (Liu et al., *Cell* 2017 Jan. 12; 168(1-2):121-134.e12). For LbuCas13a, mutation of a single residue (R1079) within the HEPN2 domain was sufficient to substantially reduce pre-crRNA processing activity. By contrast, mutations at two positions located in the helical 1 domain, R438 and K441, were shown to diminish pre-crRNA cleavage by LshCas13a (Liu et al., *Cell* 2017 Jan. 12; 168(1-2):121-134.e12). While both of these regions may be involved in pre-crRNA processing, it is unclear whether processing by LbuCas13a is inhibited by helical 1 domain mutations, and which domain is primarily responsible for crRNA maturation across the Cas13a protein family.

Figure 40B:
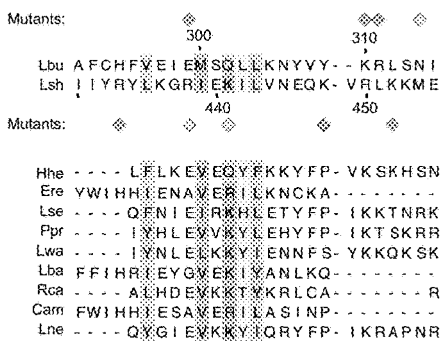
Figure 40C:
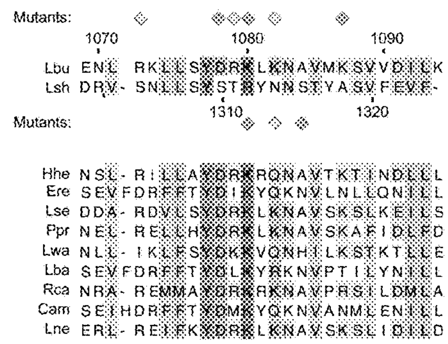

Conservation of both the helical 1 and HEPN2 domains across 19 Cas13a homologs was examined. Previously reported alignments (Liu et al., *Cell* 2017 Jan. 12; 168(1-2):121-134.e12; Shmakov et al., *Mol Cell.* 2015 Nov. 5; 60(3):385-97) conflict in the helical 1 domain region, suggesting high ambiguity in the relationship between homologs in this domain. Minimal conservation within the alignment of the helical 1 domain implicated in pre-crRNA processing was observed; in contrast, consistent conservation is present within the HEPN2 domain (FIG. 40B-40C; FIG. 41). The only pre-crRNA processing-defective homolog, HheCas13a, maintains a majority of the conserved charged residues throughout both domains, suggesting that other parts of the protein or the repeat sequence may be preventing pre-crRNA cleavage. Among the homologs used in this study, LshCas13a is the most divergent across the HEPN2 domain, potentially explaining the alternative catalytic domain and atypical cleavage site selection by this homolog.

Figure 40D:
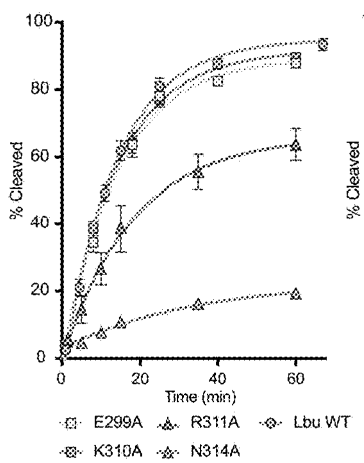
Figure 40E:
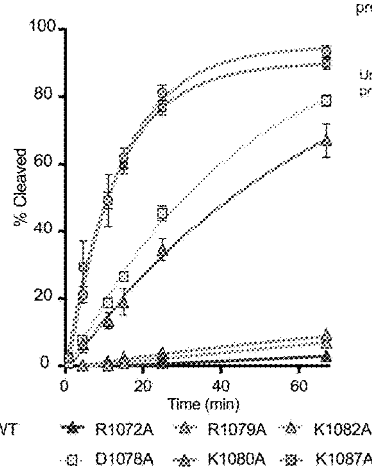

The effect of the helical 1 domain residues critical for LshCas13a pre-crRNA processing on LbuCas13a's pre-crRNA processing activity was tested. Four residues (E299, K310, R311 and N314) were tested for their role in pre-crRNA cleavage (FIGS. 40B and 40C) (Liu et al., *Cell* 2017 Jan. 12; 168(1-2):121-134.e12; Shmakov et al., *Mol Cell.* 2015 Nov. 5; 60(3):385-97). Mutation of these residues to alanine revealed a range of impacts on pre-crRNA processing efficiencies: N314A significantly reduced the cleavage rate, R311A minimally impaired activity, and E299A and K310 had no effect on pre-crRNA processing (FIG. 40D). In parallel, mutagenesis within the HEPN2 domain of LbuCas13a was performed. Alanine substitutions at R1072 and K1082 significantly reduced pre-crRNA cleavage, while other mutations in the same region (D1078A, K1080A and K1087A) had minimal impacts on pre-crRNA processing (FIG. 40E). These results suggest that the HEPN2 and to a lesser extent the helical 1 domains play significant roles in crRNA biogenesis for LbuCas13a, although the residues directly responsible for catalyzing hydrolysis remain unknown. The difference between the regions implicated in pre-crRNA processing across LbuCas13a and LshCas13a (Liu et al., *Cell* 2017 Jan. 12; 168(1-2):121-134.e12) do not necessarily contradict each other, as the 5' terminus of the crRNA is held between HEPN2 and helical 1 domains in the LshCas13a structure (Liu et al., *Cell* 2017 Jan. 12; 168(1-2):121-134.e12). Residues from both domains might play pivotal roles in pre-crRNA processing by either stabilizing substrate binding, promoting proper substrate orientation and/or catalyzing hydrolysis.

Figure 40F:
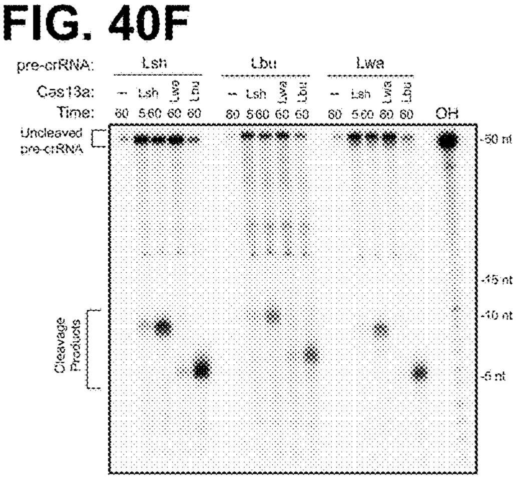

The lack of conservation within the HEPN2 domain of LshCas13a, its putative pre-crRNA processing active site, and this enzyme's atypical pre-crRNA cleavage site led us to hypothesize that LshCas13a may utilize a different region within the helical 1 domain to catalyze pre-crRNA processing. In the absence of a three-dimensional structure of a pre-crRNA-bound Cas13a homolog, this hypothesis was tested by mapping the LshCas13a cleavage sites on non-cognate pre-crRNAs (FIG. 40F). LshCas13a was able to process pre-crRNAs from LwaCas13a and LbuCas13a, generating a shifted cleavage site one nucleotide from the predicted hairpin base. In concordance with this observation, processing of the Lsh pre-crRNA by LwaCas13a and LbuCas13a occurs at the standard four-nucleotide interval from the repeat stem, differing from the cognate LshCas13a site. This supports the observations that the distinct LshCas13a processing site depends on the protein architecture, not the pre-crRNA sequence, and that LshCas13a is an outlier within the Cas13a tree with regard to pre-crRNA processing.

Cas13a Enzymes Initiate ssRNA Cleavage at Either Uridines or Adenosines

Figure 43A:
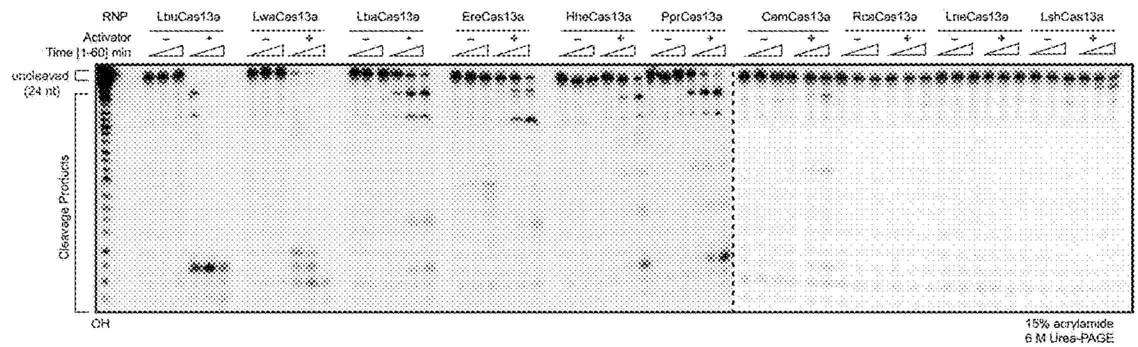
FIG. 43A-43D depict trans-ssRNA cleavage by Cas13a homologs.
Figure 43B:
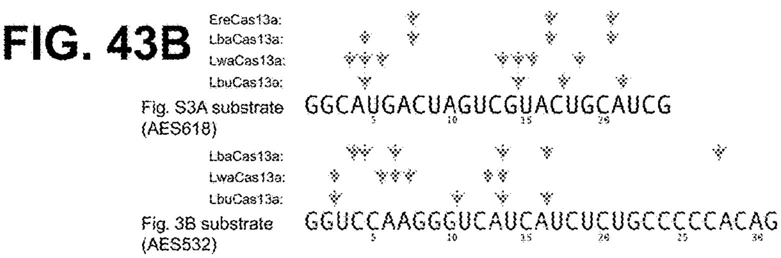

Previous studies established that Cas13a:crRNA complexes recognize and bind complementary ssRNA targets, hereby referred to as ssRNA activators, to trigger general RNase activity at exposed uridine residues (FIG. 42A). Whether the panel of homologs retained the non-specific degradation activity demonstrated by LbuCas13a and LshCas13a was tested. It was also tested whether the uridine preference within the HEPN active site is universal within the family. To systematically test general RNase activity, the ability of a ternary complex comprising Cas13a:crRNA with a bound ssRNA activator to degrade a trans-ssRNA target was monitored (FIG. 42A). Trans-ssRNA cleavage activity was detected for eight of the ten homologs over the course of one hour (FIG. 42B; FIG. 43A). Most notable of the Cas13a homologs active for trans-ssRNA cleavage is HheCas13a, which possesses no detectable pre-crRNA processing activity, yet catalyzed complete degradation of substrates guided by its cognate full-length pre-crRNA. While the previously characterized homologs LshCas13a (Abudayyeh et al., *Science.* 2016 Aug. 5; 353(6299):aaf5573) and LbuCas13a both exhibit a preference for uridine 5' to the scissile bond, products of different lengths generated by the other homologs suggests that different active site nucleotide preferences may exist within this protein family (FIG. 43B).

Figure 43C:
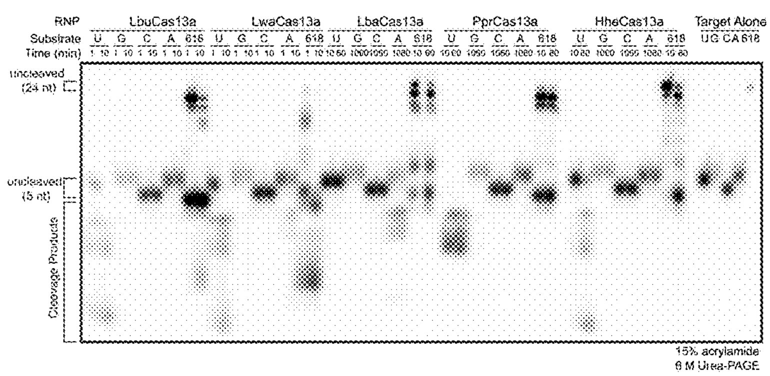
Figure 43D:
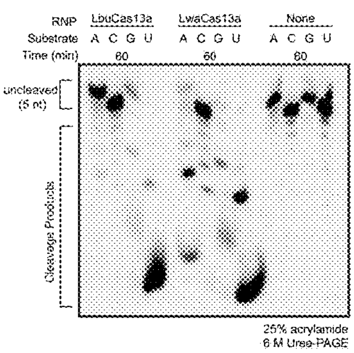

To further probe the trans-ssRNA cleavage nucleotide preferences of the Cas13a homologs, the trans-cleavage capacity of these enzymes was measured using 5-mer homopolymers of A, C, G, and U as substrates. Six homologs were able to cleave these short substrates (FIG. 42C; FIG. 43C; FIG. 50 (Table 5)). Four of the homologs, LbuCas13a, LwaCas13a, HheCas13a, and PprCas13a, exhibited preferred cleavage of the homouridine substrate, although secondary preferences were observed for the homologs with the highest activities (FIG. 42C; FIG. 43D). In contrast, LbaCas13a and EreCas13a preferred homoadenosine, in agreement with biochemically mapped cleavage sites on longer targets (FIG. 43B). Identical product generation from these long substrates by CamCas13a is consistent with adenosine preference by this clade of the Cas13a family tree (FIG. 42, FIG. 39; FIG. 43).

One notable difference between these enzymes was the rate at which trans-ssRNA cleavage reaches saturation under the tested conditions of equimolar ssRNA activator and Cas13a:crRNA interference complex. These enzymatic differences could have dramatic effects on Cas13a's biological role. The variance in trans-ssRNA cleavage within the Cas13a homolog family was quantified. A high-throughput screen utilizing a short fluorescent ssRNA reporter for RNA cleavage to account for both ssRNA activator binding and trans-ssRNA cleavage, the two core properties of Cas13a enzymes that contribute to total enzymatic output, was developed. To interrogate the sensitivity of each Cas13a homolog, decreasing amounts of complementary ssRNA activator were added to initiate the reaction, and the apparent rate of fluorescent ssRNA reporter cleavage was calculated from each of the resulting timecourses. While the calculated rates are a convolution of the ssRNA activator binding affinity and the catalytic turnover rate for each of the enzymes, they give a relative measure of cleavage activity that is comparable across homologs.

Five homologs (LbuCas13a, LwaCas13a, LbaCas13a, HheCas13a and PprCas13a) demonstrated sufficiently detectable cleavage activity within this assay for reproducible analysis. Of these five homologs, LbuCas13a exhibited the most sensitivity, with detectable reporter cleavage in the presence of only 10 fM complementary activator (FIG. 42D). Only two homologs, LwaCas13a and PprCas13a, displayed enough activity to detect the activator in the picomolar range with sensitivities of 10 pM and 100 pM, respectively. LbaCas13a and HheCas13a were much less sensitive, only becoming active at nanomolar levels of reporter, which is close to equimolar relative to the Cas13a complex. Since this assay relies on a substantial number of trans-cleavage events to produce detectable fluorescence, it can be assumed that the three homologs unable to produce detectable signal above background despite similar cleavage site preferences (EreCas13a, CamCas13a, and LshCas13a) possess even less sensitive complementary target sensitivities. The remarkably broad range in sensitivities (~$10^7$-fold) suggests a diverse capacity of Cas13a enzymes to protect a host organism from foreign RNA.

CRISPR Repeat Sequence Determines Non-Cognate Pre-crRNA Processing

The dual activities of Cas13a provide an opportunity to study the interdependence of pre-crRNA processing and targeting between distinct Type VI-A CRISPR operons. To determine the substrate requirements for both activities, the extent to which different homologs can recognize non-cognate crRNAs for guide processing and targeting was tested. Initially, it was attempted to predict bioinformatically the likely crRNA exchangeability through phylogenetic analysis of the Cas13a family and crRNA similarities. This analysis suggested that two distinct clades of homologs exist, termed alpha and beta for clarity (Stamatakis, *Bioinformatics.* 2014 May 1; 30(9):1312-3) (FIG. 44A). Five of the purified homologs exist outside of these clades with ambiguous ancestral relationships; it was questioned if the pre-crRNA (CRISPR repeat) sequence might dictate functional orthogonality. Due to the short and structured content of the CRISPR repeats, a pairwise sequence alignment score matrix was used to build a hierarchical clustering relationship between the CRISPR repeats to score the variation across the family (Burstein et al., *Nat Commun.* 2016 Feb. 3; 7:10613). Surprisingly, this analysis pointed to the existence of two crRNA clusters, overlapping but distinct from the protein clades determined by the amino acid sequences (FIGS. 44B and 44C). While cluster 1 crRNAs correlate well with a subset of the alpha-clade proteins and all the beta-clade associated crRNAs are within cluster 2, the homologs with ambiguous phylogenetic relationships are split across the two clusters (FIG. 44C).

Unable to easily predict Cas13a:crRNA orthogonality using bioinformatic analysis alone, the extent of functional exchangeability between non-cognate crRNAs for both processing and trans-ssRNA target cleavage by each of the Cas13a homologs was tested (FIGS. 44D and 44F). For pre-crRNA processing, it was found that the crRNA clusters defined by the pairwise sequence comparisons predicted their ability to be processed by their associated Cas13a proteins (FIG. 44D). For example, pre-crRNAs from cluster 1 are only processed by the proteins of clade alpha and vice versa for cluster 2 and clade beta. In contrast, the protein classification is less predictive, as most of the ambiguously classified proteins could process sequences from repeat cluster 2, independent of where their repeat sequences were clustered.

Three homologs (PprCas13a, HheCas13a, and Rca13a) were pre-crRNA processing outliers with respect to their position within the crRNA clusters. HheCas13a was unable to cleave any non-cognate pre-crRNAs, and conversely, no homolog, including HheCas13a, processed the Hhe pre-crRNA. This suggests that the inability of HheCas13a to process its cognate pre-crRNA reflects not just the divergent repeat sequence (FIG. 38; FIG. 39), but also the loss of pre-crRNA processing activity within the protein. In contrast, the deviating activity of PprCas13a and RcaCas13a is explained by crRNA repeat sequence divergence. PprCas13a and RcaCas13a process their own crRNAs, yet both also process the crRNA repeat cluster 2 non-cognate sequences. The PprCas13a crRNA repeat sequence differs from the other cluster 2 crRNA repeats across the 5' flanking region cleavage site, suggesting greater substrate flexibility for pre-crRNA processing by PprCas13a. Similarly, a distinguishing sequence feature of the RcaCas13a crRNA is an extended six-base pair stem-loop relative to the standard five-base pair stem-loop present in crRNAs of the rest of the family. It is worth noting that the positional substitution tolerance within each crRNA repeat for Cas13a pre-crRNA processing is consistent with mutation studies of the LbuCas13a:crRNA complex, discussed above, and recent structural insights obtained of the LshCas13a:crRNA complex (Liu et al., *Cell* 2017 Jan. 12; 168(1-2):121-134.e12). Overall, these results suggest that the sequence of a Type VI-A CRISPR repeat dictates its capacity for pre-crRNA processing by the Cas13a family. However, homologs that evolved in the presence of divergent repeats (PprCas13a and RcaCas13a) retain the capacity to process other cluster 2 sequences.

Two Subfamilies of Functionally Orthogonal Cas13a Enzymes

Whether the pre-crRNA processing exchangeability clusters defined in FIG. 44D were competent for directing trans-ssRNA cleavage by non-cognate Cas13a homologs was investigated. To study Cas13a-mediated trans-ssRNA cleavage directed by non-cognate pre-crRNAs and mature crRNAs, the described fluorescence assay described in the above Examples was modified, and the analysis was limited to the five homologs that exhibited significant cleavage activity in the ssRNA-cleavage experiments (see FIG. 42C). Broadly, these results mirrored the pre-crRNA processing results, with the crRNA repeat cluster identity determining functional groups, but with some striking contrasts consistent with processing and targeting being independent enzymatic activities (FIGS. 44E and 44F). For instance, the Ppr pre- and mature crRNA can direct ssRNA cleavage by non-cognate proteins LwaCas13a and LbuCas13a, despite their inability to process these pre-crRNAs. Another surprise is the promiscuity of HheCas13a, which is directed by all cluster 2 pre- and mature crRNAs for trans-ssRNA cleavage, despite lacking pre-crRNA processing activity with any of these guides. This suggests that crRNA maturation is not required for trans-ssRNA cleavage, an observation in agreement with findings that LbuCas13a pre-crRNA processing-deficient mutants possess unaffected trans-ssRNA cleavage capacity.

Figure 45A:
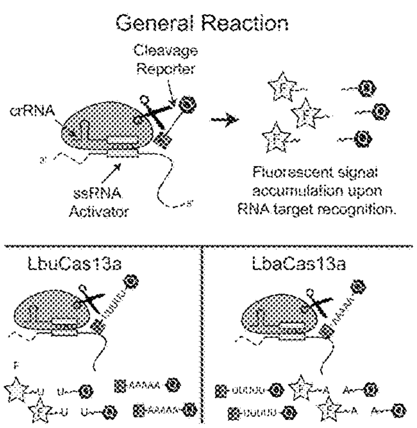
FIG. 45A-45C depict functional validation of orthogonal Cas13a subfamilies for RNA detection.
Figure 45B:
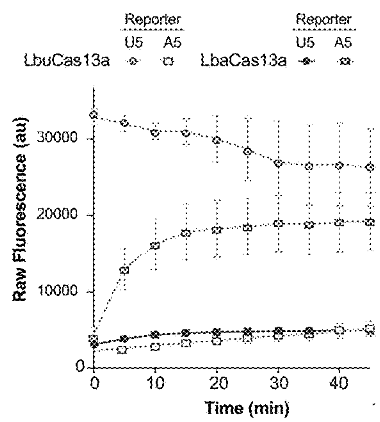
Figure 45C:
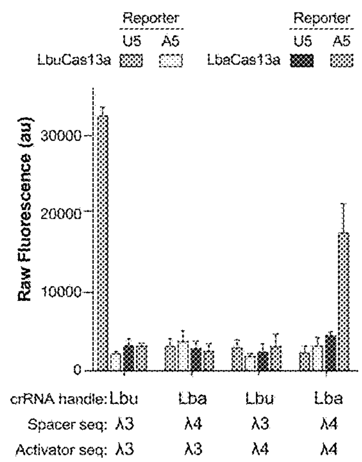

Comparison of crRNA exchangeability for both pre-crRNA processing and trans-ssRNA cleavage defines two functionally orthogonal subfamilies within the Cas13a protein family. The first group (e.g., LbuCas13a) has wide promiscuity for both pre-crRNA processing and trans-ssRNA cleavage directed by crRNAs from across the protein family. This polyphyletic group also shows a preference for uridine within the trans-ssRNA cleavage active site. The second group (e.g., LbaCas13a), defined both by crRNA and protein sequences, has a distinct crRNA exchangeability profile and preferentially cleaves at adenosines during trans-ssRNA target cleavage. To test orthogonal reactivities of these Cas13a subfamilies, it was verified that LbuCas13a and LbaCas13a cleaved homo-A or homo-U ssRNA reporters, respectively (FIGS. 45A and 45B). While the different probes generated similar amounts of fluorescent signal, it should be noted that substantially different quantities of ssRNA activator were added due the differential sensitivities of the homologs (10 pM vs 1 nM for LbuCas13a and LbaCas13a, respectively). To verify orthogonality, a panel of control reactions with all possible non-cognate combinations between crRNA, activator and reporter were tested, with no substantial signal detected except for the cognate combinations (FIG. 45C). Taken together, these results define distinct Cas13a homologs that can function in parallel within the same system.

Pre-crRNA Processing Enhances Targeting Efficiencies within the Context of a CRISPR Array One puzzling finding of this study is the lack of a stringent requirement for mature crRNA to trigger the subsequent trans-ssRNA target cleavage reaction by Cas13a. Additionally, processing deficient mutants of LbuCas13a maintain similar efficiencies of trans-ssRNA cleavage, even when directed by a pre-crRNA instead of a mature crRNA (FIG. 46; FIG. 47). This led to the hypothesis that the role of pre-crRNA processing within Type VI CRISPR loci is not necessarily for efficient ssRNA targeting but instead serves to liberate each crRNA from the confines of a long CRISPR array transcript. It was questioned whether pre-crRNA processing might relieve RNA folding constraints and potential steric hindrance of neighboring Cas13a:crRNA-spacer species during crRNA loading and/or ssRNA targeting. To test this, the efficiency of trans-ssRNA cleavage directed by a CRISPR array, using either wildtype LbuCas13a or a pre-crRNA processing-inactive mutant, was compared.

Figure 55A:
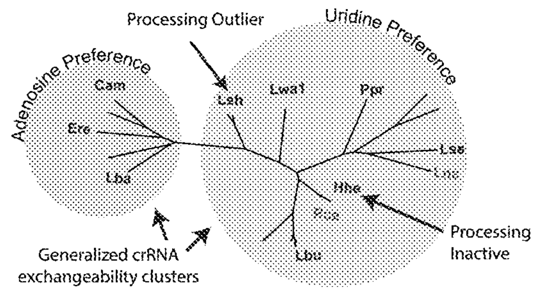
FIG. 55A-55B presents a model for Type VI-A CRISPR system function.
Figure 55B:
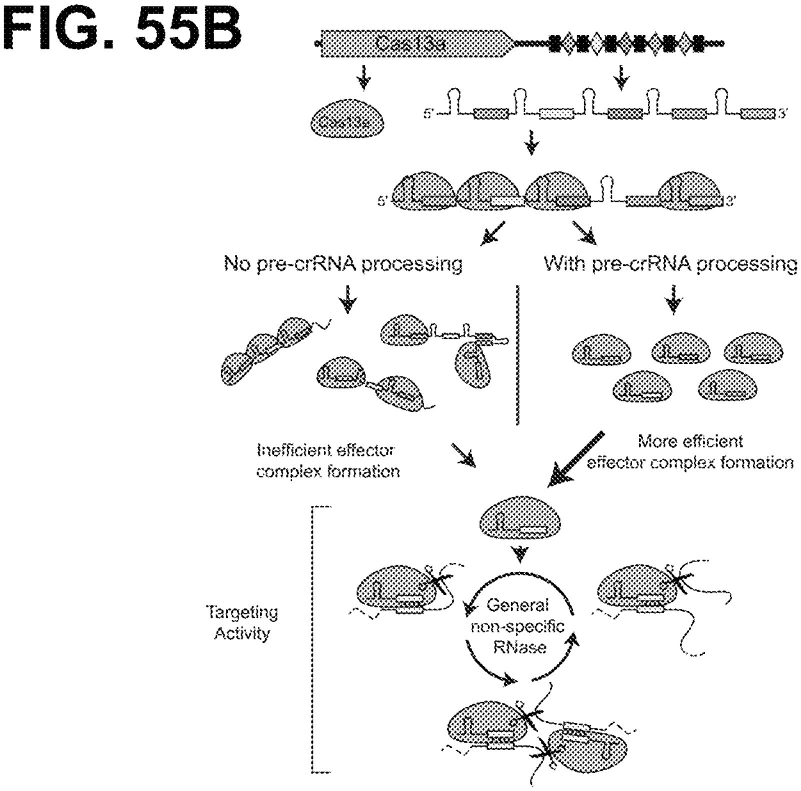
Figure 57B:
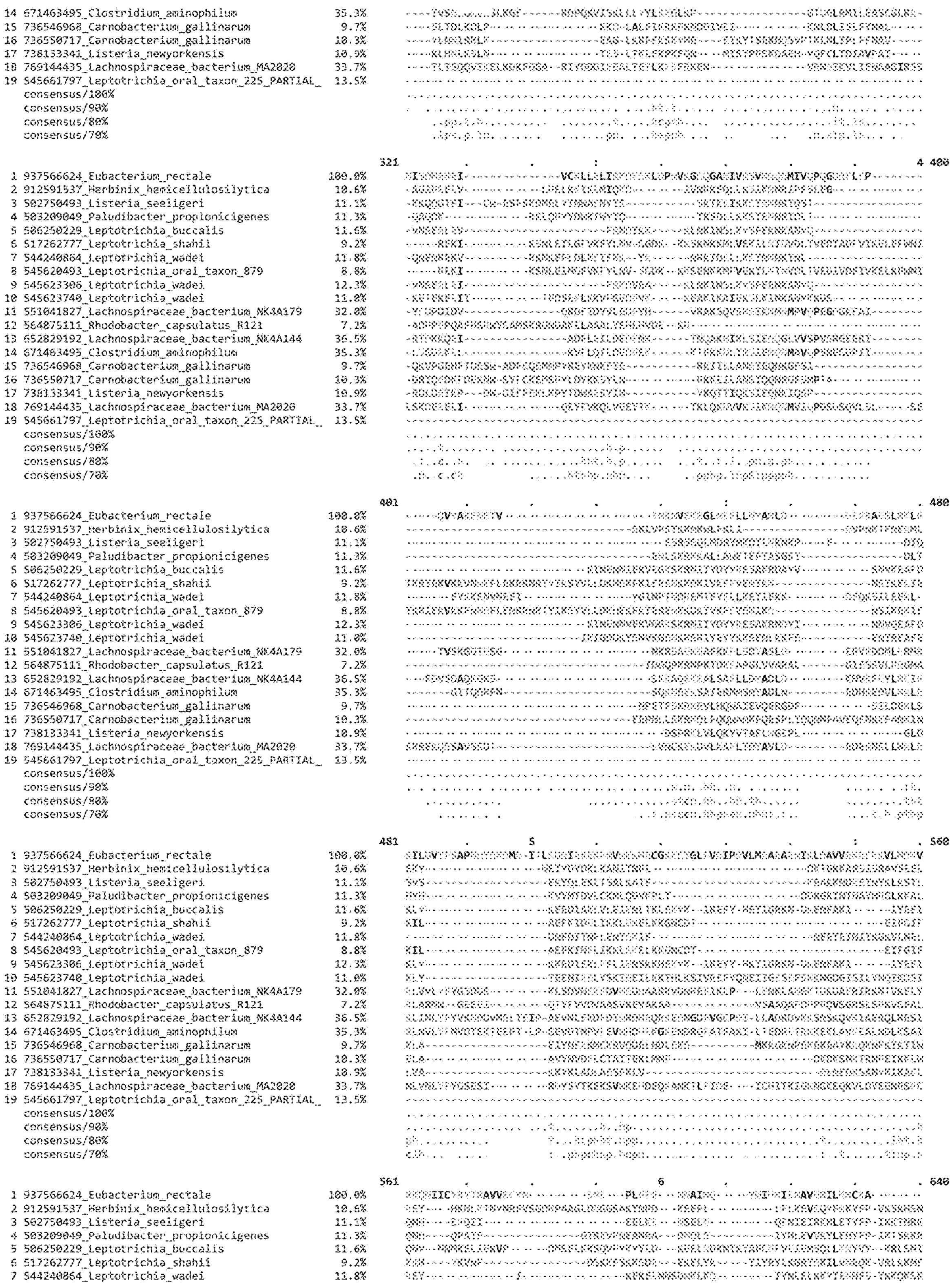
Figure 57D:
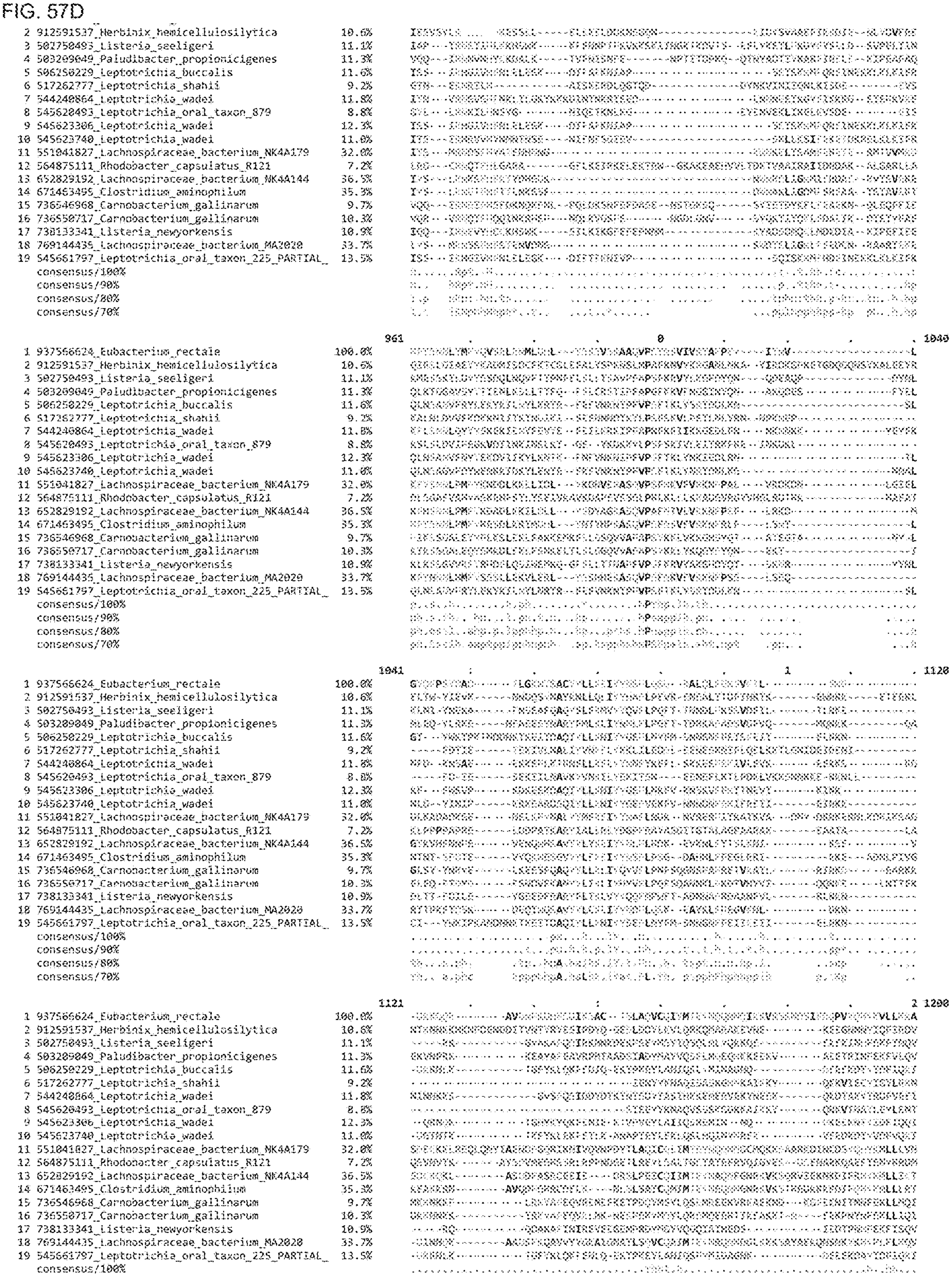
Figure 57F:
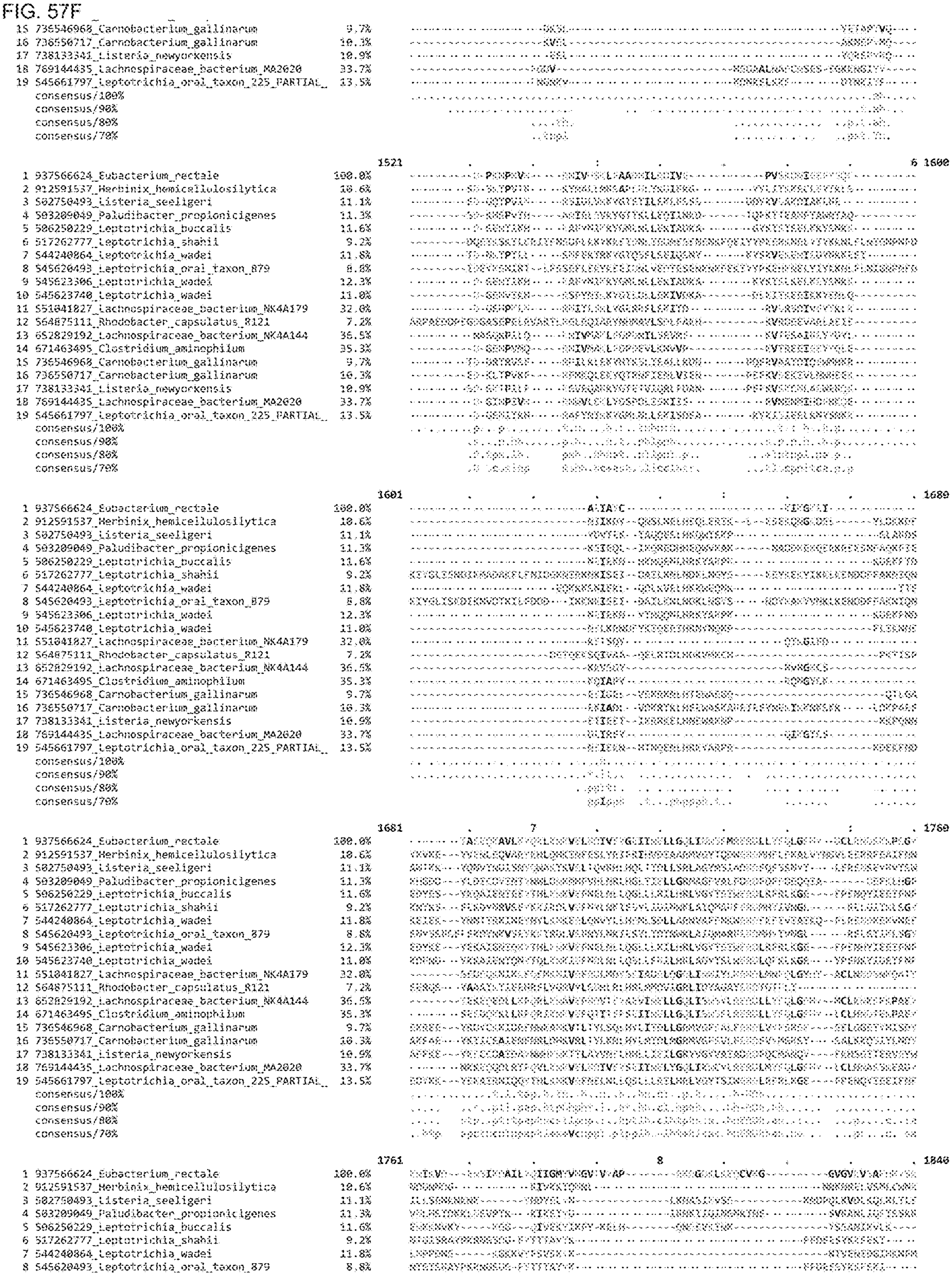
Figure 57G:
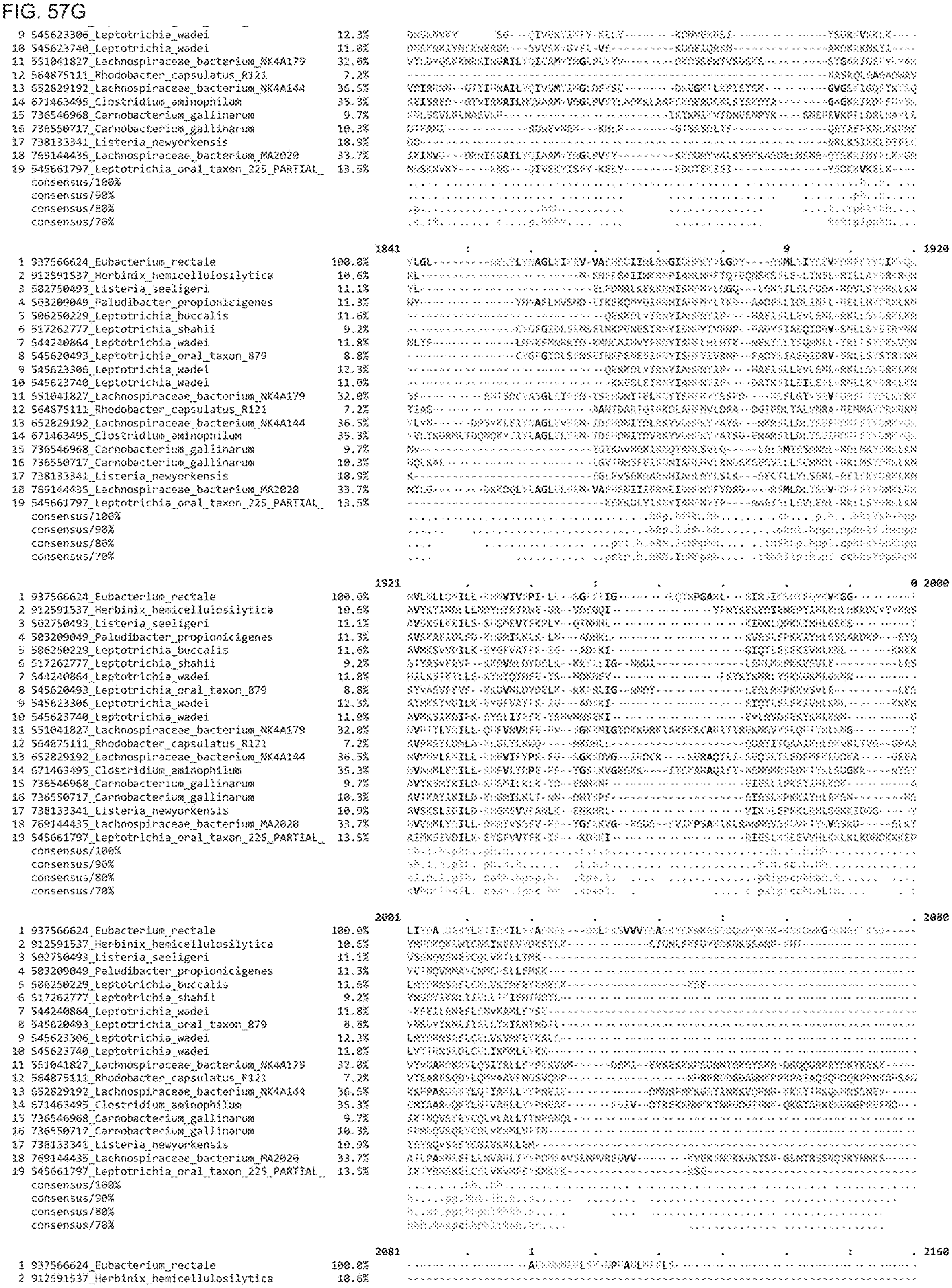

Since all processing-defective single point mutants of LbuCas13a (FIG. 40) retained low levels of pre-crRNA processing activity, a double mutant (R1079A/K1080A) was created that possessed no detectable processing activity, yet retained trans-ssRNA cleavage efficiencies similar to or greater than wildtype LbuCas13a (FIGS. 46A and 46B). This double mutant, and the wildtype LbuCas13a enzyme, were tested for ssRNA cleavage in the presence of a target RNA and a small CRISPR array transcript consisting of six distinct repeat-spacer units (FIGS. 46C and 46D). The rate of trans-ssRNA cleavage by the crRNA-processing inactive mutant was significantly reduced for all spacer sequences within the array (one-sided t-test: $p<0.001$ for all pairs). The reduced activity compared to wildtype LbuCas13a is more pronounced with each successive spacer within the array, with the last spacer directing cleavage with a rate that is only 15% of that catalyzed by the wildtype enzyme. This finding suggests that while pre-crRNA processing is not necessary for targeting, it enhances activity by liberating crRNAs from the CRISPR array, leading to a revised model for Type VI CRISPR systems (FIG. 55).

FIG. 38A-38C. Pre-crRNA processing is broadly conserved within the Cas13a protein family. (A) Schematic of crRNA biogenesis pathway catalyzed by Cas13a. pre-crRNA transcripts are cleaved by Cas13a to generate mature crRNAs. Below, a schematic of a pre-crRNA highlighting important functional features. (B) Alignment of the 5' portion of CRISPR repeat sequences from the studied type VI CRISPR systems highlighting the pre-crRNA cleavage site. Mapped cut cleavage sites are shown as red bars. Deviations from the Lbu crRNA-repeat sequence are noted in black text. Lowercase g's were required for transcription purposes and are not part of the native crRNA repeat sequences. Full CRISPR repeat sequence is diagrammed in FIG. 39B. (C) Representative gel of Cas13a-mediated pre-crRNA cleavage by 9 Cas13a homologs after 60 min incubation with 5'-radiolabelled pre-crRNA substrates.

FIG. 39A-39C. CRISPR loci and crRNA repeat architecture for Cas13a homologs used in this study (A) Maximum-likelihood phylogenetic tree of Cas13a proteins with diagrams of TypeVI-A loci adapted from (Shmakov et al., *Mol Cell.* 2015 Nov. 5; 60(3):385-97). Cas13a ORFs shown in teal. CRISPR arrays depicted as black boxes (repeats), yellow diamonds (spacers), and spacer array size for larger arrays noted above. ORFs of interest surrounding the loci are noted with the following abbreviations: T-Toxin, AT-antitoxin and TP-transposase. (B) Manual alignment of CRISPR repeat sequences from homologs used. pre-crRNA processing cleavage sites noted by red lines. Deviations from the Lbu crRNA-repeat sequence are noted in black text. Lowercase g's were required for transcription purposes and are not part of the native crRNA repeat sequences. Two separate Hhe crRNA sequences were tested, the first containing the native sequence and a second with four nucleotide extension to extend the atypically short native repeat. Neither crRNA repeat was cleaved by HheCas13a under any of the studied conditions. (C)pre-crRNA processing assay with HheCas13a on native crRNA repeat sequence across variable salt and pH conditions. No cleavage products were observed.

FIG. 40A-40F. Identification of residues important for pre-crRNA cleavage by LbuCas13a (A) LbuCas13a domain organization schematic with domains annotated based off a LshCas13a crystal structure (Liu et al., *Cell* 2017 Jan. 12; 168(1-2):121-134.e12). Multiple-sequence amino acid alignment of (B) the local region in Cas13a's helical 1 domain implicated in pre-crRNA processing by studies on LshCas13a, and (C) the region within in Cas13a's HEPN2 domain implicated in pre-crRNA processing by studies on LbuCas13a. See FIG. 41 for full family tree alignment of these regions and FIG. 57 for a complete protein alignment. Residues whose mutation severely affects pre-crRNA processing are marked by yellow diamonds, and residues whose mutation minimally affect pre-crRNA processing marked with teal diamonds. Symbols above the LbuCas13a sequences correspond to mutations made to LbuCas13a, and symbols below the LshCas13a sequence correspond to mutations made to LshCas13a by Liu et al., *Cell* 2017 Jan. 12; 168(1-2):121-134.e12. Coloration of the matrix alignment denotes residue conservation using the ClustalX scheme, with darker hues indicating the strength of the conservation. pre-crRNA processing under single turnover conditions measured for mutants in (D) the helical 1 domain, and (E) the HEPN2 domain. Quantified data were fitted with single-exponential decays with calculated pseudo-first-order rates constants (kobs) (mean±s.d., n=3) as follows: Lbu WT 0.074±0.003 min-1, E299A 0.071±0.005 min-1, K310A 0.071±0.003 min-1, R311A 0.054±0.007 min-1, N314A 0.029±0.008 min-1, R1079A 0.009±0.007 min-1, D1078A 0.023±0.002 min-1, K1080A 0.016±0.004 min-1, and K1087A 0.076±0.007 min-1, while R1072A and K1082A could not be fitted. (F) Representative gel of pre-crRNA processing of LshCas13a, LwaCas13a, and LbuCas13a pre-crRNAs by LbuCas13a, LshCas13a and LwaCas13a proteins using standard conditions. Hydrolysis ladder in right-most lane allows for relative size comparisons, although subtle sequences differences across the three pre-crRNAs will alter the migration of these small fragments.

Figure 41A:
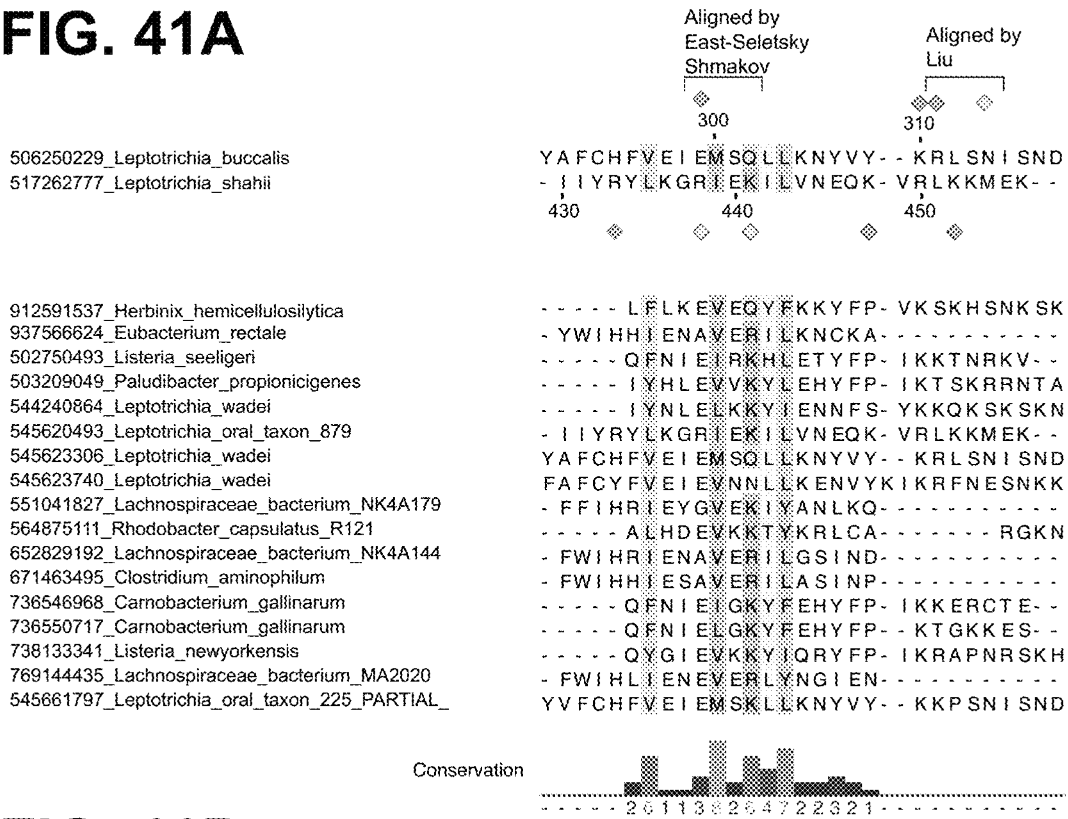
FIG. 41A-41B depict alignments of Helical 1 and HEPN domains of Cas13a family members. (Top to bottom: SEQ ID NOs: 195-232).
Figure 41B:
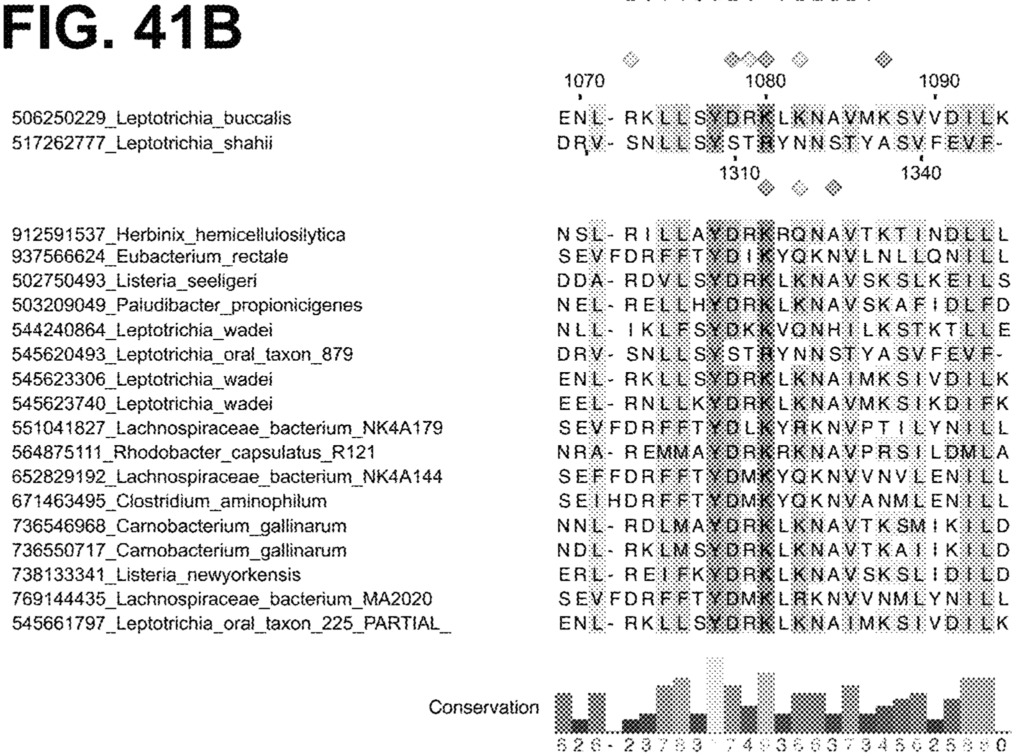

FIG. 41A-41B. Full Alignments of Helical 1 and HEPN Domains (A-B) Multiple sequence alignment of 19 Cas13a family members across (A) the helical 1 domain and (B) the HEPN2 domain. GI accession numbers are listed before each species name. Coordinates based on LbuCas13a sequence listed above the alignment and LshCas13a sequence coordinates are listed below. Mutations tested in this study are noted above the alignment by yellow and teal diamonds corresponding to alanine substitutions that negatively impacted the pre-crRNA processing reaction or those with minimal effects on pre-crRNA processing, respectively. Mutations tested by (Liu et al., *Cell* 2017 Jan. 12; 168(1-2):121-134.e12) are depicted below the LshCas13a sequence. Conservations scores were calculated by Jalview using the AMAS method.

FIG. 42A-42D. Members of the Cas13a protein family cleave ssRNA with a range of efficiencies (A) Schematic of ssRNA-targeting by Cas13a. For simplicity, trans-ssRNA cleavage was the focus of study. (B) Representative gel of Cas13a mediated trans-ssRNA cleavage by all ten homologs after 60 min incubation. Cas13a:crRNA complexes were formed as described in the methods using mature crRNA products with a final RNP complex concentration of 50 nM. <1 nM radiolabeled trans-ssRNA target was added to initiate reaction in the presence and absence of 50 nM unlabeled, crRNA-complementary ssRNA activator. Weak trans-ssRNA cleavage activity was observed by LshCas13a with product bands noted by double arrows to the right. (C) Heat map reporting Cas13a-catalyzed trans-ssRNA cleavage percentages for each 5-mer homopolymer ssRNA substrate, for six different Cas13a. Assay conditions were identical to part (B), except LbuCas13a and LwaCas13a which were incubated for 5 min instead of 60 min. (n=3, values with associated errors presented in FIG. 51 (Table 6). (D) Apparent cleavage rates of a fluorescent ssRNA reporter by five homologs across a range of ssRNA activator concentrations. Cas13a:crRNA complexes were pre-incubated at a 2:1 ratio respectively with a final active complex concentration of 50 nM. Complementary ssRNA activator and fluorescent ssRNA cleavage reporter were added to initiate reactions. Normalized reporter signal curves timecourses were fitted with single-exponential decays and the apparent rates are plotted (n=3). Some conditions plateaued before first measured time-point therefore their rates are minimally assumed to be 0.5 min-1 and are labeled with a * in the chart.

FIG. 43A-43D. trans-ssRNA cleavage by Cas13a homologs (A) Time course analysis trans-ssRNA cleavage by ten different Cas13a homlogs in the presence and absence of ssRNA activator. Time points were taken at 1, 10 and 60 min. ssRNA-activator specific cleavage products are noted for LbuCas13a, LwaCas13a, LbaCas13a, EreCas13a, HheCas13a, PprCas13a, CamCas13a, and LshCas13a. Dotted line denotes boundary between separate PAGE gels. (B) Mapped trans-ssRNA cleavage sites across multiple cleavage reactions for four Cas13a homologs. Different cleavage patterns are noted by red arrows. It appears LbaCas13a and EreCas13a may have a adenosine preference, while LwaCas13a appears to be more promiscuous with respect to nucleotide preference. (C-D) Representative trans-ssRNA cleavage gels of homopolymer ssRNA substrates by five Cas13a homologs.

FIG. 44A-44F. crRNA exchangeability within the Cas13a family (A) Maximum-likelihood phylogenetic tree of Cas13a proteins. Homologs used in this study are bolded and clades are highlighted. Bootstrapped values are located in FIG. 39. (B) Symmetrical similarity score matrix for CRISPR repeats from homologs used in this study. Rows and columns are ordered by CRISPR repeat clustering. (C) Asymmetrical similarity score matrix for CRISPR repeats from homologs used in this study. The same pairwise scores are presented here as in (B), except the rows are reordered to correspond to the Cas13a phylogenetic tree. (D-F) Functional activity matrix for (D) pre-crRNA processing by non-cognate proteins, (E) trans-ssRNA cleavage directed by pre-crRNAs, and (F) trans-ssRNA cleavage directed by mature crRNAs. Processing assays were performed using standard conditions and 60 min reaction endpoints were analyzed. trans-ssRNA cleavage assays were performed using the fluorescent ssRNA reporter assay with fitted initial rates. ssRNA activator concentrations were as follows: LbuCas13a:100 pM, LwaCas13a:100 pM, PprCas13a:100 nM, LbaCas13a:10 nM, and HheCas13a:100 nM. Initial rates were fit across three replicates to account for differences in fluorescence plateau values and normalized to each Cas13a:crRNA cognate pair. See FIGS. 52, 53, and 54 (Tables 7, 8, and 9, respectively) for numerical values and associated errors (n=3).

FIG. 45A-45C. Functional validation of orthogonal Cas13a subfamilies for RNA detection (A) Schematic of the RNA detection assay modified to use fluorescent homopolymer ssRNA reporter substrates to assay trans-ssRNA cleavage activation by either LbuCas13a or LbaCas13a. (B) Timecourse of raw fluorescence measurements generated by homopolymer reporters incubated with either LbuCas13a: Lbu-crRNA: 10 pM ssRNA activator or LbaCas13a: Lba-crRNA: 1 nM ssRNA activator (mean±s.d., n=3). (C) Raw fluorescence measurements generated by the fluorescent homopolymer ssRNA reporters across a panel of crRNA, ssRNA activator, and Cas13a protein combinations (mean±s.d., n=3).

FIG. 46A-46D. Deciphering the role of crRNA array processing for LbuCas13a (A) Quantified timecourse data of pre-crRNA processing assays for R1079A/K1080A mutant compared to wildtype LbuCas13a. Quantified data was fitted to single-exponential decays and pseudo-first-order rate constant (kobs) (mean±s.d., n=3) for LbuCas13a WT of 0.074±0.003 min-1, while the R1079A/K1080A mutant could not be fit with sufficient confidence to yield a rate constant. (B) Apparent rate of fluorescent reporter by LbuCas13a wildtype and R1079A/K1080A processing inactive mutant as directed by pre-crRNA and mature crRNAs. Cas13a:RNA complexes were pre-incubated for 60 min at a 1:1 ratio, and then 10 pM of activator and 150 nM reporter were added to initiate reaction. (mean±s.d., n=3) (C) Apparent rates of fluorescent ssRNA reporter cleavage by 300 nM wildtype LbuCas13a or R1079A/K1080A pre-crRNA processing inactive mutant as directed by 50 nM of a CRISPR array containing six crRNA repeat-spacers. Each bar group represents the addition of 100 pM of a distinct ssRNA activator sequence complementary to schematized positions within the CRISPR array indicated below each bar group. Each rate is fitted from data from three biological replicates and the standard deviation of the rate is depicted. Mutant protein rate is statistically different from the wildtype LbuCas13a for all spacer positions (one-sided t-test: p<0.001). (D) Data from (C) depicted as a percentage of wildtype LbuCAs13a activity demonstrating the positional effect of the decreased trans-ssRNA targeting efficiencies by the pre-crRNA processing inactive mutant.

Figure 47A:
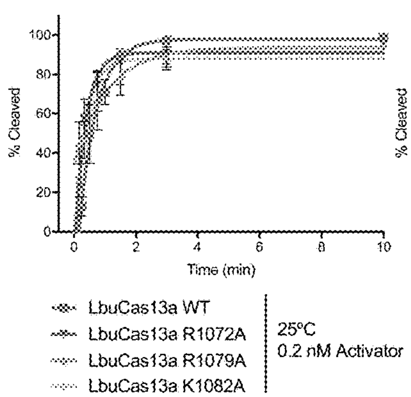
FIG. 47A-47C depict trans-cleavage by LbuCas13a point mutants in regions implicated in pre-crRNA processing.
Figure 47B:
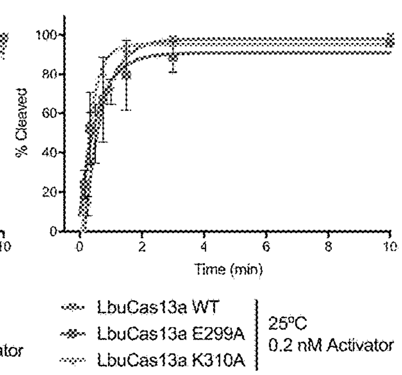
Figure 47C:
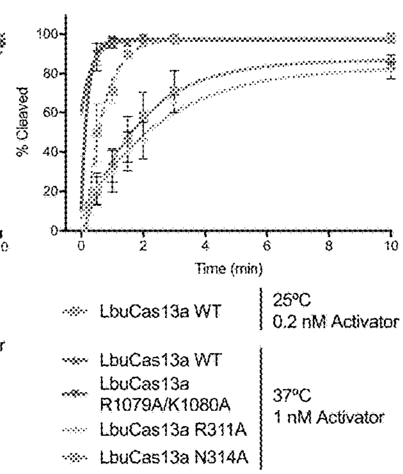

FIG. 47A-47C. trans-cleavage by LbuCas13a point mutants in regions implicated in pre-crRNA processing. (A-C) trans-ssRNA cleavage by various pre-crRNA processing 'implicated' point mutants of LbuCas13a. Cleavage reactions were performed with 50 nM Cas13a:crRNA at either 25° C. or 37° C. with 0.2 nM or 1 nM ssRNA activator as noted. Lower temperature and activator concentrations were used to slow down reaction kinetics for more accurate measurements. Fitted curves are single-exponential decays with calculated pseudo-first-order rates constants (mean±s.d., n=3) as follows: 25° C. conditions: Lbu WT 1.76±0.24 min-1, K299A 1.72±0.65 min-1, K310A 3.19±0.27 min-1, R1072A 2.95±0.53 min-1, R1079A 0.93±0.28 min-1, and K1082A 2.64±0.63 min-1 and 37° C. conditions: R311A 0.39±0.09 min-1, and N314A 0.54±0.11 min-1, while the wildtype and processing inactive mutant (R1079A/K1080A) plateaued too quickly for an accurate rate measurement: WT 2.95±1.97 min-1, and R1079A/K1080A 4.86±4.99 min-1.

Figure 48A:
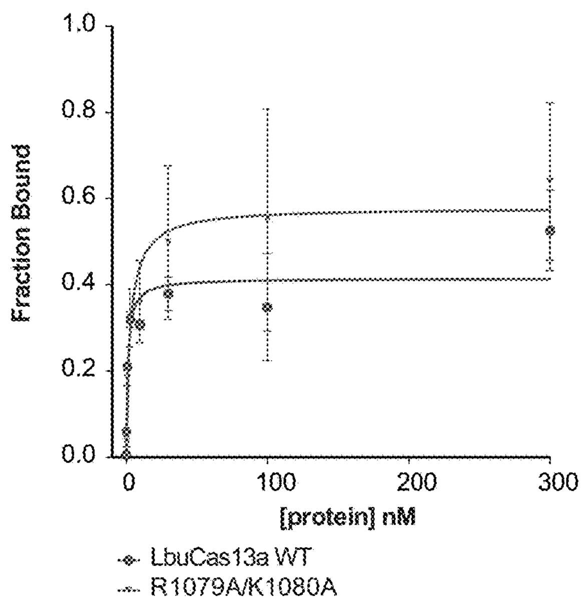
Figure 48B:
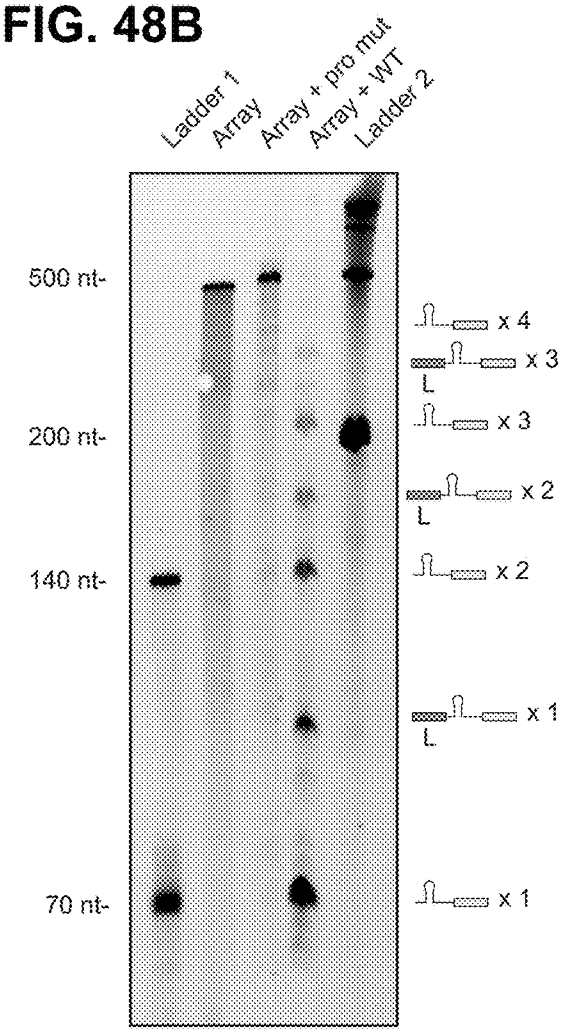

FIG. 48A-48B. crRNA processing inactive mutant R1079A/K1080A retains similar crRNA binding affinity and does not process a pre-cRNA array (A) Filter binding assays were conducted as described in the methods to determine the binding affinity of mature crRNA to LbuCas13a WT and LbuCas13a R1079A/K1080A. The quantified data were fit to standard binding isotherms. Measured dissociation constants from three independent experiments (mean±sd) were 1.21±0.57 nM (LbuCas13a WT), and 3.11±0.89 nM (LbuCas13a R1079A/K1080A). (B) pre-cRNA processing assay using a six-mer CRISPR array as the substrate with LbuCas13a and LbuCas13a R1079A/K1080A mutant along with various size markers. Product identities are depicted to the right of the gel. Due to an additional leader region that was occasionally not processed, additional sized products occasionally occurred as noted.

FIG. 49 (Table 4). CRISPR repeat consensus sequences: For homologs with multiple CRISPR loci within 10 kb of the Cas13a containing operon (RcaCas13a, LbaCas13a and EreCas13a), or long arrays with repeat variations (PprCas13a), multiple crRNA repeat sequences are listed with mutations highlighted in red text. For PprCas13a, the first crRNA repeat at the leader side of the array was chosen for this study. For RcaCas13a, LbaCas13a and EreCas13a, the crRNA repeat sequences analyzed for two factors to chose a representative crRNA for this study (1): the length of the array, and (2) capacity to direct trans-ssRNA cleavage by the cognate Cas13a protein. Sequences used in the main text are noted in the last column.

FIG. 50 (Table 5). *Oligo ID—an index number to maintain consistency for RNA substrates used in this study. **Source abbreviations: SS—single-stranded DNA oligonucleotide template was used for in-vitro transcription, HH PCR—in-vitro transcription template is a PCR product of overlapping oligonucleotides including a Hammerhead ribozyme template sequence, IDT—synthesized by IDT, PCR—in-vitro transcription template amplified from plasmid.

FIG. 51 presents Table 6. FIG. 52 presents Table 7. FIG. 53 presents Table 8. FIG. 54 presents Table 9.

FIG. 55. A revised model for Type VI-A CRISPR system function (A) Graphical summary of key findings in this study. Homologs used in this study are indicated with abbreviations in bold, with trans-ssRNA cleavage inactive homologs depicted in grey. Colored circles highlight the two orthogonal Cas13a enzyme groups, as defined by their generalized crRNA exchangeability and trans-ssRNA cleavage substrate nucleotide preference. (B) Schematic depicting a revised model for Type VI-A CRISPR system function.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting a single-stranded target RNA present in a biological sample at a concentration of from 10 fM to 1 nM, wherein the biological sample comprises a plurality of RNAs, the method comprising:

a) contacting the biological sample with:

(i) a Type VI CRISPR RNA-guided RNA endonuclease having distinct ribonuclease activities for (1) CRISPR RNA processing and (2) single-stranded RNA degradation, (ii) a guide RNA comprising a guide sequence that hybridizes to a target sequence of the single-stranded target RNA and a region that binds to the Type VI CRISPR RNA-guided RNA endonuclease, and (iii) a labeled non-target RNA, wherein the Type VI CRISPR RNA-guided RNA endonuclease cleaves the labeled non-target RNA when the guide RNA hybridizes to the target sequence; and b) measuring a detectable signal indicative of cleavage of the labeled non-target RNA by the Type VI CRISPR RNA-guided RNA endonuclease, wherein the detectable signal is indicative of the presence of the single-stranded target RNA in the biological sample.

2. The method according to claim 1, wherein the Type VI CRISPR RNA-guided RNA endonuclease cleaves at least 50% of the RNAs present in the biological sample within 1 hour of said contacting.

3. The method according to claim 1, wherein the Type VI CRISPR RNA-guided RNA endonuclease cleaves from 50% to more than 90% of the RNAs present in the biological sample within 1 minute of said contacting.

4. The method according to claim 1, wherein the Type VI CRISPR RNA-guided RNA endonuclease is not a *Leptotrichia shahii* (Lsh) C2c2 protein comprising an amino acid sequence having at least 80% amino acid sequence identity to the amino acid sequence set forth in SEQ ID NO:3.

5. The method according to claim 4, wherein the Type VI CRISPR RNA-guided RNA endonuclease cleaves the labeled non-target RNA at least 1.2-fold more efficiently than a *Leptotrichia shahii* (Lsh) C2c2 protein comprising at least 80% amino acid sequence identity to the amino acid sequence set forth in SEQ ID NO:3 or wherein the Type VI CRISPR RNA-guided RNA endonuclease cleaves the labeled non-target RNA at least 1.5-fold more efficiently than a *Leptotrichia shahii* (Lsh) C2c2 protein comprising the amino acid sequence set forth in SEQ ID NO:3.

6. The method according to claim 1, wherein the Type VI CRISPR RNA-guided RNA endonuclease comprises:

(i) an amino acid sequence having 80% or more amino acid sequence identity with the amino acid sequence set forth in any one of SEQ ID NOs: 1, 2, 4-6, 301, 304, 307, 310, 312-314, 316, or 321;

(ii) the amino acid sequence set forth in any one of SEQ ID NOs: 1, 2, 4-6, 301, 304, 307, 310, 312-314, 316, or 321;

(iii) an amino acid sequence having at least 80% amino acid sequence identity to the amino acid sequence set forth in SEQ ID NO:2, and comprises a substitution of one or more of R472, H477, R1048, and H1053;

(iv) an amino acid sequence having at least 80% amino acid sequence identity to the amino acid sequence set forth in SEQ ID NO:2, and comprises a substitution of amino acids R472 and H477; or (v) an amino acid sequence having at least 80% amino acid sequence identity to the amino acid sequence set forth in SEQ ID NO:2, and comprises a substitution of amino acids R1048 and H1053.

7. The method according to claim 1, wherein the sample is contacted for 1 hour or less prior to said measuring.

8. The method according to claim 1, comprising determining an amount of the single-stranded target RNA present in the sample and, optionally, wherein said determining comprises:

(a) measuring the detectable signal to generate a test measurement; measuring a detectable signal produced by a reference sample to generate a reference measurement; and comparing the test measurement to the reference measurement to determine an amount of the single-stranded target RNA present in the sample, or (b) measuring the detectable signal to generate a test measurement; measuring a detectable signal produced by each of two or more reference samples, wherein the two or more reference samples each include a different amount of a positive control RNA, to generate two or more reference measurements; and comparing the test measurement to the two or more reference measurements to determine an amount of the single-stranded target RNA present in the sample.

9. The method according to claim 1, wherein the plurality of RNAs comprises from 10 to $10^6$ RNAs that differ from one another in sequence.

10. The method according to claim 1, wherein measuring the detectable signal comprises one or more of: visual based detection, sensor based detection, color detection, gold nanoparticle based detection, fluorescence polarization, colloid phase transition/dispersion, electrochemical detection, fluorescent signal detection, and semiconductor-based sensing.

11. The method according to claim 1, wherein:

(i) the labeled non-target RNA comprises a fluorescence-emitting dye pair, and (ii) the detectable signal is produced by the fluorescence-emitting dye pair upon cleavage of the labeled non-target RNA by the Type VI CRISPR RNA-guided RNA endonuclease.

12. The method of according to claim 11, wherein the labeled non-target RNA comprises a fluorescence resonance energy transfer (FRET) pair or a quencher/fluor pair.

13. The method of according to claim 11, wherein:

(i) the labeled non-target RNA produces an amount of detectable signal prior to being cleaved, and the amount of detectable signal is reduced when the labeled non-target RNA is cleaved, (ii) the labeled non-target RNA produces a first detectable signal prior to being cleaved and a second detectable signal when the labeled non-target RNA is cleaved, (iii) the detectable signal is produced when the labeled non-target RNA is cleaved, or (iv) an amount of detectable signal increases when the labeled non-target RNA is cleaved.

14. The method according to claim 1, wherein the labeled non-target RNA comprises one or more of: a non-natural internucleoside linkage, a nucleic acid mimetic, a modified nucleobase, a modified sugar moiety, a locked nucleic acid (LNA), a peptide nucleic acid (PNA), a morpholino nucleic acid, and a cyclohexenyl nucleic acid (CeNA).

15. The method according to claim 1, wherein said contacting is carried out in an acellular sample or wherein said contacting is carried out in a cell in vitro, ex vivo, or in vivo.

16. The method according to claim 1, wherein the sample comprises RNAs from a cell lysate.

17. The method according to claim 1, wherein the measuring comprises measuring a change in the detectable signal over a period of time or wherein the measuring comprises measuring a change in the detectable signal in real time.

18. The method according to claim 1, further comprising lysing the sample prior to the contacting.

19. The method according to claim 17, wherein the Type VI CRISPR RNA-guided RNA endonuclease is not denatured prior to the measuring.

* * * * *